(12) United States Patent
Powell et al.

(10) Patent No.: US 8,574,588 B2
(45) Date of Patent: Nov. 5, 2013

(54) FUSION PROTEINS COMPRISING FLAGELLIN AND DENGUE VIRAL ENVELOPE PROTEINS

(75) Inventors: Thomas J. Powell, Madison, CT (US); Valerian Nakaar, Hamden, CT (US); Langzhou Song, Freehold, NJ (US); James W. Huleatt, Nazareth, PA (US); William F. McDonald, Madison, CT (US); Duane D. Hewitt, Hamilton (CA)

(73) Assignee: VanInnate Corporation, Cranbury, NJ (US)

( * ) Notice: Subject to any disclaimer, the term of this patent is extended or adjusted under 35 U.S.C. 154(b) by 898 days.

(21) Appl. No.: 11/879,695

(22) Filed: Jul. 18, 2007

(65) Prior Publication Data

US 2008/0063657 A1    Mar. 13, 2008

Related U.S. Application Data

(63) Continuation-in-part of application No. PCT/US2006/001623, filed on Jan. 19, 2006.

(60) Provisional application No. 60/723,409, filed on Oct. 4, 2005, provisional application No. 60/725,919, filed on Oct. 11, 2005, provisional application No. 60/645,170, filed on Jan. 19, 2005, provisional application No. 60/653,405, filed on Feb. 15, 2005, provisional application No. 60/704,160, filed on Jul. 29, 2005.

(51) Int. Cl.
    *A61K 39/295* (2006.01)
(52) U.S. Cl.
    USPC ........................................... 424/201.1
(58) Field of Classification Search
    None
    See application file for complete search history.

(56) References Cited

U.S. PATENT DOCUMENTS

| | | | |
|---|---|---|---|
| 4,666,839 A | 5/1987 | Souza | |
| 5,777,095 A | 7/1998 | Barbour et al. | |
| 5,871,747 A | 2/1999 | Gengoux-Sedlik et al. | |
| 5,891,992 A | 4/1999 | Stevens | |
| 5,895,651 A | 4/1999 | Simmons et al. | |
| 5,965,714 A | 10/1999 | Ryall | |
| 5,968,776 A | 10/1999 | Klein et al. | |
| 6,130,082 A | 10/2000 | Majarian et al. | |
| 6,562,798 B1 | 5/2003 | Schwartz | |
| 6,589,940 B1 | 7/2003 | Raz et al. | |
| 7,129,222 B2 | 10/2006 | Van Nest et al. | |
| 7,183,111 B2 | 2/2007 | Van Nest et al. | |
| 8,420,102 B2 | 4/2013 | Song et al. | |
| 2003/0044429 A1* | 3/2003 | Aderem et al. | 424/234.1 |
| 2003/0175287 A1 | 9/2003 | Medzhitov | |
| 2003/0232055 A1 | 12/2003 | Medzhitov et al. | |
| 2007/0122421 A1 | 5/2007 | Medzhitov | |
| 2008/0124361 A1 | 5/2008 | Mizel et al. | |
| 2008/0193487 A1 | 8/2008 | Schild et al. | |
| 2008/0220011 A1 | 9/2008 | Mizel | |
| 2009/0162400 A1 | 6/2009 | Powell et al. | |
| 2010/0015170 A1 | 1/2010 | Takeshita et al. | |

FOREIGN PATENT DOCUMENTS

| | | |
|---|---|---|
| AU | 49273 90 | 8/1990 |
| WO | WO 89/10967 | 11/1989 |
| WO | WO 96/37624 | 11/1996 |
| WO | WO 98/23735 | 6/1998 |
| WO | WO 00/32228 | 8/2000 |
| WO | WO 01/40280 A2 | 6/2001 |
| WO | WO 2005/042564 A1 | 5/2005 |
| WO | WO 2005/077408 A2 | 8/2005 |
| WO | WO 2006/040076 A2 | 4/2006 |
| WO | WO 2006/069262 A2 | 6/2006 |
| WO | WO 2006/078657 A2 | 7/2006 |
| WO | WO 2007/031034 A | 3/2007 |

OTHER PUBLICATIONS

Feighny et al. (Am. J. Trop. Med. Hyg., 50:322-328, 1994).*
Mizel, Steven B., et al., "Flagellin-F1-V Fusion Protein is an Effective Plague Vaccine in Mice and Two Species of Nonhuman Primates," *Clinical and Vaccine Immunology* 16(1): pp. 21-28 (Jan. 2009).
Weimer, Eric T., et al., "A Fusion Protein Vaccine Containing OprF Epitope 8, OprI, and Type A and B Flagellins Promotes Enhanced Clearance of Nonmucoid *Pseudomonas aeruginosa*," *Infection and Immunity* 77(6): pp. 2356-2366 (Jun. 2009).
Weimer, E.T., et al., "Immunization of Young African Green Monkeys with OprF Epitope 8-OprI-Type A- and B-flagellin Fusion Proteins Promotes the Production of Protective Antibodies Against Nonmucoid *Pseudomonas aeruginosa*," Vaccine, doi:10.1016/j.vaccine.2009.08.080 (pp. 1-8), (2009).
Akira, S., et al., "Recognition of Pathogen-associated Molecular Patterns by TLR Family," *Immuno. Letters*, 85:85-95 (2003).
Allen, et al., "Influenza Virus RNA Segment 7 Has the Coding Capacity for Two Polypeptides," *Virology*, 107:548-551 (1980).
Applequist, S.E., et al. "Activation of Innate Immunity, Inflammation, and Potentiation of DNA Vaccination through Mammalian Expression of the TLR5 Agonist Flagellin" *J Immunol.* 175:3882-3891 (2005).
Arnon, R. et al. "Peptide-based Synthetic Recombinant Vaccines with Anti-viral Efficacy" *Biologicals*, 29:237-242 (2001).
Bamps, Bart, Insertion of Nucleoprotein T-Cell Epitope of the Influrnza A Virus in the M2 Hepatitis B Core Fusion Protein (1996-1997

(56) References Cited

OTHER PUBLICATIONS

Bhardwaj, S., et al., "Biophysical Characterization and Vector-specific Antagonist Activity of Domain III of the Tick-borne Flavivirus Envelope Protein," *J. of Virology*, 75(8):4002-4007 (2001).

Black, R.A., et al., "Antibody Response to the M2 Protein of Influenza A Virus Expressed in Insect Cells," *J. of General Virology* 74:143-146 (1993).

Borisova, G.P., et al., "Recombinant Core Particles of Hepatitis B Virus Exposing Foreign Antigenic Determinants on Their Surface," *FEBS Letters*, 259:121-124 (1989).

Brown, A.L., et al., "Foreign Epitopes in Immunodominant Regions of Hepatitis B Core Particles are Highly Immunogenic and Conformationally Restricted," *Vaccine*, 9:595-601 (1991).

Charbit, A., et al., "Probing and Topology of a Bacterial membrane Protein by Genetic Insertion of a Foreign Epitope; Expression at the Cell Surface," *EMBO J.*, 5:3029-3037 (1986).

Charbit, A., et al., "Presentation of Two Epitopes of the preS2 Region of Hepatitis B Virus on Live Recombinant Bacteria," *J. Immunol.*, 139:1658-1664 (1987).

Clarke, B.E., et al., "Improved Immunogenicity of a Peptide Epitope After Fusion to Hepatitis B Core Protein," *Nature*, 330:381-384 (1987).

Clarke, B.E., et al., "Presentation and Immunogenicity of Viral Epitopes on the Surface of a Hybrid Hepatitis B Virus Core Particles Produced in Bacteria," *J. General Virology*, 71:1109-1117 (1990).

Cox, et al., "Identification of Sequence Changes in the Cold-Adapted, Live Attenuated Influenza Vaccine Strain, A/Ann Arbor/6/60 (H2N2)," *Virology*, 167:554-567 (1988).

Crill, W.D., et al., "Monoclonal Antibodies that Bind to Domain III of Dengue Virus E Glycoprotein are the Most Efficient Blockers of Virus Adsorption to Vero Cells," *J. of Virology*, 75(16):7769-7773 (2001).

Cuadros, C., et al., "Flagellin Fusion Proteins as Adjuvants or Vaccines Induce Specific Immune Responses," *Infection and Immunity*, 72(5):2810-2816 (2004).

das Gracas Luna, M., et al., "*Salmonella* Flagellin Fused with a Linear Epitope of Colonization Factor Antigen I (CFA/I) Can Prime Antibody Responses Against Homologous and Heterologous Fimbriae of Entertoxigenic *Escherichia coli*," *Research in Microbiology*, 151: 575-582 (2000).

Donnelly, M. A. et al. "Two Nonadjacent Regions in Enteroaggregative *Escherichia coli* Flagellin Are Required for Activation of Toll-like Receptor 5" *J. Biol. Chem.* 277(43):40456-40461 (2002).

Francis, M.J., et al., "Immunological Properties of Hepatitis B Core Antigen Fusion Proteins," *Proc. Natl. Acad. Sci.*, 87:2545-2549 (1990).

Francis, M.J., et al., "Peptide Vaccines Based on Enhanced Immunogenicity of Peptide Epitopes Presented with T-Cell Determinants or Hepatitis B Core Protein," In: *Antibodies, Antigens, and Molecular Mimicry, Methods in Enzymology* vol. 178, JJ. Langone, editor, pp. 659-676, Academic Press, Inc., New York (1989).

Hongo, S., et al., "Characterization of a Second Protein (CM2) Encoded by RNA Segment 6 of Influenza C Virus," *J. of Virol.*, 71(4): 143-146 (1993).

Honko, A.N., et al., "Mucosal Administration of Flagellin Induces Innate Immunity in the Mouse Lung," *Infection and Immunity*, 72(11):6676-6679 (2004).

Jeon, S.H. et al., "Intranasal Immunization with Synthetic Recombinant Vaccine Containing Multiple Epitopes of Influenza Virus," *Vaccine*, 20:2772-2780 (2002).

Kovacsovics-Bankowski, M., et al., "Efficient Major Histocompatibility Complex Class I Presentation of Exogeneous Antigen Upon Phagocytosis by Macrophages," *PNAS*, 90:4942-4946 (1993).

Levi, R. and Arnon, R., "Synthetic Recombinant Influenza Vaccine Induces Efficient Long-Term Immunity and Cross-Strain Protection," A148(1): 85-92 (1996).

McEwen, J., et al., "Synthetic Recombinant Vaccine Expressing Influenza Heamagglutinin Epitope in *Salmonella* Flagellin Leads to Partial Protection in Mice," *Vaccine*, 10(6): 405-411 (1992).

McQuiston, J.R., et al., "Sequencing and Comparative Analysis of Flagellin Genes flicC, fljB, and flpA from *Salmonella*," *J. of Clinical Micro.*, 42(5):1923-1932 (2004).

McSorley, S.J., et al. "Bacterial Flagellin Is an Effective Adjuvant for CD4+ T Cells in Vivo" *J. Immunol.* 169:3914-3919 (2002).

Milich, D.R., et al., "The Hepatitis Nucleocapsid as a Vaccine Carrier Moiety," *Ann N Y Acad Sci.*, 754:187-201 (1995).

Murthy, K.G.K. et al. "Identification of Conserved Domains in *Salmonella muenchen* Flagellin That Are Essential for Its Ability to Activate TLR5 and to Induce an Inflammatory Response in Vitro" *J. Biol. Chem.*, 279:5667-5675 (2004).

Obert, M., et al., "Protection of Mice Against SV40 Tumours by Pam3Cys, MTP-PE and Pam3Cys Conjugated with the SV40 T Antigen-derived Peptide, K(698)-T(708)," *Vaccine*, 16(2/3):161-169 (1998).

Pouwels, et al., "The Potential of *Lactobacillus* as a Carrier for Oral Immunication: Development and Preliminary Characterization of Vector Systems for Targeted Delivery of Antigens," *J. of Biotechnol.*, 44:183-192 (1996).

Pumpens, P., et al., "Hepatitis B Virus Core Particles as Epitope Carriers," *Intervirology*, 38:63-74 (1995).

Singh, B.P., et al., "Toll-like Receptors and Their Role in Innate Immunity," *Current Science*, 85(8):1156-1164 (2003).

Smith, K.D., et al., "Toll-like Receptor 5 Recognizes a Conserved Site on Flagellin Required for Protofilament Formation and Bacterial Motility," *Nat. Immunology*, 4(12):1247-1253 (2003).

Stocker, B.A.D., et al., "*Immune Responses to Epitopes Inserted in Salmonella Flagellin*," *Intern. Rev. Immunol*, 11:167-178 (1994).

Ulrich, R., "Core Particles of Hepatitis B Virus as Carrier for Foreign Epitopes," *Advances in Virus Research*, 50:141-182 (1998).

Vlaycheva, L., et al., "Yellow Fever 17D Virus: Pseudo-revertant Suppression of Defective Virus Penetration and Spread by Mutations in Domains II and III of the E Protein," *Virology*, 327:41-49 (2004).

von Brun, A., et al., "Principal Neutralizing Domain of HIV-1 is Highly Immunogenic when Expressed on the Surface of Hepatitis B Core Particles," *Vaccine*, 11:817-824 (1993).

Wells, J.M., et al., "*Lactococcus lactis*: High-level Expression of Tetanus Toxin Fragment C and Protection Against Lethal Challenge," *Molecular Microbiology* 8(6):1155-1162 (1993).

Wu, J.Y., et al., "Expression of Immunogenic Epitopes of Hepatitis B Surface Antigen with Hybrid Flagellin Proteins by a Vaccine Strain of *Salmonella*," *Proc. Nat. Acad. Sci. USA*, 86:4726-4730 (1989).

Wu, S-C., et al., "The Domain III Fragment of Japanese Encephalitis Virus Envelope Protein Mouse Immunogenicity and Liposome Adjuvanticity," *Vaccine*, 21:2516-2522 (2003).

Wyant, T.L., et al., "Potent Immunoregulatory Effects of *Salmonella typhi* Flagella on Antigenic Stimulation of Human Peripheral Blood Mononuclear Cells," *Infection and Immunity*, 67(3):1338-1346 (1999).

Wyant, T.L., et al., "*Salmonella typhi* Flagella are Potent Inducers of Proinflammatory Cytokine Secretion by Human Monocytes," *Infection and Immunity*, 67(7):3619-3624 (1999).

Ben-Yedidia, T. and Arnon, R., "Towards an Epitope-Based Human Vaccine for Influenza," *Human Vaccines* 1(3):95-101 (2005).

De Filette, M., et al., "Universal Influenza A Vaccine: Optimization of M2-Based Constructs," *Virology* 337:149-161 (2005).

Geisse, S., et al., "Eukaryotic Expression Systems: A Comparison," *Protein Expression and Purification* 8:271-282 (1996).

Huleatt, J.W., et al., "Vaccination with Recombinant Fusion Proteins Incorporating Toll-Like Receptor Ligands Induces Rapid Cellular and Humoral Immunity," *Vaccine* 25:763-775 (2007).

Jegerlehner, A., et al., "A Molecular Assembly System that Renders Antigens of Choice Highly Repetitive for Induction of Protective B Cell Responses," *Vaccine* 20:3104-3112 (2002).

Treanor, J.J., et al., "Safety and Immunogenicity of a Recombinant Hemagglutinin Vaccine for H5 Influenza in Humans," *Vaccine* 19:1732-1737 (2001).

EMBL U02084, H1N1 M1 and M2 genes, *VRL* May 2, 2006.

Data of M2e linked 2 STF 2, pp. 1-4 (2004).
de Vries,N., et al., "Production of Monoclonal Antibodies Specific for the i and 1,2 Flagellar Antigens of *Salmonella typhimurium* and Characterization of Their Respective Epitopes," *Applied and Environmental Microbiology*, 64(12): 5033-5038 (1998).

(56) References Cited

OTHER PUBLICATIONS

Eaves-Pyles, T.D. et al., "*Salmonella* Flagellin-Dependent Proinflammatory Responses are Localized to the Conserved Amino and Carboxyl Regions of the Protein," *The Journal of Immunology*, 167: 7009-7016 (2001).

Simmons, M., et al., "Short Report: Antibody Responses of Mice Immunized with a Tetravalent Dengue Recombinant Protein Subunit Vaccine," *Am. Jour. Tropical Med. & Hygeine*, 65(2): 159-161 (2001).

Extended European Search Report dated Aug. 26, 2011 for European Application No. 10180988.7-2406.

Andersen-Nissen, E., et al., "A Conserved Surface on Toll-Like Receptor 5 Recognizes Bacterial Flagellin," *Journal of Experimental Medicine*, 204(2):393-403 (Feb. 2007).

Andersen-Nissen, E., et al., "Evasion of Toll-like Receptor 5 by Flagellated Bacteria," *Proc. Natl. Acad. Sci. USA*, 102(26):9247-9252 (Jun. 13, 2005).

Barton, G. M. and Medzhitov, R., "Control of Adaptive Immune Responses by Toll-like Receptors," *Curr. Opin. Immunol.*, 14(3):380-383 (2002).

Fearon, D. T., and Locksley, R. M., "The Instructive Role of Innate Immunity in the Acquired Immune Response," *Science*, 272(5258):50-54 (Apr. 5, 1996).

Hayashi, F., et al., "The Innate Immune Response to Bacterial Flagellin is Mediated by Toll-Like Receptor 5," *Nature*, 410(6832):1099-1103 (Apr. 26, 2001).

Kopp, E.B. and Medzhitov, R., "The Toll-Receptor Family and Control of Innate Immunity," *Current Opinion in Immunology*, 11:13-18 (1999).

Means, T. K., et al., "The Toll-Like Receptor 5 Stimulus Bacterial Flagellin Induces Maturation and Chemokine Production in Human Dendritic Cells," *J. Immunol.*, 170(10):5165-5175 (2003).

Medzhitov, R., and Janeway, C., Jr., "Innate Immune Recognition: Mechanisms and Pathways," *Immunological Reviews*, 173:89-97 (2000).

Medzhitov, R., and Janeway, C. A., Jr., "Innate Immune Recognition and Control of Adaptive Immune Responses," *Seminars in Immunology*, 10:351-353 (1998).

Medzhitov, R., and Janeway, C. A., Jr., "Innate Immunity Impact on the Adaptive Immune Response," *Current Opinion in Immunology*, 9(1):4-9 (1997).

Medzhitov, R., and Janeway, C. A., Jr., "Innate Immunity: The Virtues of a Nonclonal System of Recognition," *Cell*, 91:295-298 (Oct. 1997).

Medzhitov, R., and Janeway, C., Jr., "Innate Immunity," *New England Journal of Medicine*, 343:338-344 (Aug. 3, 2000).

Medzhitov, R., and Janeway, C., Jr., "The Toll Receptor Family and Microbial Recognition," *Trends in Microbiology*, 8(10):452-456 (Oct. 10, 2000).

Medzhitov, R., and Janeway, C. A., Jr., "How Does the Immune System Distinguish Self from Nonself?" *Seminars in Immunology*, 12:185-188 (2000).

Medzhitov, R., "Toll-Like Receptors and Innate Immunity," *Nature Reviews Immunology*, 1:135-145 (Nov. 2001).

Newton, S. M. C., et al., "Immune Response to Cholera Toxin Epitope Inserted in *Salmonella* Flagellin," *Science*, 244(4900):70-72 (Apr. 1989).

Schnare, M., et al., "Toll-Like Receptors Control Activation of Adaptive Immune Responses," *Nature Immunology*, 2(10):947-950 (Oct. 2001).

Westerlund-Wikström, B., et al., "Functional Expression of Adhesive Peptides as Fusions to *Escherichia coli* Flagellin," *Protein Engineering*, 10(11):1319-1326 (1997).

Simmons, M., et al., Evaluation of the Protective Efficacy of a Recombinant Dengue Envelope B Domain Fusion Protein Against Dengue 2 Virus Infection in Mice, Am. J. Trop. Med. Hyg., 58(5): 655-662 (1998).

Simmons, M., et al., "Characterization of Antibody Responses to Combinations of a Dengue Virus Type 2 DNA Vaccine and Two Dengue Virus Type 2 Protein Vaccines in Thesus Macaques," Journal of Virology,80(19): 9577-9585 (2006).

\* cited by examiner

SEQ ID NO: 1 - fljB/STF2 amino acid sequence (hinge region underlined)

MAQVINTNSLSLLTQNNLNKSQSALGTAIERLSSGLRINSAKDDAAGQAIANRFTA
NIKGLTQASRNANDGISIAQTTEGALNEINNNLQRVRELAVQSANSTNSQSDLDSI
QAEITQRLNEIDRVSGQTQFNGVKVLAQDNTLTIQVGANDGETIDIDLKQINSQTL
GLDSLNVQKAYDVKDTAVTTKAYANNGTTLDVSGLDDAAIKAATGGTNGTASVTGG
AVKFDADNNKYFVTIGGFTGADAAKNGDYEVNVATDGTVTLAAGATKTTMPAGATT
KTEVQELKDTPAVVSADAKNALIAGGVDATDANGAELVKMSYTDKNGKTIEGGYAL
KAGDKYYAADYDEATGAIKAKTTSYTAADGTTKTAANQLGGVDGKTEVVTIDGKTY
NASKAAGHDFKAQPELAEAAAKTTENPLQKIDAALAQVDALRSDLGAVQNRFNSAI
TNLGNTVNNLSEARSRIEDSDYATEVSNMSRAQILQQAGTSVLAQANQVPQNVLSL
LR

Figure 1

SEQ ID NO: 2 - fljB/STF2 nucleic acid sequence (hinge region underlined)

ATGGCACAAGTAATCAACACTAACAGTCTGTCGCTGCTGACCCAGAATAACCTGAA
CAAATCCCAGTCCGCACTGGGCACCGCTATCGAGCGTCTGTCTTCTGGTCTGCGTA
TCAACAGCGCGAAAGACGATGCGGCAGGTCAGGCGATTGCTAACCGTTTCACCGCG
AACATCAAAGGTCTGACTCAGGCTTCCCGTAACGCTAACGACGGTATCTCCATTGC
GCAGACCACTGAAGGCGCGCTGAACGAAATCAACAACAACCTGCAGCGTGTGCGTG
AACTGGCGGTTCAGTCTGCTAACAGCACCAACTCCCAGTCTGACCTCGACTCCATC
CAGGCTGAAATCACCCAGCGCCTGAACGAAATCGACCGTGTATCCGGCCAGACTCA
GTTCAACGGCGTGAAAGTCCTGGCGCAGGACAACACCCTGACCATCCAGGTTGGCG
CCAACGACGGTGAAACTATCGATATCGATCTGAAGCAGATCAACTCTCAGACCCTG
GGTCTGGACTCACTGAACGTGCAGAAAGCGTATGATGTGAAAGATACAGCAGTAAC
AACGAAAGCTTATGCCAATAATGGTACTACACTGGATGTATCGGGTCTTGATGATG
CAGCTATTAAAGCGGCTACGGGTGGTACGAATGGTACGGCTTCTGTAACCGGTGGT
GCGGTTAAATTTGACGCAGATAATAACAAGTACTTTGTTACTATTGGTGGCTTTAC
TGGTGCTGATGCCGCCAAAAATGGCGATTATGAAGTTAACGTTGCTACTGACGGTA
CAGTAACCCTTGCGGCTGGCGCAACTAAAACCACAATGCCTGCTGGTGCGACAACT
AAAACAGAAGTACAGGAGTTAAAAGATACACCGGCAGTTGTTTCAGCAGATGCTAA
AAATGCCTTAATTGCTGGCGGCGTTGACGCTACCGATGCTAATGGCGCTGAGTTGG
TCAAAATGTCTTATACCGATAAAAATGGTAAGACAATTGAAGGCGGTTATGCGCTT
AAAGCTGGCGATAAGTATTACGCCGCAGATTACGATGAAGCGACAGGAGCAATTAA
AGCTAAAACTACAAGTTATACTGCTGCTGACGGCACTACCAAAACAGCGGCTAACC
AACTGGGTGGCGTAGACGGTAAAACCGAAGTCGTTACTATCGACGGTAAAACCTAC
AATGCCAGCAAAGCCGCTGGTCATGATTTCAAAGCACAACCAGAGCTGGCGGAAGC
AGCCGCTAAAACCACCGAAAACCCGCTGCAGAAAATTGATGCCGCGCTGGCGCAGG
TGGATGCGCTGCGCTCTGATCTGGGTGCGGTACAAAACCGTTTCAACTCTGCTATC
ACCAACCTGGGCAATACCGTAAACAATCTGTCTGAAGCGCGTAGCCGTATCGAAGA
TTCCGACTACGCGACCGAAGTTTCCAACATGTCTCGCGCGCAGATTCTGCAGCAGG
CCGGTACTTCCGTTCTGGCGCAGGCTAACCAGGTCCCGCAGAACGTGCTGTCTCTG
TTACGT

Figure 2

SEQ ID NO: 3 - fljB/STF2Δ amino acid sequence

MAQVINTNSLSLLTQNNLNKSQSALGTAIERLSSGLRINSAKDDAAGQAIANRFTA
NIKGLTQASRNANDGISIAQTTEGALNEINNNLQRVRELAVQSANSTNSQSDLDSI
QAEITQRLNEIDRVSGQTQFNGVKVLAQDNTLTIQVGANDGETIDIDLKQINSQTL
GLDSLNVHGAPVDPASPWTENPLQKIDAALAQVDALRSDLGAVQNRFNSAITNLGN
TVNNLSEARSRIEDSDYATEVSNMSRAQILQQAGTSVLAQANQVPQNVLSLLR

Figure 3

SEQ ID NO: 4 - fljB/STF2Δ nucleic acid sequence

ATGGCACAAGTAATCAACACTAACAGTCTGTCGCTGCTGACCCAGAATAACCTGAA
CAAATCCCAGTCCGCACTGGGCACCGCTATCGAGCGTCTGTCTTCTGGTCTGCGTA
TCAACAGCGCGAAAGACGATGCGGCAGGTCAGGCGATTGCTAACCGTTTCACCGCG
AACATCAAAGGTCTGACTCAGGCTTCCCGTAACGCTAACGACGGTATCTCCATTGC
GCAGACCACTGAAGGCGCGCTGAACGAAATCAACAACAACCTGCAGCGTGTGCGTG
AACTGGCGGTTCAGTCTGCTAACAGCACCAACTCCCAGTCTGACCTCGACTCCATC
CAGGCTGAAATCACCCAGCGCCTGAACGAAATCGACCGTGTATCCGGCCAGACTCA
GTTCAACGGCGTGAAAGTCCTGGCGCAGGACAACACCCTGACCATCCAGGTTGGCG
CCAACGACGGTGAAACTATCGATATCGATCTGAAGCAGATCAACTCTCAGACCCTG
GGTCTGGACTCACTGAACGTGCATGGAGCGCCGGTGGATCCTGCTAGCCCATGGAC
CGAAAACCCGCTGCAGAAAATTGATGCCGCGCTGGCGCAGGTGGATGCGCTGCGCT
CTGATCTGGGTGCGGTACAAAACCGTTTCAACTCTGCTATCACCAACCTGGGCAAT
ACCGTAAACAATCTGTCTGAAGCGCGTAGCCGTATCGAAGATTCCGACTACGCGAC
CGAAGTTTCCAACATGTCTCGCGCGCAGATTTTGCAGCAGGCCGGTACTTCCGTTC
TGGCGCAGGCTAACCAGGTCCCGCAGAACGTGCTGTCTCTGTTACGTG

Figure 4

SEQ ID NO: 5 - pET/STF2Δ.JEIII+ nucleic acid sequence

ATGGCACAAGTAATCAACACTAACAGTCTGTCGCTGCTGACCCAGAATAACCTGAA
CAAATCCCAGTCCGCACTGGGCACCGCTATCGAGCGTCTGTCTTCTGGTCTGCGTA
TCAACAGCGCGAAAGACGATGCGGCAGGTCAGGCGATTGCTAACCGTTTCACCGCG
AACATCAAAGGTCTGACTCAGGCTTCCCGTAACGCTAACGACGGTATCTCCATTGC
GCAGACCACTGAAGGCGCGCTGAACGAAATCAACAACAACCTGCAGCGTGTGCGTG
AACTGGCGGTTCAGTCTGCTAACAGCACCAACTCCCAGTCTGACCTCGACTCCATC
CAGGCTGAAATCACCCAGCGCCTGAACGAAATCGACCGTGTATCCGGCCAGACTCA
GTTCAACGGCGTGAAAGTCCTGGCGCAGGACAACACCCTGACCATCCAGGTTGGCG
CCAACGACGGTGAAACTATCGATATCGATCTGAAGCAGATCAACTCTCAGACCCTG
GGTCTGGACTCACTGAACGTG<u>CATGGAGCGCCGGTGGATCCTGCTAGCCCATGG</u>AC
CGAAAACCCGCTGCAGAAAATTGATGCCGCGCTGGCGCAGGTGGATGCGCTGCGCT
CTGATCTGGGTGCGGTACAAAACCGTTTCAACTCTGCTATCACCAACCTGGGCAAT
ACCGTAAACAATCTGTCTGAAGCGCGTAGCCGTATCGAAGATTCCGACTACGCGAC
CGAAGTTTCCAACATGTCTCGCGCGCAGATTTTGCAGCAGGCCGGTACTTCCGTTC
TGGCGCAGGCTAACCAGGTCCCGCAGAACGTGCTGTCTCTGTTACGTGAATTCTGC
AGATATCCAGCACAGTGGCGGCCGCTC***ATGGACAAACTGGCTCTGAAAGGCACAAC
CTATGGCATGTGTACAGAAAAATTCTCGTTCGCGAAAAATCCGGTGGACACTGGTC
ACGGAACAGTTGTCATTGAACTCTCCTACTCTGGGAGTGATGGCCCCTGCAAAATT
CCGATTGTTTCCGTTGCGAGCCTCAATGACATGACCCCCGTTGGGCGGCTGGTGAC
AGTGAACCCCTTCGTCGCGACTTCCAGTGCCAACTCAAAGGTGCTGGTCGAGATGG
AACCCCCCTTCGGAGACTCCTACATCGTAGTTGGAAGGGGAGACAAGCAGATCAAC
CACCATTGGCACAAAGCTGGAAGCACGCTGGGCAAGGCC***

Figure 5

SEQ ID NO: 6 - pET/STF2.JEIII+ amino acid sequence

MAQVINTNSLSLLTQNNLNKSQSALGTAIERLSSGLRINSAKDDAAGQAIANRFTANIKG
LTQASRNANDGISIAQTTEGALNEINNNLQRVRELAVQSANSTNSQSDLDSIQAEITQRL
NEIDRVSGQTQFNGVKVLAQDNTLTIQVGANDGETIDIDLKQINSQTLGLDSLN<u>VHGAPV
DPASPW</u>TENPLQKIDAALAQVDALRSDLGAVQNRFNSAITNLGNTVNNLSEARSRIEDSD
YATEVSNMSRAQILQQAGTSVLAQANQVPQNVLSLL<u>REFCRYPAQWRPL</u>***MDKLALKGTTY
GMCTEKFSFAKNPVDTGHGTVVIELSYSGSDGPCKIPIVSVASLNDMTPVGRLVTVNPFV
ATSSANSKVLVEMEPPFGDSYIVVGRGDKQINHHWHKAGSTLGKA***

Figure 6

SEQ ID NO: 29 - STF2.EIII+ nucleic acid sequence

ATGGCACAAGTAATCAACACTAACAGTCTGTCGCTGCTGACCCAGAATAACCTGAACAAA
TCCCAGTCCGCACTGGGCACCGCTATCGAGCGTCTGTCTTCTGGTCTGCGTATCAACAGC
GCGAAAGACGATGCGGCAGGTCAGGCGATTGCTAACCGTTTCACCGCGAACATCAAAGGT
CTGACTCAGGCTTCCCGTAACGCTAACGACGGTATCTCCATTGCGCAGACCACTGAAGGC
GCGCTGAACGAAATCAACAACAACCTGCAGCGTGTGCGTGAACTGGCGGTTCAGTCTGCT
AACAGCACCAACTCCCAGTCTGACCTCGACTCCATCCAGGCTGAAATCACCCAGCGCCTG
AACGAAATCGACCGTGTATCCGGCCAGACTCAGTTCAACGGCGTGAAAGTCCTGGCGCAG
GACAACACCCTGACCATCCAGGTTGGCGCCAACGACGGTGAAACTATCGATATCGATCTG
AAGCAGATCAACTCTCAGACCCTGGGTCTGGACTCACTGAACGTGCAGAAAGCGTATGAT
GTGAAAGATACAGCAGTAACAACGAAAGCTTATGCCAATAATGGTACTACACTGGATGTA
TCGGGTCTTGATGATGCAGCTATTAAAGCGGCTACGGGTGGTACGAATGGTACGGCTTCT
GTAACCGGTGGTGCGGTTAAATTTGACGCAGATAATAACAAGTACTTTGTTACTATTGGT
GGCTTTACTGGTGCTGATGCCGCCAAAAATGGCGATTATGAAGTTAACGTTGCTACTGAC
GGTACAGTAACCCTTGCGGCTGGCGCAACTAAAACCACAATGCCTGCTGGTGCGACAACT
AAAACAGAAGTACAGGAGTTAAAAGATACACCGGCAGTTGTTTCAGCAGATGCTAAAAAT
GCCTTAATTGCTGGCGGCGTTGACGCTACCGATGCTAATGGCGCTGAGTTGGTCAAAATG
TCTTATACCGATAAAAATGGTAAGACAATTGAAGGCGGTTATGCGCTTAAAGCTGGCGAT
AAGTATTACGCCGCAGATTACGATGAAGCGACAGGAGCAATTAAAGCTAAAACTACAAGT
TATACTGCTGCTGACGGCACTACCAAAACAGCGGCTAACCAACTGGGTGGCGTAGACGGT
AAAACCGAAGTCGTTACTATCGACGGTAAAACCTACAATGCCAGCAAAGCCGCTGGTCAT
GATTTCAAAGCACAACCAGAGCTGGCGGAAGCAGCCGCTAAAACCACCGAAAACCCGCTG
CAGAAAATTGATGCCGCGCTGGCGCAGGTGGATGCGCTGCGCTCTGATCTGGGTGCGGTA
CAAAACCGTTTCAACTCTGCTATCACCAACCTGGGCAATACCGTAAACAATCTGTCTGAA
GCGCGTAGCCGTATCGAAGATTCCGACTACGCGACCGAAGTTTCCAACATGTCTCGCGCG
CAGATTCTGCAGCAGGCCGGTACTTCCGTTCTGGCGCAGGCTAACCAGGTCCCGCAGAAC
GTGCTGTCTCTGTTACGTATGGAAAAATTGCAGTTGAAGGGAACAACCTATGGCGTCTGT

TCAAAGGCTTTCAAGTTTCTTGGGACTCCGCAGACACAGGTCACGGCACTGTGGTGTTG
GAATTGCAGTACACTGGCACGGATGGACCTTGCAAAGTTCCTATCTCGTCAGTGGCTTCA
TTGAACGACCTAACGCCAGTGGGCAGATTGGTCACTGTCAACCCTTTTGTTTCAGTGGCC
ACGGCCAACGCTAAGGTCCTGATTGAATTGGAACCACCCTTTGGAGACTCATACATAGTG
GTGGGCAGAGGAGAACAACAGATCAATCACCATTGGCACAAGTCTGGAAGCAGCATTGGC
AAA

Figure 7

SEQ ID NO: 30 - fljB/STF2.EIII+ amino acid sequence of SEQ ID NO: 29

MAQVINTNSLSLLTQNNLNKSQSALGTAIERLSSGLRINSAKDDAAGQAIANRFTA
NIKGLTQASRNANDGISIAQTTEGALNEINNNLQRVRELAVQSANSTNSQSDLDSI
QAEITQRLNEIDRVSGQTQFNGVKVLAQDNTLTIQVGANDGETIDIDLKQINSQTL
GLDSLNVQKAYDVKDTAVTTKAYANNGTTLDVSGLDDAAIKAATGGTNGTASVTGG
AVKFDADNNKYFVTIGGFTGADAAKNGDYEVNVATDGTVTLAAGATKTTMPAGATT
KTEVQELKDTPAVVSADAKNALIAGGVDATDANGAELVKMSYTDKNGKTIEGGYAL
KAGDKYYAADYDEATGAIKAKTTSYTAADGTTKTAANQLGGVDGKTEVVTIDGKTY
NASKAAGHDFKAQPELAEAAAKTTENPLQKIDAALAQVDALRSDLGAVQNRFNSAI
TNLGNTVNNLSEARSRIEDSDYATEVSNMSRAQILQQAGTSVLAQANQVPQNVLSL
LRMEKLQLKGTTYGVCSKAFKFLGTPADTGHGTVVLELQYTGTDGPCKVPISSVAS
LNDLTPVGRLVTVNPFVSVATANAKVLIELEPPFGDSYIVVGREQQINHHWHKSG
SSIGK

Figure 8

SEQ ID NO: 31 - STF2Δ .EIII+ nucleic acid sequence

ATGGCACAAGTAATCAACACTAACAGTCTGTCGCTGCTGACCCAGAATAACCTGAA
CAAATCCCAGTCCGCACTGGGCACCGCTATCGAGCGTCTGTCTTCTGGTCTGCGTA
TCAACAGCGCGAAAGACGATGCGGCAGGTCAGGCGATTGCTAACCGTTTCACCGCG
AACATCAAAGGTCTGACTCAGGCTTCCCGTAACGCTAACGACGGTATCTCCATTGC
GCAGACCACTGAAGGCGCGCTGAACGAAATCAACAACAACCTGCAGCGTGTGCGTG
AACTGGCGGTTCAGTCTGCTAACAGCACCAACTCCCAGTCTGACCTCGACTCCATC
CAGGCTGAAATCACCCAGCGCCTGAACGAAATCGACCGTGTATCCGGCCAGACTCA
GTTCAACGGCGTGAAAGTCCTGGCGCAGGACAACACCCTGACCATCCAGGTTGGCG
CCAACGACGGTGAAACTATCGATATCGATCTGAAGCAGATCAACTCTCAGACCCTG
GGTCTGGACTCACTGAACGTGC<u>ATGGAGCGCCGGTGGATCCTGCTAGCCCATGGAC
CGAAAACCCGCTGCAGAAAATTGATGCCGCGCTGGCGCAGGTGGATGCGCTGCGCT
CTGATCTGGGTGCGGTACAAAACCGTTTCAACTCTGCTATCACCAACCTGGGCAAT
ACCGTAAACAATCTGTCTGAAGCGCGTAGCCGTATCGAAGATTCCGACTACGCGAC
CGAAGTTTCCAACATGTCTCGCGCGCAGATTTTGCAGCAGGCCGGTACTTCCGTTC
TGGCGCAGGCTAACCAGGTCCCGCAGAACGTGCTGTCTCTGTTACGT</u>***ATGGAAAAA
TTGCAGTTGAAGGGAACAACCTATGGCGTCTGTTCAAAGGCTTTCAAGTTTCTTGG
GACTCCCGCAGACACAGGTCACGGCACTGTGGTGTTGGAATTGCAGTACACTGGCA
CGGATGGACCTTGCAAAGTTCCTATCTCGTCAGTGGCTTCATTGAACGACCTAACG
CCAGTGGGCAGATTGGTCACTGTCAACCCTTTTGTTTCAGTGGCCACGGCCAACGC
TAAGGTCCTGATTGAATTGGAACCACCCTTTGGAGACTCATACATAGTGGTGGGCA
GAGGAGAACAACAGATCAATCACCATTGGCACAAGTCTGGAAGCAGCATTGGCAAA***

Figure 9

SEQ ID NO: 32 - fljB/STF2Δ.EIII⁺ amino acid sequence of SEQ ID NO: 31

MAQVINTNSLSLLTQNNLNKSQSALGTAIERLSSGLRINSAKDDAA
GQAIANRFTANIKGLTQASRNANDGISIAQTTEGALNEINNNLQRV
RELAVQSANSTNSQSDLDSIQAEITQRLNEIDRVSGQTQFNGVKVL
AQDNTLTIQVGANDGETIDIDLKQINSQTLGLDSLNV<u>HGAPVDPAS
PW</u>TENPLQKIDAALAQVDALRSDLGAVQNRFNSAITNLGNTVNNLS
EARSRIEDSDYATEVSNMSRAQILQQAGTSVLAQANQVPQNVLSLL
R*MEKLQ*LKGTTYGVCSKAFKFLGTPADTGHGTVVLELQYTGTDGPC
KVPISSVASLNDLTPVGRLVTVNPFVSVATANAKVLIELEPPFGDS
YIVVGREQQINHHWHKSGSSIGK

Figure 10

SEQ ID NO: 33 - STF2Δ.EIII+ nucleic acid sequence

ATGGCACAAGTAATCAACACTAACAGTCTGTCGCTGCTGACCCAGA
ATAACCTGAACAAATCCCAGTCCGCACTGGGCACCGCTATCGAGCG
TCTGTCTTCTGGTCTGCGTATCAACAGCGCGAAAGACGATGCGGCA
GGTCAGGCGATTGCTAACCGTTTCACCGCGAACATCAAAGGTCTGA
CTCAGGCTTCCCGTAACGCTAACGACGGTATCTCCATTGCGCAGAC
CACTGAAGGCGCGCTGAACGAAATCAACAACAACCTGCAGCGTGTG
CGTGAACTGGCGGTTCAGTCTGCTAACAGCACCAACTCCCAGTCTG
ACCTCGACTCCATCCAGGCTGAAATCACCCAGCGCCTGAACGAAAT
CGACCGTGTATCCGGCCAGACTCAGTTCAACGGCGTGAAAGTCCTG
GCGCAGGACAACACCCTGACCATCCAGGTTGGCGCCAACGACGGTG
AAACTATCGATATCGATCTGAAGCAGATCAACTCTCAGACCCTGGG
TCTGGACTCACTGAACGTG<u>CATGGAGCGCCGGTGGATCCTGCTAGC
CCATGGA</u>CCGAAAACCCGCTGCAGAAAATTGATGCCGCGCTGGCGC
AGGTGGATGCGCTGCGCTCTGATCTGGGTGCGGTACAAAACCGTTT
CAACTCTGCTATCACCAACCTGGGCAATACCGTAAACAATCTGTCT
GAAGCGCGTAGCCGTATCGAAGATTCCGACTACGCGACCGAAGTTT
CCAACATGTCTCGCGCGCAGATTTTGCAGCAGGCCGGTACTTCCGT
TCTGGCGCAGGCTAACCAGGTCCCGCAGAACGTGCTGTCTCTGTTA
CGT<u>GAATTCTGCAGATATCCAGCACAGTGGCGGCCGCT</u>***CATGGAAA
AATTGCAGTTGAAGGGAACAACCTATGGCGTCTGTTCAAAGGCTTT
CAAGTTTCTTGGGACTCCCGCAGACACAGGTCACGGCACTGTGGTG
TTGGAATTGCAGTACACTGGCACGGATGGACCTTGCAAAGTTCCTA
TCTCGTCAGTGGCTTCATTGAACGACCTAACGCCAGTGGGCAGATT
GGTCACTGTCAACCCTTTTGTTTCAGTGGCCACGGCCAACGCTAAG
GTCCTGATTGAATTGGAACCACCCTTTGGAGACTCATACATAGTGG
TGGGCAGAGGAGAACAACAGATCAATCACCATTGGCACAAGTCTGG
AAGCAGCATTGGCAAA***CCCTTAATAAGC

Figure 11

SEQ ID NO: 34 - fljB/STF2Δ.EIII+ amino acid sequence of SEQ ID NO: 33

MAQVINTNSLSLLTQNNLNKSQSALGTAIERLSSGLRINSAKDDAA
GQAIANRFTANIKGLTQASRNANDGISIAQTTEGALNEINNNLQRV
RELAVQSANSTNSQSDLDSIQAEITQRLNEIDRVSGQTQFNGVKVL
AQDNTLTIQVGANDGETIDIDLKQINSQTLGLDSLNV<u>HGAPVDPAS</u>
<u>P</u>WTENPLQKIDAALAQVDALRSDLGAVQNRFNSAITNLGNTVNNLS
EARSRIEDSDYATEVSNMSRAQILQQAGTSVLAQANQVPQNVLSLL
<u>REFCRYPAQWRPL</u>*MEKLQLKGTTYGVCSKAFKFLGTPADTGHGTVV*
*LELQYTGTDGPCKVPISSVASLNDLTPVGRLVTVNPFVSVATANAK*
*VLIELEPPFGDSYIVVGRGEQQINHHWHKSGSSIGKPLIS*

Figure 12

SEQ ID NO: 35 - STF2.EIII+- STF2 nucleic acid sequence

```
ATGGCACAAGTAATCAACACTAACAGTCTGTCGCTGCTGACCCAGAATAACCTGAACAAA
TCCCAGTCCGCACTGGGCACCGCTATCGAGCGTCTGTCTTCTGGTCTGCGTATCAACAGC
GCGAAAGACGATGCGGCAGGTCAGGCGATTGCTAACCGTTTCACCGCGAACATCAAAGGT
CTGACTCAGGCTTCCCGTAACGCTAACGACGGTATCTCCATTGCGCAGACCACTGAAGGC
GCGCTGAACGAAATCAACAACAACCTGCAGCGTGTGCGTGAACTGGCGGTTCAGTCTGCT
AACAGCACCAACTCCCAGTCTGACCTCGACTCCATCCAGGCTGAAATCACCCAGCGCCTG
AACGAAATCGACCGTGTATCCGGCCAGACTCAGTTCAACGGCGTGAAAGTCCTGGCGCAG
GACAACACCCTGACCATCCAGGTTGGCGCCAACGACGGTGAAACTATCGATATCGATCTG
AAGCAGATCAACTCTCAGACCCTGGGTCTGGACTCACTGAACGTGCAGAAAGCGTATGAT
GTGAAAGATACAGCAGTAACAACGAAAGCTTATGCCAATAATGGTACTACACTGGATGTA
TCGGGTCTTGATGATGCAGCTATTAAAGCGGCTACGGGTGGTACGAATGGTACGGCTTCT
GTAACCGGTGGTGCGGTTAAATTTGACGCAGATAATAACAAGTACTTTGTTACTATTGGT
GGCTTTACTGGTGCTGATGCCGCCAAAAATGGCGATTATGAAGTTAACGTTGCTACTGAC
GGTACAGTAACCCTTGCGGCTGGCGCAACTAAAACCACAATGCCTGCTGGTGCGACAACT
AAAACAGAAGTACAGGAGTTAAAAGATACACCGGCAGTTGTTTCAGCAGATGCTAAAAAT
GCCTTAATTGCTGGCGGCGTTGACGCTACCGATGCTAATGGCGCTGAGTTGGTCAAAATG
TCTTATACCGATAAAAATGGTAAGACAATTGAAGGCGGTTATGCGCTTAAAGCTGGCGAT
AAGTATTACGCCGCAGATTACGATGAAGCGACAGGAGCAATTAAAGCTAAAACTACAAGT
TATACTGCTGCTGACGGCACTACCAAAACAGCGGCTAACCAACTGGGTGGCGTAGACGGT
AAAACCGAAGTCGTTACTATCGACGGTAAAACCTACAATGCCAGCAAAGCCGCTGGTCAT
GATTTCAAAGCACAACCAGAGCTGGCGGAAGCAGCCGCTAAAACCACCGAAAACCCGCTG
CAGAAAATTGATGCCGCGCTGGCGCAGGTGGATGCGCTGCGCTCTGATCTGGGTGCGGTA
CAAAACCGTTTCAACTCTGCTATCACCAACCTGGGCAATACCGTAAACAATCTGTCTGAA
GCGCGTAGCCGTATCGAAGATTCCGACTACGCGACCGAAGTTTCCAACATGTCTCGCGCG
CAGATTCTGCAGCAGGCCGGTACTTCCGTTCTGGCGCAGGCTAACCAGGTCCCGCAGAAC
GTGCTGTCTCTGTTACGTGAATTCTGCAGATATCCAGCACAGTGGCGGCCGCTCATGG
AAAAATTGCAGTTGAAGGGAACAACCTATGGCGTCTGTTCAAAGGCTTTCAAGTTTCT
TGGGACTCCCGCAGACACAGGTCACGGCACTGTGGTGTTGGAATTGCAGTACACTGGC
ACGGATGGACCTTGCAAAGTTCCTATCTCGTCAGTGGCTTCATTGAACGACCTAACGC
CAGTGGGCAGATTGGTCACTGTCAACCCTTTTGTTTCAGTGGCCACGGCCAACGCTAA
GGTCCTGATTGAATTGGAACCACCCTTTGGAGACTCATACATAGTGGTGGGCAGAGGA
GAACAACAGATCAATCACCATTGGCACAAGTCTGGAAGCAGCATTGGCAAA
```

Figure 13

SEQ ID NO: 36 - fljB/STF2.EIII+ amino acid sequence of SEQ ID NO: 35

MAQVINTNSLSLLTQNNLNKSQSALGTAIERLSSGLRINSAKDDAAGQAIA
NRFTANIKGLTQASRNANDGISIAQTTEGALNEINNNLQRVRELAVQSANS
TNSQSDLDSIQAEITQRLNEIDRVSGQTQFNGVKVLAQDNTLTIQVGANDG
ETIDIDLKQINSQTLGLDSLNVQKAYDVKDTAVTTKAYANNGTTLDVSGLD
DAAIKAATGGTNGTASVTGGAVKFDADNNKYFVTIGGFTGADAAKNGDYEV
NVATDGTVTLAAGATKTTMPAGATTKTEVQELKDTPAVVSADAKNALIAGG
VDATDANGAELVKMSYTDKNGKTIEGGYALKAGDKYYAADYDEATGAIKAK
TTSYTAADGTTKTAANQLGGVDGKTEVVTIDGKTYNASKAAGHDFKAQPEL
AEAAAKTTENPLQKIDAALAQVDALRSDLGAVQNRFNSAITNLGNTVNNLS
EARSRIEDSDYATEVSNMSRAQILQQAGTSVLAQANQVPQNVLSLLR**EFCR
YPAQWRPL*MEKL*QLKGTTYGVCSKAFKFLGTPADTGHGTVVLELQYTGTDG
PCKVPISSVASLNDLTPVGRLVTVNPFVSVATANAKVLIELEPPFGDSYIV
VGRGEQQINHHWHKSGSSIGK**

Figure 14

SEQ ID NO: 37 - fljB/STF2Δ.EIII+ nucleic acid sequence of SEQ ID NO: 38

ATGGCACAAGTAATCAACACTAACAGTCTGTCGCTGCTGACCCAGAATAACCTGAA
CAAATCCCAGTCCGCACTGGGCACCGCTATCGAGCGTCTGTCTTCTGGTCTGCGTA
TCAACAGCGCGAAAGACGATGCGGCAGGTCAGGCGATTGCTAACCGTTTCACCGCG
AACATCAAAGGTCTGACTCAGGCTTCCCGTAACGCTAACGACGGTATCTCCATTGC
GCAGACCACTGAAGGCGCGCTGAACGAAATCAACAACAACCTGCAGCGTGTGCGTG
AACTGGCGGTTCAGTCTGCTAACAGCACCAACTCCCAGTCTGACCTCGACTCCATC
CAGGCTGAAATCACCCAGCGCCTGAACGAAATCGACCGTGTATCCGGCCAGACTCA
GTTCAACGGCGTGAAAGTCCTGGCGCAGGACAACACCCTGACCATCCAGGTTGGCG
CCAACGACGGTGAAACTATCGATATCGATCTGAAGCAGATCAACTCTCAGACCCTG
GGTCTGGACTCACTGAACGTGACCGAAAACCCGCTGCAGAAAATTGATGCCGCGCT
GGCGCAGGTGGATGCGCTGCGCTCTGATCTGGGTGCGGTACAAAACCGTTTCAACT
CTGCTATCACCAACCTGGGCAATACCGTAAACAATCTGTCTGAAGCGCGTAGCCGT
ATCGAAGATTCCGACTACGCGACCGAAGTTTCCAACATGTCTCGCGCGCAGATTCT
GCAGCAGGCCGGTACTTCCGTTCTGGCGCAGGCTAACCAGGTCCCGCAGAACGTGC
TGTCTCTGTTACGT**ATGGAAAAATTGCAGTTGAAGGGAACAACCTATGGCGTCTGT
TCAAAGGCTTTCAAGTTTCTTGGGACTCCCGCAGACACAGGTCACGGCACTGTGGT
GTTGGAATTGCAGTACACTGGCACGGATGGACCTTGCAAAGTTCCTATCTCGTCAG
TGGCTTCATTGAACGACCTAACGCCAGTGGGCAGATTGGTCACTGTCAACCCTTTT
GTTTCAGTGGCCACGGCCAACGCTAAGGTCCTGATTGAATTGGAACCACCCTTTGG
AGACTCATACATAGTGGTGGGCAGAGGAGAACAACAGATCAATCACCATTGGCACA
AGTCTGGAAGCAGCATTGGCAAA**

Figure 15

SEQ ID NO: 38 - fljB/STF2Δ.EIII+ amino acid sequence of SEQ ID NO: 37

MAQVINTNSLSLLTQNNLNKSQSALGTAIERLSSGLRINSAKDDAAGQAIANRFTA
NIKGLTQASRNANDGISIAQTTEGALNEINNNLQRVRELAVQSANSTNSQSDLDSI
QAEITQRLNEIDRVSGQTQFNGVKVLAQDNTLTIQVGANDGETIDIDLKQINSQTL
GLDSLNVTENPLQKIDAALAQVDALRSDLGAVQNRFNSAITNLGNTVNNLSEARSR
IEDSDYATEVSNMSRAQILQQAGTSVLAQANQVPQNVLSLLR*MEKLQLKGTTYGVC*
*SKAFKFLGTPADTGHGTVVLELQYTGTDGPCKVPISSVASLNDLTPVGRLVTVNPF*
*VSVATANAKVLIELEPPFGDSYIVVGRGEQQINHHWHKSGSSIGK*

Figure 16

SEQ ID NO: 54 - fljB/STF2.EIII+ nucleic acid sequence

ATGGCACAAGTAATCAACACTAACAGTCTGTCGCTGCTGACCCAGAATAACCTGAACAAA
TCCCAGTCCGCACTGGGCACCGCTATCGAGCGTCTGTCTTCTGGTCTGCGTATCAACAGC
GCGAAAGACGATGCGGCAGGTCAGGCGATTGCTAACCGTTTCACCGCGAACATCAAAGGT
CTGACTCAGGCTTCCCGTAACGCTAACGACGGTATCTCCATTGCGCAGACCACTGAAGGC
GCGCTGAACGAAATCAACAACAACCTGCAGCGTGTGCGTGAACTGGCGGTTCAGTCTGCT
AACAGCACCAACTCCCAGTCTGACCTCGACTCCATCCAGGCTGAAATCACCCAGCGCCTG
AACGAAATCGACCGTGTATCCGGCCAGACTCAGTTCAACGGCGTGAAAGTCCTGGCGCAG
GACAACACCCTGACCATCCAGGTTGGCGCCAACGACGGTGAAACTATCGATATCGATCTG
AAGCAGATCAACTCTCAGACCCTGGGTCTGGACTCACTGAACGTGCAGAAAGCGTATGAT
GTGAAAGATACAGCAGTAACAACGAAAGCTTATGCCAATAATGGTACTACACTGGATGTA
TCGGGTCTTGATGATGCAGCTATTAAAGCGGCTACGGGTGGTACGAATGGTACGGCTTCT
GTAACCGGTGGTGCGGTTAAATTTGACGCAGATAATAACAAGTACTTTGTTACTATTGGT
GGCTTTACTGGTGCTGATGCCGCCAAAAATGGCGATTATGAAGTTAACGTTGCTACTGAC
GGTACAGTAACCCTTGCGGCTGGCGCAACTAAAACCACAATGCCTGCTGGTGCGACAACT
AAAACAGAAGTACAGGAGTTAAAAGATACACCGGCAGTTGTTTCAGCAGATGCTAAAAAT
GCCTTAATTGCTGGCGGCGTTGACGCTACCGATGCTAATGGCGCTGAGTTGGTCAAAATG
TCTTATACCGATAAAAATGGTAAGACAATTGAAGGCGGTTATGCGCTTAAAGCTGGCGAT
AAGTATTACGCCGCAGATTACGATGAAGCGACAGGAGCAATTAAAGCTAAAACTACAAGT
TATACTGCTGCTGACGGCACTACCAAAACAGCGGCTAACCAACTGGGTGGCGTAGACGGT
AAAACCGAAGTCGTTACTATCGACGGTAAAACCTACAATGCCAGCAAAGCCGCTGGTCAT
GATTTCAAAGCACAACCAGAGCTGGCGGAAGCAGCCGCTAAAACCACCGAAAACCCGCTG
CAGAAAATTGATGCCGCGCTGGCGCAGGTGGATGCGCTGCGCTCTGATCTGGGTGCGGTA
CAAAACCGTTTCAACTCTGCTATCACCAACCTGGGCAATACCGTAAACAATCTGTCTGAA
GCGCGTAGCCGTATCGAAGATTCCGACTACGCGACCGAAGTTTCCAACATGTCTCGCGCG
CAGATTCTGCAGCAGGCCGGTACTTCCGTTCTGGCGCAGGCTAACCAGGTCCCGCAGAAC
GTGCTGTCTCTGTTACGT**AAGGGCAATTCGAAGCTTGAAGGTCAATTGGAATTCCCTAGG
ACTAGT**ATGGAAAAATTGCAGTTGAAGGGAACAACCTATGGCGTCTGTTCAAAGGCTTTC
AAGTTTCTTGGGACTCCCGCAGACACAGGTCACGGCACTGTGGTGTTGGAATTGCAGTAC
ACTGGCACGGATGGACCTTGCAAAGTTCCTATCTCGTCAGTGGCTTCATTGAACGACCTA
ACGCCAGTGGGCAGATTGGTCACTGTCAACCCTTTTGTTTCAGTGGCCACGGCCAACGCT
AAGGTCCTGATTGAATTGGAACCACCCTTTGGAGACTCATACATAGTGGTGGGCAGAGGA
GAACAACAGATCAATCACCATTGGCACAAGTCTGGAAGCAGCATTGGCAAA

Figure 17

SEQ ID NO: 55 - fljB/STF2.EIII+ amino acid sequence

MAQVINTNSLSLLTQNNLNKSQSALGTAIERLSSGLRINSAKDDAAGQAIANRFTANIKG
LTQASRNANDGISIAQTTEGALNEINNNLQRVRELAVQSANSTNSQSDLDSIQAEITQRL
NEIDRVSGQTQFNGVKVLAQDNTLTIQVGANDGETIDIDLKQINSQTLGLDSLNVQKAYD
VKDTAVTTKAYANNGTTLDVSGLDDAAIKAATGGTNGTASVTGGAVKFDADNNKYFVTIG
GFTGADAAKNGDYEVNVATDGTVTLAAGATKTTMPAGATTKTEVQELKDTPAVVSADAKN
ALIAGGVDATDANGAELVKMSYTDKNGKTIEGGYALKAGDKYYAADYDEATGAIKAKTTS
YTAADGTTKTAANQLGGVDGKTEVVTIDGKTYNASKAAGHDFKAQPELAEAAAKTTENPL
QKIDAALAQVDALRSDLGAVQNRFNSAITNLGNTVNNLSEARSRIEDSDYATEVSNMSRA
QILQQAGTSVLAQANQVPQNVLSLLRKGNSKLEGQLEFPRTS*MEKLQL*KGTTYGVCSKAF
KFLGTPADTGHGTVVLELQYTGTDGPCKVPISSVASL*NDL*TPVGRLVTVNPFVSVATANA
KVLIELEPPFGDSYIVVGRGEQQINHHWHKSGSSIGK

Figure 18

SEQ ID NO: 58 - *Salmonella muenchen* flagellin fliC amino acid sequence (hinge underlined)

MAQVINTNSLSLLTQNNLNKSQSALGTAIERLSSGLRINSAKDDAAGQAIANRFTA
NIKGLTQASRNANDGISIAQTTEGALNEINNNLQRVRELAVQSANGTNSQSDLDSI
QAEITQRLNEIDRVSGQTQFNGVKVLAQDNTLTIQVGANDGETIDIDLKEISSKTL
GLDKLNVQDAYTPKETAVTVDKTTYKNGTDTITAQSNTDIQTAIGGGATGVTGADI
KFKDGQYYLDVKGGASAGVYKATYDETTKKVNIDTTDKTPLATAEATAIRGTATIT
HNQIAEVTKEGVDTTTVAAQLAAAGVTGADKDNTSLVKLSFEDKNGKVIDGGYAVK
MGDDFYAATYDEKTGTITAKTTTYTDGAGVAQTGAVKFGGANGKSEVVTATDGKTY
LASDLDKHNFRTGGELKEVNTDKTENPLQKIDAALAQVDTLRSDLGAVQNRFNSAI
TNLGNTVNNLSSARSRIEDSDYATEVSNMSRAQILQQAGTSVLAQANQVPQNVLSL
LR

Figure 19

SEQ ID NO: 59 - *Salmonella muenchen* flagellin fliC nucleic acid sequence (hinge underlined)

ATGGCACAAGTCATTAATACAAACAGCCTGTCGCTGTTGACCCAGAATAACCTGAA
CAAATCCCAGTCCGCTCTGGGCACCGCTATCGAGCGTCTGTCTTCCGGTCTGCGTA
TCAACAGCGCGAAAGACGATGCGGCAGGTCAGGCGATTGCTAACCGTTTCACCGCG
AACATCAAAGGTCTGACTCAGGCTTCCCGTAACGCTAACGACGGTATCTCCATTGC
GCAGACCACTGAAGGCGCGCTGAACGAAATCAACAACAACCTGCAGCGTGTGCGTG
AACTGGCGGTTCAGTCTGCTAACGGTACTAACTCCCAGTCTGACCTTGACTCTATC
CAGGCTGAAATCACCCAGCGTCTGAACGAAATCGACCGTGTATCCGGTCAGACTCA
GTTCAACGGCGTGAAAGTCCTGGCGCAGGACAACACCCTGACCATCCAGGTTGGTG
CCAACGACGGTGAAACTATTGATATTGATTTAAAAGAAATTAGCTCTAAAACACTG
GGACTTGATAAGCTTAATGTCCAGGATGCCTACACCCCGAAAGAAACTGCTGTAAC
CGTTGATAAAACTACCTATAAAAATGGTACAGATACTATTACAGCCCAGAGCAATA
CTGATATCCAAACTGCAATTGGCGGTGGTGCAACGGGGGTTACTGGGGCTGATATC
<u>AAATTTAAAGATGGTCAATACTATTTAGATGTTAAAGGCGGTGCTTCTGCTGGTGT
TTATAAAGCCACTTATGATGAAACTACAAAGAAAGTTAATATTGATACGACTGATA
AAACTCCGTTAGCAACTGCGGAAGCTACAGCTATTCGGGGAACGGCCACTATAACC
CACAACCAAATTGCTGAAGTAACAAAAGAGGGTGTTGATACGACCACAGTTGCGGC
TCAACTTGCTGCTGCAGGGGTTACTGGTGCCGATAAGGACAATACTAGCCTTGTAA
AACTATCGTTTGAGGATAAAAACGGTAAGGTTATTGATGGTGGCTATGCAGTGAAA
ATGGGCGACGATTTCTATGCCGCTACATATGATGAGAAACAGGTACAATTACTGC
TAAAACAACCACTTATACAGATGGTGCTGGCGTTGCTCAAACTGGAGCTGTGAAAT
TTGGTGGCGCAAATGGTAAATCTGAAGTTGTTACTGCTACCGATGGTAAAACTTAC
TTAGCAAGCGACCTTGACAAACATAACTTCAGAACAGGCGGTGAGCTTAAAGAGGT
TAATACAGATAAGACTG</u>AAAACCCACTGCAGAAAATTGATGCTGCCTTGGCACAGG
TTGATACACTTCGTTCTGACCTGGGTGCGGTACAGAACCGTTTCAACTCCGCTATC
ACCAACCTGGGCAATACCGTAAATAACCTGTCTTCTGCCCGTAGCCGTATCGAAGA
TTCCGACTACGCGACCGAAGTCTCCAACATGTCTCGCGCGCAGATTCTGCAGCAGG
CCGGTACCTCCGTTCTGGCGCAGGCTAACCAGGTTCCGCAAAACGTCCTCTCTTTA
CTGCGTTAA

Figure 20

SEQ ID NO: 63 - linker nucleic acid sequence

AAGGGCAATTCGAAGCTTGAAGGTCAATTGGAATTCCCTAGGACTAGTC
CAGTGTGGTGGAATTCTGCAGATATCCAGCACAGTGGCGGCCGCCAGTG
TGATGGATATCTGCAGAATTCGCCCTTGCGGCCGCTC

Figure 21

SEQ ID NO: 64 - Hepatitis C E1 amino acid sequence

YQVRNSTGLYHVTNDCPNSSIVYEAADAILHTPGCVPCVREGNASRCWVA
MTPTVATRDGKLPATQLRRHIDLLVGSATLCSALYVGDLCGSVFLVGQLFT
FSPRRHWTTQGCNCSIYPGHITGHRMAWDMMMNWSPTTALVMAQLLRIPQ
AILDMIAGAHWGVLAGIAYFSMVGNWAKVLVVLLLFAGVDA

Figure 22

SEQ ID NO: 65 - Hepatitis C E2 amino acid sequence

ETHVTGGSAGHTVSGFVSLLAPGAKQNVQLINTNGSWHLNSTALNCNDSLN
TGWLAGLFYHHKFNSSGCPERLASCRPLTDFDQGWGPISYANGSGPDQRPY
CWHYPPKPCGIVPAKSVCGPVYCFTPSPVVVGTTDRSGAPTYSWGENDTDV
FVLNNTRPPLGNWFGCTWMNSTGF

SEQ ID NO: 66 - Hepatitis C E1 nucleic acid sequence

TACCAAGTGCGCAACTCCACGGGGCTCTACCACGTCACCAATGATTGCC
CTAACTCGAGTATTGTGTACGAGGCGGCCGATGCCATCCTGCACACTCCG
GGGTGCGTCCCTTGCGTTCGCGAGGGCAACGCCTCGAGGTGTTGGGTGG
CGATGACCCCTACGGTGGCCACCAGGGATGGCAAACTCCCCGCGACGCA
GCTTCGACGTCACATCGATCTGCTTGTCGGGAGCGCCACCCTCTGTTCGG
CCCTCTACGTGGGGGACCTGTGCGGGTCTGTCTTTCTTGTCGGCCAACTG
TTTACCTTCTCTCCCAGGCGCCACTGGACGACGCAAGGTTGCAATTGCTC
TATCTATCCCGGCCATATAACGGTCACCGCATGGCATGGGATATGATG
ATGAACTGGTCCCCTACGACGGCGTTGGTAATGGCTCAGCTGCTCCGGAT
CCCACAAGCCATCTTGGACATGATCGCTGGTGCTCACTGGGGAGTCCTG
GCGGGCATAGCGTATTTCTCCATGGTGGGGAACTGGGCGAAGGTCCTGG
TAGTGCTGCTGCTATTTGCCGGCGTCGACGCG

Figure 24

SEQ ID NO: 67 - Hepatitis C E2 nucleic acid sequence

GAAACCCACGTCACCGGGGGAAGTGCCGGCCACACTGTGTCTGGATTTG
TTAGCCTCCTCGCACCAGGCGCCAAGCAGAACGTCCAGCTGATCAACAC
CAACGGCAGTTGGCACCTCAATAGCACGGCCCTGAACTGCAATGATAGC
CTCAACACCGGCTGGTTGGCAGGGCTTTTCTATCACCACAAGTTCAACTC
TTCAGGCTGTCCTGAGAGGCTAGCCAGCTGCCGACCCCTTACCGATTTTG
ACCAGGGCTGGGGCCCTATCAGTTATGCCAACGGAAGCGGCCCCGACCA
GCGCCCCTACTGCTGGCACTACCCCCAAAACCTTGCGGTATTGTGCCCG
CGAAGAGTGTGTGTGGTCCGGTATATTGCTTACTCCCAGCCCCGTGGTG
GTGGGAACGACCGACAGGTCGGGCGCGCCCACCTACAGCTGGGGTGAA
AATGATACGGACGTCTTCGTCCTTAACAATACCAGGCCACCGCTGGGCA
ATTGGTTCGGTTGTACCTGGATGAACTCAACTGGATTCACCAAAGTGTGC
GGAGCGCCTCCTTGTGTCATCGGAGGGGCGGGCAACAACACCCTGCACT
GCCCCACTGATTGCTTCCGCAAGCATCCGGACGCCACATACTCTCGGTGC
GGCTCCGGTCCCTGGATCACACCCAGGTGCCTGGTCGACTACCCGTATAG
GCTTTGGCATTATCCTTGTACCATCAACTACACTATATTTAAAATCAGGA
TGTACGTGGGAGGGGTCGAGCACAGGCTGGAAGCTGCCTGCAACTGGAC
GCGGGGCGAACGTTGCGATCTGGAAGATAGGGACAGGTCCGAGCTCAGC
CCGTTACTGCTGACCACTACACAGTGGCAGGTCCTCCCGTGTTCCTTCAC
AACCCTGCCAGCCTTGTCCACCGGCCTCATCCACCTCCACCAGAACATTG
TGGACGTGCAGTACTTGTACGGGGTGGGGTCAAGCATCGCGTCCTGGGC
CATTAAGTGGGAGTACGTCGTCCTCCTGTTCCTTCTGCTTGCAGACGCGC
GCGTCTGCTCCTGCTTGTGGATGATGCTACTCATATCCCAAGCGGAAGCG

Figure 25

SEQ ID NO: 68 - *E. coli* fliC amino acid sequence (hinge region underlined)

MAQVINTNSLSLITQNNINKNQSALSSSIERLSSGLRINSAKDDAAGQAIANRFTS
NIKGLTQAARNANDGISVAQTTEGALSEINNNLQRIRELTVQASTGTNSDSDLDSI
QDEIKSRLDEIDRVSGQTQFNGVNVLAKDGSMKIQVGANDGQTITIDLKKIDSDTL
GL<u>NGFNVNGSGTIANKAATISDLTAAKMDAATNTITTTNNALTASKALDQLKDGDT
VTIKADAAQTATVYTYNASAGNFSFSNVSNNTSAKAGDVAASLLPPAGQTASGVYK
AASGEVNFDVDANGKITIGGQKAYLTSDGNLTTNDAGGATAATLDGLFKKAGDGQS
IGFKKTASVTMGGTTYNFKTGADADAATANAGVSFTDTASKETVLNKVATAKQGKA
VAADGDTSATITYKSGVQTYQAVFAAGDGTASAKYADKADVSNATATYTDADGEMT
TIGSYTTKYSIDANNGKVTVDSGTGTGKYAPKVGAEVYVSANGTLTTDATSEGTVT</u>
KDPLKALDEAISSIDKFRSSLGAIQNRLDSAVTNLNNTTTNLSEAQSRIQDADYAT
EVSNMSKAQIIQQAGNSVLAKANQVPQQVLSLLQG

Figure 26

SEQ ID NO: 69 - *E. coli* fliC nucleic acid sequence (hinge region underlined)

ATGGCACAAGTCATTAATACCAACAGCCTCTCGCTGATCACTCAAAATAATATCAA
CAAGAACCAGTCTGCGCTGTCGAGTTCTATCGAGCGTCTGTCTTCTGGCTTGCGTA
TTAACAGCGCGAAGGATGACGCAGCGGGTCAGGCGATTGCTAACCGTTTCACCTCT
AACATTAAAGGCCTGACTCAGGCGGCCCGTAACGCAACGACGGTATCTCCGTTGC
GCAGACCACCGAAGGCGCGCTGTCCGAAATCAACAACAACTTACAGCGTATCCGTG
AACTGACGGTTCAGGCTTCTACCGGGACTAACTCCGATTCGGATCTGGACTCCATT
CAGGACGAAATCAAATCCCGTCTGGACGAAATTGACCGCGTATCTGGCCAGACCCA
GTTCAACGGCGTGAACGTACTGGCGAAAGACGGTTCAATGAAAATTCAGGTTGGTG
CGAATGACGGCCAGACTATCACGATTGATCTGAAGAAAATTGACTCAGATACGCTG
GGGCTGAATGGTTTTAACGTGAATGGTTCCGGTACGATAGCCAATAAAGCGGCGAC
CATTAGCGACCTGACAGCAGCGAAAATGGATGCTGCAACTAATACTATAACTACAA
CAAATAATGCGCTGACTGCATCAAAGGCGCTTGATCAACTGAAAGATGGTGACACT
GTTACTATCAAAGCAGATGCTGCTCAAACTGCCACGGTTTATACATACAATGCATC
AGCTGGTAACTTCTCATTCAGTAATGTATCGAATAATACTTCAGCAAAAGCAGGTG
ATGTAGCAGCTAGCCTTCTCCCGCCGGCTGGGCAAACTGCTAGTGGTGTTTATAAA
GCAGCAAGCGGTGAAGTGAACTTTGATGTTGATGCGAATGGTAAAATCACAATCGG
AGGACAGAAAGCATATTTAACTAGTGATGGTAACTTAACTACAAACGATGCTGGTG
GTGCGACTGCGGCTACGCTTGATGGTTTATTCAAGAAAGCTGGTGATGGTCAATCA
ATCGGGTTTAAGAAGACTGCATCAGTCACGATGGGGGGAACAACTTATAACTTTAA
AACGGGTGCTGATGCTGATGCTGCAACTGCTAACGCAGGGGTATCGTTCACTGATA
CAGCTAGCAAAGAAACCGTTTTAAATAAAGTGGCTACAGCTAAACAAGGCAAAGCA
GTTGCAGCTGACGGTGATACATCCGCAACAATTACCTATAAATCTGGCGTTCAGAC
GTATCAGGCTGTATTTGCCGCAGGTGACGGTACTGCTAGCGCAAAATATGCCGATA
AAGCTGACGTTTCTAATGCAACAGCAACATACACTGATGCTGATGGTGAAATGACT
ACAATTGGTTCATACACCACGAAGTATTCAATCGATGCTAACAACGGCAAGGTAAC
TGTTGATTCTGGAACTGGTACGGGTAAATATGCGCCGAAAGTAGGGGCTGAAGTAT
ATGTTAGTGCTAATGGTACTTTAACAACAGATGCAACTAGCGAAGGCACAGTAACA
AAAGATCCACTGAAAGCTCTGGATGAAGCTATCAGCTCCATCGACAAATTCCGTTC
TTCCCTGGGTGCTATCCAGAACCGTCTGGATTCCGCAGTCACCAACCTGAACAACA
CCACTACCAACCTGTCCGAAGCGCAGTCCCGTATTCAGGACGCCGACTATGCGACC
GAAGTGTCCAACATGTCGAAAGCGCAGATCATTCAGCAGGCCGGTAACTCCGTGCT
GGCAAAAGCCAACCAGGTACCGCAGCAGGTTCTGTCTCTGCTGCAGGGTTAA

Figure 27

SEQ ID NO: 70 - STF2Δ.EIII+ nucleic acid sequence

ATGGCACAAGTAATCAACACTAACAGTCTGTCGCTGCTGACCCAGA
ATAACCTGAACAAATCCCAGTCCGCACTGGGCACCGCTATCGAGCG
TCTGTCTTCTGGTCTGCGTATCAACAGCGCGAAAGACGATGCGGCA
GGTCAGGCGATTGCTAACCGTTTCACCGCAACATCAAAGGTCTGA
CTCAGGCTTCCCGTAACGCTAACGACGGTATCTCCATTGCGCAGAC
CACTGAAGGCGCGCTGAACGAAATCAACAACAACCTGCAGCGTGTG
CGTGAACTGGCGGTTCAGTCTGCTAACAGCACCAACTCCCAGTCTG
ACCTCGACTCCATCCAGGCTGAAATCACCCAGCGCCTGAACGAAAT
CGACCGTGTATCCGGCCAGACTCAGTTCAACGGCGTGAAAGTCCTG
GCGCAGGACAACACCCTGACCATCCAGGTTGGCGCCAACGACGGTG
AAACTATCGATATCGATCTGAAGCAGATCAACTCTCAGACCCTGGG
TCTGGACTCACTGAACGTG<u>CATGGAGCGCCGGTGGATCCTGCTAGC
CCATGG</u>ACCGAAAACCCGCTGCAGAAATTGATGCCGCGCTGGCGC
AGGTGGATGCGCTGCGCTCTGATCTGGGTGCGGTACAAAACCGTTT
CAACTCTGCTATCACCAACCTGGGCAATACCGTAAACAATCTGTCT
GAAGCGCGTAGCCGTATCGAAGATTCCGACTACGCGACCGAAGTTT
CCAACATGTCTCGCGCGCAGATTTTGCAGCAGGCCGGTACTTCCGT
TCTGGCGCAGGCTAACCAGGTCCCGCAGAACGTGCTGTCTCTGTTA
CGT<u>GAATTCTGCAGATATCCAGCACAGTGGCGGCCGCTC</u>**ATGGAAA
AATTGCAGTTGAAGGGAACAACCTATGGCGTCTGTTCAAAGGCTTT
CAAGTTTCTTGGGACTCCCGCAGACACAGGTCACGGCACTGTGGTG
TTGGAATTGCAGTACACTGGCACGGATGGACCTTGCAAAGTTCCTA
TCTCGTCAGTGGCTTCATTGAACGACCTAACGCCAGTGGGCAGATT
GGTCACTGTCAACCCTTTTGTTTCAGTGGCCACGGCCAACGCTAAG
GTCCTGATTGAATTGGAACCACCCTTTGGAGACTCATACATAGTGG
TGGGCAGAGGAGAACAACAGATCAATCACCATTGGCACAAGTCTGG
AAGCAGCATTGGCAAA**CCCTTAATAAGC

Figure 28

SEQ ID NO: 71 - STF2Δ.EIII+ amino acid sequence of SEQ ID NO: 70

MAQVINTNSLSLLTQNNLNKSQSALGTAIERLSSGLRINSAKDDAA
GQAIANRFTANIKGLTQASRNANDGISIAQTTEGALNEINNNLQRV
RELAVQSANSTNSQSDLDSIQAEITQRLNEIDRVSGQTQFNGVKVL
AQDNTLTIQVGANDGETIDIDLKQINSQTLGLDSLNV<u>HGAPVDPAS</u>
<u>PW</u>TENPLQKIDAALAQVDALRSDLGAVQNRFNSAITNLGNTVNNLS
EARSRIEDSDYATEVSNMSRAQILQQAGTSVLAQANQVPQNVLSLL
REFCRYPAQWRPL*MEKLQLKGTTYGVCSKAFKFLGTPADTGHGTVV*
*LELQYTGTDGPCKVPISSVASLNDLTPVGRLVTVNPFVSVATANAK*
*VLIELEPPFGDSYIVVGRGEQQINHHWHKSGSSIGK*PLIS

Figure 29

SEQ ID NO: 72 - STF2Δ.EIIIs+ (Cys-Ser mutation) amino acid sequence (linker underlined)

MAQVINTNSLSLLTQNNLNKSQSALGTAIERLSSGLRINSAKDDAA
GQAIANRFTANIKGLTQASRNANDGISIAQTTEGALNEINNNLQRV
RELAVQSANSTNSQSDLDSIQAEITQRLNEIDRVSGQTQFNGVKVL
AQDNTLTIQVGANDGETIDIDLKQINSQTLGLDSLNV<u>HGAPVDPAS
PW</u>TENPLQKIDAALAQVDALRSDLGAVQNRFNSAITNLGNTVNNLS
EARSRIEDSDYATEVSNMSRAQILQQAGTSVLAQANQVPQNVLSLL
REF<u>SRYPAQWRPL</u>*MEKLQLKGTTYGVCSKAFKFLGTPADTGHGTVV*
*LELQYTGTDGPCKVPISSVASLNDLTPVGRLVTVNPFVSVATANAK*
*VLIELEPPFGDSYIVVGRGEQQINHHWHKSGSSIGKPLIS*

Figure 30

SEQ ID NO: 73 - STF2Δ.EIIIs+ (Cys-Ser mutation) nucleic acid sequence of SEQ ID NO: 72 (linker underlined)

ATGGCACAAGTAATCAACACTAACAGTCTGTCGCTGCTGACCCAGA
ATAACCTGAACAAATCCCAGTCCGCACTGGGCACCGCTATCGAGCG
TCTGTCTTCTGGTCTGCGTATCAACAGCGCGAAAGACGATGCGGCA
GGTCAGGCGATTGCTAACCGTTTCACCGCGAACATCAAAGGTCTGA
CTCAGGCTTCCCGTAACGCTAACGACGGTATCTCCATTGCGCAGAC
CACTGAAGGCGCGCTGAACGAAATCAACAACAACCTGCAGCGTGTG
CGTGAACTGGCGGTTCAGTCTGCTAACAGCACCAACTCCCAGTCTG
ACCTCGACTCCATCCAGGCTGAAATCACCCAGCGCCTGAACGAAAT
CGACCGTGTATCCGGCCAGACTCAGTTCAACGGCGTGAAAGTCCTG
GCGCAGGACAACACCCTGACCATCCAGGTTGGCGCCAACGACGGTG
AAACTATCGATATCGATCTGAAGCAGATCAACTCTCAGACCCTGGG
TCTGGACTCACTGAACGTG<u>CATGGAGCGCCGGTGGATCCTGCTAGC</u>
<u>CCATGG</u>ACCGAAAACCCGCTGCAGAAAATTGATGCCGCGCTGGCGC
AGGTGGATGCGCTGCGCTCTGATCTGGGTGCGGTACAAAACCGTTT
CAACTCTGCTATCACCAACCTGGGCAATACCGTAAACAATCTGTCT
GAAGCGCGTAGCCGTATCGAAGATTCCGACTACGCGACCGAAGTTT
CCAACATGTCTCGCGCGCAGATTTTGCAGCAGGCCGGTACTTCCGT
TCTGGCGCAGGCTAACCAGGTCCCGCAGAACGTGCTGTCTCTGTTA
CGTG<u>AATTCTCTAGATATCCAGCACAGTGGCGGCCGCTC</u>ATGGAAA
AATTGCAGTTGAAGGGAACAACCTATGGCGTCTGTTCAAAGGCTTT
CAAGTTTCTTGGGACTCCCGCAGACACAGGTCACGGCACTGTGGTG
TTGGAATTGCAGTACACTGGCACGGATGGACCTTGCAAAGTTCCTA
TCTCGTCAGTGGCTTCATTGAACGACCTAACGCCAGTGGGCAGATT
GGTCACTGTCAACCCTTTTGTTTCAGTGGCCACGGCCAACGCTAAG
GTCCTGATTGAATTGGAACCACCCTTTGGAGACTCATACATAGTGG
TGGGCAGAGGAGAACAACAGATCAATCACCATTGGCACAAGTCTGG
AAGCAGCATTGGCAAACCCTTAATAAGCTGA

Figure 31

SEQ ID NO: 76 - pET/STF2Δ.JEIIIs+ amino acid sequence (Cys-ser mutation in linker region)

MAQVINTNSLSLLTQNNLNKSQSALGTAIERLSSGLRINSAKDDAAGQAIANRFTANIKG
LTQASRNANDGISIAQTTEGALNEINNNLQRVRELAVQSANSTNSQSDLDSIQAEITQRL
NEIDRVSGQTQFNGVKVLAQDNTLTIQVGANDGETIDIDLKQINSQTLGLDSLNV<u>HGAPV
DPASPW</u>TENPLQKIDAALAQVDALRSDLGAVQNRFNSAITNLGNTVNNLSEARSRIEDSD
YATEVSNMSRAQILQQAGTSVLAQANQVPQNVLSLLR<u>EFSRYPAQWRPL</u>*MDKLALKGTTY*
*GMCTEKFSFAKNPVDTGHGTVVIELSYSGSDGPCKIPIVSVASLNDMTPVGRLVTVNPFV*
*ATSSANSKVLVEMEPPFGDSYIVVGRGDKQINHHWHKAGSTLGKA*

Figure 32

SEQ ID NO: 77 - pET/STF2 Δ.JEIIIs+ nucleic acid sequence(Cys-ser mutation in linker region)

ATGGCACAAGTAATCAACACTAACAGTCTGTCGCTGCTGACCCAGAATAACCTGAACAAA
TCCCAGTCCGCACTGGGCACCGCTATCGAGCGTCTGTCTTCTGGTCTGCGTATCAACAGC
GCGAAAGACGATGCGGCAGGTCAGGCGATTGCTAACCGTTTCACCGCGAACATCAAAGGT
CTGACTCAGGCTTCCCGTAACGCTAACGACGGTATCTCCATTGCGCAGACCACTGAAGGC
GCGCTGAACGAAATCAACAACAACCTGCAGCGTGTGCGTGAACTGGCGGTTCAGTCTGCT
AACAGCACCAACTCCCAGTCTGACCTCGACTCCATCCAGGCTGAAATCACCCAGCGCCTG
AACGAAATCGACCGTGTATCCGGCCAGACTCAGTTCAACGGCGTGAAAGTCCTGGCGCAG
GACAACACCCTGACCATCCAGGTTGGCGCCAACGACGGTGAAACTATCGATATCGATCTG
AAGCAGATCAACTCTCAGACCCTGGGTCTGGACTCACTGAACGTG<ins>CATGGAGCGCCGGTG
GATCCTGCTAGCCCATGG</ins>ACCGAAAACCCGCTGCAGAAAATTGATGCCGCGCTGGCGCAG
GTGGATGCGCTGCGCTCTGATCTGGGTGCGGTACAAAACCGTTTCAACTCTGCTATCACC
AACCTGGGCAATACCGTAAACAATCTGTCTGAAGCGCGTAGCCGTATCGAAGATTCCGAC
TACGCGACCGAAGTTTCCAACATGTCTCGCGCGCAGATTTTGCAGCAGGCCGGTACTTCC
GTTCTGGCGCAGGCTAACCAGGTCCCGCAGAACGTGCTGTCTCTGTTACGT<ins>GAATTCAGC
AGATATCCAGCACAGTGGCGGCCGCTC</ins>*ATGGACAAACTGGCTCTG*AAAGGCACAACCTAT
GGCATGTGTACAGAAAAATTCTCGTTCGCGAAAAATCCGGTGGACACTGGTCACGGAACA
GTTGTCATTGAACTCTCCTACTCTGGGAGTGATGGCCCCTGCAAAATTCCGATTGTTTCC
GTTGCGAGCCTCAATGACATGACCCCCGTTGGGCGGCTGGTGACAGTGAACCCCTTCGTC
GCGACTTCCAGTGCCAACTCAAAGGTGCTGGTCGAGATGGAACCCCCCTTCGGAGACTCC
TACATCGTAGTTGGAAGGGGAGACAAGCAGATCAACCACCATTGGCACAAAGCTGGAAGC
ACGCTGGGCAAGGCC

Figure 33

SEQ ID NO: 78 - JEIII+ nucleic acid sequence

ATGGACAAACTGGCTCTGAAAGGCACAACCTATGGCATGTGTACAGAAAAATTCTCGTTCGC
GAAAAATCCGGTGGACACTGGTCACGGAACAGTTGTCATTGAACTCTCCTACTCTGGGAGTG
ATGGCCCCTGCAAAATTCCGATTGTTTCCGTTGCGAGCCTCAATGACATGACCCCCGTTGGG
CGGCTGGTGACAGTGAACCCCTTCGTCGCGACTTCCAGTGCCAACTCAAAGGTGCTGGTCGA
GATGGAACCCCCCTTCGGAGACTCCTACATCGTAGTTGGAAGGGGAGACAAGCAGATCAACC
ACCATTGGCACAAAGCTGGAAGCACGCTGGGCAAGGCC

Figure 34

SEQ ID NO: 79 - JEIII+ amino acid sequence

*MDKLAL* KGTTYGMCTEKFSFAKNPVDTGHGTVVIELSYSGSDGPCKIPIVSVASLND
MTPVGRLVTVNPFVATSSANSKVLVEMEPPFGDSYIVVGRGDKQINHHWHKAGSTL
GKA

Figure 35

SEQ ID NO: 80 - pET/STF2Δ.Den1 EIII amino acid sequence

MAQVINTNSLSLLTQNNLNKSQSALGTAIERLSSGLRINSAKDDAAGQAIANRFTANIKG
LTQASRNANDGISIAQTTEGALNEINNNLQRVRELAVQSANSTNSQSDLDSIQAEITQRL
NEIDRVSGQTQFNGVKVLAQDNTLTIQVGANDGETIDIDLKQINSQTLGLDSLNV<u>HGAPV</u>
<u>DPASPW</u>TENPLQKIDAALAQVDALRSDLGAVQNRFNSAITNLGNTVNNLSEARSRIEDSD
YATEVSNMSRAQILQQAGTSVLAQANQVPQNVLSLLR<u>EFSRYPAQWRPL</u>KGMSYVMCTGS
FKLEKEVAETQHGTVLVQVKYEGTDAPCKIPFSTQD

SEQ ID NO: 81 - pET/STF2Δ.Den1 EIII nucleic acid sequence

ATGGCACAAGTAATCAACACTAACAGTCTGTCGCTGCTGACCCAGAATAACCTGAACAAATCCCA
GTCCGCACTGGGCACCGCTATCGAGCGTCTGTCTTCTGGTCTGCGTATCAACAGCGCGAAAGACG
ATGCGGCAGGTCAGGCGATTGCTAACCGTTTCACCGCGAACATCAAAGGTCTGACTCAGGCTTCC
CGTAACGCTAACGACGGTATCTCCATTGCGCAGACCACTGAAGGCGCGCTGAACGAAATCAACAA
CAACCTGCAGCGTGTGCGTGAACTGGCGGTTCAGTCTGCTAACAGCACCAACTCCCAGTCTGACC
TCGACTCCATCCAGGCTGAAATCACCCAGCGCCTGAACGAAATCGACCGTGTATCCGGCCAGACT
CAGTTCAACGGCGTGAAAGTCCTGGCGCAGGACAACACCCTGACCATCCAGGTTGGCGCCAACGA
CGGTGAAACTATCGATATCGATCTGAAGCAGATCAACTCTCAGACCCTGGGTCTGGACTCACTGA
ACGTGCATGGAGCGCCGGTGGATCCTGCTAGCCCATGGACCGAAAACCCGCTGCAGAAAATTGAT
GCCGCGCTGGCGCAGGTGGATGCGCTGCGCTCTGATCTGGGTGCGGTACAAAACCGTTTCAACTC
TGCTATCACCAACCTGGGCAATACCGTAAACAATCTGTCTGAAGCGCGTAGCCGTATCGAAGATT
CCGACTACGCGACCGAAGTTTCCAACATGTCTCGCGCGCAGATTTTGCAGCAGGCCGGTACTTCC
GTTCTGGCGCAGGCTAACCAGGTCCCGCAGAACGTGCTGTCTCTGTTACGTGAATTCAGCAGATA
TCCAGCACAGTGGCGGCCGCTCAAAGGAATGTCTTACGTAATGTGCACAGGCAGTTTCAAGCTGG
AAAAAGAAGTTGCCGAAACACAGCATGGCACGGTACTAGTCCAAGTGAAATATGAGGGAACAGAC
GCGCCATGTAAGATACCATTTTCCACTCAAGATGAGAAAGGGGCGACTCAGAACGGAAGATTGAT
AACCGCAAATCCTATCGTAACCGACAAGGAAAAGCCCGTGAATATTGAGGCAGAGCCTCCGTTTG
GGGAGTCGTATATCGTCGTTGGTGCTGGTGAAAAGGCTTTAAAGCTCAGTTGGTTCAAAAAGGGG
TCAAGCATTGGTAAA

Figure 37

SEQ ID NO: 82 - pET/STF2Δ.Den2 EIII amino acid sequence

MAQVINTNSLSLLTQNNLNKSQSALGTAIERLSSGLRINSAKDDAAGQAIANRFTANIKG
LTQASRNANDGISIAQTTEGALNEINNNLQRVRELAVQSANSTNSQSDLDSIQAEITQRL
NEIDRVSGQTQFNGVKVLAQDNTLTIQVGANDGETIDIDLKQINSQTLGLDSLNV<u>HGAPV</u>
<u>DPASPW</u>TENPLQKIDAALAQVDALRSDLGAVQNRFNSAITNLGNTVNNLSEARSRIEDSD
YATEVSNMSRAQILQQAGTSVLAQANQVPQNVLSLLR<u>EFSRYPAQWRPL</u>KGMSYSMCTGK
FKVVKEIAETQHGTIVIRVQYEGD

SEQ ID NO: 83 - pET/STF2Δ.Den2 EIII nucleic acid sequence

ATGGCACAAGTAATCAACACTAACAGTCTGTCGCTGCTGACCCAGAATAACCTGAACAAAT
CCCAGTCCGCACTGGGCACCGCTATCGAGCGTCTGTCTTCTGGTCTGCGTATCAACAGCGC
GAAAGACGATGCGGCAGGTCAGGCGATTGCTAACCGTTTCACCGCGAACATCAAAGGTCTG
ACTCAGGCTTCCCGTAACGCTAACGACGGTATCTCCATTGCGCAGACCACTGAAGGCGCGC
TGAACGAAATCAACAACAACCTGCAGCGTGTGCGTGAACTGGCGGTTCAGTCTGCTAACAG
CACCAACTCCCAGTCTGACCTCGACTCCATCCAGGCTGAAATCACCCAGCGCCTGAACGAA
ATCGACCGTGTATCCGGCCAGACTCAGTTCAACGGCGTGAAAGTCCTGGCGCAGGACAACA
CCCTGACCATCCAGGTTGGCGCCAACGACGGTGAAACTATCGATATCGATCTGAAGCAGAT
CAACTCTCAGACCCTGGGTCTGGACTCACTGAACGTGCATGGAGCGCCGGTGGATCCTGCT
AGCCCATGGACCGAAAACCCGCTGCAGAAAATTGATGCCGCGCTGGCGCAGGTGGATGCGC
TGCGCTCTGATCTGGGTGCGGTACAAAACCGTTTCAACTCTGCTATCACCAACCTGGGCAA
TACCGTAAACAATCTGTCTGAAGCGCGTAGCCGTATCGAAGATTCCGACTACGCGACCGAA
GTTTCCAACATGTCTCGCGCGCAGATTTTGCAGCAGGCCGGTACTTCCGTTCTGGCGCAGG
CTAACCAGGTCCCGCAGAACGTGCTGTCTCTGTTACGTGAATTCAGCAGATATCCAGCACA
GTGGCGGCCGCTCAAAGGTATGAGCTATAGCATGTGTACCGGTAAATTTAAAGTTGTTAAA
GAAATTGCGGAAACCCAGCATGGTACCATTGTTATTCGTGTTCAGTATGAAGGTGATGGTA
GCCCGTGTAAAATTCCGTTTGAAATTATGGATCTGGAAAAACGTCATGTTCTGGGTCGTCT
GATTACCGTTAATCCGATTGTTACCGAAAAAGATAGCCCGGTTAATATTGAAGCGGAACCG
CCGTTTGGTGATAGCTATATTATTATTGGTGTTGAACCGGGTCAGCTGAAACTGAATTGGT
TTAAAAAAGGTAGCAGCATTGGTCAG

Figure 39

SEQ ID NO: 84 - pET/STF2Δ.Den3 EIII amino acid sequence

MAQVINTNSLSLLTQNNLNKSQSALGTAIERLSSGLRINSAKDDAAGQAIANRFTANIKG
LTQASRNANDGISIAQTTEGALNEINNNLQRVRELAVQSANSTNSQSDLDSIQAEITQRL
NEIDRVSGQTQFNGVKVLAQDNTLTIQVGANDGETIDIDLKQINSQTLGLDSLNV<u>HGAPV</u>
<u>DPASPW</u>TENPLQKIDAALAQVDALRSDLGAVQNRFNSAITNLGNTVNNLSEARSRIEDSD
YATEVSNMSRAQILQQAGTSVLAQANQVPQNVLSLLR<u>EFSRYPAQWRPL</u>KGMSYAMCLNT
FVLKKEVSETQHGTILIKVEYKGEDAPCKIPFS

SEQ ID NO: 85 - pET/STF2Δ.Den3 EIII nucleic acid sequence

ATGGCACAAGTAATCAACACTAACAGTCTGTCGCTGCTGACCCAGAATAACCTGAACAAAT
CCCAGTCCGCACTGGGCACCGCTATCGAGCGTCTGTCTTCTGGTCTGCGTATCAACAGCGC
GAAAGACGATGCGGCAGGTCAGGCGATTGCTAACCGTTTCACCGCGAACATCAAAGGTCTG
ACTCAGGCTTCCCGTAACGCTAACGACGGTATCTCCATTGCGCAGACCACTGAAGGCGCGC
TGAACGAAATCAACAACAACCTGCAGCGTGTGCGTGAACTGGCGGTTCAGTCTGCTAACAG
CACCAACTCCCAGTCTGACCTCGACTCCATCCAGGCTGAAATCACCCAGCGCCTGAACGAA
ATCGACCGTGTATCCGGCCAGACTCAGTTCAACGGCGTGAAAGTCCTGGCGCAGGACAACA
CCCTGACCATCCAGGTTGGCGCCAACGACGGTGAAACTATCGATATCGATCTGAAGCAGAT
CAACTCTCAGACCCTGGGTCTGGACTCACTGAACGTG<u>CATGGAGCGCCGGTGGATCCTGCT
AGCCCATGG</u>ACCGAAAACCCGCTGCAGAAAATTGATGCCGCGCTGGCGCAGGTGGATGCGC
TGCGCTCTGATCTGGGTGCGGTACAAAACCGTTTCAACTCTGCTATCACCAACCTGGGCAA
TACCGTAAACAATCTGTCTGAAGCGCGTAGCCGTATCGAAGATTCCGACTACGCGACCGAA
GTTTCCAACATGTCTCGCGCGCAGATTTTGCAGCAGGCCGGTACTTCCGTTCTGGCGCAGG
CTAACCAGGTCCCGCAGAACGTGCTGTCTCTGTTACGT<u>GAATTCAGCAGATATCCAGCACA
GTGGCGGCCGCTC</u>AAAGGAATGAGTTATGCAATGTGTTTAAATACATTTGTATTAAAAAAA
GAAGTAAGTGAAACACAACATGGAACAATATTAATAAAAGTAGAATATAAAGGAGAAGATG
CACCATGTAAAATACCATTTAGTACAGAAGATGGACAAGGAAAAGCACATAATGGAAGATT
AATAACAGCAAATCCAGTAGTAACAAAAAAAGAAGAACCAGTAAATATAGAAGCAG
AACCACCATTTGGAGAAAGTAATATAGTAATAGGAATAGGAGATAAAGCATTAAAA
ATAAATTGGTATAGAAAAGGAAGTAGTATAGGAAAA

Figure 41

SEQ ID NO: 86 - pET/STF2Δ.Den4 EIII amino acid sequence

MAQVINTNSLSLLTQNNLNKSQSALGTAIERLSSGLRINSAKDDAAGQAIANRFTANIKG
LTQASRNANDGISIAQTTEGALNEINNNLQRVRELAVQSANSTNSQSDLDSIQAEITQRL
NEIDRVSGQTQFNGVKVLAQDNTLTIQVGANDGETIDIDLKQINSQTLGLDSLNVHGAPV
DPASPWTENPLQKIDAALAQVDALRSDLGAVQNRFNSAITNLGNTVNNLSEARSRIEDSD
YATEVSNMSRAQILQQAGTSVLAQANQVPQNVLSLLREFSRYPAQWRPLKGMSYTMCSGK
FSIDKEMAETQHGTTVVKVKYEGAGAPCKVPIEIRDVNKEKVVGRIISPTPFAENTNSVT
NIELERPLDSYIVIGVGDSALTLHWFRK

Figure 42

SEQ ID NO: 87 - pET/STF2Δ.Den4 EIII nucleic acid sequence

ATGGCACAAGTAATCAACACTAACAGTCTGTCGCTGCTGACCCAGAATAACCTGAACAAAT
CCCAGTCCGCACTGGGCACCGCTATCGAGCGTCTGTCTTCTGGTCTGCGTATCAACAGCGC
GAAAGACGATGCGGCAGGTCAGGCGATTGCTAACCGTTTCACCGCGAACATCAAAGGTCTG
ACTCAGGCTTCCCGTAACGCTAACGACGGTATCTCCATTGCGCAGACCACTGAAGGCGCGC
TGAACGAAATCAACAACAACCTGCAGCGTGTGCGTGAACTGGCGGTTCAGTCTGCTAACAG
CACCAACTCCCAGTCTGACCTCGACTCCATCCAGGCTGAAATCACCCAGCGCCTGAACGAA
ATCGACCGTGTATCCGGCCAGACTCAGTTCAACGGCGTGAAAGTCCTGGCGCAGGACAACA
CCCTGACCATCCAGGTTGGCGCCAACGACGGTGAAACTATCGATATCGATCTGAAGCAGAT
CAACTCTCAGACCCTGGGTCTGGACTCACTGAACGTGCATGGAGCGCCGGTGGATCCTGCT
AGCCCATGGACCGAAAACCCGCTGCAGAAAATTGATGCCGCGCTGGCGCAGGTGGATGCGC
TGCGCTCTGATCTGGGTGCGGTACAAAACCGTTTCAACTCTGCTATCACCAACCTGGGCAA
TACCGTAAACAATCTGTCTGAAGCGCGTAGCCGTATCGAAGATTCCGACTACGCGACCGAA
GTTTCCAACATGTCTCGCGCGCAGATTTTGCAGCAGGCCGGTACTTCCGTTCTGGCGCAGG
CTAACCAGGTCCCGCAGAACGTGCTGTCTCTGTTACGTGAATTCAGCAGATATCCAGCACA
GTGGCGGCCGCTCAAGGGAATGTCATACACGATGTGTAGTGGTAAATTCTCTATAGACAAA
GAGATGGCAGAGACACAACACGGGACAACCGTCGTGAAGGTTAAGTATGAAGGAGCTGGCG
CACCGTGCAAAGTACCCATCGAAATTAGGGATGTAAACAAAGAGAAGGTCGTTGGGCGTAT
CATTAGCTCAACCCCACTTGCGGAAAATACTAATTCTGTAACGAACATAGAGTTGGAACCA
CCTTTTGGTGATAGCTATATAGTTATTGGTGTGGGCAATAGTGCCTTAACTCTACATTGGT
TTAGAAAAGGATCCTCGATCGGGAAA

Figure 43

SEQ ID NO: 174: - Tick-borne encephalitis envelope protein amino acid sequence

SRCTHLENRDFVTGTQGTTRVTLVLELGGCVTITAEGKPSMDVWLDSIYQENPAKTREY
CLHAKLSDTKVAARCPTMGPATLTEEHQSGTVCKRDQSDRGWGNHCGLFGKGSIVTCVK
VACEAKKKAIGHVYDANKIVYTVKVEPHTGDYVAANETHSGRKTASFTVSSEKTILTMG
DYGDVPLLCRVASGVDLAQTVILELDKTLEHLPTAWQVHRDWFNDLALPWKHEGAQQWN
NAERLVEFGAPHAVKMDVYNLGDQTGVLLKSLAGVPVAHIDGTKYHLKSGHVTCEVGLE
KLKMKGLTYTMCDKTKFAWKRTPTDSGHDTVVMEVTFSGTKPCRIPVRAVAHGSPDVNV
AMLITPNPTIENNGGGFIEMQLPPGDNIIYVGELSHQWFQKGSSIGRVFQKTRKGIERL
TVIGEHAWDFGSTGGFLTSVGKALHTVLGGAFNSIFGGVGFLPKLLLGVALAWLGLNMR
NPTMSMSFLLAGGLVLAMTLGVGA

Figure 44

SEQ ID NO: 39 – West Nile virus envelope protein amino acid sequence

```
FNCLGMSNRDFLEGVSGATWVDLVLEGDSCVTIMSKDKPTIDVKMMNMEAANLAEVRSYC    60
YLATVSDLSTKAACPTMGEAHNDKRADPAFVCRQGVVDRGWGNGCGLFGKGSIDTCAKFA   120
CSTKAIGRTILKENIKYEVAIFVHGPTTVESHGNYSTQVGATQAGRFSITPAAPSYTLKL   180
GEYGEVTVDCEPRSGIDTNAYYVMTVGTKTFLVHREWFMDLNLPWSSAGSTVWRNRETLM   240
EFEEPHATKQSVIALGSQEGALHQALAGAIPVEFSSNTVKLTSGHLKCRVKMEKLQLKGT   300
TYGVCSKAFKFLGTPADTGHGTVVLELQYTGTDGPCKVPISSVASLNDLTPVGRLVTVNP   360
FVSVATANAKVLIELEPPFGDSYIVVGRGEQQINHHWHKSGSSIGK                 406
```

| | | |
|---|---|---|
| E2-21 1 | CRVKMEKLQLKGTTYGVCSK | SEQ ID NO: 100 |
| E2-21-1 | SRVKMEKLQLKGTTYGVCSK | SEQ ID NO: 101 |
| E2-21-2 | CRVKMEKLQLKGTTYGVSSK | SEQ ID NO: 102 |
| E2-21-3 | SRVKMEKLQLKGTTYGVSSK | SEQ ID NO: 103 |
| E2-21-4 | CRVKMEKLQLKGTTYGVCSK | SEQ ID NO: 104 |
| E2-21-5 | ARVKMEKLQLKGTTYGVCSK | SEQ ID NO: 105 |
| E2-21-6 | CAVKMEKLQLKGTTYGVCSK | SEQ ID NO: 106 |
| E2-21-7 | CRAKMEKLQLKGTTYGVCSK | SEQ ID NO: 107 |
| E2-21-8 | CRVAMEKLQLKGTTYGVCSK | SEQ ID NO: 108 |
| E2-21-9 | CRVKAEKLQLKGTTYGVCSK | SEQ ID NO: 109 |
| E2-21-10 | CRVKMAKLQLKGTTYGVCSK | SEQ ID NO: 110 |
| E2-21-11 | CRVKMEALQLKGTTYGVCSK | SEQ ID NO: 111 |
| E2-21-12 | CRVKMEKAQLKGTTYGVCSK | SEQ ID NO: 112 |
| E2-21-13 | CRVKMEKLALKGTTYGVCSK | SEQ ID NO: 113 |
| E2-21-14 | CRVKMEKLQAKGTTYGVCSK | SEQ ID NO: 114 |
| E2-21-15 | CRVKMEKLQLAGTTYGVCSK | SEQ ID NO: 115 |
| E2-21-16 | CRVKMEKLQLKATTYGVCSK | SEQ ID NO: 116 |
| E2-21-17 | CRVKMEKLQLKGATYGVCSK | SEQ ID NO: 117 |
| E2-21-18 | CRVKMEKLQLKGTAYGVCSK | SEQ ID NO: 118 |
| E2-21-19 | CRVKMEKLQLKGTTAGVCSK | SEQ ID NO: 119 |
| E2-21-20 | CRVKMEKLQLKGTTYAVCSK | SEQ ID NO: 120 |
| E2-21-21 | CRVKMEKLQLKGTTYGACSK | SEQ ID NO: 121 |
| E2-21-22 | CRVKMEKLQLKGTTYGVASK | SEQ ID NO: 122 |
| E2-21-23 | CRVKMEKLQLKGTTYGVCAK | SEQ ID NO: 123 |
| E2-21-24 | CRVKMEKLQLKGTTYGVCSA | SEQ ID NO: 124 |

Figure 57

Flavivirus Envelope Protein Domain I/III
junction
(domain I 280-297, domain III 298-406)

WN aa 281-307
WN    LTSGHLK<u>CRVKMEKLQLKGTTYGVCSK</u>(SEQ ID NO: 88)
JE    LTSGHLKCRLKMDKLALKGTTYGMCTE (SEQ ID NO: 89)
D1    IFAGHLKCRLKMDKLTLKGMSYVMCTG (SEQ ID NO: 90)
D2    LFTGHLKCRLRMDKLQLKGMSYSMCTG (SEQ ID NO: 91)
D3    IFAGHLKCRLKMDKLKLKGMSYAMCLN (SEQ ID NO: 92)
D4    MFAGHLKCKVRMEKLRIKGMSYTMCSG (SEQ ID NO: 93)
      xxxGHLKCRxxMxKLxLKGxxYxxCxx (SEQ ID NO: 94)
         GHLKCRMKLLKGYC           (SEQ ID NO: 95)

Figure 59

| | | |
|---|---|---|
| E2-21 | CRVKMEKLQLKGTTYGVCSK | SEQ ID NO: 125 |
| E27 | SNTVKLTSGHLKCRVKMEKL | SEQ ID NO: 126 |
| E28 | NTVKLTSGHLKCRVKMEKLQ | SEQ ID NO: 127 |
| E29 | TVKLTSGHLKCRVKMEKLQL | SEQ ID NO: 128 |
| E30 | VKLTSGHLKCRVKMEKLQLK | SEQ ID NO: 129 |
| E31 | KLTSGHLKCRVKMEKLQLKG | SEQ ID NO: 130 |
| E32 | LTSGHLKCRVKMEKLQLKGT | SEQ ID NO: 131 |
| E33 | TSGHLKCRVKMEKLQLKGTT | SEQ ID NO: 132 |
| E34 | SGHLKCRVKMEKLQLKGTTY | SEQ ID NO: 133 |
| E35 | GHLKCRVKMEKLQLKGTTYG | SEQ ID NO: 134 |
| E36 | HLKCRVKMEKLQLKGTTYGV | SEQ ID NO: 135 |
| E37 | LKCRVKMEKLQLKGTTYGVC | SEQ ID NO: 136 |
| E38 | KCRVKMEKLQLKGTTYGVCS | SEQ ID NO: 137 |
| E39 | CRVKMEKLQLKGTTYGVCSK | SEQ ID NO: 138 |
| E40 | RVKMEKLQLKGTTYGVCSKA | SEQ ID NO: 139 |
| E41 | VKMEKLQLKGTTYGVCSKAF | SEQ ID NO: 140 |
| E42 | KMEKLQLKGTTYGVCSKAFK | SEQ ID NO: 141 |
| E43 | MEKLQLKGTTYGVCSKAFKF | SEQ ID NO: 142 |
| E44 | EKLQLKGTTYGVCSKAFKFL | SEQ ID NO: 143 |
| E45 | KLQLKGTTYGVCSKAFKFLG | SEQ ID NO: 144 |
| E46 | LQLKGTTYGVCSKAFKFLGT | SEQ ID NO: 145 |
| E47 | QLKGTTYGVCSKAFKFLGTP | SEQ ID NO: 146 |
| E48 | LKGTTYGVCSKAFKFLGTPA | SEQ ID NO: 147 |
| E49 | KGTTYGVCSKAFKFLGTPAD | SEQ ID NO: 148 |
| E50 | GTTYGVCSKAFKFLGTPADT | SEQ ID NO: 149 |
| E51 | TTYGVCSKAFKFLGTPADTG | SEQ ID NO: 150 |
| E52 | TYGVCSKAFKFLGTPADTGH | SEQ ID NO: 151 |

Figure 60

SEQ ID NO: 152 - STF2.OVA nucleic acid sequence

ATGGCACAAGTAATCAACACTAACAGTCTGTCGCTGCTGACCCAGAATAACCTGAACAAA
TCCCAGTCCGCACTGGGCACCGCTATCGAGCGTCTGTCTTCTGGTCTGCGTATCAACAGC
GCGAAAGACGATGCGGCAGGTCAGGCGATTGCTAACCGTTTCACCGCGAACATCAAAGGT
CTGACTCAGGCTTCCCGTAACGCTAACGACGGTATCTCCATTGCGCAGACCACTGAAGGC
GCGCTGAACGAAATCAACAACAACCTGCAGCGTGTGCGTGAACTGGCGGTTCAGTCTGCT
AACAGCACCAACTCCCAGTCTGACCTCGACTCCATCCAGGCTGAAATCACCCAGCGCCTG
AACGAAATCGACCGTGTATCCGGCCAGACTCAGTTCAACGGCGTGAAAGTCCTGGCGCAG
GACAACACCCTGACCATCCAGGTTGGCGCCAACGACGGTGAAACTATCGATATCGATCTG
AAGCAGATCAACTCTCAGACCCTGGGTCTGGACTCACTGAACGTGCAGAAAGCGTATGAT
GTGAAAGATACAGCAGTAACAACGAAAGCTTATGCCAATAATGGTACTACACTGGATGTA
TCGGGTCTTGATGATGCAGCTATTAAAGCGGCTACGGGTGGTACGAATGGTACGGCTTCT
GTAACCGGTGGTGCGGTTAAATTTGACGCAGATAATAACAAGTACTTTGTTACTATTGGT
GGCTTTACTGGTGCTGATGCCGCCAAAAATGGCGATTATGAAGTTAACGTTGCTACTGAC
GGTACAGTAACCCTTGCGGCTGGCGCAACTAAAACCACAATGCCTGCTGGTGCGACAACT
AAAACAGAAGTACAGGAGTTAAAAGATACACCGGCAGTTGTTTCAGCAGATGCTAAAAAT
GCCTTAATTGCTGGCGGCGTTGACGCTACCGATGCTAATGGCGCTGAGTTGGTCAAAATG
TCTTATACCGATAAAAATGGTAAGACAATTGAAGGCGGTTATGCGCTTAAAGCTGGCGAT
AAGTATTACGCCGCAGATTACGATGAAGCGACAGGAGCAATTAAAGCTAAAACCACAAGT
TATACTGCTGCTGACGGCACTACCAAAACAGCGGCTAACCAACTGGGTGGCGTAGACGGT
AAAACCGAAGTCGTTACTATCGACGGTAAAACCTACAATGCCAGCAAAGCCGCTGGTCAT
GATTTCAAAGCACAACCAGAGCTGGCGGAAGCAGCCGCTAAAACCACCGAAAACCCGCTG
CAGAAAATTGATGCCGCGCTGGCGCAGGTGGATGCGCTGCGCTCTGATCTGGGTGCGGTA
CAAAACCGTTTCAACTCTGCTATCACCAACCTGGGCAATACCGTAAACAATCTGTCTGAA
GCGCGTAGCCGTATCGAAGATTCCGACTACGCGACCGAAGTTTCCAACATGTCTCGCGCG
CAGATTTTGCAGCAGGCCGGTACTTCCGTTCTGGCGCAGGCTAACCAGGTCCCGCAGAAC
GTGCTGTCTCTGTTACGTCTCGAGGGCTCCATCGGCGCAGCAAGCATGGAATTTTGTTTT
GATGTATTCAAGGAGCTCAAAGTCCACCATGCCAATGAGAACATCTTCTACTGCCCCATT
GCCATCATGTCAGCTCTAGCCATGGTATACCTGGGTGCAAAAGACAGCACCAGGACACAA
ATAAATAAGGTTGTTCGCTTTGATAAACTTCCAGGATTCGGAGACAGTATTGAAGCTCAG
TGTGGCACATCTGTAAACGTTCACTCTTCACTTAGAGACATCCTCAACCAAATCACCAAA
CCAAATGATGTTTATTCGTTCAGCCTTGCCAGTAGACTTTATGCTGAAGAGAGATACCCA
ATCCTGCCAGAATACTTGCAGTGTGTGAAGGAACTGTATAGAGGAGGCTTGGAACCTATC
AACTTTCAAACAGCTGCAGATCAAGCCAGAGAGCTCATCAATTCCTGGGTAGAAAGTCAG
ACAAATGGAATTATCAGAAATGTCCTTCAGCCAAGCTCCGTGGATTCTCAAACTGCAATG
GTTCTGGTTAATGCCATTGTCTTCAAAGGACTGTGGGAGAAAGCATTTAAGGATGAAGAC
ACACAAGCAATGCCTTTCAGAGTGACTGAGCAAGAAAGCAAACCTGTGCAGATGATGTAC
CAGATTGGTTTATTTAGAGTGGCATCAATGGCTTCTGAGAAAATGAAGATCCTGGAGCTT
CCATTTGCCAGTGGGACAATGAGCATGTTGGTGCTGTTGCCTGATGAAGTCTCAGGCCTT
GAGCAGCTTGAGAGTATAATCAACTTTGAAAAACTGACTGAATGGACCAGTTCTAATGTT
ATGGAAGAGAGGAAGATCAAAGTGTACTTACCTCGCATGAAGATGGAGGAAAAATACAAC
CTCACATCTGTCTTAATGGCTATGGGCATTACTGACGTGTTTAGCTCTTCAGCCAATCTG
TCTGGCATCTCCTCAGCAGAGAGCCTGAAGATATCTCAAGCTGTCCATGCAGCACATGCA
GAAATCAATGAAGCAGGCAGAGAGGTGGTAGGGTCAGCAGAGGCTGGAGTGGATGCTGCA
AGCGTCTCTGAAGAATTTAGGGCTGACCATCCATTCCTCTTCTGTATCAAGCACATCGCA
ACCAACGCCGTTCTCTTCTTTGGCAGATGTGTTTCCCCT**TCGAAGCTTGAAGGTAAGCCT
ATCCCTAACCCTCTCCTCGGTCTCGATTCTACGCGTACCGGTCATCATCACCATCACCAT**

Figure 61

SEQ ID NO: 153 - STF2.OVA amino acid sequence

MAQVINTNSLSLLTQNNLNKSQSALGTAIERLSSGLRINSAKDDAAGQAIANRFTANIKG
LTQASRNANDGISIAQTTEGALNEINNNLQRVRELAVQSANSTNSQSDLDSIQAEITQRL
NEIDRVSGQTQFNGVKVLAQDNTLTIQVGANDGETIDIDLKQINSQTLGLDSLNVQKAYD
VKDTAVTTKAYANNGTTLDVSGLDDAAIKAATGGTNGTASVTGGAVKFDADNNKYFVTIG
GFTGADAAKNGDYEVNVATDGTVTLAAGATKTTMPAGATTKTEVQELKDTPAVVSADAKN
ALIAGGVDATDANGAELVKMSYTDKNGKTIEGGYALKAGDKYYAADYDEATGAIKAKTTS
YTAADGTTKTAANQLGGVDGKTEVVTIDGKTYNASKAAGHDFKAQPELAEAAAKTTENPL
QKIDAALAQVDALRSDLGAVQNRFNSAITNLGNTVNNLSEARSRIEDSDYATEVSNMSRA
QILQQAGTSVLAQANQVPQNVLSLLRLEGSIGAASMEFCFDVFKELKVHHANENIFYCPI
AIMSALAMVYLGAKDSTRTQINKVVRFDKLPGFGDSIEAQCGTSVNVHSSLRDILNQITK
PNDVYSFSLASRLYAEERYPILPEYLQCVKELYRGGLEPINFQTAADQARELINSWVESQ
TNGIIRNVLQPSSVDSQTAMVLVNAIVFKGLWEKAFKDEDTQAMPFRVTEQESKPVQMMY
QIGLFRVASMASEKMKILELPFASGTMSMLVLLPDEVSGLEQLESIINFEKLTEWTSSNV
MEERKIKVYLPRMKMEEKYNLTSVLMAMGITDVFSSSANLSGISSAESLKISQAVHAAHA
EINEAGREVVGSAEAGVDAASVSEEFRADHPFLFCIKHIATNAVLFFGRCVSP**SKLEGKP
IPNPLLGLDSTRTGHHHHHH**

Figure 62

SEQ ID NO: 154 - Ovalbumin (OVA) amino acid sequence

GSIGAASMEFCFDVFKELKVHHANENIFYCPIAIMSALAMVYLGAKDSTRTQINKVVRFD
KLPGFGDSIEAQCGTSVNVHSSLRDILNQITKPNDVYSFSLASRLYAEERYPILPEYLQC
VKELYRGGLEPINFQTAADQARELINSWVESQTNGIIRNVLQPSSVDSQTAMVLVNAIVF
KGLWEKAFKDEDTQAMPFRVTEQESKPVQMMYQIGLFRVASMASEKMKILELPFASGTMS
MLVLLPDEVSGLEQLESIINFEKLTEWTSSNVMEERKIKVYLPRMKMEEKYNLTSVLMAM
GITDVFSSSANLSGISSAESLKISQAVHAAHAEINEAGREVVGSAEAGVDAASVSEEFRA
DHPFLFCIKHIATNAVLFFGRCVSP

Figure 63

SEQ ID NO: 155 - Ovalbumin (OVA) nucleic acid sequence

GGGCTCCATCGGCGCAGCAAGCATGGAATTTTGTTTTGATGTATTCAAGGAGCTCAAAGT
CCACCATGCCAATGAGAACATCTTCTACTGCCCCATTGCCATCATGTCAGCTCTAGCCAT
GGTATACCTGGGTGCAAAAGACAGCACCAGGACACAAATAAATAAGGTTGTTCGCTTTGA
TAAACTTCCAGGATTCGGAGACAGTATTGAAGCTCAGTGTGGCACATCTGTAAACGTTCA
CTCTTCACTTAGAGACATCCTCAACCAAATCACCAAACCAAATGATGTTTATTCGTTCAG
CCTTGCCAGTAGACTTTATGCTGAAGAGAGATACCCAATCCTGCCAGAATACTTGCAGTG
TGTGAAGGAACTGTATAGAGGAGGCTTGGAACCTATCAACTTTCAAACAGCTGCAGATCA
AGCCAGAGAGCTCATCAATTCCTGGGTAGAAAGTCAGACAAATGGAATTATCAGAAATGT
CCTTCAGCCAAGCTCCGTGGATTCTCAAACTGCAATGGTTCTGGTTAATGCCATTGTCTT
CAAAGGACTGTGGGAGAAAGCATTTAAGGATGAAGACACACAAGCAATGCCTTTCAGAGT
GACTGAGCAAGAAAGCAAACCTGTGCAGATGATGTACCAGATTGGTTTATTTAGAGTGGC
ATCAATGGCTTCTGAGAAAATGAAGATCCTGGAGCTTCCATTTGCCAGTGGGACAATGAG
CATGTTGGTGCTGTTGCCTGATGAAGTCTCAGGCCTTGAGCAGCTTGAGAGTATAATCAA
CTTTGAAAAACTGACTGAATGGACCAGTTCTAATGTTATGGAAGAGAGGAAGATCAAAGT
GTACTTACCTCGCATGAAGATGGAGGAAAAATACAACCTCACATCTGTCTTAATGGCTAT
GGGCATTACTGACGTGTTTAGCTCTTCAGCCAATCTGTCTGGCATCTCCTCAGCAGAGAG
CCTGAAGATATCTCAAGCTGTCCATGCAGCACATGCAGAAATCAATGAAGCAGGCAGAGA
GGTGGTAGGGTCAGCAGAGGCTGGAGTGGATGCTGCAAGCGTCTCTGAAGAATTTAGGGC
TGACCATCCATTCCTCTTCTGTATCAAGCACATCGCAACCAACGCCGTTCTCTTCTTTGG
CAGATGTGTTTCCCCT

Figure 64

SEQ ID NO: 158 - STF2.E nucleic acid sequence

ATGGCACAAGTAATCAACACTAACAGTCTGTCGCTGCTGACCCAGAATAACCTGAACAAA
TCCCAGTCCGCACTGGGCACCGCTATCGAGCGTCTGTCTTCTGGTCTGCGTATCAACAGC
GCGAAAGACGATGCGGCAGGTCAGGCGATTGCTAACCGTTTCACCGCGAACATCAAAGGT
CTGACTCAGGCTTCCCGTAACGCTAACGACGGTATCTCCATTGCGCAGACCACTGAAGGC
GCGCTGAACGAAATCAACAACAACCTGCAGCGTGTGCGTGAACTGGCGGTTCAGTCTGCT
AACAGCACCAACTCCCAGTCTGACCTCGACTCCATCCAGGCTGAAATCACCCAGCGCCTG
AACGAAATCGACCGTGTATCCGGCCAGACTCAGTTCAACGGCGTGAAAGTCCTGGCGCAG
GACAACACCCTGACCATCCAGGTTGGCGCCAACGACGGTGAAACTATCGATATCGATCTG
AAGCAGATCAACTCTCAGACCCTGGGTCTGGACTCACTGAACGTGCAGAAAGCGTATGAT
GTGAAAGATACAGCAGTAACAACGAAAGCTTATGCCAATAATGGTACTACACTGGATGTA
TCGGGTCTTGATGATGCAGCTATTAAAGCGGCTACGGGTGGTACGAATGGTACGGCTTCT
GTAACCGGTGGTGCGGTTAAATTTGACGCAGATAATAACAAGTACTTTGTTACTATTGGT
GGCTTTACTGGTGCTGATGCCGCCAAAAATGGCGATTATGAAGTTAACGTTGCTACTGAC
GGTACAGTAACCCTTGCGGCTGGCGCAACTAAAACCACAATGCCTGCTGGTGCGACAACT
AAAACAGAAGTACAGGAGTTAAAAGATACACCGGCAGTTGTTTCAGCAGATGCTAAAAAT
GCCTTAATTGCTGGCGGCGTTGACGCTACCGATGCTAATGGCGCTGAGTTGGTCAAAATG
TCTTATACCGATAAAAATGGTAAGACAATTGAAGGCGGTTATGCGCTTAAAGCTGGCGAT
AAGTATTACGCCGCAGATTACGATGAAGCGACAGGAGCAATTAAAGCTAAAACCACAAGT
TATACTGCTGCTGACGGCACTACCAAAACAGCGGCTAACCAACTGGGTGGCGTAGACGGT
AAAACCGAAGTCGTTACTATCGACGGTAAAACCTACAATGCCAGCAAAGCCGCTGGTCAT
GATTTCAAAGCACAACCAGAGCTGGCGGAAGCAGCCGCTAAAACCACCGAAAACCCGCTG
CAGAAAATTGATGCCGCGCTGGCGCAGGTGGATGCGCTGCGCTCTGATCTGGGTGCGGTA
CAAAACCGTTTCAACTCTGCTATCACCAACCTGGGCAATACCGTAAACAATCTGTCTGAA
GCGCGTAGCCGTATCGAAGATTCCGACTACGCGACCGAAGTTTCCAACATGTCTCGCGCG
CAGATTTTGCAGCAGGCCGGTACTTCCGTTCTGGCGCAGGCTAACCAGGTCCCGCAGAAC
GTGCTGTCTCTGTTACGTTTCAACTGCCTTGGAATGAGCAACAGAGACTTCTTGGAAGGA
GTGTCTGGAGCAACATGGGTGGATTTGGTTCTCGAAGGCGACAGCTGCGTGACTATCATG
TCTAAGGACAAGCCTACCATCGATGTGAAGATGATGAATATGGAGGCGGCCAACCTGGCA
GAGGTCCGCAGTTATTGCTATTTGGCTACCGTCAGCGATCTCTCCACCAAAGCTGCGTGC
CCGACCATGGGAGAAGCTCACAATGACAAACGTGCTGACCCAGCTTTTGTGTGCAGACAA
GGAGTGGTGGACAGGGGCTGGGGCAACGGCTGCGGACTATTTGGCAAAGGAAGCATTGAC
ACATGCGCCAAATTTGCCTGCTCTACCAAGGCAATAGGAAGAACCATCTTGAAAGAGAAT
ATCAAGTACGAAGTGGCCATTTTTGTCCATGGACCAACTACTGTGGAGTCGCACGGAAAC
TACTCCACACAGGTTGGAGCCACTCAGGCAGGGAGATTCAGCATCACTCCTGCAGCGCCT
TCATACACACTAAAGCTTGGAGAATATGGAGAGGTGACAGTGGACTGTGAACCACGGTCA
GGGATTGACACCAATGCATACTACGTGATGACTGTTGGAACAAAGACGTTCTTGGTCCAT
CGTGAGTGGTTCATGGACCTCAACCTCCCTTGGAGCAGTGCTGGAAGTACTGTGTGGAGG
AACAGAGAGACGTTAATGGAGTTTGAGGAACCACACGCCACGAAGCAGTCTGTGATAGCA
TTGGGCTCACAAGAGGGAGCTCTGCATCAAGCTTTGGCTGGAGCCATTCCTGTGGAATTT
TCAAGCAACACTGTCAAGTTGACGTCGGGTCATTTGAAGTGTAGAGTGAAGATGGAAAAA
TTGCAGTTGAAGGGAACAACCTATGGCGTCTGTTCAAAGGCTTTCAAGTTTCTTGGGACT
CCCGCAGACACAGGTCACGGCACTGTGGTGTTGGAATTGCAGTACACTGGCACGGATGGA
CCTTGCAAAGTTCCTATCTCGTCAGTGGCTTCATTGAACGACCTAACGCCAGTGGGCAGA
TTGGTCACTGTCAACCCTTTTGTTTCAGTGGCCACGGCCAACGCTAAGGTCCTGATTGAA
TTGGAACCACCCTTTGGAGACTCATACATAGTGGTGGGCAGAGGAGAACAACAGATCAAT
CACCATTGGCACAAGTCTGGAAGCAGCATTGGCAAA

Figure 65

SEQ ID NO: 159 - STF2.E amino acid sequence

MAQVINTNSLSLLTQNNLNKSQSALGTAIERLSSGLRINSAKDDAAGQAIANRFTANIKG
LTQASRNANDGISIAQTTEGALNEINNNLQRVRELAVQSANSTNSQSDLDSIQAEITQRL
NEIDRVSGQTQFNGVKVLAQDNTLTIQVGANDGETIDIDLKQINSQTLGLDSLNVQKAYD
VKDTAVTTKAYANNGTTLDVSGLDDAAIKAATGGTNGTASVTGGAVKFDADNNKYFVTIG
GFTGADAAKNGDYEVNVATDGTVTLAAGATKTTMPAGATTKTEVQELKDTPAVVSADAKN
ALIAGGVDATDANGAELVKMSYTDKNGKTIEGGYALKAGDKYYAADYDEATGAIKAKTTS
YTAADGTTKTAANQLGGVDGKTEVVTIDGKTYNASKAAGHDFKAQPELAEAAAKTTENPL
QKIDAALAQVDALRSDLGAVQNRFNSAITNLGNTVNNLSEARSRIEDSDYATEVSNMSRA
QILQQAGTSVLAQANQVPQNVLSLL<u>RFNCLGMSNRDFLEGVSGATWVDLVLEGDSCVTIM
SKDKPTIDVKMMNMEAANLAEVRSYCYLATVSDLSTKAACPTMGEAHNDKRADPAFVCRQ
GVVDRGWGNGCGLFGKGSIDTCAKFACSTKAIGRTILKENIKYEVAIFVHGPTTVESHGN
YSTQVGATQAGRFSITPAAPSYTLKLGEYGEVTVDCEPRSGIDTNAYYVMTVGTKTFLVH
REWFMDLNLPWSSAGSTVWRNRETLMEFEEPHATKQSVIALGSQEGALHQALAGAIPVEF
SSNTVKLTSGHLKCRVKMEKLQLKGTTYGVCSKAFKFLGTPADTGHGTVVLELQYTGTDG
PCKVPISSVASLNDLTPVGRLVTVNPFVSVATANAKVLIELEPPFGDSYIVVGRGEQQIN
HHWHKSGSSIGK</u>

Figure 66

SEQ ID NO: 57 - E protein nucleic acid sequence

TTCAACTGCCTTGGAATGAGCAACAGAGACTTCTTGGAAGGAGTGTCTGGAGCAACATGG
GTGGATTTGGTTCTCGAAGGCGACAGCTGCGTGACTATCATGTCTAAGGACAAGCCTACC
ATCGATGTGAAGATGATGAATATGGAGGCGGCCAACCTGGCAGAGGTCCGCAGTTATTGC
TATTTGGCTACCGTCAGCGATCTCTCCACCAAAGCTGCGTGCCCGACCATGGGAGAAGCT
CACAATGACAAACGTGCTGACCCAGCTTTTGTGTGCAGACAAGGAGTGGTGGACAGGGGC
TGGGGCAACGGCTGCGGACTATTTGGCAAAGGAAGCATTGACACATGCGCCAAATTTGCC
TGCTCTACCAAGGCAATAGGAAGAACCATCTTGAAAGAGAATATCAAGTACGAAGTGGCC
ATTTTTGTCCATGGACCAACTACTGTGGAGTCGCACGGAAACTACTCCACACAGGTTGGA
GCCACTCAGGCAGGGAGATTCAGCATCACTCCTGCAGCGCCTTCATACACACTAAAGCTT
GGAGAATATGGAGAGGTGACAGTGGACTGTGAACCACGGTCAGGGATTGACACCAATGCA
TACTACGTGATGACTGTTGGAACAAAGACGTTCTTGGTCCATCGTGAGTGGTTCATGGAC
CTCAACCTCCCTTGGAGCAGTGCTGGAAGTACTGTGTGGAGGAACAGAGAGACGTTAATG
GAGTTTGAGGAACCACACGCCACGAAGCAGTCTGTGATAGCATTGGGCTCACAAGAGGGA
GCTCTGCATCAAGCTTTGGCTGGAGCCATTCCTGTGGAATTTTCAAGCAACACTGTCAAG
TTGACGTCGGGTCATTTGAAGTGTAGAGTGAAGATGGAAAAATTGCAGTTGAAGGGAACA
ACCTATGGCGTCTGTTCAAAGGCTTTCAAGTTTCTTGGGACTCCCGCAGACACAGGTCAC
GGCACTGTGGTGTTGGAATTGCAGTACACTGGCACGGATGGACCTTGCAAAGTTCCTATC
TCGTCAGTGGCTTCATTGAACGACCTAACGCCAGTGGGCAGATTGGTCACTGTCAACCCT
TTTGTTTCAGTGGCCACGGCCAACGCTAAGGTCCTGATTGAATTGGAACCACCCTTTGGA
GACTCATACATAGTGGTGGGCAGAGGAGAACAACAGATCAATCACCATTGGCACAAGTCT
GGAAGCAGCATTGGCAAA

Figure 67

SEQ ID NO: 160 - Den-1 amino acid sequence

MRCVGIGNRDFVEGLSGATWVDVVLEHGSCVTTMAKNKPTLDIELLKTEVTNPAVLRKLCIEAKI
SNTTTDSRCPTQGEATLVEEQDANFVCRRTFVDRGWGNGCGLFGKGSLITCAKFKCVTKLEGKIA
QYENLKYSVIVTVHTGDQHQVGNETTEHGTTATITPQAPTSEIQLTDYGTLTLDCSPRTGLDFNE
MVLLTMKKKSWLVHKQWFLDLPLPWTSGALTSQETWNRQDLLVTFKTAHAKKQEVVVLGSQEGAM
HTALTGATEIQTSGTTTIFAGHLKCRLKMDKLTLKGMSYVMCTGSFKLEKEVAETQHGTVLVQVK
YEGTDAPCKIPFSTQDEKGATQNGRLITANPIVTDKEKPVNIEAEPPFGESYIVVGAGEKALKLS
WFKKGSSIGKMFEATARGARRMAILGDTAWDFGSIGGVFTSMGKLVHQVFGTAYGVLFSGVSWTM
KIGIGILLTWLGLNSRNTSLSVMCIAVGMVTLYLGVMVQA

Figure 68

SEQ ID NO: 161 - Den-1 nucleic acid sequence

ATGCGATGCGTGGGAATAGGCAACAGAGACTTCGTGGAAGGACTGTCAGGAGCAACATGGGTGGAT
GTGGTACTGGAGCATGGAAGTTGCGTCACCACCATGGCAAAAAACAAACCAACACTGGACATTGAA
CTCTTGAAGACGGAGGTCACAAACCCTGCAGTTCTGCGTAAATTGTGCATTGAAGCTAAAATATCA
AACACCACCACCGATTCGAGATGTCCAACACAAGGAGAAGCCACACTGGTGGAAGAACAAGACGCG
AACTTTGTGTGCCGACGAACGTTCGTGGACAGAGGCTGGGGCAATGGCTGTGGGCTATTCGGAAAA
GGTAGTCTAATAACGTGTGCCAAGTTTAAGTGTGTGACAAAACTAGAAGGAAAGATAGCTCAATAT
GAAAACCTAAAATATTCAGTGATAGTCACCGTCCACACTGGAGATCAGCACCAGGTGGGAAATGAG
ACTACAGAACATGGAACAACTGCAACCATAACACCTCAAGCTCCTACGTCGGAAATACAGCTGACC
GACTACGGAACCCTTACATTAGATTGTTCACCTAGGACAGGGCTAGATTTTAACGAGATGGTGTTG
CTGACAATGAAAAAGAAATCATGGCTTGTCCACAAACAGTGGTTTCTAGACTTACCACTGCCTTGG
ACCTCTGGGGCTTTAACATCCCAAGAGACTTGGAACAGACAAGATTTACTGGTCACATTTAAGACA
GCTCATGCAAAGAAGCAGGAAGTAGTCGTACTAGGATCACAAGAAGGAGCAATGCACACTGCGCTG
ACTGGAGCGACAGAAATCCAAACGTCAGGAACGACAACAATTTTCGCAGGACACCTAAAATGCAGA
CTAAAAATGGACAAACTAACTTTAAAAGGGATGTCATATGTGATGTGCACAGGCTCATTCAAGTTA
GAGAAAGAAGTGGCTGAGACCCAGCATGGAACTGTTCTGGTGCAGGTTAAATATGAAGGAACAGAC
GCACCATGCAAGATTCCCTTTTCGACCCAAGATGAGAAAGGAGCAACCCAGAATGGGAGATTAATA
ACAGCCAACCCCATAGTCACTGACAAAGAAAAACCAGTCAATATTGAGGCAGAACCACCCTTTGGT
GAGAGCTACATCGTGGTAGGAGCAGGTGAAAAAGCTTTGAAACTAAGCTGGTTCAAGAAAGGAAGC
AGCATAGGGAAAATGTTTGAAGCAACTGCCCGAGGAGCACGAAGGATGGCCATTCTGGGAGACACC
GCATGGGACTTCGGTTCTATAGGAGGAGTGTTCACGTCTATGGGAAAACTGGTACACCAGGTTTTT
GGAACTGCATATGGAGTTTTGTTTAGCGGAGTTTCTTGGACCATGAAAATAGGAATAGGGATTCTG
CTGACATGGCTAGGATTAAATTCAAGGAACACGTCCCTTTCGGTGATGTGCATCGCAGTTGGCATG
GTCACACTGTACCTAGGAGTCATGGTTCAGGCA

Figure 69

SEQ ID NO: 162 - Den-2 amino acid sequence

MRCIGMSNRDFVEGVSGGSWVDIVLEHGSCVTTMAKNKPTLDFELIKTEAKQPATLRKYC
IEAKLTNTTTESRCPTQGEPSLNEEQDKRFVCKHSMVDRGWGNGCGLFGKGGIVTCAMFR
CKKNMEGKVVQPENLEYTIVITPHSGEEHAVGNDTGKHGKEIKITPQSSTTEAELTGYGT
VTMECSPRTGLDFNEMVLLQMENKAWLVHRQWFLDLPLPWLPGADTQGSNWIQKETLVTF
KNPHAKKQDVVVLGSQEGAMHTALTGATEIQMSSGNLLFTGHLKCRLRMDKLQLKGMSYS
MCTGKFKVVKEIAETQHGTIVIRVQYEGDGSPCKIPFEIMDLEKRHVLGRLITVNPIVTE
KDSPVNIEAEPPFGDSYIIIGVEPGQLKLNWFKKGSSIGQMFETTMRGAKRMAILGDTAW
DFGSLGGVFTSIGKALHQVFGAIYGAAFSGVSWTMKILIGVIITWIGMNSRSTSLSVTLV
LVGIVTLYLGVMVQA

Figure 70

SEQ ID NO: 163 - Den-2 nucleic acid sequence

ATGCGTTGCATAGGAATGTCAAATAGAGACTTTGTGGAAGGGGTTTCAGGAGGAAGCTGGGTTGAC
ATAGTCTTAGAACATGGAAGCTGTGTGACGACGATGGCAAAAAACAAACCAACATTGGATTTTGAA
CTGATAAAAACAGAAGCCAAACAGCCTGCCACCCTAAGGAAGTACTGTATAGAGGCAAAGCTAACC
AACACAACAACAGAATCTCGCTGCCCAACACAAGGGGAACCCAGCCTAAATGAAGAGCAGGACAAA
AGGTTCGTCTGCAAACACTCCATGGTAGACAGAGGATGGGGAAATGGATGTGGACTATTTGGAAAG
GGAGGCATTGTGACCTGTGCTATGTTCAGATGCAAAAAGAACATGGAAGGAAAAGTTGTGCAACCA
GAAAACTTGGAATACACCATTGTGATAACACCTCACTCAGGGGAAGAGCATGCAGTCGGAAATGAC
ACAGGAAAACATGGCAAGGAAATCAAAATAACACCACAGAGTTCCACCACAGAAGCAGAATTGACA
GGTTATGGCACTGTCACAATGGAGTGCTCTCCAAGAACGGGCCTCGACTTCAATGAGATGGTGTTG
CTGCAGATGGAAAATAAAGCTTGGCTGGTGCACAGGCAATGGTTCCTAGACCTGCCGTTACCATGG
TTGCCCGGAGCGGACACACAAGGGTCAAATTGGATACAGAAAGAGACATTGGTCACTTTCAAAAAT
CCCCATGCGAAGAAACAGGATGTTGTTGTTTTAGGATCCCAAGAAGGGGCCATGCACACAGCACTT
ACAGGGGCCACAGAAATCCAAATGTCATCAGGAAACTTACTCTTCACAGGACATCTCAAGTGCAGG
CTGAGAATGGACAAGCTACAGCTCAAAGGAATGTCATACTCTATGTGCACAGGAAAGTTTAAAGTT
GTGAAGGAAATAGCAGAAACACAACATGGAACAATAGTTATCAGAGTGCAATATGAAGGGGACGGC
TCTCCATGCAAGATCCCTTTTGAGATAATGGATTTGGAAAAAGACATGTCTTAGGTCGCCTGATT
ACAGTCAACCCAATTGTGACAGAAAAGATAGCCCAGTCAACATAGAAGCAGAACCTCCATTCGGA
GACAGCTACATCATCATAGGAGTAGAGCCGGGACAACTGAAGCTCAACTGGTTTAAGAAAGGAAGT
TCTATCGGCCAAATGTTTGAGACAACAATGAGGGGGGCGAAGAGAATGGCCATTTTAGGTGACACA
GCCTGGGATTTTGGATCCTTGGGAGGAGTGTTTACATCTATAGGAAAGGCTCTCCACCAAGTCTTT
GGAGCAATCTATGGAGCTGCCTTCAGTGGGGTTTCATGGACTATGAAAATCCTCATAGGAGTCATT
ATCACATGGATAGGAATGAATTCACGCAGCACCTCACTGTCTGTGACACTAGTATTGGTGGGAATT
GTGACACTGTATTTGGGAGTCATGGTGCAGGCC

Figure 71

SEQ ID NO: 164 - Den-3 amino acid sequence

MRCVGVGNRDFVEGLSGATWVDVVLEHGGCVTTMAKNKPTLDIELQKTEATQLATLRKLCIEGKIT
NITTDSRCPTQGEAILPEEQDQNYVCKHTYVDRGWGNGCGLFGKGSLVTCAKFQCLEPIEGKVVQH
ENLKYTVIITVHTGDQHQVGNDTQGVTVEITPQASTVEAILPEYGTLGLECSPRTGLDFNEMILLT
MKNKAWMVHRQWFFDLPLPWTSGATTETPTWNRKELLVTFKNAHAKKQEVVVLGSQEGAMHTALTG
ATEIQNSGGTSIFAGHLKCRLKMDKLELKGMSYAMCLNTFVLKKEVSETQHGTILIKVEYKGEDAP
CKIPFSTEDGQGKAHNGRLITANPVVTKKEEPVNIEAEPPFGESNIVIGIGDKALKINWYKKGSSI
GKMFEATARGARRMAILGDTAWDFGSVGGVLNSLGKMVHQIFGSAYTALFSGVSWIMKIGIGVLLT
WIGLNSKNTSMSFSCIAIGIITLYLGAVVQA

Figure 72

SEQ ID NO: 165 - Den-3 nucleic acid sequence

ATGAGATGCGTGGGAGTAGGAAACAGAGATTTTGTGGAAGGTCTGTCGGGAGCTACGTGGGTTGAT
GTGGTGCTCGAGCACGGAGGGTGTGTGACCACCATGGCTAAGAACAAGCCTACGCTGGACATAGAG
CTCCAGAAGACCGAGGCCACCCAACTGGCGACCCTAAGAAAGTTATGCATTGAGGGAAAAATTACC
AACATAACAACTGACTCAAGGTGTCCTACCCAGGGGAAGCGATTTTACCTGAGGAGCAGGACCAG
AACTACGTATGTAAGCACACATACGTGGATAGAGGTTGGGGAAACGGTTGTGGTTTGTTTGGAAAA
GGAAGCTTGGTGACATGCGCGAAATTTCAATGTCTAGAACCAATAGAGGGAAAAGTGGTGCAACAT
GAGAACCTCAAATACACTGTCATCATCACAGTGCACACAGGAGACCAACACCAGGTGGGAAATGAC
ACGCAGGGAGTCACGGTTGAGATAACACCCCAGGCATCAACCGTTGAAGCTATCTTGCCTGAATAT
GGAACCCTTGGGCTAGAATGTTCACCACGGACAGGTTTGGATTTCAACGAAATGATTTTATTGACA
ATGAAGAACAAAGCATGGATGGTACATAGGCAATGGTTCTTTGACCTACCCCTACCATGGACATCA
GGAGCTACAACAGAGACACCAACTTGGAACAGGAAAGAGCTCCTTGTGACATTCAAGAATGCACAT
GCAAAAAAGCAAGAAGTAGTTGTCCTTGGATCGCAAGAGGGAGCAATGCACACAGCGCTGACAGGA
GCTACAGAGATTCAAAACTCAGGAGGTACAAGCATTTTTGCGGGGCACTTGAAATGTAGACTTAAG
ATGGACAAATTGGAACTCAAGGGGATGAGCTATGCAATGTGCTTGAATACCTTTGTGTTGAAGAAA
GAAGTCTCTGAAACGCAGCATGGGACAATACTCATCAAGGTTGAGTACAAAGGGGAAGATGCACCT
TGCAAGATTCCTTTCTCCACAGAGGATGGACAAGGGAAAGCTCACAATGGTAGACTGATCACAGCC
AACCCAGTGGTGACCAAGAAGGAGGAGCCTGTCAACATTGAGGCTGAACCTCCTTTTGGGGAAAGT
AACATAGTGATTGGGATTGGAGACAAAGCCTTGAAAATTAACTGGTACAAGAAGGGAAGCTCGATT
GGAAAGATGTTCGAGGCTACTGCCAGAGGTGCAAGGCGCATGGCCATCTTGGGAGACACAGCCTGG
GATTTTGGTTCAGTGGGTGGTGTTCTGAATTCATTAGGGAAAATGGTACACCAAATATTCGGAAGT
GCTTACACAGCCCTGTTTAGTGGAGTCTCATGGATAATGAAAATTGGAATAGGTGTCCTCTTAACC
TGGATAGGGTTGAATTCAAAAAACACTTCCATGTCATTTTCATGCATTGCGATAGGAATTATTACA
CTCTATCTGGGAGCCGTGGTACAAGCT

Figure 73

SEQ ID NO: 166 - Den-4 amino acid sequence

```
MRCVGVGNRDFVEGVSGGAWVDLVLEHGGCVTTMAQGKPTLDFELTKTTAKEVALLRTYCIEASIS
NITTATRCPTQGEPYLKEEQDQQYICRRDVVDRGWGNGCGLFGKGGVVTCAKFSCSGKITGNLVRI
ENLEYTVVVTVHNGDTHAVGNDTSNHGVTAMITPRSPSVEVKLPDYGELTLDCEPRSGIDFNEMIL
MKMKKKTWLVHKQWFLDLPLPWTAGADTSEVHWNYKERMVTFKVPHAKRQDVTVLGSQEGAMHSAL
AGATEVDSGDGNHMFAGHLKCEVRMEKLRIKGMSYTMCSGKFSIDKEMAETQHGTTVVKVKYEGAG
APCKVPIEIRDVNKEKVVGRIISSTPLAENTNSVTNIELEPPFGDSYIVIGVGNSALTHWFRKGS
SIGKMFESTYRGAKRMAILGETAWDFGSVGGLFTSLGKAVHQVFGSVYTTMFGGVSWMIRILIGF
LVLWIGTNSRNTSMAMTCIAVGGITLFLGF
```

Figure 74

SEQ ID NO: 167 - Den-4 nucleic acid sequence

ATGCGATGCGTAGGAGTAGGAAACAGAGACTTTGTGGAAGGAGTCTCAGGTGGAGCATGGGTCGACC
TGGTGCTAGAACATGGAGGATGCGTCACAACCATGGCCCAGGGAAAACCAACCTTGGATTTTGAACT
GACCAAGACAACAGCCAAGGAAGTGGCTCTGTTAAGAACCTATTGCATTGAAGCCTCAATATCAAAC
ATAACTACGGCAACAAGATGTCCAACGCAAGGAGAGCCTTATCTGAAAGAGGAACAGGACCAACAGT
ACATTTGCCGGAGAGATGTGGTAGACAGAGGGTGGGGCAATGGCTGTGGCTTGTTTGGAAAAGGAGG
AGTTGTGACATGTGCGAAGTTTTCATGTTCGGGGAAGATAACAGGCAATTTGGTCCGAATTGAGAAC
CTTGAATACACAGTGGTGGTAACAGTCCACAATGGAGACACCCATGCAGTAGGAAATGACACATCCA
ATCATGGAGTTACAGCCATGATAACCCCCAGGTCACCATCGGTGGAAGTCAAATTGCCGGACTATGG
AGAACTAACACTCGATTGTGAACCCAGGTCTGGAATTGACTTTAATGAGATGATTCTGATGAAAATG
AAAAAGAAAACATGGCTCGTGCATAAGCAATGGTTTTTGGATCTGCCTCTTCCATGGACAGCAGGAG
CAGACACATCAGAGGTTCACTGGAATTACAAAGAGAGAATGGTGACATTTAAGGTTCCTCATGCCAA
GAGACAGGATGTGACAGTGCTGGGATCTCAGGAAGGAGCCATGCATTCTGCCCTCGCTGGAGCCACA
GAAGTGGACTCCGGTGATGGAAATCACATGTTTGCAGGACATCTCAAGTGCGAAGTCCGTATGGAGA
AATTGAGAATCAAGGGAATGTCATACACGATGTGTTCAGGAAAGTTTTCAATTGACAAAGAGATGGC
AGAAACACAGCATGGGACAACAGTGGTGAAAGTCAAGTATGAAGGTGCTGGAGCTCCGTGTAAAGTC
CCCATAGAGATAAGAGATGTAAACAAGGAAAAAGTGGTTGGGCGTATCATCTCATCCACCCCTTTGG
CTGAGAATACCAACAGTGTAACCAACATAGAATTAGAACCCCCCTTTGGGGACAGCTACATAGTGAT
AGGTGTTGGAAACAGCGCATTAACACTCCATTGGTTCAGGAAGGGAGTTCCATTGGCAAGATGTTT
GAGTCCACATACAGAGGTGCAAAACGAATGGCCATTCTAGGTGAAACAGCTTGGGATTTTGGTTCCG
TTGGTGGATTGTTCACATCATTGGGAAAGGCTGTGCACCAGGTTTTTGGAAGTGTGTATACAACCAT
GTTTGGAGGAGTCTCATGGATGATTAGAATCCTAATTGGGTTCTTAGTGTTGTGGATTGGCACGAAC
TCAAGGAACACTTCAATGGCTATGACGTGCATAGCTGTTGGAGGAATCACTCTGTTTCTGGGCTTC

Figure 75

SEQ ID NO: 170 - JE nucleic acid sequence

```
TTTAATTGTCTGGGAATGGGCAATCGTGACTTCATAGAAGGAGCCAGTGGAGCCGCTTGGGTGACTTGGTGCTA
GAAGGAGACAGCTGCTTGACAATCATGGCAAACGACAAACCAACATTGGACGTCCGCATGATTAACATCGAAGC
TAGCCAACTTGCTGAGGTCAGAAGTTACTGCTATCATGCTTCAGTCACTGACATCTCGACGGTGGCTCGGTGCC
CCACGACTGGAGAAGCCCACAACGAGAAGCGAGCTGATAGTAGCTATGTGTGCAAACAAGGCTTCACTGACCGT
GGGTGGGGCAACGGATGTGGATTTTTCGGGAAGGGAAGCATTGACACATGTGCAAAATTCTCCTGCACCAGTAA
AGCGATTGGGAGAACAATCCAGCCAGAAAACATCAAATACAAAGTTGGCATTTTTGTGCATGGAACCACCACTT
CGGAAAACCATGGGAATTATTCAGCGCAAGTTGGGGCGTCCCAGGCGGCAAAGTTTACAGTAACACCCAATGCT
CCTTCGGTAGCCCTCAAACTTGGTGACTACGGAGAAGTCACACTGGACTGTGAGCCAAGGAGTGGACTGAACAC
TGAAGCGTTTTACGTCATGACCGTGGGGTCAAAGTCATTTCTGGTCCATAGGGAGTGGTTTCATGACCTCGCTC
TCCCCTGGACGTCCCCTTCGAGCACAGCGTGGAGAAACAGAGAACTCCTCATGGAATTTGAAGGGGCGCACGCC
ACAAAACAGTCCGTTGTTGCTCTTGGGTCACAGGAAGGAGGCCTCCATCATGCGTTGGCAGGAGCCATCGTGGT
GGAGTACTCAAGCTCAGTGATGTTAACATCAGGCCACCTGAAATGTAGGCTGAAAATGGACAAACTGGCTCTGA
AAGGCACAACCTATGGCATGTGTACAGAAAAATTCTCGTTCGCGAAAAATCCGGTGGACACTGGTCACGGAACA
GTTGTCATTGAACTCTCCTACTCTGGGAGTGATGGCCCCTGCAAAATTCCGATTGTTTCCGTTGCGAGCCTCAA
TGACATGACCCCCGTTGGGCGGCTGGTGACAGTGAACCCCTTCGTCGCGACTTCCAGTGCCAACTCAAAGGTGC
TGGTCGAGATGGAACCCCCCTTCGGAGACTCCTACATCGTAGTTGGAAGGGGAGACAAGCAGATCAACCACCAT
TGGCACAAAGCTGGAAGCACGCTGGGCAAGGCC
```

Figure 76

SEQ ID NO: 171 - JE amino acid sequence

FNCLGMGNRDFIEGASGAAWVDLVLEGDSCLTIMANDKPTLDVRMINIEASQLAEVRSYCYHASVTDISTV
ARCPTTGEAHNEKRADSSYVCKQGFTDRGWGNGCGFFGKGSIDTCAKFSCTSKAIGRTIQPENIKYKVGIF
VHGTTTSENHGNYSAQVGASQAAKFTVTPNAPSVALKLGDYGEVTLDCEPRSGLNTEAFYVMTVGSKSFLV
HREWFHDLALPWTSPSSTAWRNRELLMEFEGAHATKQSVVALGSQEGGLHHALAGAIVVEYSSSVMLTSGH
LKCRLKMDKLALKGTTYGMCTEKFSFAKNPVDTGHGTVVIELSYSGSDGPCKIPIVSVASLNDMTPVGRLV
TVNPFVATSSANSKVLVEMEPPFGDSYIVVGRGDKQINHHWHKAGSTLGKA

Figure 77

SEQ ID NO: 175 - Tick-borne encephalitis envelope protein nucleic acid sequence

TCGCGGTGCACACATTTGGAGAACAGGGACTTTGTCACTGGTACTCAGGGAACCAC
GAGAGTGACTCTGGTGTTGGAGCTGGGGGGATGTGTCACGATCACTGCTGAGGGGA
AGCCCTCAATGGATGTGTGGCTCGATTCCATCTATCAGGAGAACCCTGCCAAGACA
CGCGAGTACTGTCTGCATGCCAAGCTGTCGGACACCAAAGTTGCGGCCAGATGCCC
AACAATGGGGCCTGCCACTCTGACTGAGGAGCATCAGAGTGGTACGGTGTGCAAGA
GAGACCAGAGTGACCGAGGCTGGGGCAATCACTGCGGATTGTTTGGAAAGGGCAGT
ATTGTGACCTGTGTCAAGGTGGCTTGTGAGGCAAAGAAGAAGGCCATTGGACATGT
GTATGATGCCAACAAGATCGTGTACACCGTTAAGGTTGAGCCACACACGGGGGACT
ATGTTGCCGCCAATGAAACCCACAGTGGGAGGAAGACGGCATCCTTCACGGTCTCC
TCAGAAAAGACCATCTTGACTATGGGGACTATGGAGATGTGCCCTTGTTGTGCAG
AGTCGCCAGTGGCGTTGACTTGGCTCAGACTGTCATTCTTGAGCTTGACAAGACTC
TGGAACACCTTCCAACAGCCTGGCAGGTCCATCGTGACTGGTTCAATGATCTGGCT
CTACCGTGGAAACACGAAGGAGCGCAACAATGGAACAATGCTGAGCGACTGGTTGA
ATTTGGAGCTCCGCATGCCGTTAAAATGGACGTGTATAACCTTGGAGATCAAACTG
GGGTGTTGTTGAAGTCACTTGCTGGGGTTCCTGTGGCGCACATTGATGGAACAAAG
TACCACCTAAAAAGCGGCCATGTAACATGCGAGGTTGGACTAGAAAAGCTCAAAAT
GAAGGGTCTCACATACACAATGTGTGACAAAACGAAGTTCGCATGGAAGCGGACTC
CAACAGACAGCGGACATGACACAGTGGTCATGGAGGTCACGTTCTCTGGAACAAAA
CCTTGCAGGATCCCAGTGCGGGCAGTGGCACACGGCTCTCCAGATGTAAATGTGGC
CATGCTGATAACACCAAACCCCACCATTGAGAACAATGGAGGTGGCTTCATAGAGA
TGCAGCTACCCCCAGGGGATAACATCATCTATGTTGGGGAACTAAGCCATCAGTGG
TTCCAGAAGGGGAGCAGCATCGGAAGGGTGTTTCAAAAGACCAGGAAGGGCATCGA
GAGACTGACAGTGATAGGAGAACACGCCTGGGACTTCGGTTCCACTGGAGGTTTCT
TGACTTCGGTAGGCAAAGCGCTGCACAGTCCTCGGCGGAGCCTTCAACAGCATC
TTTGGGGGAGTGGGGTTTCTGCCCAAGCTCCTGTTGGGTGTGGCCTTAGCCTGGTT
GGGCCTGAACATGAGGAACCCCACCATGTCCATGAGTTTCCTCTTGGCTGGGGGAC
TGGTCCTGGCTATGACACTTGGAGTGGGTGCT

Figure 78

SEQ ID NO: 178 Nucleic acid sequence of EIII+

ATGGAAAAATTGCAGTTGAAGGGAACAACCTATGGCGTCTGTTCAAA
GGCTTTCAAGTTTCTTGGGACTCCCGCAGACACAGGTCACGGCACTG
TGGTGTTGGAATTGCAGTACACTGGCACGGATGGACCTTGCAAAGTT
CCTATCTCGTCAGTGGCTTCATTGAACGACCTAACGCCAGTGGGCAG
ATTGGTCACTGTCAACCCTTTTGTTTCAGTGGCCACGGCCAACGCTAA
GGTCCTGATTGAATTGGAACCACCCTTTGGAGACTCATACATAGTGG
TGGGCAGAGGAGAACAACAGATCAATCACCATTGGCACAAGTCTGG
AAGCAGCATTGGCAAA

Figure 79

| Group | # Mice | Test Sample | Survivors | Percent Survival |
|---|---|---|---|---|
| 1 | 10 | PBS (negative control) | 3/10 | 30 |
| 2 | 10 | JE Vax (positive control) | 10/10 | 100 |
| 3 | 10 | STF2Δ.JEIIIs+ | 10/10 | 100 |

Figure 85

FUSION PROTEINS COMPRISING FLAGELLIN AND DENGUE VIRAL ENVELOPE PROTEINS

RELATED APPLICATIONS

This application is a continuation-in-part application of International Application No. PCT/US2006/001623, which designated the United States and was filed on Jan. 19, 2006, published in English, which claims the benefit of U.S. Provisional Application Nos. 60/645,170, filed Jan. 19, 2005; 60/653,405, filed Feb. 15, 2005; 60/704,160, filed Jul. 29, 2005; 60/723,409, filed Oct. 4, 2005; and 60/725,919, filed Oct. 11, 2005. The teachings of the above applications are incorporated herein by reference.

BACKGROUND OF THE INVENTION

Infections with viruses, including flaviviruses, such as West Nile flavivirus, Dengue flavivirus, Japanese encephalitis flavivirus, Langat flavivirus, Kunjin flavivirus, Murray Valley encephalitis flavivirus, Tick-borne flavivirus and Yellow fever flavivirus, can result in serious disease and, possibly death. Mosquitos and ticks transmit many of the flaviviruses. For example, severe symptoms of West Nile virus infection include high fever, headache, neck stiffness, stupor, disorientation, coma, tremors, convulsions, muscle weakness, vision loss, numbness, meningoencephalitis and paralysis. These symptoms may last several weeks, and neurological effects may be permanent. In cases with milder symptoms (e.g., fever, headache, and body aches, nausea, vomiting, and sometimes swollen lymph glands or a skin rash on the chest, stomach and back), certain symptoms, such as fever and aches, can pass on their own. In more severe cases, people usually require hospitalization for treatment, such as administration of intravenous fluids and assistance with breathing.

Methods to prevent flavivirus infection include compositions of live attenuated and inactivated virus. However, such compositions may be less than optimally immunogenic, may result in unknown hazards if improperly prepared and may have adverse side effects. There is a need to develop new compositions and methods to prevent flavivirus infection.

SUMMARY OF THE INVENTION

The present invention relates to compositions, fusion proteins and polypeptides of at least a portion of an antigen and a flagellin that lacks a hinge region; and at least a portion of at least one pathogen-associated molecular pattern (PAMP) and at least a portion of at least one flavivirus. The compositions, fusion protein and polypeptides of the invention can be employed in methods to stimulate an immune response and protective immunity in a subject.

In one embodiment, the invention is a composition comprising at least a portion of at least one antigen and at least a portion of at least one flagellin, wherein at least one of the flagellin lacks at least a portion of a hinge region.

In another embodiment, the invention is a fusion protein comprising at least a portion of at least one antigen and at least a portion of at least one flagellin, wherein at least one of the flagellin lacks at least a portion of a hinge region.

In an additional embodiment, the invention is a composition comprising at least a portion of at least one pathogen-associated molecular pattern and at least a portion of at least one viral protein selected from the group consisting of a West Nile viral protein, a Langat viral protein, a Kunjin viral protein, a Murray Valley encephalitis viral protein, a Japanese encephalitis viral protein, a tickborne encephalitis viral protein, and a Yellow fever viral protein.

In yet another embodiment, the invention is a composition comprising at least a portion of at least one pathogen-associated molecular pattern and at least a portion of at least one Den2 viral envelope protein, wherein the Den2 viral envelope protein is at least one member selected from the group consisting of SEQ ID NO: 22 and SEQ ID NO: 40.

In another embodiment, the invention is a composition comprising at least a portion of at least one pathogen-associated molecular pattern and at least a portion of at least one member selected from the group consisting of a Den1 viral envelope protein, a Den2 viral envelope protein, a Den3 viral envelope protein and a Den4 viral envelope protein.

In still another embodiment, the invention is a fusion protein comprising at least a portion of at least one pathogen-associated molecular pattern and at least a portion of at least one viral protein selected from the group consisting of a West Nile viral protein, a Langat viral protein, a Kunjin viral protein, a Murray Valley encephalitis viral protein, a Japanese encephalitis viral protein, a tickborne encephalitis viral protein, and a Yellow fever viral protein.

An additional embodiment of the invention is a fusion protein comprising at least a portion of at least one member selected from the group consisting of a *Salmonella typhimurium* flagellin type 2 (fljB/STF2), an *E. coli* fliC, and a *S. muenchen* fliC and at least a portion of at least one member selected from the group consisting of a Den1 viral envelope protein, a Den2 viral envelope protein, a Den3 viral envelope protein and a Den4 viral envelope protein.

In another embodiment, the invention is a fusion protein comprising at least a portion of at least one pathogen-associated molecular pattern and at least a portion of at least one member selected from the group consisting of a Den1 viral envelope protein, a Den2 viral envelope protein, a Den3 viral envelope protein and a Den4 viral envelope protein.

Another embodiment of the invention is a polypeptide encoded by SEQ ID NO: 29.

In yet another embodiment, the invention is a polypeptide that includes SEQ ID NO: 30.

In a further embodiment, the invention is a polypeptide having at least about 85% identity to SEQ ID NO: 30.

In still another embodiment, the invention is a polypeptide encoded by SEQ ID NO: 31.

In another embodiment, the invention is a polypeptide that includes SEQ ID NO: 32.

In an additional embodiment, the invention is a polypeptide having at least about 70% identity to SEQ ID NO: 32.

In yet another embodiment, the invention is a polypeptide encoded by SEQ ID NO: 33.

In another embodiment, the invention is a polypeptide that includes SEQ ID NO: 34.

In still another embodiment, the invention is a polypeptide having at least about 70% identity to SEQ ID NO: 34.

In an additional embodiment, the invention is a polypeptide encoded by SEQ ID NO: 35.

In a further embodiment, the invention is a polypeptide that includes SEQ ID NO: 36.

In yet another embodiment, the invention is a polypeptide having at least 80% identity to SEQ ID NO: 36.

In another embodiment, the invention is a polypeptide encoded by SEQ ID NO: 37.

In still another embodiment, the invention is a polypeptide that includes SEQ ID NO: 38.

In another embodiment, the invention is a polypeptide having at least 70% identity to SEQ ID NO: 38.

In an additional embodiment, the invention is a polypeptide encoded by SEQ ID NO: 54.

In another embodiment, the invention is a polypeptide that includes SEQ ID NO: 55.

Another embodiment of the invention is a polypeptide having at least about 70% identity to SEQ ID NO: 55.

In still another embodiment, the invention is a polypeptide that includes at least one member selected from the group consisting of SEQ ID NO: 71 and SEQ ID NO: 72.

In another embodiment, the invention is a polypeptide encoded by at least one member selected from the group consisting of SEQ ID NO: 70 and SEQ ID NO: 73.

In yet another embodiment, the invention is a polypeptide having at least about 70% identity to at least one member selected from the group consisting of SEQ ID NO: 71 and SEQ ID NO: 72.

In still another embodiment, the invention is a polypeptide that includes at least one member selected from the group consisting of SEQ ID NO: 76 and SEQ ID NO: 6.

In a further embodiment, the invention is a polypeptide encoded by at least one member selected from the group consisting of SEQ ID NO: 77 and SEQ ID NO: 5.

In another embodiment, the invention is a polypeptide having at least about 70% identity to at least one member selected from the group consisting of SEQ ID NO: 76 and SEQ ID NO: 6.

In an additional embodiment, the invention is a polypeptide that includes at least one member selected from the group consisting of SEQ ID NO: 80, SEQ ID NO: 82, SEQ ID NO: 84 and SEQ ID NO: 86.

In still another embodiment, the invention is a polypeptide encoded by at least one member selected from the group consisting of SEQ ID NO: 81, SEQ ID NO: 83, SEQ ID NO: 85 and SEQ ID NO: 87.

In a further embodiment, the invention is a polypeptide having at least about 70% identity to at least one member selected from the group consisting of SEQ ID NO: 80, SEQ ID NO: 82, SEQ ID NO: 84 and SEQ ID NO: 86.

In an additional embodiment, the invention is a polypeptide that includes SEQ ID NO: 159.

In yet another embodiment, the invention is a polypeptide encoded by SEQ ID NO: 158.

In another embodiment, the invention is a polypeptide having at least about 70% identity to SEQ ID NO: 159.

In yet another embodiment, the invention is a composition comprising at least one Pam3Cys and at least a portion of at least one flavivirus protein.

In an additional embodiment, the invention is a composition comprising at least one Pam2Cys and at least a portion of at least one flavivirus protein.

In still another embodiment, the invention is a method of stimulating an immune response in a subject, comprising the step of administering to the subject a composition that includes at least a portion of at least one pathogen-associated molecular pattern and at least a portion of at least one viral protein selected from the group consisting of a West Nile viral protein, a Langat viral protein, a Kunjin viral protein, a Murray Valley encephalitis viral protein, a Japanese encephalitis viral protein, a tickborne encephalitis viral protein, and a Yellow fever virus protein.

In a further embodiment, the invention is a method of stimulating an immune response in a subject, comprising the step of administering to the subject a composition that includes at least a portion of at least one pathogen-associated molecular pattern and at least a portion of at least one Den2 envelope protein, wherein the Den2 envelope protein is selected from the group consisting of SEQ ID NO: 20 and SEQ ID NO: 40.

In yet another embodiment, the invention is a method of stimulating an immune response in a subject, comprising the step of administering to the subject a fusion protein that includes at least a portion of at least one pathogen-associated molecular pattern and at least a portion of at least one viral protein selected from the group consisting of a West Nile viral protein, a Langat viral protein, a Kunjin viral protein, a Murray Valley encephalitis viral protein, a Japanese encephalitis viral protein, a tickborne encephalitis viral protein and a Yellow fever viral protein.

In another embodiment, the invention is a method of stimulating an immune response in a subject, comprising the step of administering to the subject a composition that includes at least a portion of at least one pathogen-associated molecular pattern and at least a portion of at least one member selected from the group consisting of a Den1 viral envelope protein, a Den2 viral envelope protein, a Den3 viral envelope protein and a Den4 viral envelope protein.

In still another embodiment, the invention is a method of stimulating an immune response in a subject, comprising the step of administering to the subject a fusion protein that includes at least a portion of at least one member selected from the group consisting of a *Salmonella typhimurium* flagellin type 2 (fljB/STF2), an *E. coli* fliC, and a *S. muenchen* fliC and at least a portion of at least one member selected from the group consisting of a Den1 viral envelope protein, a Den2 viral envelope protein, a Den3 viral envelope protein and a Den4 viral envelope protein.

In an additional embodiment, the invention is a method of stimulating an immune response in a subject, comprising the step of administering to the subject a fusion protein that includes at least a portion of at least one pathogen-associated molecular pattern and at least a portion of at least one member selected from the group consisting of a Den1 viral envelope protein, a Den2 viral envelope protein, a Den3 viral envelope protein and a Den4 viral envelope protein.

In a further embodiment, the invention is a method of stimulating an immune response in a subject, comprising the step of administering to the subject a composition comprising at least a portion of at least one antigen and at least a portion of at least one flagellin, wherein at least one of the flagellins lack at least a portion of a hinge region.

In another embodiment, the invention is a method of stimulating an immune response in a subject, comprising the step of administering to the subject a fusion protein comprising at least a portion of at least one antigen and at least a portion of at least one flagellin, wherein at least one of the flagellins lack at least a portion of a hinge region.

In another embodiment, the invention is a method of stimulating protective immunity in a subject, comprising the step of administering to the subject a composition that includes at least a portion of at least one pathogen-associated molecular pattern and at least a portion of at least one viral protein selected from the group consisting of a West Nile viral protein, a Langat viral protein, a Kunjin viral protein, a Murray Valley encephalitis viral protein, a Japanese encephalitis viral protein, a Tick-borne encephalitis viral protein, and a Yellow fever virus protein.

In a further embodiment, the invention is a method of stimulating protective immunity in a subject, comprising the step of administering to the subject a composition that includes at least a portion of at least one pathogen-associated molecular pattern and at least a portion of at least one Den2 envelope protein, wherein the Den2 envelope protein is at least one member selected from the group consisting of SEQ ID NO: 22, SEQ ID NO: 40 and SEQ ID NO: 97.

In still another embodiment, the invention is a method of stimulating protective immunity in a subject, comprising the step of administering to the subject a fusion protein that includes at least a portion of at least one pathogen-associated molecular pattern and at least a portion of at least one viral protein selected from the group consisting of a West Nile viral protein, a Langat viral protein, a Kunjin viral protein, a Murray Valley encephalitis viral protein, a Japanese encephalitis viral protein, a Tick-borne encephalitis viral protein and a Yellow fever viral protein.

In an additional embodiment, the invention is a method of stimulating protective immunity in a subject, comprising the step of administering to the subject a composition that includes at least a portion of at least one pathogen-associated molecular pattern and at least a portion of at least one member selected from the group consisting of a Den1 viral envelope protein, a Den2 viral envelope protein, a Den3 viral envelope protein and a Den4 viral envelope protein.

In another embodiment, the invention is a method of stimulating protective immunity in a subject, comprising the step of administering to the subject a fusion protein that includes at least a portion of at least one member selected from the group consisting of a *Salmonella typhimurium* flagellin type 2 (fljB/STF2), an *E. coli* fliC, and a *S. muenchen* fliC and at least a portion of at least one member selected from the group consisting of a Den1 viral envelope protein, a Den2 viral envelope protein, a Den3 viral envelope protein and a Den4 viral envelope protein.

In a further embodiment, the invention is a method of stimulating protective immunity in a subject, comprising the step of administering to the subject a fusion protein that includes at least a portion of at least one pathogen-associated molecular pattern and at least a portion of at least one member selected from the group consisting of a Den1 viral envelope protein, a Den2 viral envelope protein, a Den3 viral envelope protein and a Den4 viral envelope protein.

In yet another embodiment, the invention is a method of stimulating protective immunity in a subject, comprising the step of administering to the subject a composition comprising at least a portion of at least one antigen and at least a portion of at least one flagellin, wherein at least one of the flagellins lacks at least a portion of a hinge region.

In yet another embodiment, the invention is a method of stimulating protective immunity in a subject, comprising the step of administering to the subject a fusion protein comprising at least a portion of at least one antigen and at least a portion of at least one flagellin, wherein at least one of the flagellins lacks at least a portion of a hinge region.

The compositions, fusions proteins and polypeptides of the invention can be employed to stimulate an immune response or protective immunity in a subject. Advantages of the claimed invention can include, for example, prevention of flavivirus infection in a subject in a manner specific for a particular antigen or virus, such as a flavivirus protein, that has effective immunogenicity and reduced side effects. The claimed compositions, fusion proteins, polypeptides and methods can be employed to prevent or treat infection and, therefore, avoid serious diseases consequent to antigen or viral infection.

BRIEF DESCRIPTION OF THE FIGURES

FIG. 1 depicts the amino acid sequence (SEQ ID NO: 1) of *Salmonella typhimurium* flagellin type 2 (fljB/STF2, also referred to herein as "STF2"). The hinge region (also referred to herein as "the hypervariable" or the "hypervariable hinge region") is underlined.

FIG. 2 depicts the nucleic acid sequence (SEQ ID NO: 2) encoding SEQ ID NO: 1. The nucleic acid sequence encoding the hinge region is underlined.

FIG. 3 depicts the amino acid sequence (SEQ ID NO: 3) of a fljB/STF2Δ (also referred to herein as "fljB/STF2Δ" or "STF2Δ"). STF2Δ is a STF2 lacking at least a portion of the hinge region. The artificial hinge region is underlined.

FIG. 4 depicts the nucleic acid sequence (SEQ ID NO: 4) encoding SEQ ID NO: 3. The nucleic acid sequence encoding the artificial hinge region is underlined.

FIG. 5 depicts the nucleic acid sequence (SEQ ID NO: 5) encoding a pET/STF2Δ.JEIII+ fusion protein. The nucleic acid sequence encoding the artificial hinge region is double underlined. The nucleic acid sequence encoding the linker between STF2Δ and JEIII+ is underlined. The nucleic acid sequence encoding JEIII+ is bolded.

FIG. 6 depicts the amino acid sequence (SEQ ID NO: 6) encoded by SEQ ID NO: 5. The artificial hinge is double underlined. The linker between STF2Δ and JEIII+ is underlined. The amino acid sequence of JEIII+ is bolded.

FIG. 7 depicts the nucleic acid sequence (SEQ ID NO: 29) encoding a STF2.EIII+ fusion protein. The nucleic acid sequence encoding the hinge region of STF2 is underlined.

FIG. 8 depicts the amino acid sequence (SEQ ID NO: 30) encoded by SEQ ID NO: 29. The hinge region of STF2 is underlined.

FIG. 9 depicts the nucleic acid sequence (SEQ ID NO: 31) encoding a STF2Δ.EIII+ fusion protein. The naturally occurring hinge region of STF2 has been removed and replaced with an artificial hinge region. The nucleic acid sequence encoding the artificial hinge region is underlined. The nucleic acid sequence encoding EIII+ is bolded.

FIG. 10 depicts the amino acid sequence (SEQ ID NO: 32) encoded by SEQ ID NO: 31. The artificial hinge region is underlined. The EIII+ amino acid sequence is bolded.

FIG. 11 depicts the nucleic acid sequence (SEQ ID NO: 33) of a STF2Δ.EIII+ fusion protein. The nucleic acid sequence encoding the artificial hinge region is double underlined. The nucleic acid sequence encoding a linker between STF2Δ and EIII+ is underlined. The nucleic acid sequence encoding EIII+ is bolded. Vector sequence is unbolded at the 3' end of the nucleic acid sequence.

FIG. 12 depicts the amino acid sequence (SEQ ID NO: 34) encoded by SEQ ID NO: 33. The artificial hinge region is double underlined. The linker between STF2Δ and EIII+ is underlined. The amino acid sequence of the EIII+ is bolded. Domain I of the West Nile virus protein is bolded and italicized (MEKLQ, SEQ ID NO: 172). The remainder of the bolded sequence (LKGTTYGVCSKAFKFLGTPADTGH-GTVVLELQYTGTDGPCKVPISSVASLNDL TPVGR-LVTVNPFVSVATANAKVLIELEPPF-GDSYIVVGRGEQQINHHWHKSGSS IGK, SEQ ID NO: 176) is domain III of the envelope protein of the West Nile virus. Vector sequence at the carboxy-terminus is not bolded at the carboxy-terminus.

FIG. 13 depicts the nucleic acid sequence (SEQ ID NO: 35) of a STF2.EIII+ fusion protein. The nucleic acid sequence encoding the hinge region of STF2 is underlined. The nucleic acid sequence encoding a linker between STF2 and EIII+ is bolded and underlined. The nucleic acid sequence encoding EIII+ is bolded.

FIG. 14 depicts the amino acid sequence (SEQ ID NO: 36) encoded by SEQ ID NO: 35. The hinge region is underlined.

Figure 46:
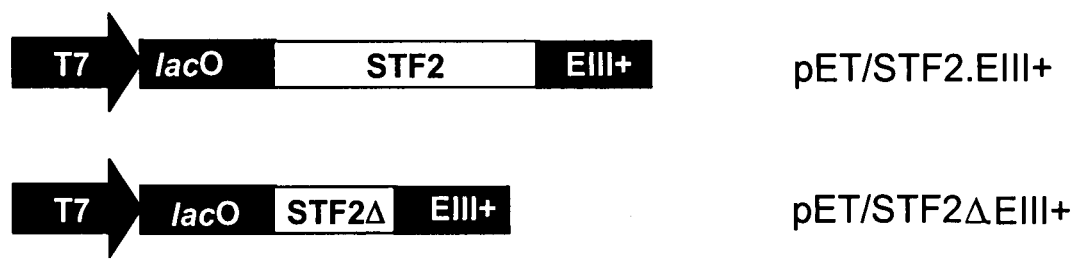

The linker between STF2 and EIII+ is bolded and underlined. The amino acid sequence of EIII+ is bolded.

FIG. 15 depicts the nucleic acid sequence (SEQ ID NO: 37) encoding a fljB/STF2Δ.EIII+ fusion protein. There is no linker between STFΔ and EIII+.

FIG. 16 depicts the amino acid sequence (SEQ ID NO: 38) encoded by SEQ ID NO: 37. The amino acid sequence of EIII+ is bolded.

FIG. 17 depicts the nucleic acid sequence (SEQ ID NO: 54) of a fljB/STF2.EIII+ fusion protein. The nucleic acid sequence encoding the hinge region of STF2 is underlined. The nucleic acid sequence encoding a linker between STF2 and EIII+ is bolded and underlined. The nucleic acid sequence encoding EIII+ is bolded.

FIG. 18 depicts the amino acid sequence (SEQ ID NO: 55) encoded by SEQ ID NO: 54. The amino acid sequence of the hinge region of STF2 is underlined. The amino acid sequence of the linker between STF2 and EIII+ is bolded and underlined. The amino acid sequence of EIII+ is bolded.

FIG. 19 depicts the amino acid sequence (SEQ ID NO: 58) of *Salmonella muenchen* flagellin fliC. The amino acid sequence of the hinge region is underlined.

FIG. 20 depicts the nucleic acid sequence (SEQ ID NO: 59) encoding SEQ ID NO: 58. The nucleic acid sequence encoding the hinge region is underlined.

FIG. 21 depicts the nucleic acid sequence (SEQ ID NO: 63) of a linker.

FIG. 22 depicts the amino acid sequence (SEQ ID NO: 64) of Hepatitis C E1.

FIG. 23 depicts the amino acid sequence (SEQ ID NO: 65) of Hepatitis C E2.

FIG. 24 depicts the nucleic acid sequence (SEQ ID NO: 66) encoding SEQ ID NO: 64.

FIG. 25 depicts the nucleic acid sequence (SEQ ID NO: 67) encoding SEQ ID NO: 65.

FIG. 26 depicts the amino acid sequence (SEQ ID NO: 68) of *E. Coli* fliC. The amino acid sequence of the hinge region is underlined.

FIG. 27 depicts the nucleic acid sequence (SEQ ID NO: 69) encoding SEQ ID NO: 68. The nucleic acid sequence encoding the hinge region is underlined.

FIG. 28 depicts the nucleic acid sequence (SEQ ID NO: 70) encoding a fljB/STF2Δ.EIII+ fusion protein. The nucleic acid sequence encoding the artificial hinge region is double underlined. The nucleic acid sequence encoding a linker between STF2Δ and EIII+ is underlined. The nucleic acid sequence encoding the EIII+ is bolded. Vector sequence is not bolded at the 3' end of the sequence.

FIG. 29 depicts the amino acid sequence (SEQ ID NO: 71) encoded by SEQ ID NO: 70. The artificial hinge region is double underlined. The amino acid sequence of the linker between STF2Δ and EIII+ is underlined. The amino acid sequence of the EIII+ is bolded. Vector sequence at the carboxy-terminus is not bolded.

FIG. 30 depicts the amino acid sequence (SEQ ID NO: 72) of a fljB/STF2Δ.EIIIs+ fusion protein. The artificial hinge region is double underlined. The amino acid sequence encoding the linker between STF2Δ and EIII+ is underlined. Domain I of the West Nile virus protein is bolded and italicized (SEQ ID NO: 172). The remainder of the bolded sequence is domain III of the envelope protein (SEQ ID NO: 176) of the West Nile virus. Portions of domains I and III are referred to as EIII+. Vector sequence at the carboxy-terminus of the protein is unbolded. The serine residue of the linker region is bolded and is a substitution of the cysteine residue in the same region of the linker of SEQ ID NO: 71 of FIG. 29.

FIG. 31 depicts the nucleic acid sequence (SEQ ID NO: 73) encoding SEQ ID NO: 72. The nucleic acid sequence encoding the artificial hinge region is double underlined. The nucleic acid sequence encoding the linker between STF2Δ and EIII+ is underlined with the codon encoding the serine residue bolded. The nucleic acid sequence encoding EIII+ is indicated by bolded text. Linker sequence is unbolded text at the 3' end.

FIG. 32 depicts the amino acid sequence (SEQ ID NO: 76) of a pET/STF2Δ.JEIII+ fusion protein. The artificial hinge region is double underlined. The amino acid sequence of the linker between STF2Δ and JEIII+ is underlined. The amino acid sequence of a portion of domain I of the Japanese encephalitis virus is bolded and italicized (MDKLAL, SEQ ID NO: 173). The amino acid sequence of a portion of the domain III of the Japanese encephalitis virus is bolded (KGTTYGMCTEKFSFAKNPVDTGHGTVVIELSYSGSD GPCKIPIVSVASLNDMTP VGRLVTVNPFVATSSAN-SKVLVEMEPPFGDSYIVVGRGDKQINHHWHKAGSTL GKA, SEQ ID NO: 177). Portions of domains I and III are referred to as "JEIII+."

FIG. 33 depicts the nucleic acid sequence (SEQ ID NO: 77) encoding SEQ ID NO: 76. The nucleic acid sequence encoding the artificial hinge region is double underlined. The nucleic acid sequence encoding a linker between STF2Δ and JEIII+ is underlined. The nucleic acid sequence encoding a portion of domain I of the Japanese encephalitis virus is bolded and italicized. The nucleic acid sequence encoding a portion of domain III of the Japanese encephalitis virus is bolded. Portions of domains I and III are referred to as "JEIII+."

FIG. 34 depicts the nucleic acid sequence (SEQ ID NO: 78) encoding JEIII+. The nucleic acid sequence encoding at least a portion of domain I of the envelope protein is underlined. The remaining nucleic acid sequence encodes at least a portion of domain III of the envelope protein.

FIG. 35 depicts the amino acid sequence (SEQ ID NO: 79) encoded by SEQ ID NO: 78. At least a portion of domain I of the envelope protein is bolded and italicized. The remaining sequence is at least a portion of domain III of the envelope protein.

FIG. 36 depicts the amino acid sequence (SEQ ID NO: 80) of a pET/STF2Δ.Den1 EIII fusion protein. The artificial hinge region is double underlined. A linker between STF2Δ and Den1 EIII is underlined.

FIG. 37 depicts the nucleic acid sequence (SEQ ID NO: 81) encoding SEQ ID NO: 80. The nucleic acid sequence encoding the artificial hinge region is double underlined. The nucleic acid sequence encoding the linker between STF2Δ and Den1 EIII is underlined.

FIG. 38 depicts the amino acid sequence (SEQ ID NO: 82) of a pET/STF2Δ.Den2 EIII fusion protein. The artificial hinge region is double underlined. The amino acid sequence of the linker between STF2Δ and Den2 EIII is underlined.

FIG. 39 depicts the nucleic acid sequence (SEQ ID NO: 83) encoded by SEQ ID NO: 82. The nucleic acid sequence encoding the artificial hinge region is double underlined. The nucleic acid sequence encoding the linker between STF2Δ and Den2 EIII is underlined.

FIG. 40 depicts the amino acid sequence (SEQ ID NO: 84) of a pET/STF2Δ.Den3 EIII fusion protein. The artificial hinge region is double underlined. The amino acid sequence of the linker between STF2Δ and Den3 EIII is underlined.

FIG. 41 depicts the nucleic acid sequence (SEQ ID NO: 85) encoding SEQ ID NO: 84. The nucleic acid sequence encoding the artificial hinge region is double underlined. The nucleic acid sequence encoding the linker between STF2Δ and Den3 EIII is underlined.

FIG. 42 depicts the amino acid sequence (SEQ ID NO: 86) of a pET/STF2Δ.Den4 EIII fusion protein. The artificial hinge region is double underlined. The amino acid sequence of the linker between STF2Δ and Den4 EIII is underlined.

FIG. 43 depicts the nucleic acid sequence (SEQ ID NO: 87) encoding SEQ ID NO: 86. The nucleic acid sequence encoding the artificial hinge region is double underlined. The nucleic acid sequence encoding the linker between STF2Δ and Den4 EIII is underlined.

FIG. 44 depicts the amino acid sequence (SEQ ID NO: 174) of the envelope protein of the Tick-borne encephalitis envelope protein.

FIG. 45 depicts the amino acid sequence (SEQ ID NO: 39) of a West Nile virus envelope protein (WNE) (amino acids 1-406). The amino acid sequence incorporated into EIII+ constructs is underlined (amino acids 292-406). Amino acids 292-297 correspond to a portion of domain I; amino acids 298-406 correspond to domain III. SEQ ID NO: 39 is encoded by SEQ ID NO: 57 (FIG. 67).

FIG. 46 depicts fusion constructs in a pET24 vector. T7:T7 promoter; lacO: lac operator; STF2: *Salmonella typhimurium* flagellin; STF2Δ=STF2 with the hinge region deleted; EIII+ is domain III of a West Nile envelope protein with 6 amino acids of domain I amino acid.

Figure 47A:
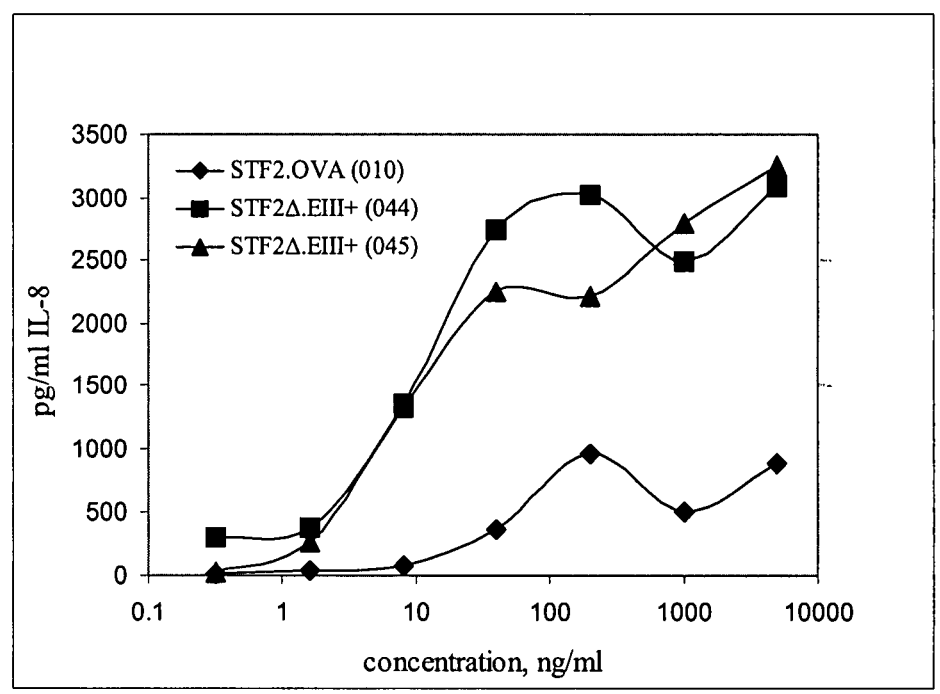
Figure 47B:
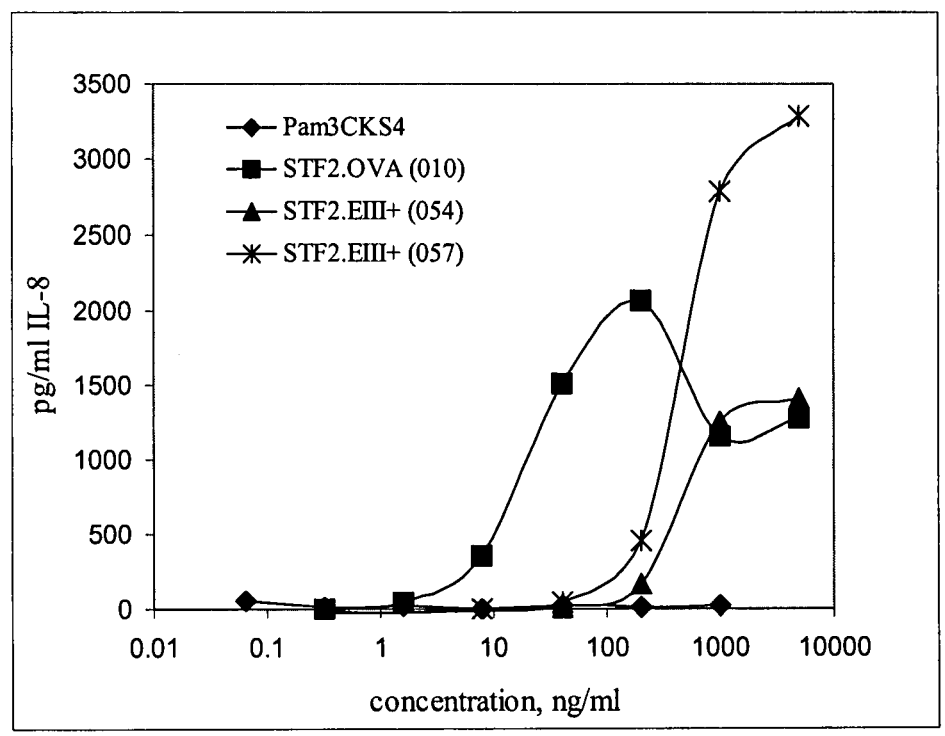

FIGS. 47A and 47B depict TLR-5 bioactivity of STF2.EIII+ (SEQ ID NOS: 54, 55) and STF2ΔEIII+ (SEQ ID NOS: 70, 71) fusion proteins. Serial dilutions of purified proteins were added to HEK293 (TLR5+) cells overnight and IL-8 content of the supernatants measured by ELISA. Purified STF2.OVA was used as a positive control (FIG. 47A). The TLR-2 agonist Pam3CSK4 was used as a negative control (FIG. 47B).

Figure 48:
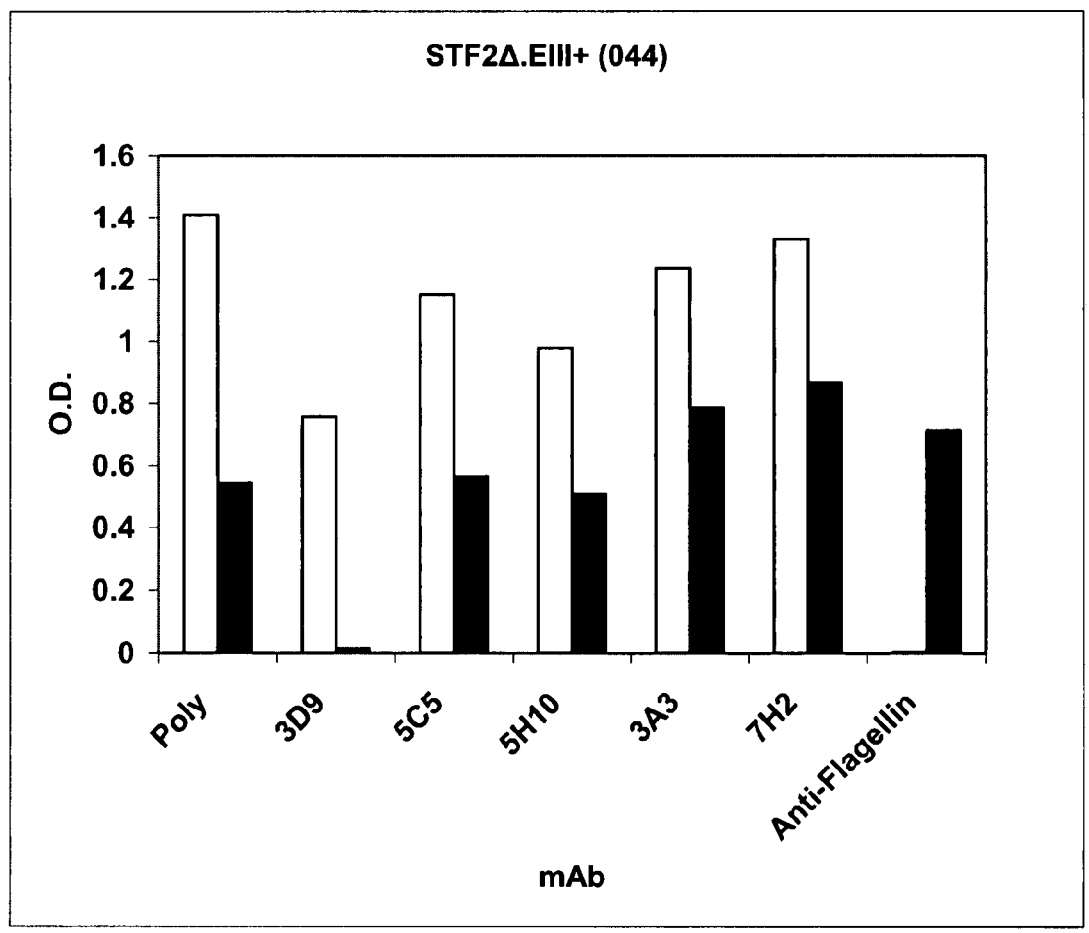
Figure 49A:
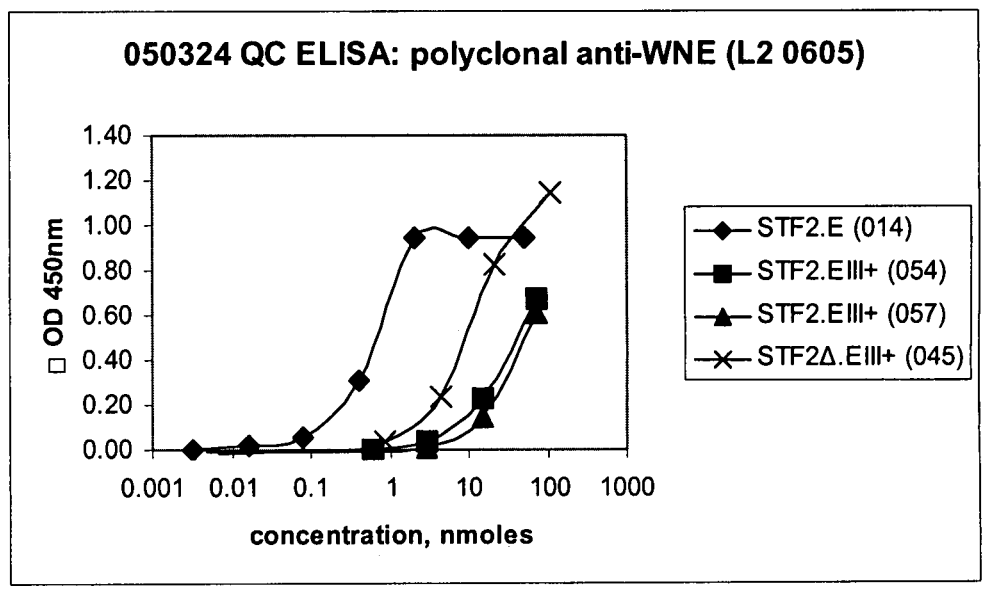
Figure 49B:
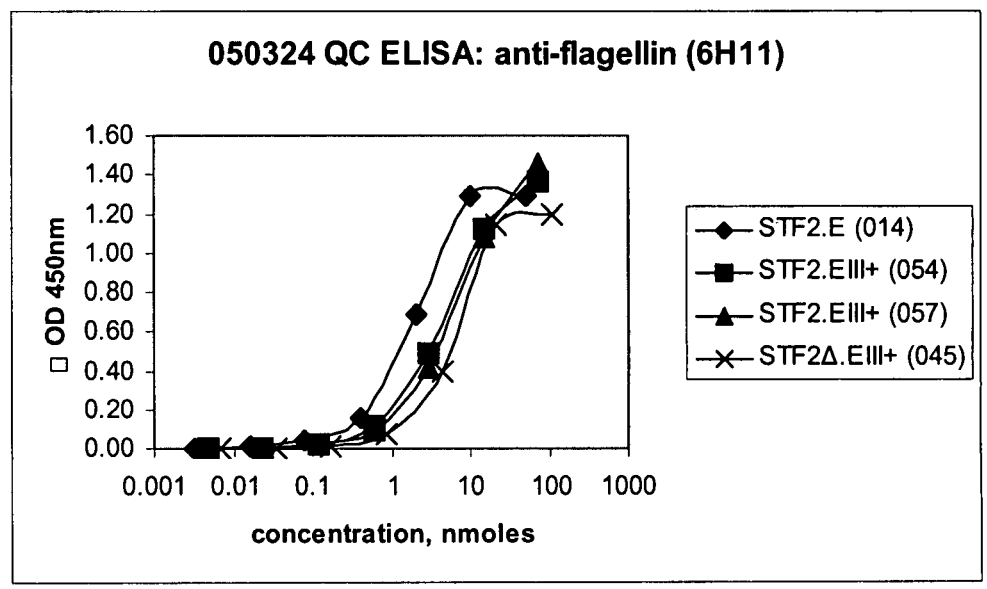
Figure 49C:
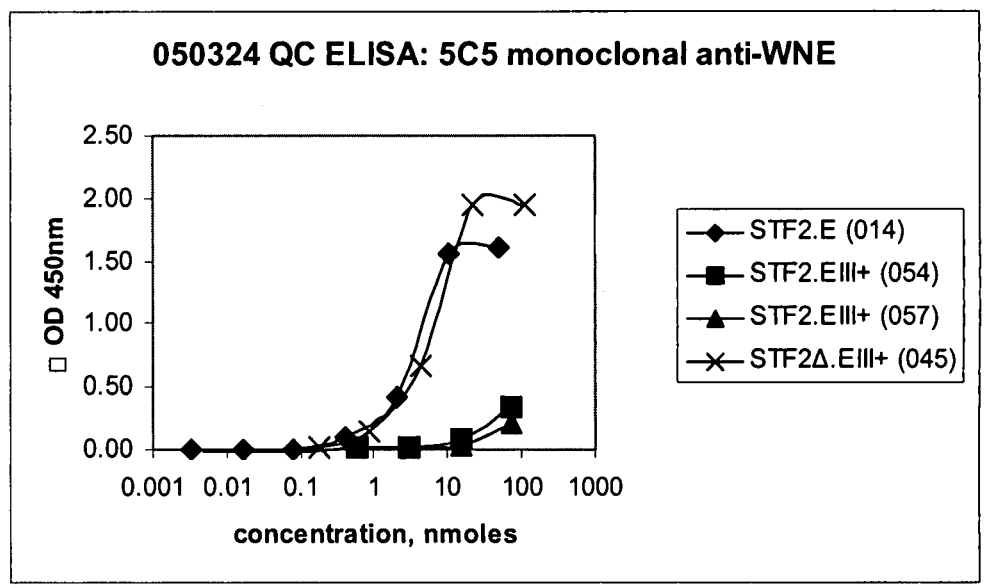
Figure 49D:
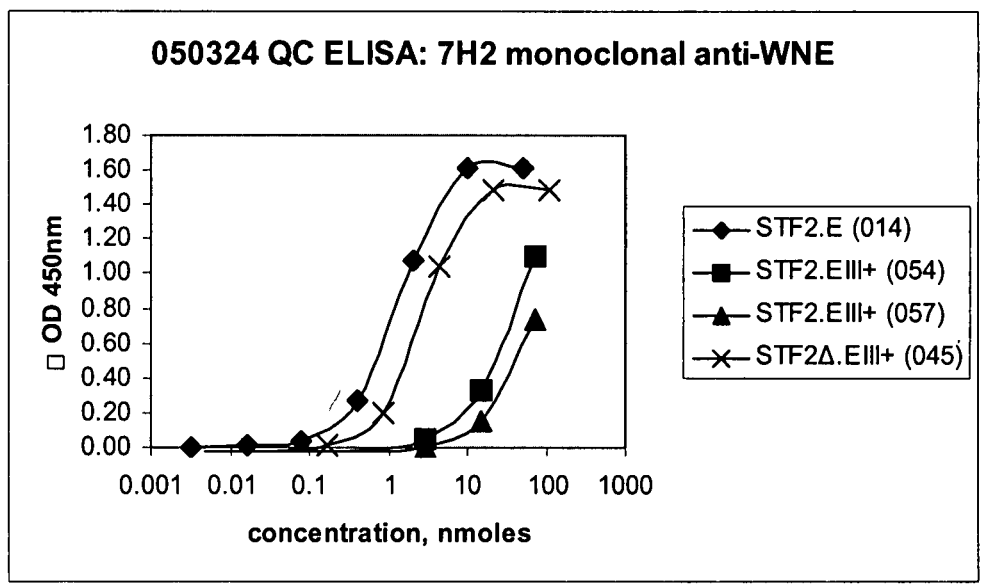

FIG. 48 depicts STF2Δ.EIII+ antigenic epitopes assessed by ELISA. Plates were coated with full-length WNE (open bars) (SEQ ID NO: 39) or STF2Δ.EIII+ (SEQ ID NOS: 70, 71) and probed with the indicated antibodies (mAb). Poly=polyclonal antiserum to WNE; 3D9 through 7H2=neutralizing monoclonal antibodies to WNE epitopes; anti-flagellin=monoclonal antibody to flagellin.

FIGS. 49A, 49B, 49C and 49D depict reactivity of STF2.E (SEQ ID NOS: 158, 159); STF2.EIII+ (SEQ ID NOS: 54, 55) and STF2Δ.EIII+ (SEQ ID NOS: 70, 71) fusion proteins with antibodies to WNE and flagellin. Plates were coated with fusion proteins, blocked and incubated with antibodies to WNE or flagellin. Antibody reactivity was detected following incubation with HRP-labeled species specific IgG. Plates were developed in the presence of TMB substrate and O.D.450/650 using a TECAN plate reader and Magellian software.

Figure 50:
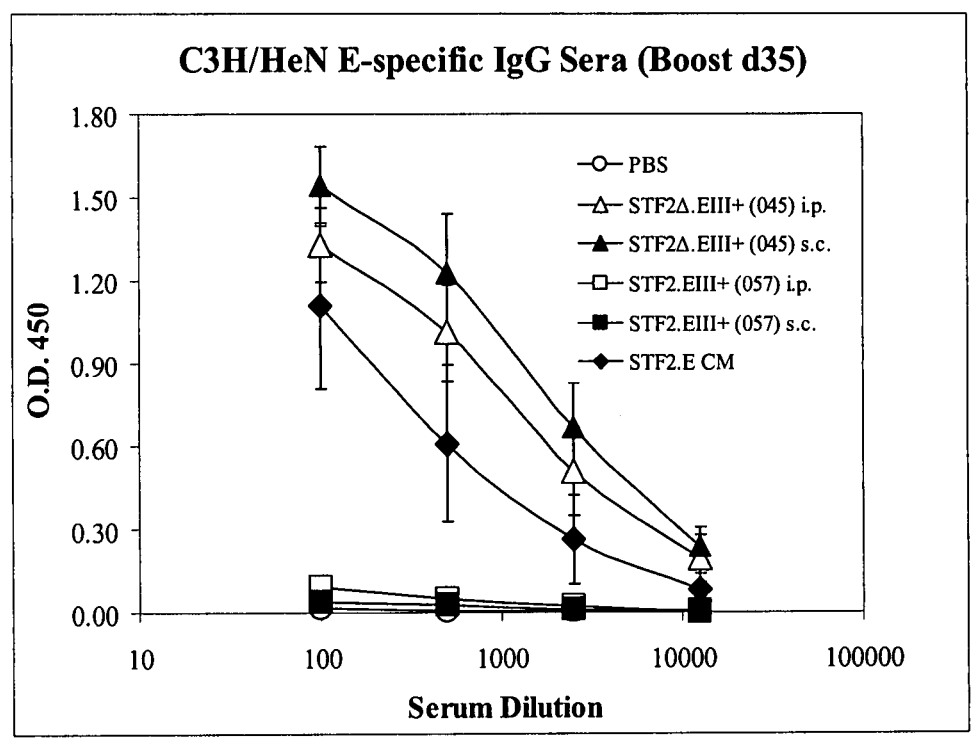

FIG. 50 depicts IgG serum following injection with fusion proteins. Mice were immunized with either PBS, *Drosophila* conditioned medium containing STF2.E (CM, positive control), 25 µg of STF2Δ.EIII+ (SEQ ID NOS: 70, 71) i.p., 25 µg STF2Δ.EIII+ s.c., 25 µg STF2.EIII+ (SEQ ID NO: 54, 55) i.p., 25 µg STF2.EIII+ (SEQ ID NOS: 54, 55) or 25 µg STF2.E (SEQ ID NOS: 158, 159). On day 35, immunized animals were challenged with WNV. Sera from individual mice (day 35) were characterized by direct ELISA to determine IgG levels. Purified WNV-E protein (SEQ ID NO: 39) was used as the antigen in this assay. This antigen (60) was produced in *Drosophila* as a his-tagged protein.

Figure 51:
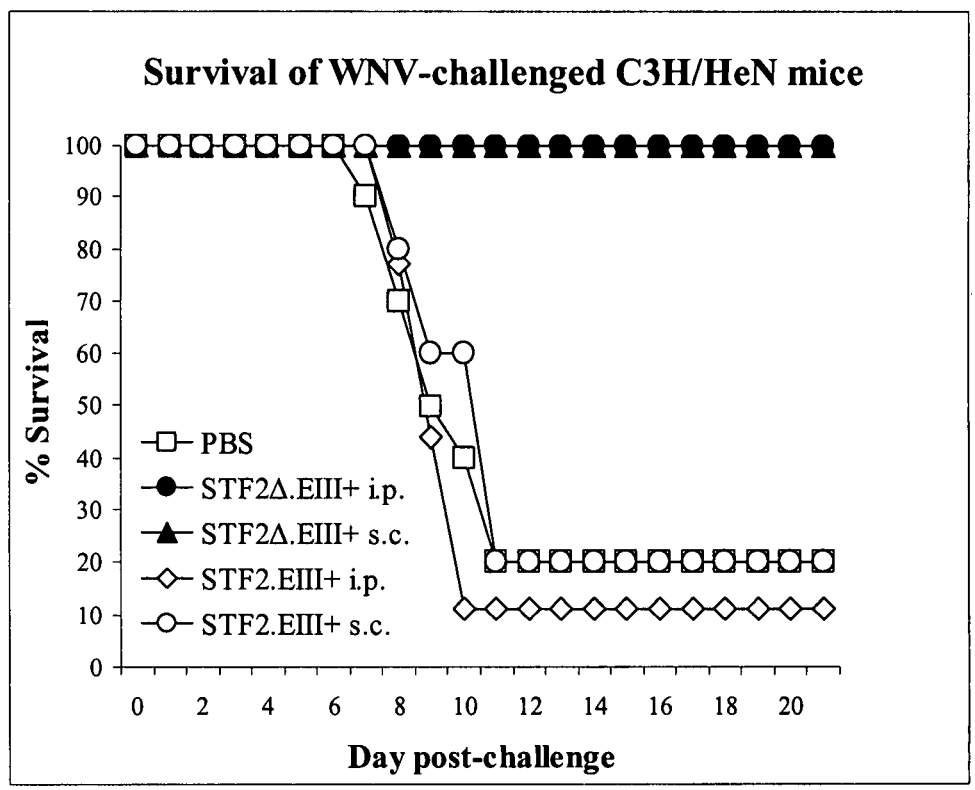

FIG. 51 depicts STF2Δ.EIII+ (SEQ ID NOS: 70, 71) and STF2.EIII+ (SEQ ID NOS: 54, 55) protective immunity to WNV viral challenge. Mice were immunized and challenged with a lethal dose of WNV strain 2741 on day 35. Survival was monitored for 21 days.

Figure 52:
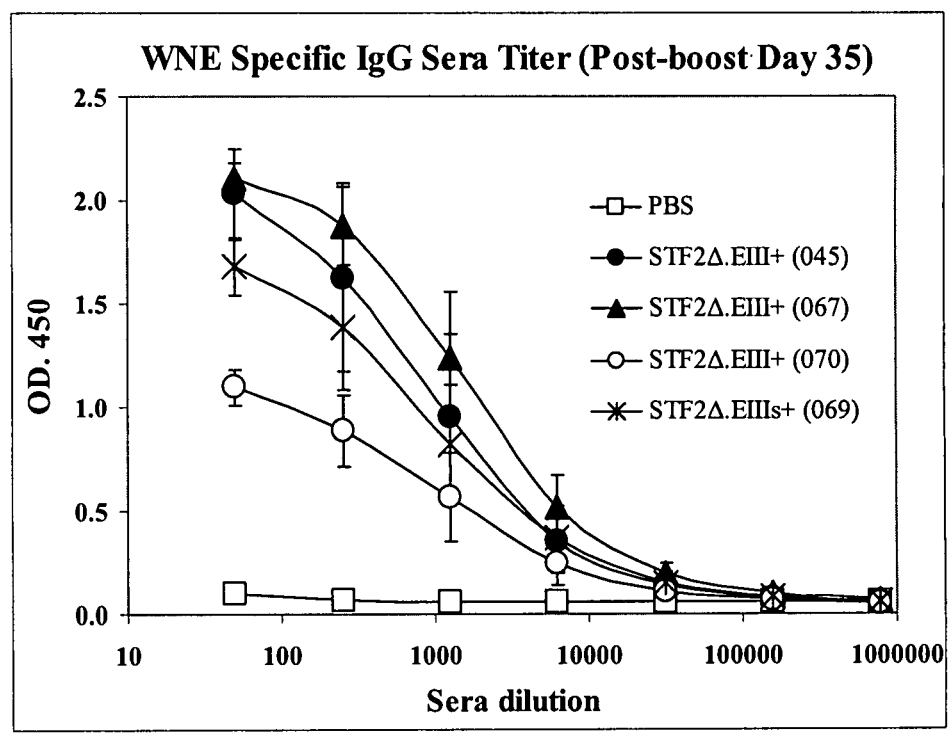

FIG. 52 depicts IgG sera titers following immunization with fusion proteins. STF2Δ.EIII+ proteins induce WNV-specific IgG antibodies. Mice were immunized s.c. on days 0, 14 and 28 with PBS alone or about 25 µg of STF2Δ.EIII+ (SEQ ID NOS: 70, 71) (045 [positive control]), STF2Δ.EIII+ (067, trimer), STF2Δ.EIII+ (070, monomer) or STF2Δ.EIIIs+ (SEQ ID NOS: 72, 73) (069). On day 35 sera from individual mice were characterized by direct ELISA to determine IgG levels. Purified WNV-E protein (060, produced in *Drosophila* as a his-tagged protein) was used as the antigen in this assay.

Figure 53:
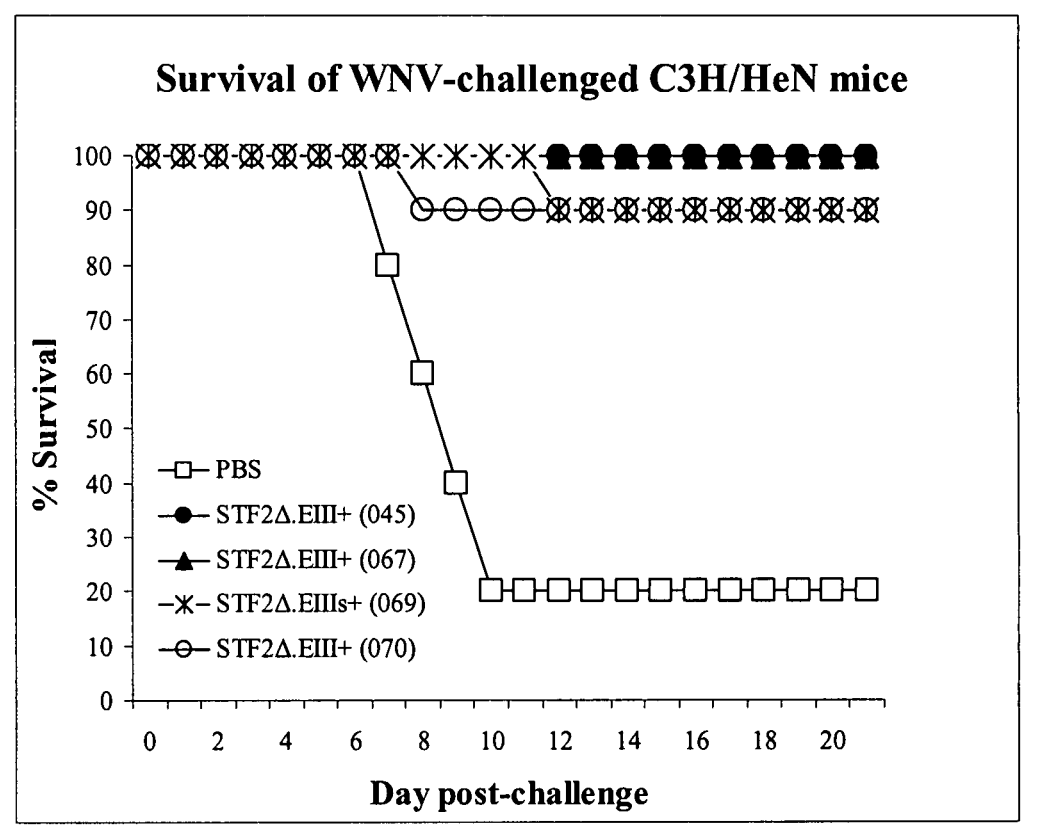

FIG. 53 depicts STF2Δ.EIII+ (SEQ ID NOS: 70, 71) and STF2Δ.EIIIs+ (SEQ ID NOS: 72, 73) protective immunity in mice from WNV lethal challenge. On day 38 following immunization with fusion proteins, all groups were challenged with a lethal dose of WNV strain 2741 and survival was monitored for 21 days. Survival for each group (10 mice/group) is indicated as a percentage.

Figure 54:
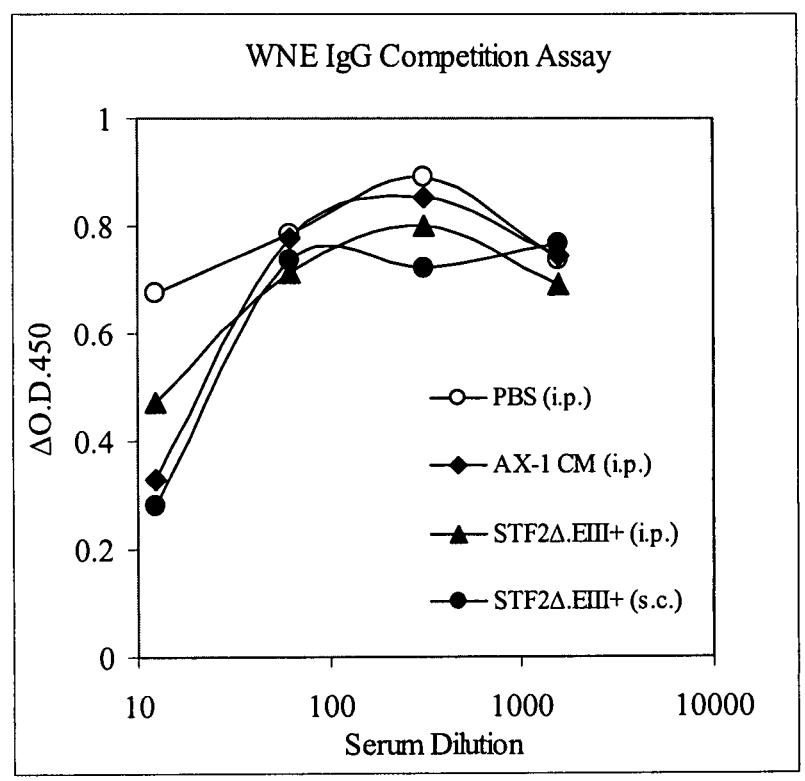

FIG. 54 depicts competition assays. Serial dilutions (five fold starting at 1:25) of antisera from immunized animals were incubated with biotinylated WNE protein (SEQ ID NO: 39) and then added to the wells of ELISA plates coated with mAb 7H2 at about 2 mg/ml. Wells were developed using avidin-HRP to determine inhibition of West Nile protein binding as a results of competition with mAb 7H2.

Figure 55:
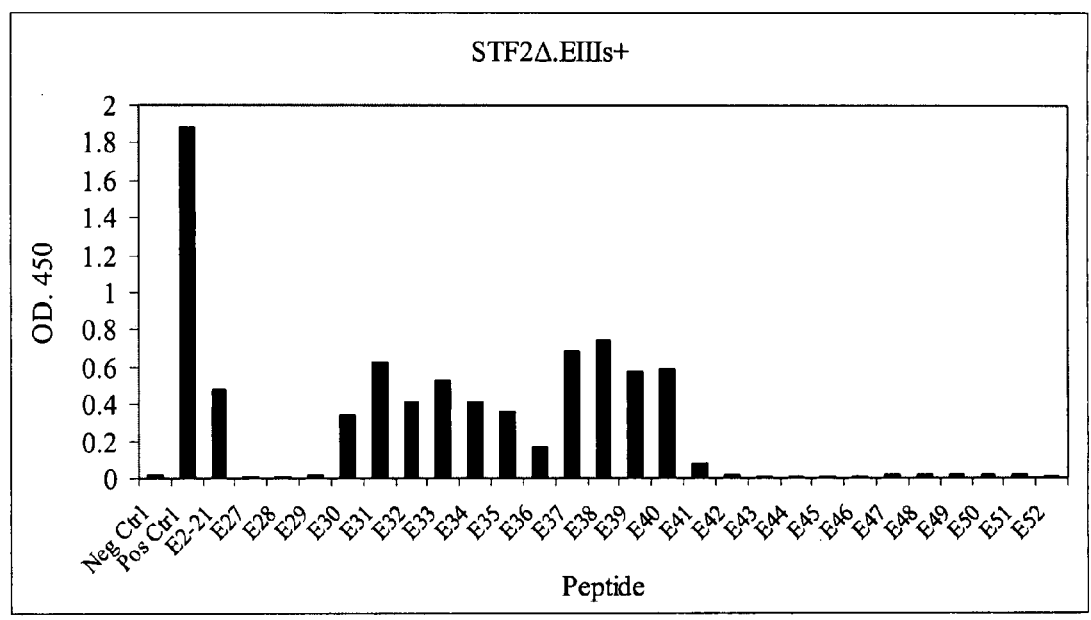

FIG. 55 depicts epitope mapping of the antibody response induced by STF2Δ.EIII+ (SEQ ID NOS: 72, 73) fusion proteins. Immune sera from animals immunized with indicated STF2Δ-fusion proteins (E2-21, E27-E52, FIG. 60) were examined for the ability to recognize overlapping peptides corresponding to the junction of domains I and III of the WNV envelope protein.

Figure 56:
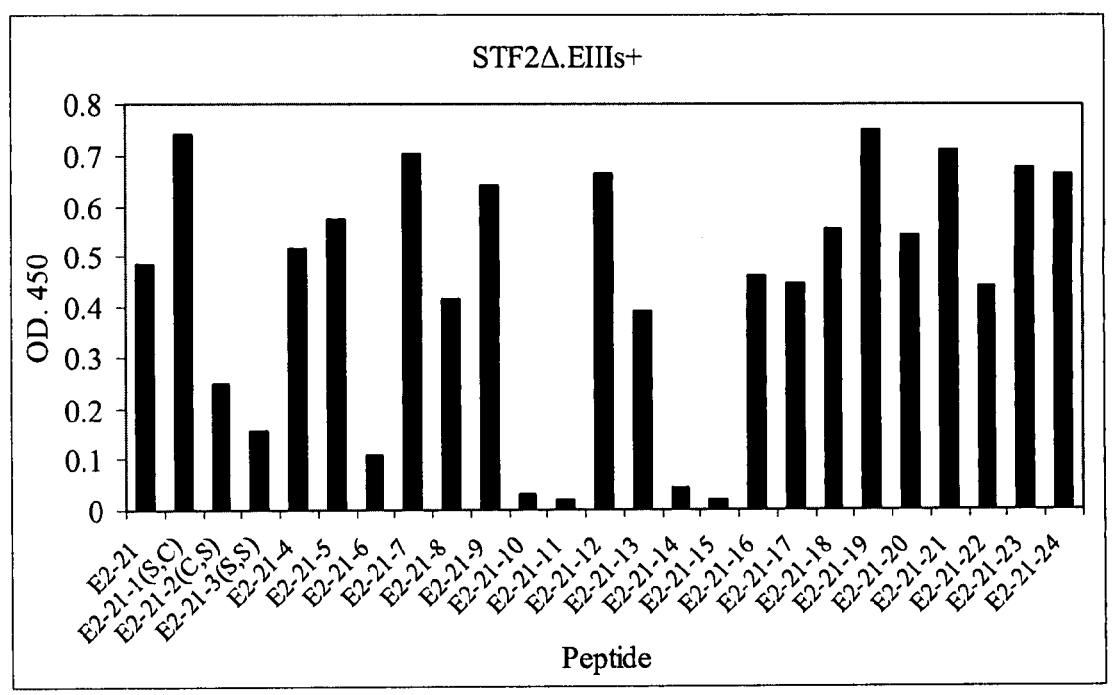

FIG. 56 depicts epitope mapping of the antibody response induced by STFΔ.EIIIs+ (SEQ ID NOS: 72, 73) E-21 (envelope protein) epitope fusion proteins. Immune sera from animals immunized with the indicated STF2Δ-fusion proteins (E2-21, E2-21-1(S,C), E2-21-2(C,S), E2-21-2(C,S) and E2-21-4 through E2-21-24, see FIG. 57) were evaluated to identify the residues defining the E-21 epitope of West Nile envelope protein. Data reflects the response of sera to E-21 following the substitution of cysteine with serine (indicated by C,S); and the sequential replacement of amino acids with alanine. The peptides tested are listed in FIG. 57.

FIG. 57 depicts EIII+ peptide arrays. The sequences include domains I and III of the West Nile virus envelope protein. Amino acids that correspond to domain III are underlined. Amino acids that are not underlined correspond to domain I.

Figure 58:
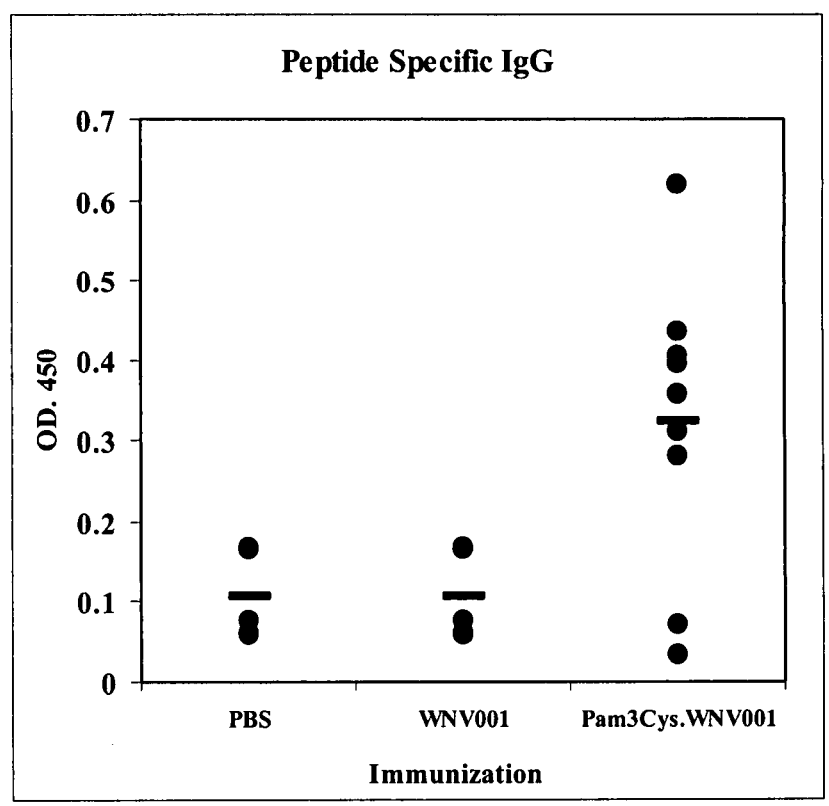

FIG. 58 depicts Pam3Cys.WNV001 (SEQ ID NO: 168) inducing EIII specific IgG antibodies. Mice were immunized s.c. on days 0, 14 and 28 with PBS alone, 22 mg of unmodified WNV001 (SEQ ID NO: 168) or 30 µg of Pam3Cys.WNV001. On day 35 sera from individual mice were characterized by direct ELISA to determine IgG levels to synthetic WNV001 peptide.

FIG. 59 depicts the amino acid sequences (SEQ ID NOS: 88-95) of the EI/EIII junction for West Nile, Japanese encephalitis and Dengue (serotypes 1 through 4) viruses. The West Nile epitope identified using antisera from STF2Δ.EIIIs+ immunized animals is underlined. This sequence corresponds to peptide E2-21 (SEQ ID NO: 125).

FIG. 60 depicts E2-21 peptide (SEQ ID NOS: 125-151) alanine scan array. Amino acids that correspond to domain III of the West Nile virus envelope protein are underlined. Amino acids that are not underlined correspond to domain I of the West Nile virus.

FIG. 61 depicts a STF2.OVA nucleic acid sequence (SEQ ID NO: 152). The nucleic acid sequence encoding the linker between STF2 and ovalbumin (OVA) is underlined. Vector sequence at the 3' end is bolded and underlined.

FIG. 62 depicts an amino acid sequence (SEQ ID NO: 153) encoded by SEQ ID NO: 152. The linker sequence between STF2 and OVA is underlined. Vector sequence is underlined and bolded.

FIG. 63 depicts the amino acid sequence (SEQ ID NO: 154) of ovalbumin.

FIG. 64 depicts the nucleic acid sequence (SEQ ID NO: 155) of ovalbumin.

FIG. 65 depicts the nucleic acid sequence (SEQ ID NO: 158) encoding a STF2.E fusion protein. The nucleic acid sequence encoding the full-length West Nile virus envelope protein (E) is underlined.

FIG. 66 depicts the amino acid sequence (SEQ ID NO: 159) encoded by SEQ ID NO: 158. The amino acid sequence of the West Nile virus envelope protein is underlined.

FIG. 67 depicts the nucleic acid sequence (SEQ ID NO: 57) encoding SEQ ID NO: 39 (FIG. 45). The full length sequence of the West Nile virus envelope protein is depicted.

FIG. 68 depicts the amino acid sequence (SEQ ID NO: 160) of the Dengue 1 virus (also referred to herein as "Den-1," "Den 1" or "Den1").

FIG. 69 depicts the nucleic acid sequence (SEQ ID NO: 161) encoding SEQ ID NO: 160.

FIG. 70 depicts the amino acid sequence (SEQ ID NO: 162) of the Dengue 2 virus (also referred to herein as "Den-2," "Den 2" or "Den2").

FIG. 71 depicts the nucleic acid sequence (SEQ ID NO: 163) encoding SEQ ID NO: 162.

FIG. 72 depicts the amino acid sequence (SEQ ID NO: 164) of the Dengue 3 virus (also referred to herein as "Den-3," "Den 3" or "Den3").

FIG. 73 depicts the nucleic acid sequence (SEQ ID NO: 165) encoding SEQ ID NO: 164).

FIG. 74 depicts the amino acid sequence (SEQ ID NO: 166) of the Dengue 4 virus (also referred to here in as "Den-4," "Den 4" or "Den4").

FIG. 75 depicts the nucleic acid sequence (SEQ ID NO: 167) encoding SEQ ID NO: 166.

FIG. 76 depicts the nucleic acid sequence (SEQ ID NO: 170) encoding a Japanese encephalitis virus.

FIG. 77 depicts the amino acid sequence (SEQ ID NO: 171) encoded by SEQ ID NO: 170.

FIG. 78 depicts the nucleic acid sequence (SEQ ID NO: 175) encoding SEQ ID NO: 174, depicted in FIG. 44.

FIG. 79 depicts the nucleic acid sequence (SEQ ID NO: 178) encoding EIII+ (amino acids of 292-406 of SEQ ID NO: 39, depicted in FIG. 45 and SEQ ID NO: 7).

Figure 80:
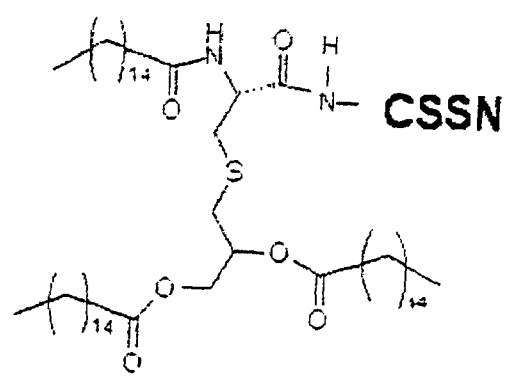

FIG. 80 depicts a tripalmitoylated peptide.

Figure 81A:
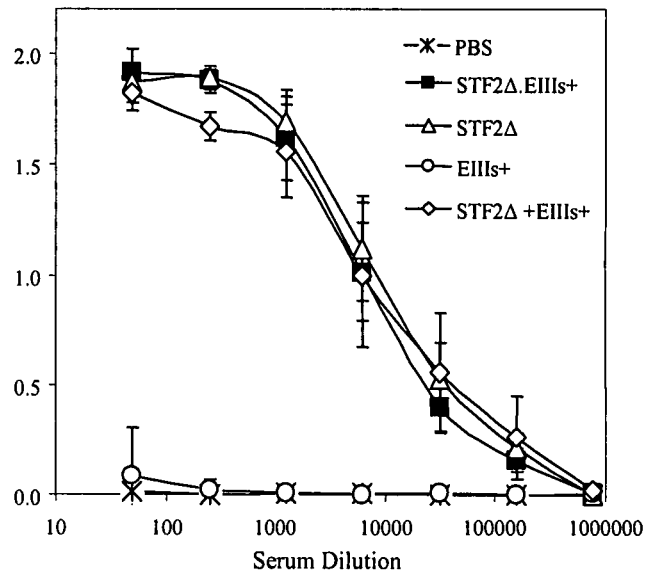
Figure 81B:
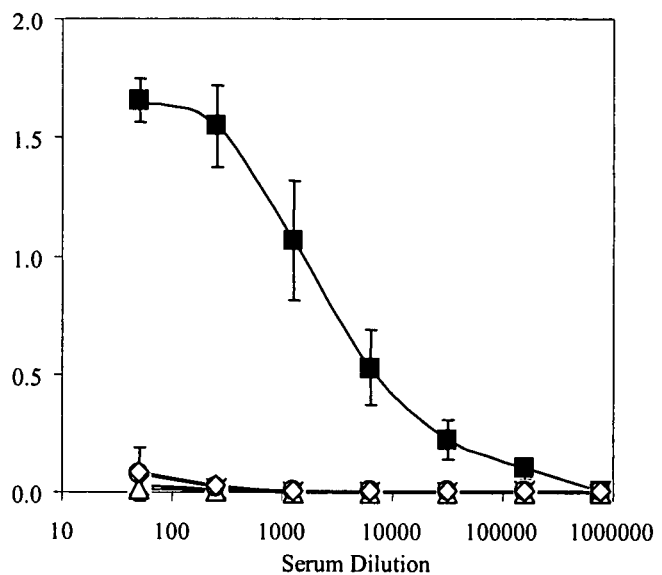

FIGS. 81A and 81B depict anti-flagellin and anti-WNV-E specific IgG responses in mice. Five groups of C3H/HeN mice (10 mice per group) were immunized on days 0, 14 and 28 days s.c. with STF2Δ.EIII (SEQ ID NO: 72; 25 μg), STF2Δ (18 μg), WNV-EIIIs+ (7 μg), and a mixture of STF2Δ (18 μg) and WNV-EIIIs+ (7 μg). Doses were chosen to ensure that molar equivalents of each antigen were administered in PBS. On day 35, sera were harvested and tested by ELISA for flagellin (81A) and WNV-E (81B)-specific IgG responses. Purified flagellin (STF2) and 80% WNE-E protein were used as antigens for antibody detection. Results reflect the mean±standard error $OD_{450}$ values obtained from 10 individual animals per group.

Figure 82:
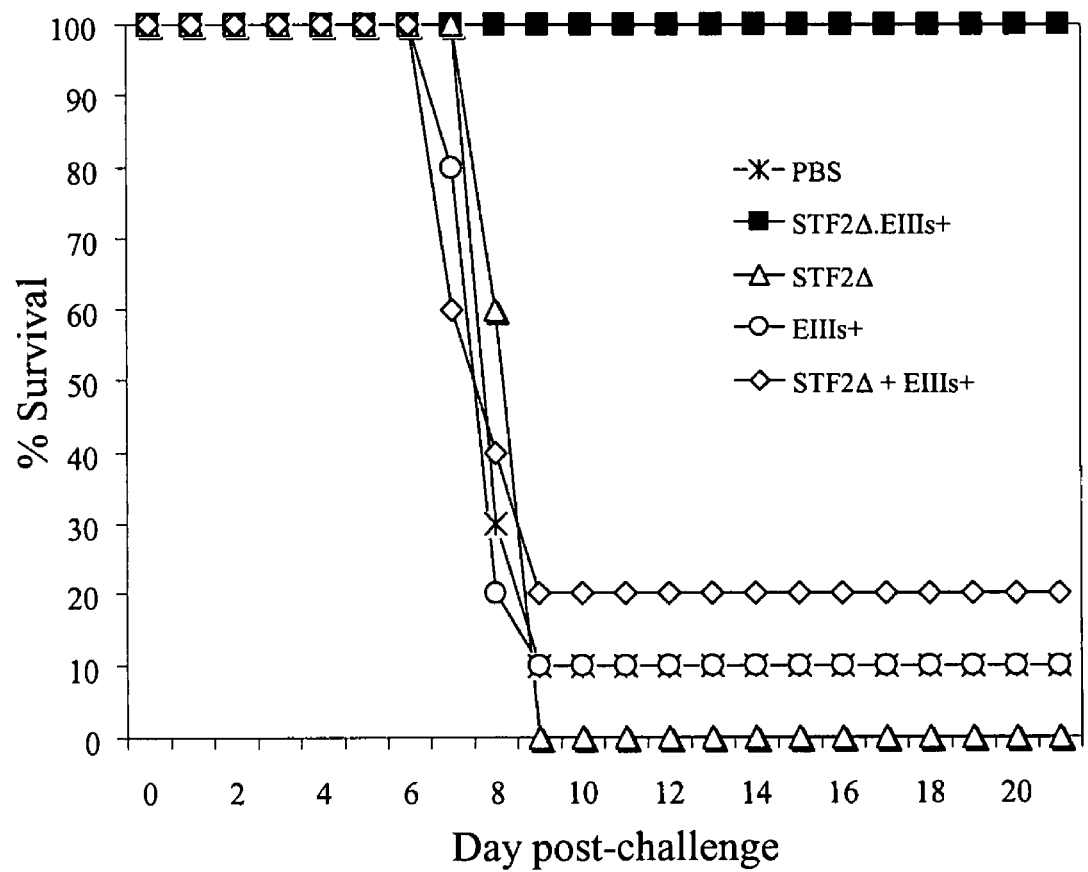

FIG. 82 depicts percent survival of immunized mice depicted in FIGS. 81A and 81B challenged with a lethal dose ($LD_{90}$) of WNV-strain 2741 and monitored for survival for 21 days.

Figure 83A:
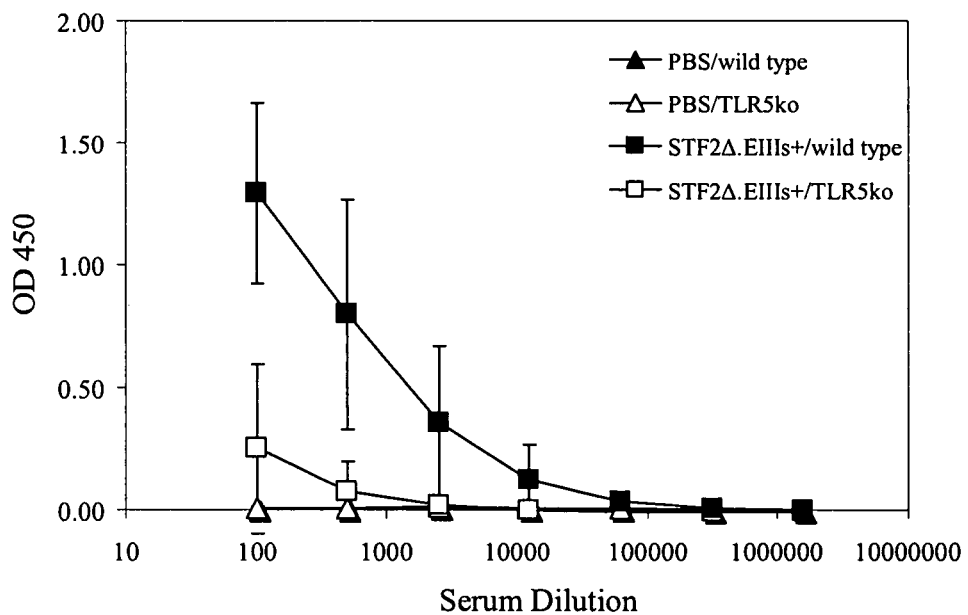
Figure 83B:
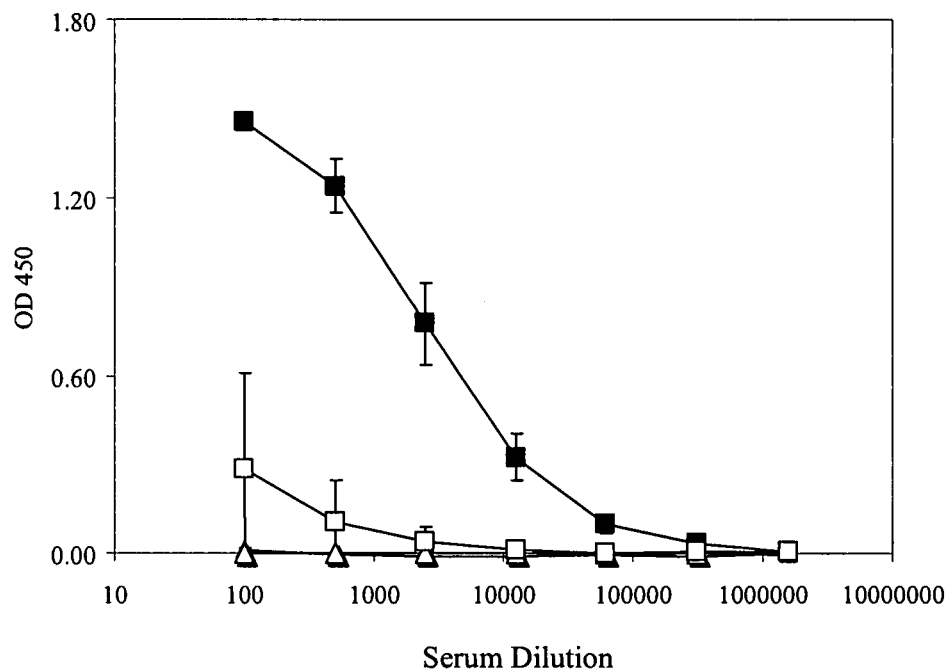

FIGS. 83A and 83B depict IgG responses following immunization of wild type or TLR5 knockout (ko) C57BL/6 mice with the STF2Δ.EIII+ fusion protein (SEQ ID NO: 72). Wild type and TLR5ko mice (5 mice per group) were immunized with PBS, or 25 μg of the STF2Δ.EIII+ fusion protein s.c. on days 0 and 21, and sera were collected on day 28. Anti-flagellin and anti-E IgG responses were examined by ELISA. The data depict the mean±standard deviation of 5 individual sera per group.

Figure 84A:
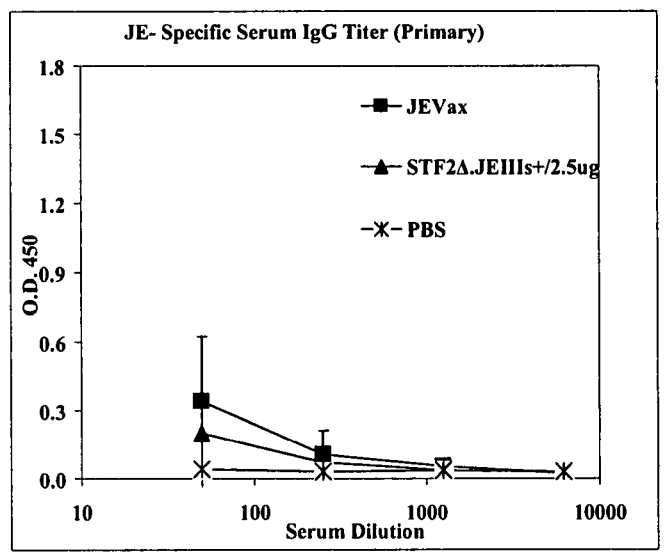
Figure 84B:
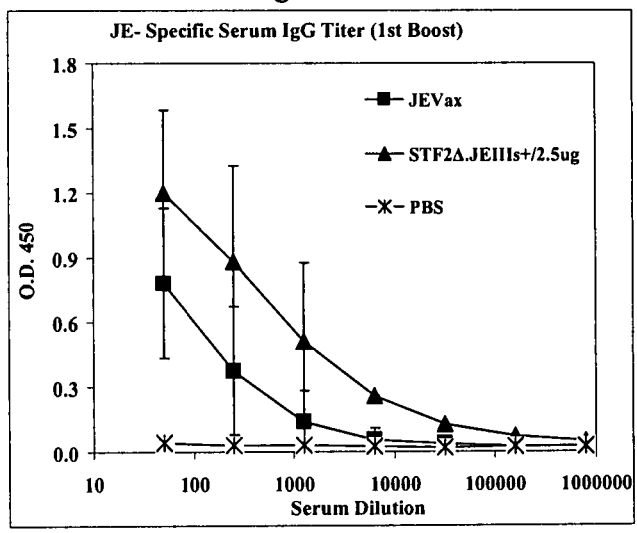
Figure 84C:
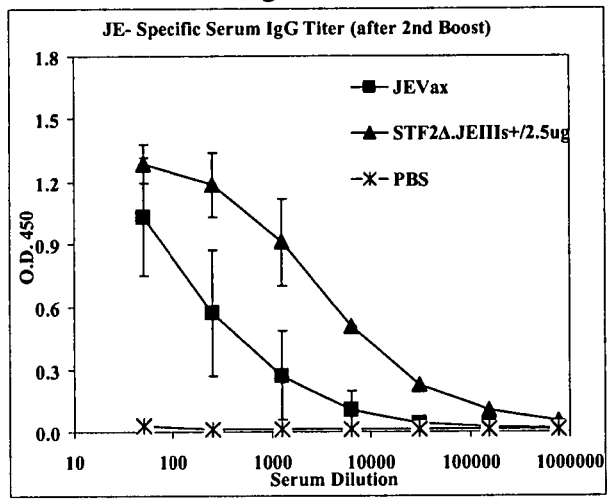

FIGS. 84A, 84B and 84C depict immunogenicity of STF2Δ.JEIII+ (SEQ ID NO: 76) in C57BL/6 mice. Mice (20 mice per group) were immunized with PBS, 2.5 μg of STF2Δ.JEIIIs+ (SEQ ID NO: 76) on days 0, 14, or 28 and bled on day 7 (primary), day 21 (boost 1), and day 35 (boost 2). Anti-JE-his IgG responses were examined by ELISA. The data depict the mean±SD of 20 individual sera per group.

FIG. 85 depicts the percent survival of mice depicted in FIGS. 84A, 84B and 84C. Following the third immunization, 10 mice from each group were challenged with of the Nakayama JE virus by i.p. administration with a viral dose of $10 \times LD_{50}$. Survival was monitored for 21 days.

DETAILED DESCRIPTION OF THE INVENTION

The features and other details of the invention, either as steps of the invention or as a combination of parts of the invention, will now be more particularly described and pointed out in the claims. It will be understood that the particular embodiments of the invention are shown by way of illustration and not as limitations of the invention. The principle features of this invention can be employed in various embodiments without departing from the scope of the invention.

The present invention relates to compositions, fusion proteins and polypeptides of at least a portion of at least one antigen and at least a portion of a flagellin that lacks a hinge region; and at least a portion of at least one pathogen-associated molecular pattern (PAMP) and at least a portion of at least one flavivirus. The compositions, fusion proteins and polypeptides of the invention can be employed in methods to stimulate an immune response and protective immunity in a subject.

In one embodiment, the invention is a composition comprising at least a portion of at least one antigen and at least a portion of at least one flagellin, wherein at least one of the flagellins lacks at least a portion of a hinge region.

Pathogen-associated molecular pattern (PAMP), such as a flagellin or a bacterial lipoprotein, refers to a class of molecules (e.g., protein, peptide, carbohydrate, lipid, lipopeptide, nucleic acid) found in microorganisms that, when bound to a pattern recognition receptor (PRR), can trigger an innate immune response. The PRR can be a Toll-like receptor (TLR). Toll-like receptors refer to a family of receptor proteins that are homologous to the *Drosophila melangogaster* Toll protein. Toll-like receptors are type I transmembrane signaling receptor proteins characterized by an extracellular leucine-rich repeat domain and an intracellular domain homologous to an interleukin 1 receptor. Toll-like receptors include TLR1, TLR2, TLR3, TLR4, TLR5, TLR6, TLR7, TLR 8, TLR9, TLR10, TLR11 and TLR12.

The pathogen-associated molecular pattern can be an agonist of a toll-like receptor, for example, a TLR2 agonist (i.e., Pam2Cys, Pam3Cys, a bacterial lipoprotein) or a TLR5 agonist, such as a flagellin. "Agonist," as used herein in referring to a TLR, means a molecule that activates a TLR signaling pathway. A TLR signaling pathway is an intracellular signal transduction pathway employed by a particular TLR that can be activated by a TLR ligand or a TLR agonist. Common intracellular pathways are employed by TLRs and include, for example, NF-κB, Jun N-terminal kinase and mitogen-activated protein kinase. The pathogen-associated molecular pattern can include at least one member selected from the group consisting of a TLR1 agonist, a TLR2 agonist (e.g., Pam3Cys, Pam2Cys, bacterial lipoprotein), a TLR3 agonist (e.g., dsRNA), a TLR4 agonist (e.g., bacterial lipopolysaccharide), a TLR5 agonist (e.g., a flagellin), a TLR6 agonist, a TLR7 agonist, a TLR8 agonist, a TLR9 agonist (e.g., unmethylated DNA motifs), TLR10 agonist, a TLR11 agonist and a TLR12 agonist.

TLR4 ligands (e.g., TLR4 agonists) for use in the compositions and methods of the invention can include at least one member selected from the group consisting of SEQ ID NOS: 184-231 (see, PCT/US 2006/002906/WO 2006/083706; PCT/US 2006/003285/WO 2006/083792; PCT/US 2006/041865; PCT/US 2006/042051; U.S. application Ser. No. 11/714,873).

```
GGKSGRTG      (SEQ ID NO: 184)
KGYDWLVVG     (SEQ ID NO: 185)
EDMVYRIGVP    (SEQ ID NO: 186)
VKLSGS        (SEQ ID NO: 187)
GMLSLALF      (SEQ ID NO: 188)
CVVGSVR       (SEQ ID NO: 189)
IVRGCLGW      (SEQ ID NO: 190)
AAEERTLG      (SEQ ID NO: 191)
WARVVGWLR     (SEQ ID NO: 192)
SEGYRLFGG     (SEQ ID NO: 193)
LVGGVVRRGS    (SEQ ID NO: 194)
GRVNDLWLAA    (SEQ ID NO: 195)
SGWMLWREGS    (SEQ ID NO: 196)
ERMEDRGGDL    (SEQ ID NO: 197)
KLCCFTECM     (SEQ ID NO: 198)
AVGSMERGRG    (SEQ ID NO: 199)
RDWVGGDLV     (SEQ ID NO: 200)
FFEVAKISQQ    (SEQ ID NO: 201)
WWYWC         (SEQ ID NO: 202)
MHLCSHA       (SEQ ID NO: 203)
WLFRRIG       (SEQ ID NO: 204)
YWFWRIG       (SEQ ID NO: 205)
MHLYCIA       (SEQ ID NO: 206)
WPLFPWIV      (SEQ ID NO: 207)
DMRSHAR       (SEQ ID NO: 208)
MHLCTHA       (SEQ ID NO: 209)
NLFPFY        (SEQ ID NO: 210)
MHLCTRA       (SEQ ID NO: 211)
RHLWYHA       (SEQ ID NO: 212)
WPFSAYW       (SEQ ID NO: 213)
WYLRGS        (SEQ ID NO: 214)
GKGTDLG       (SEQ ID NO: 215)
IFVRMR        (SEQ ID NO: 216)
WLFRPVF       (SEQ ID NO: 217)
FLGWLMG       (SEQ ID NO: 218)
MHLWHHA       (SEQ ID NO: 219)
WWFPWKA       (SEQ ID NO: 220)
WYLPWLG       (SEQ ID NO: 221)
WPFPRTF       (SEQ ID NO: 222)
WPFPAYW       (SEQ ID NO: 223)
FLGLRWL       (SEQ ID NO: 224)
SRTDVGVLEV    (SEQ ID NO: 225)
REKVSRGDKG    (SEQ ID NO: 226)
DWDAVESEYM    (SEQ ID NO: 227)
VSSAQEVRVP    (SEQ ID NO: 228)
LTYGGLEALG    (SEQ ID NO: 229)
VEEYSSSGVS    (SEQ ID NO: 230)
VCEVSDSVMA    (SEQ ID NO: 231)
```

TLR2 ligands (e.g., TLR2 agonists) for use in the compositions and methods of the invention can also include at least one member selected from the group consisting of SEQ ID NOS: 232-271 (see, PCT/US 2006/002906/WO 2006/083706; PCT/US 2006/003285/WO 2006/083792; PCT/US 2006/041865; PCT/US 2006/042051; U.S. application Ser. No. 11/714,873).

```
NPPTT         (SEQ ID NO: 232)
MRRIL         (SEQ ID NO: 233)
MISS          (SEQ ID NO: 234)
RGGSK         (SEQ ID NO: 235)
RGGF          (SEQ ID NO: 236)
NRTVF         (SEQ ID NO: 237)
NRFGL         (SEQ ID NO: 238)
SRHGR         (SEQ ID NO: 239)
IMRHP         (SEQ ID NO: 240)
EVCAP         (SEQ ID NO: 241)
ACGVY         (SEQ ID NO: 242)
```

-continued

| | |
|---|---|
| CGPKL | (SEQ ID NO: 243) |
| AGCFS | (SEQ ID NO: 244) |
| SGGLF | (SEQ ID NO: 245) |
| AVRLS | (SEQ ID NO: 246) |
| GGKLS | (SEQ ID NO: 247) |
| VSEGV | (SEQ ID NO: 248) |
| KCQSF | (SEQ ID NO: 249) |
| FCGLG | (SEQ ID NO: 250) |
| PESGV | (SEQ ID NO: 251) |
| DPDSG | (SEQ ID NO: 252) |
| IGRFR | (SEQ ID NO: 253) |
| MGTLP | (SEQ ID NO: 254) |
| ADTHQ | (SEQ ID NO: 255) |
| HLLPG | (SEQ ID NO: 256) |
| GPLLH | (SEQ ID NO: 257) |
| NYRRW | (SEQ ID NO: 258) |
| LRQGR | (SEQ ID NO: 259) |
| IMWFP | (SEQ ID NO: 260) |
| RVVAP | (SEQ ID NO: 261) |
| IHVVP | (SEQ ID NO: 262) |
| MFGVP | (SEQ ID NO: 263) |
| CVWLQ | (SEQ ID NO: 264) |
| IYKLA | (SEQ ID NO: 265) |
| KGWF | (SEQ ID NO: 266) |
| KYMPH | (SEQ ID NO: 267) |
| VGKND | (SEQ ID NO: 268) |
| THKPK | (SEQ ID NO: 269) |
| SHIAL | (SEQ ID NO: 270) |
| AWAGT | (SEQ ID NO: 271) |

The TLR2 ligand (e.g., TLR2 agonist) can also include at least a portion of at least one member selected from the group consisting of flagellin modification protein FlmB of *Caulobacter crescentus*; Bacterial Type III secretion system protein; invasin protein of *Salmonella*; Type 4 fimbrial biogenesis protein (PilX) of *Pseudomonas; Salmonella* SciJ protein; putative integral membrane protein of *Streptomyces*; membrane protein of *Pseudomonas*; adhesin of *Bordetella pertussis*; peptidase B of *Vibrio cholerae*; virulence sensor protein of *Bordetella*; putative integral membrane protein of *Neisseria meningitidis*; fusion of flagellar biosynthesis proteins FliR and FlhB of *Clostridium*; outer membrane protein (porin) of *Acinetobacter*; flagellar biosynthesis protein FlhF of *Helicobacter*; ompA related protein of *Xanthomonas*; omp2a porin of *Brucella*; putative porin/fimbrial assembly protein (LHrE) of *Salmonella*; wbdk of *Salmonella*; Glycosyltransferase involved in LPS biosynthesis; *Salmonella* putative permease.

The TLR2 ligand (e.g., TLR agonist) can include at least a portion of at least one member selected from the group consisting of lipoprotein/lipopeptides (a variety of pathogens); peptidoglycan (Gram-positive bacteria); lipoteichoic acid (Gram-positive bacteria); lipoarabinomannan (mycobacteria); a phenol-soluble modulin (*Staphylococcus epidermidis*); glycoinositolphospholipids (*Trypanosoma Cruzi*); glycolipids (*Treponema maltophilum*); porins (*Neisseria*); zymosan (fungi) and atypical LPS (*Leptospira interrogans* and *Porphyromonas gingivalis*).

The TLR2 ligand (e.g., TLR2 agonist) can also include at least one member selected from the group consisting of SEQ ID NOS: 272-274 (see, PCT/US 2006/002906/WO 2006/083706; PCT/US 2006/003285/WO 2006/083792; PCT/US 2006/041865; PCT/US 2006/042051; U.S. application Ser. No. 11/714,873).

| | |
|---|---|
| KGGVGPVRRSSRLRRTTQPG | (SEQ ID NO: 272) |
| GRRGLCRGCRTRGRIKQLQSAHK | (SEQ ID NO: 273) |
| RWGYHLRDRKYKGVRSHKGVPR | (SEQ ID NO: 274) |

In a particular embodiment, the TLR2 agonist is a bacterial lipoprotein, such as Pam2Cys, Pam3Cys or *Pseudomonas aeruginosa* OprI lipoprotein (OprI). Exemplary OprI lipoproteins include MNNVLKFSALALAAVLATGCSSH (SEQ ID NO: 179), encoded by ATGAAAGCTACTAAACTGG-TACTGGGCGCGGTAATCCTGGGTTCTACTCTGC TGGCAGGTTGCTCCAGCAAC (SEQ ID NO: 180). An exemplary *E. coli* bacterial lipoprotein for use in the invention described herein is MKATKLVLGAVILGSTLLAGCSSN (SEQ ID NO: 181) encoded by ATGAAAGCTAC-TAAACTGGTACTGGGCGCGGTAATC-CTGGGTTCTACTCTGC TGGCAGGTTGCTCCAG-CAAC (SEQ ID NO: 182). A bacterial lipoprotein that activates a TLR2 signaling pathway (a TLR2 agonist) is a bacterial protein that includes a palmitoleic acid (Omueti, K. O., et al., *J. Biol. Chem.* 280: 36616-36625 (2005)). For example, expression of SEQ ID NOS: 180 and 182 in bacterial expression systems (e.g., *E. coli*) results in the addition of a palmitoleic acid moiety to a cysteine residue of the resulting protein (e.g., SEQ ID NOS: 179, 181) thereby generating a TLR2 agonist for use in the compositions, fusion proteins and polypeptides of the invention. Production of tripalmitoylated-lipoproteins (also referred to as triacyl-lipoproteins) in bacteria occurs through the addition of a diacylglycerol group to the sulfhydryl group of a cysteine (Cysteine 21 of SEQ ID NO: 181) followed by cleavage of the signal sequence and addition of a third acyl chain to the free N-terminal group of the same cysteine (Cysteine 21 of SEQ ID NO: 181) (Sankaran, K., et al., *J. Biol. Chem.* 269:19706 (1994)), to generate a tripalmitylated peptide (a TLR2 agonist) as shown, for example, in FIG. 80.

An antigen is any molecule (e.g., protein, peptide, glycoprotein, glycopeptide, carbohydrate, lipid, lipopeptide, polysaccharide) that generates an immune response in a subject either when employed in combination with a PAMP (e.g., a flagellin, Pam2Cys, Pam3Cys) or in the absence of a PAMP. The antigen can be a fragment or portion of a naturally occurring antigen or a synthetic molecule that mimics the naturally occurring antigen or a portion of the naturally occurring antigen.

The antigen can be a viral antigen. A "viral antigen," as used herein, refers to any portion of a virus (e.g., flavivirus) that generates an immune response in a subject either when employed in combination with a PAMP (e.g., a flagellin, Pam2Cys, Pam3Cys) or in the absence of a PAMP. The viral antigen can be a portion or a fragment of a naturally occurring virus or a synthetic molecule that mimics a naturally occurring virus, such as a recombinant or synthetic protein (e.g., a flavivirus), peptide, lipid, carbohydrate, that generates an immune response in the subject. "At least a portion," as used herein in reference to at least a portion of an antigen (e.g., a viral antigen), means any part of the antigen or the entirety of the antigen. For example, at least a portion of a flaviviral antigen can be an envelope protein, or a domain (e.g., domain I, II, III) of an envelope protein of a flavivirus antigen.

The flagellin employed in the compositions, fusion proteins and polypeptides of the invention can lack at least a portion of a hinge region. Hinge regions are the hypervariable regions of a flagellin that link the amino-terminus and carboxy-terminus of the flagellin. Hinge regions of a flagellin are also referred to herein as "hypervariable regions" or "hypervariable hinge regions." "Lack," as used herein in reference to a hinge region of a flagellin, means that at least one amino acid or at least one nucleic acid codon encoding at least one amino acid that comprises the hinge region of a flagellin is absent in the flagellin. Example of hinge regions include amino acids 176-415 of SEQ ID NO: 1, which are encoded by nucleic acids 528-1245 of SEQ ID NO: 2; amino acids 174-422 of SEQ ID NO: 68, which are encoded by nucleic acids 522-1266 of SEQ ID NO: 69; or amino acids 173-464 of SEQ ID NO: 58, which are encoded by nucleic acids 519-1392 of SEQ ID NO: 59. Thus, if amino acids 176-415 were absent from the flagellin of SEQ ID NO: 1, the flagellin would lack a hinge region. A flagellin lacking at least a portion of a hinge region is also referred to herein as a "truncated version" of a flagellin.

"At least a portion of a hinge region," as used herein, refers to any part of the hinge region of the PAMP (e.g., flagellin), or the entirety of the hinge region. "At least a portion of a hinge region" is also referred to herein as a "fragment of a hinge region." For example, the hinge region of *S. typhimurium* flagellin B (fljB, also referred to herein as "fljB/STF2" or "STF2") is amino acids 176-416 of SEQ ID NO: 1, which is encoded by nucleic acids at position 528-1245 of SEQ ID NO: 2. At least a portion of the hinge region of fljB/STF2 can be, for example, amino acids 200-300 of SEQ ID NO: 1. Thus, if amino acids 200-300 were absent from SEQ ID NO: 1, the resulting amino acid sequence of STF2 would lack at least a portion of a hinge region.

At least a portion of a naturally occurring a flagellin can be replaced with at least a portion of an artificial hinge region. "Naturally occurring," as used herein in reference to a hinge region of a flagellin, means the hinge region that is present in the native flagellin. For example, amino acids 176-415 of SEQ ID NO: 1, amino acids 174-422 of SEQ ID NO: 68 and amino acids 173-464 of SEQ ID NO: 58, are the amino acids corresponding to the natural hinge region of STF2, *E. coli* fliC and *S. muenchen* flagellins, fliC, respectively. "Artificial," as used herein in reference to a hinge region of a flagellin, means a hinge region that is inserted in the native flagellin in any region of the flagellin that contains or contained the native hinge region. For example, SEQ ID NO: 32 lacks the naturally occurring hinge region, which has been replaced by amino acids 176-186, the artificial hinge region.

An artificial hinge region may be employed in a flagellin that lacks at least a portion of a hinge region to facilitate interaction of the carboxy- and amino-terminus of the flagellin for binding to TLR5 and, thus, activation of the TLR5 innate signal transduction pathway. A flagellin lacking at least a portion of a hinge region is designated by the name of the flagellin followed by a "Δ." For example, an STF2 (e.g., SEQ ID NO: 1) that lacks at least a portion of a hinge region is referenced to as "STF2Δ" or "fljB/STF2Δ" (e.g., SEQ ID NO: 3).

The flagellin employed in the compositions, fusion proteins and polypeptides of the invention can be at least one member selected from the group consisting of fljB/STF2 (*S. typhimurium* flagellin B, Genbank Accession Number AF045151), a fragment of fljB/STF2, *E. coli* flagellin fliC (also referred to herein as *E. coli* fliC) (Genbank Accession Number AB028476), a fragment of *E. coli* flagellin fliC, *S. muenchen* flagellin fliC (also referred to herein as *S. muenchen* fliC), and a fragment of *S. muenchen* flagellin fliC.

The flagellin employed in the compositions, fusion proteins and polypeptides of the invention include the polypeptides of SEQ ID NO: 1, SEQ ID NO: 3, SEQ ID NO: 58 and SEQ ID NO: 68; at least a portion of SEQ ID NO: 1, at least a portion of SEQ ID NO: 3, at least a portion of SEQ ID NO: 58 and at least a portion of SEQ ID NO: 68; and a polypeptide encoded by SEQ ID NO: 2, SEQ ID NO: 4, SEQ ID NO: 59 and SEQ ID NO: 69; or at least a portion of a polypeptide encoded by SEQ ID NO: 2, SEQ ID NO: 4, SEQ ID NO: 59 and SEQ ID NO: 69.

In another embodiment, the invention is a fusion protein comprising at least a portion of at least one antigen and at least a portion of at least one flagellin, wherein at least one of the flagellins lack at least a portion of a hinge region.

"Fusion protein," as used herein, refers to a protein generated from at least two similar or distinct components (e.g., Pam2Cys, Pam3Cys, PAMP, at least a portion of an antigen, at least a portion of a viral protein) that are linked covalently or noncovalently. The components of the fusion protein can be made, for example, synthetically (e.g., Pam3Cys, Pam2Cys) or by recombinant nucleic acid techniques (e.g., transfection of a host cell with a nucleic acid sequence encoding a component of the fusion protein, such as at least a portion of a PAMP, or at least a portion of an antigen or a viral protein). One component of the fusion protein (e.g., Pam2Cys, Pam3Cys, PAMP, at least a portion of an antigen or at least a portion of a viral protein) can be linked to another component of the fusion protein (e.g., Pam2Cys, Pam3Cys, PAMP, at least a portion of an antigen or at least a portion of a viral protein) using chemical conjugation techniques, including peptide conjugation, or using molecular biological techniques, including recombinant technology, such as the generation of a fusion protein construct. Chemical conjugation (also referred to herein as "chemical coupling") can include conjugation by a reactive group, such as a thiol group (e.g., a cysteine residue) or by derivatization of a primary (e.g., a amino-terminal) or secondary (e.g., lysine) group. Exemplary fusion proteins of the invention include SEQ ID NOS: 6, 71, 72, 76, 80, 82, 84, 86 and 159 (FIGS. 6, 29, 30, 32, 36, 38, 40 and 42), encoded by SEQ ID NOS: 5, 70, 73, 77, 81, 83, 85, 87 and 158 (FIGS. 5, 28, 31, 33, 37, 39, 41 and 43)

Fusion proteins of the invention can be designated by components of the fusion proteins separated by a "." or "-." For example, "STF2.EIII" refers to a fusion protein comprising one fljB/STF2 protein and at least a portion of domain III (see, infra) of at least one West Nile virus envelope protein; and "STF2Δ.EIII" refers to a fusion protein comprising one fljB/STF2 protein lacking at least a portion of its hinge region and having at least a portion of domain III of at least one West Nile virus envelope protein.

In yet another embodiment, the invention is a composition comprising at least a portion of at least one pathogen-associated molecular pattern and at least a portion of at least one viral protein selected from the group consisting of a West Nile viral protein, a Langat viral protein, a Kunjin viral protein, a Murray Valley encephalitis viral protein, a Japanese encephalitis viral protein, a Tick-borne encephalitis viral protein, and a Yellow fever viral protein, which are flaviviral proteins. The pathogen-associated molecular pattern and viral protein can be components of a fusion protein.

The genus flavivirus is in the virus family Flaviviridae and consists of about 70 viruses. Mosquito or ticks transmit most of these viruses. Several flaviviruses are significant human pathogens, including the four dengue viruses (Den1, Den2, Den3 and Den4), yellow fever (YF), Japanese encephalitis (JE), West Nile (WN, also referred to herein as "WNV") and Tick-borne encephalitis (TBE) (Weaver S. C., et al., *Nat Rev Microbiol* 10: 789-801 (2004)). The flavivirus genus is divided into a number of serogroups based on cross-neutralization tests, including the dengue serogroup that contains four serologically and genetically distinct viruses termed DEN-1, DEN-2, DEN-3 and DEN-4.

Flaviviruses are small, enveloped viruses with icosahedral capsids. The flavivirus genome is a single-stranded positive-sense RNA (about 11 kb) that is directly translated by the host cell machinery following infection. The viral genome is translated as a single polypeptide that undergoes co- and post-translational cleavage by viral and cellular enzymes to generate three structural proteins of the flavivirus (the capsid (C), the membrane (M) and the envelope (E) proteins); and seven nonstructural proteins (NS1, NS2A, NS2B, NS3, NS4A, NS4B, and NS5) (Weaver, et al., *Annu Rev Microbiol* 1990:44-649 (2004)). The flavivirus genome organization is depicted in FIG. 44. The viral capsid is composed of the C-protein, while both the M- and envelope proteins are located on the envelope surface of the virion (Weaver, S. C., et al., *Nat. Rev. Microbiol.* 10:789-801 (2004); Chambers et al., *Annu Rev. Microbiol.* 44: 649-688 (1990)). A major immunogen for flaviviruses is the membrane envelope protein.

The flavivirus envelope protein plays a role in virus assembly. These proteins form a protective shell around the virus, which serves as a cage for the genetic material inside, sheltering the virus until it is released inside a host cell. While simple viruses consist of only a protein shell and genetic information, more complex viruses, such as flaviviruses, also contain a lipid bilayer between the protein shell and viral genome. A flavivirus can enter a host cell when the viral envelope protein binds to a receptor and responds by conformational rearrangement to the reduced pH of an endosome. The conformational change induces fusion of viral and host-cell membranes.

The envelope of a flavivirus may function as a receptor binding protein and to facilitate fusion of the virus and host cell membrane. As a receptor binding protein, the envelope protein is a determinant of host range, cell tropism, virulence and elicits neutralizing antibodies during the immune response (Roehrig, *Adv Virus Res* 59: 141-175 (2003)). The envelope protein is responsible for fusing the virus and host membranes (Chu, et al., *J. Virol* 78:10543-10555 (2004); Heinz, et al., *Adv Virus Res* 59:63-97 (2003); Chu, et al., *J. Gen Virol* 86:405-412 (2005)). Crystallographic structures of the Tick-borne encephalitis virus envelope protein and the Dengue-2 (Den 2) virus envelope protein have been determined (Rey, et al., *Nature* 375:291-298(1995); Modis, et al., *Proc Natl Acad Sci USA* 100:6986-6991(2003)). Envelope proteins of flaviviruses have common structural (domains I, II and III) and functional features (receptor binding of virus and host cell and fusion functions) and are class II fusion glycoproteins (Lescar et al., *Cell* 105:137-148 (2001)).

In the pre-fusion conformation, envelope proteins form homodimers on the outer surface of the virus particles (Rey, et al., *Nature* 375:291-298); Kuhn, et al., *Cell* 108:717-725 (2002); Mukhopadhyay, et al., *Science* 302:248 (2003)). Each envelope protein monomer folds into three structural domains (domains I, II and III) predominantly composed of β-strands. Domain I (also referred to herein as "I" or "DI") is centrally located in the structure and has an N-glycosylation site in glycosylated envelope proteins. Domain II (also referred to herein as "II" or "DII") of the envelope protein promotes dimerization and has a fusion loop that inserts into the target host membrane during the pH-dependent fusion of the virus (Modis, et al., *Nature* 427:313-319 (2004); Bressanelli, et al., *EMBO J* 23:728-738 (2004)). Domain III (also referred to herein as "III" or "DIII") is at the carboxy-terminus of the envelope protein. Domain III is also referred to as "domain B" in earlier antigenic mapping studies. Domain III has several epitopes that can elicit virus-neutralizing antibodies (Roehrig, *Adv Virus Res* 59:141-175 (2003)). In addition, studies with several flaviviruses, including Tick-borne encephalitis (Mandle, et al., *J. Virol* 75:5627-5637 (2001)), indicate that domain III, which has a fold typical of an immunoglobulin constant domain, may mediate flavivirus attachment to host cells (Anderson, *Adv Virus Res* 59:229-274 (2003)) and, thus, be a receptor-binding domain.

The crystal structure of domains I, II and III of the envelope protein from the Tick-borne encephalitis flavivirus and the Dengue 2 flavivirus has been determined (Rey, F. A., et al., *Nature* 375:291-298 (1995); Modis, Y., et al., *Nature* 427: 313-319 (2004), respectively). Domain I of the Tick-borne encephalitis envelope protein corresponds to amino acids 1-51, 137-189 and 285-302 of SEQ ID NO: 174; domain II of the Tick-borne encephalitis envelope protein of SEQ ID NO: 174 corresponds to amino acids 52-136 and 190-284; and domain III corresponds to amino acids 303-395 of SEQ ID NO: 174. (Rey, F. A., et al., *Nature* 375:291-298 (1995)). SEQ ID NO: 174 (FIG. 44) is encoded by SEQ ID NO: 175 (FIG. 78). Domain I of the Dengue 2 flavivirus envelope protein corresponds to amino acids 1-52, 132-193 and 280-296 of SEQ ID NO: 160 (FIG. 70); domain II corresponds to amino acids 53-131 and 194-279 of SEQ ID NO: 160; and domain III corresponds to amino acids 297-495 of SEQ ID NO: 160 (Modis, Y., et al., *Nature* 427:313-319 (2004)). The location of domains I, II and III of other flavivirus (e.g., West Nile virus, Japanese encephalitis, Dengue 1 virus, Dengue 3 virus and Dengue 4 virus) is based on homology of the Tick-borne encephalitis envelope protein domains and the Dengue 2 envelope protein domains. Thus, reference herein to domains of flavivirus proteins, in particular, flaviviruses other than Tick-borne encephalitis flavivirus envelope proteins and Dengue 2 flavivirus envelope proteins, are based on homology to domains in the Tick-borne encephalitis flavivirus envelope protein and the Dengue 2 flavivirus envelope protein.

The domain III of the envelope protein of the DEN flavivirus encodes the majority of the flavivirus type-specific contiguous critical/dominant neutralizing epitopes (Roehring, J. T., *Adv. Virus Res.* 59:141 (2003)), including the four DEN (DEN1, DEN2, DEN3, DEN4) viruses. Flavivirus envelope proteins are highly homologous. Exemplary envelope protein sequences are shown in FIGS. 45, 68, 70, 72, 74 and 77 (SEQ ID NOs: 39, 160, 162, 164, 166 and 171, respectively).

The seven nonstructural proteins of flavivirus envelope proteins are involved in the replication of the virus. NS3 is a multifunctional enzyme that encodes a serine protease at the aminus-terminal region; and helicase, RNA triphosphatase and NTPase activities in the carboxy-terminal region. NS5 encodes a methyltransferase and the RNA-dependent-RNA polymerase. NS2A, NS2B, NS4A and NS4B are four poorly characterized proteins. The central domain of NS2B is a co-factor for the NS3 serine protease while NS2A and NS4A are known to be components of the replication complex. NS1 is located at both the plasma membrane and in the lumen of intracellular vesicles of virus-infected cells. NS1 is a multifunctional protein that is associated with an early step in the replication cycle either prior to or early in negative-strand RNA synthesis and is also thought to be involved in virus maturation and/or release (Brinton, M. A., *Annu Rev Microbiol* 56:371 (2002)).

West Nile virus (WNV) is a single-stranded positive sense RNA envelope virus. It was first isolated and identified in the West Nile region of Uganda in 1937 from a febrile female adult (Smithburn, et al., *Am J Trop Med Hyg* 3:9-18 (1954)). West Nile Virus has been classified as a member of the family Flaviviridae using cross-neutralization tests with polyclonal antisera (Boctor, et al., *J. Virol Methods* 26:305-311 (1989)). West Nile virus is neuroinvasive (George, et al., *Bull W H O* 62:879-882 (1984)); and severe human meningoencephalitis might occur consequent to infection with West Nile virus, as seen in the outbreaks in North America (CDC, Update: West Nile Virus Encephalitis—New York 1999, *MMWR Morbid Mortal Wkly Rep* 48:994-946; CDC, Update: West Nile Virus Encephalitis—New York 1999. *MMWR Morbid Mortal Wkly Rep* 51:1135-1136). During 1999-2002, WNV extended its range throughout much of the eastern part of the United States, and its range within the western hemisphere is expected to continue to expand. Birds are the natural reservoir hosts, and WNV is maintained in nature in a mosquito-bird-mosquito transmission cycle primarily involving Culex species mosquitoes.

Recently, West Nile virus has emerged in temperate regions of Europe and North America, presenting a threat to public and animal health. The most serious manifestation of WNV infection is fatal encephalitis (inflammation of the brain) in humans and horses, as well as mortality in certain domestic and wild birds. West Nile virus infection has also been a significant cause of human illness in the United States. The envelope glycoprotein of the West Nile virus (WNV-E) and other flaviviruses may be important in formulating compositions to stimulate an immune response to generate neutralizing and protective antibodies. Currently, there are no compositions that prevent West Nile virus infection, for example, by stimulating an immune response in a subject.

Japanese encephalitis (JE) virus is localized in Asia and northern Australia (about 50,000 cases with about 10,000 deaths annually). A composition comprising an inactivated virus was recently associated with a case of acute disseminated encephalomyelitis, prompting the Japanese Ministry of Health, Labor and Welfare to recommend the nationwide suspension of compositions comprising inactivated virus.

The Dengue (DEN) disease is caused by four mosquito-borne, serologically related flaviviruses known as DEN-1 (also referred to herein as "Den1" or Den 1"), DEN-2 (also referred to herein as "Den2" or "Den 2"), DEN-3 (also referred to herein as "Den3" or "Den 3"), and DEN-4 (also referred to herein as "Den4" or Den 4"), and is an important arboviral disease of humans. DEN is a major public health problem in all tropical areas of the world. About three billion people are at risk for DEN and about 50 to about 100 million cases of dengue fever (DF) and hundreds of thousands of cases of dengue hemorrhagic fever (DHF) occur in the tropics each year, including Mexico, the Caribbean and parts of Asia and the South Pacific (Gubler, D. J., *Ann Acad Med Singapore* 27: 227-34 (1998)). Dengue viruses are transmitted by peridomestic Aedes spp. mosquitoes, which inhabit the tropics, allowing endemicity of DF in these areas. Infection by one virus causes Dengue Fever (DF), a febrile illness, which is not normally life-threatening, and leads to life-long protective immunity against the infecting DEN serotype/virus. However, individuals that are infected by one serotype/virus remain susceptible to infection by the other three DEN serotypes/viruses. Subsequent infection by one of the other DEN serotypes/viruses can lead to Dengue hemorrhagic fever (DHF) or dengue shock syndrome (DSS), which are life-threatening diseases.

DHF may be the result of an antibody dependent enhancement (ADE) where non-neutralizing antibodies induced by the primary DEN infection form virus-antibody complexes in secondary infections that are taken up into macrophages by Fc receptors and, thus, enhance virus infection. About 500,000 cases of DHF occur each year, mostly in children, with a fatality rate of about 5%. About 600 million children are at risk for DEN infections, about 60 million may get DEN infections each year, and about 60,000 may be hospitalized. In addition, to the public health problem, military personnel are often sent overseas to tropical areas of the world where DEN viruses are found. Significant numbers of soldiers succumb to DEN while performing overseas, such as in Somalia, Grenada, Viet Nam and the Gulf conflicts. Attempts to develop a DEN vaccine have proved difficult due to the need to develop a tetravalent vaccine that protects against all four DEN serotypes/viruses.

Methods to prevent flavivirus disease include vaccines to the flaviviruses (Barrett, A. D., *Ann. N.Y. Acad. Sci* 951:262 (2001). These compositions can be divided into two categories: live attenuated and inactivated. Compositions comprising live flavivirus have been developed for YF and JE based on strains 17D and SA14-14-2, respectively, and were derived by empirical passage in chicken and hamster tissue, respectively. SA14-14-2 is produced in the People's Republic of China, grown in primary hamster kidney cell culture and very recently has been approved for use outside China. Both compositions are efficacious and require one or two doses, respectively, to develop protective immunity. There are inactivated virus compositions for JE and TBE. The inactivated JE compositions are based on strains Nakayama, Beijing-1 or P3, while inactivated TBE compositions are based on Central European TBE strains Neudorfl and K23, and Russian Spring Summer encephalitis strains Sofjin and 205. These killed flavivirus compositions require about two doses (given about 1 week to about 2 months apart), a booster dose at about one year and periodic boosters about every 3 to about 4 years. The antibody-mediated immunity, in particular neutralizing antibodies, may be important in preventing flavivirus disease. Long-lived neutralizing antibody responses following administration of compositions to treat flavivirus disease or to prevent flavivirus disease may also be important.

Many different approaches have been taken to develop compositions to prevent flavivirus infection, but many have not been successful. With respect to the disease DEN, which is the result of four related viruses (DEN1, DEN2, DEN3, DEN4), a composition may need to be developed to one or more the DEN flaviviruses. For example, a tetravalent (DEN1, DEN2, DEN3 and DEN4) composition may stimulate an immune response simultaneously against all four DEN viruses and thereby eliminate the potential of antibody dependent enhancement.

Currently, there is no effective compositions to prevent infection by many flaviviruses, including West Nile virus, Dengue virus, Tick-borne virus, Kunjun virus, Murray Valley encephalitis virus and Yellow fever virus (Chang, G. J., et al., *Expert Rev. Vaccine* 3:199 (2004)). Attenuation and immunogenicity may occur in compositions with live attenuated flavivirus. Furthermore, compositions with tetravalent live Dengue flaviviruses may have problems with interference and imbalanced immune response resulting in many compositions being tested with variation in the quantity of each of the four DEN viruses. Compositions comprising inactivated flavivirus may have problems with immunogenicity and the need for multiple doses. In addition, the production of inactivated flavivirus compositions in infected mouse brains or cell culture can be complex, tedious, may result in unknown hazards if not properly inactivated and may result in adverse effects when administered to subjects. Thus, there is a need to develop new compositions for use in the prevention of flavivirus infection in subjects.

The compositions, fusion proteins and polypeptides of the invention employ pathogen-associated molecular patterns that trigger cellular events resulting in the expression of costimulatory molecules, secretion of critical cytokines and chemokines; and efficient processing and presentation of antigens to T-cells. As discussed above, TLRs recognize PAMPs including bacterial cell wall components (e.g., bacterial lipoproteins and lipopolysaccharides), bacterial DNA sequences that contain unmethylated CpG residues and bacterial flagellin. TLRs act as initiators of the innate immune response and gatekeepers of the adaptive immune response (Medzhitov, R., et al., *Cold Springs Harb. Symp. Quant. Biol.* 64:429 (1999); Pasare, C., et al., *Semin, Immunol* 16:23 (2004); Medzhitov, R., et al., *Nature* 388:394 (1997); Barton, G. M., et al., *Curr. Opin. Immunol* 14:380 (2002); Bendelac, A., et al., *J. Exp. Med.* 195:F19 (2002)).

As discussed above, the binding of PAMPs to TLRs activates immune pathways for use in the compositions, fusion proteins and polypeptides of the invention, which can be employed in stimulating the immune system in a subject. The compositions, fusion proteins and polypeptides of the invention can trigger an immune response to an antigen (e.g., a viral protein, such as a flaviviral protein) and trigger signal transduction pathways of the innate and adaptive immune system of the subject to thereby stimulate the immune system of a subject. Stimulation of the immune system of the subject may prevent infection by an antigen or a virus (e.g., a flavivirus) and thereby treat the subject or prevent the subject from disease, illness and, possibly, death.

The compositions, fusion proteins and polypeptides of the invention, can include, for example, one, two, three, four, five, six or more pathogen-associated molecular patterns (e.g., Pam2Cys, Pam3Cys, flagellin) and one, two, three, four, five, six or more antigens. When two or more PAMPs and/or two or more antigens and/or viral proteins comprise the compositions, fusion proteins and polypeptides of the invention, they are also referred to as "multimers."

The pathogen-associated molecular pattern can be a TLR5 agonist (e.g., at least a portion of at least one flagellin). The flagellin can be at least one member selected from the group consisting of a fljB/STF2, an *E. coli* fliC, and a *S. muenchen* fliC. The flagellin can include fljB/STF2 (e.g., SEQ ID NO: 1) or a flagellin lacking a hinge region (e.g., SEQ ID NO: 3).

The pathogen-associated molecular pattern can be a TLR2 agonist. The TLR2 agonist includes at least one member selected from the group consisting of a Pam2Cys and a Pam3Cys. Pam3Cys is ([Palmitoyl]-Cys((RS)-2,3-di(palmitoyloxy)-propyl cysteine). Pam3Cys is also referred to herein as "P2." Pam2Cys is (S-[2,3-bis(palmitoyloxy)propyl]cysteine).

The viral protein for use in the compositions, fusion proteins and polypeptides of the invention can be an envelope protein of at least one member selected from the group consisting of a West Nile viral envelope protein, a Langat viral envelope protein, a Kunjin viral envelope protein, a Murray Valley encephalitis viral envelope protein, a Japanese encephalitis viral envelope protein, a Tick-borne encephalitis viral envelope protein, a Yellow fever viral envelope protein and a Dengue viral envelope protein.

The compositions, fusion proteins and polypeptides of the invention can employ any portion of the envelope protein of a flavivirus. The compositions, fusion proteins and polypeptides of the invention can include at least a portion of at least one member selected from the group consisting of domain I, domain II and domain III of an envelope protein of a flavivirus. "At least a portion," as used herein, in reference to a domain of an envelope protein, means any part of the envelope protein domain or the entirety of the envelope protein. For example, SEQ ID NOS: 88 and 100-151, include at least a portion of domain III of the West Nile virus envelope protein.

"EI," "EII," and "EIII," as used herein, refer to domains I, II and III, respectively, of the West Nile flavivirus envelope protein. "JEI," "JEII," and "JEIII," as used herein, refer to domains I, II and III, respectively, of the Japanese encephalitis flavivirus envelope protein. "Den1 I," "Den1 II," and "Den1 III," as used herein refer to domains I, II and III, respectively, of the Dengue 1 flavivirus envelope protein. Likewise, designations for the domains of envelope proteins of other flaviviruses are referenced by the flavivirus name followed by the domain number (e.g., (Tick-borne) TBI (Tick-borne), TBII, TBIII, Den2 I, Den2 II, Den2 III).

The portion of an envelope protein of a flavivirus employed in the compositions, fusion proteins and polypeptides of the invention can include at least one member selected from the group consisting of at least a portion of domain I, at least a portion of domain II and at least a portion of domain III. When a domain is designated with a "+," for example "EIII+" or "JEIII+," the portion of the envelope protein referenced as "III" is one component of the total of that domain plus at least one of at least a portion of either or both of domains I and II. For example, "EIII+," as used herein, means the compositions, fusion proteins and polypeptides of the invention include domain III and at least a portion of domain I. "EIII+" is also referred to as "EI/III." "JEIII+" is also referred to as "JEI/III." Similarly, when compositions, fusion proteins and polypeptides of the invention include domains of envelope proteins of flavivirus, the domains can be any combination of domains I, II, and III and can be designated based on the domain. For example, EI/II includes domain I and II of the West Nile flavivirus. The absence of a "+" in reference to a domain (e.g., EIII, JEIII, Den1 III) of an envelope protein employed in the compositions, fusion proteins and polypeptides of the invention means that the composition, fusion protein and polypeptide includes the referenced domain. For example, "Den1 III" means the compositions, fusion proteins and compositions include domain III, not domains I and II, of the Dengue 1 virus.

The West Nile viral envelope protein for use in the compositions, fusion proteins and polypeptides of the invention can include at least a portion of at least one member selected from the group consisting of MEKLQLKGTTYGVCSKAF-KFLGTPADTGHGTVVLELQYTGTDGPCKVPISSVA SLNDLTPVGRLVTVNPFVSVATANAKV-LIELEPPFGDSYIVVGRGEQQINHHWH KSGSSIGK (SEQ ID NO: 7, which is an EIII+ amino acid sequence, the italicized amino acids are domain I of the envelope protein and the remaining sequence is domain III of the envelope protein); GTTYGVCSKAFKFARTPADTGHGTVV-LELQYTGKDGPCKVPISSVASLNDLTP VGRLVTVN-PFVSVATANSKVLIELEPPFGDSYIV-VGRGEQQINHHWHKSG (SEQ ID NO: 8, West Nile virus, Stanford, Conn., also referred to as "West Nile S");

GTTYGVCSKAFKFLGTPADTGHGTVV-
LELQYTGTDGPCKVPISSVASLNDLTPV GRLVTVN-
PFVSVATANAKVLIELEPPFGDSYV-
VGRGEQQINHHWHKSG (SEQ ID NO: 9, West Nile virus, New York, N.Y., also referred to as "West Nile NY"); and ELEPPFGDSYIVVGRGEQQINHHWHKS (SEQ ID NO: 10). SEQ ID NO: 7 is encoded by ATGGAAAAATTGCAGT-
TGAAGGGAACAACCTATGGCGTCTGTTCAAAGGCT
TTCAAGTTTCTTGGGACTCCCGCAGACA-
CAGGTCACGGCACTGTGGTGTTGG AATTGCAGTA-
CACTGGCACGGATGGACCTTGCAAAGT-
TCCTATCTCGTCAGT
GGCTTCATTGAACGACCTAACGC-
CAGTGGGCAGATTGGTCACTGTCAACCCT
TTTGTTTCAGTGGCCACGGC-
CAACGCTAAGGTCCTGATTGAATTGGAACCAC
CCTTTGGAGACTCATACATAGTG-
GTGGGCAGAGGAGAACAACAGATCAATC ACCAT-
TGGCACAAGTCTGGAAGCAGCATTGGCAAA (SEQ ID NO: 11). The West Nile viral envelope protein can include a protein that has at least about 70% identity, at least about 75% identity, at least about 80% identity, at least about 85% identity, at least about 90% identity, at least about 95% identity and at least about 99% identity to a polypeptide that includes SEQ ID NO: 7, which include portions of domains I and III (referred to herein as "EIII+") of the West Nile virus.

The Langat virus envelope protein for use in the compositions, fusion proteins and polypeptides of the invention can include at least a portion of GLTYTVCDKTK-
FTWKRAPTDSGHDTVVMEVGFSGTR-
PCRIPVRAVAHGVPEV NVAMLITPNPTMENNGGGFI-
EMQLPPGDNIIYVGDLNHQWFQKG (SEQ ID NO: 12). The Kunjin virus envelope protein can include at least a portion of GTTYGVCSKAFRFLGTPADTGHGTVV-
LELQYTGTDGPCKIPISSVASLNDLTPV GRLVTVN-
PFVSVSTANAKVLIELEPPFGDSYIV-
VGRGEQQINHHWHKSG (SEQ ID NO: 13). The Murray Valley encephalitis envelope protein can include at least a portion of GTTYGMCTEKFTFSKNPADTGHGTVV-
LELQYTGSDGPCKIPISSVASLNDMTPV GRMVTAN-
PYVASSTANAKVLVEIEPPFGDSYIV-
VGRGDKQINHHWHKEG (SEQ ID NO: 14). The Japanese encephalitis envelope protein can include at least one member selected from the group consisting of at least a portion of GTTYGMCTEKFSFAKNPADTGHGTV-
VIELSYSGSDGPCKIPIVSVASLNDMTPV GRLVTVN-
PFVATSSANSKVLVEMEPPFGSDYIVVG-
MGDKQINHHWHKAG (SEQ ID NO: 15) and EMEPPFGDSYIVVMGDKQINHHWHKA (SEQ ID NO: 16). The Tick-borne encephalitis envelope protein can include at least a portion of GLTYTMCDKTK-
FTWKRAPTDSGHDTVVMEVTFSGTK-
PCRIPVRAVAHGSPDV NVAMLITPNPTIENNGGGFI-
EMQLPPGDNIIYVGELSHQWFQK (SEQ ID NO: 17). The Yellow fever virus envelope protein can include at least a portion of GLTYTMCDKTFTWKRAPTDSGHDTV-
VMEVTFSGTKPCRIPVRAVAHGSPDVN VAMLITPNP-
TIENNGGGFIEMQLPPGDNIIYVGELSHQWFQK (SEQ ID NO: 18). The envelope protein of a flavivirus can include at least a portion of at least one member selected from the group consisting of GTTYGMCSKKFTFRPADTGHGTVV-
LELQYSGDGPCKIPISVASKNDLTPVGRLV TVN-
PFVSSTANAKVLIEMEPPFGDSYIV-
VGGEQINHHWHKG (SEQ ID NO: 19) and GMSYSMCTGKFKVVKEIAETQHG-
TIVIRVQYEGDGSPCKIPFEIMDLEKRHVLG RLITVN-
PIVTEKDSPVNIEAEPPFGDSYIIIGVE-
PGQLKLNWFKK (SEQ ID NO: 40). SEQ ID NOS: 12, 13, 14, 15, 16, 17, 18, 19 and 40 are portions of domain III of the viral envelope protein.

In another embodiment, the invention is a composition comprising at least a portion of at least one pathogen-associated molecular pattern and at least a portion of at least one Den2 viral envelope protein, wherein the Den2 viral envelope protein is at least one member selected from the group consisting of EAEPPFGDSYIIIGVEPQQLKLNWFKK (SEQ ID NO: 22), SEQ ID NO: 40 and SEQ ID NO: 97.

The compositions, fusion proteins and polypeptides of the invention can include Den 1 (EAEPPFGESYIV-
VGAGEKALKLSWFKK (SEQ ID NO.: 20); Den 1 PR 94 (Puerto Rico, 1994) (ETEPPFGESYIV-
VGAGEKALKLSWFKK (SEQ ID NO: 21)); Den 3 (EAEP-
PFGESNIVIGIGDKALKINWYKK (SEQ ID NO: 23)); and Den 4 (ELEPPFGESYIVIGVGNSALTLHWFRK (SEQ ID NO: 24)). SEQ ID NOS: 20, 21, 22, 23 and 24 are portions of domain III of Den1, Den2, Den3 and Den4 flaviviruses. At least a portion of domain III of the four Dengue viruses can be employed together or separately in the compositions, fusion proteins or polypeptides of the invention. For example, domain III of Den1 (strain 16007), Den2 (strain 516803), Den3 (strain H53489) and Den4 (strain 703) can be employed separately or in combination. The pathogen-associated molecular pattern and Den2 envelope viral protein can be components of a fusion protein.

In still another embodiment, the invention is a composition comprising at least a portion of at least one pathogen-associated molecular pattern and at least a portion of at least one member selected from the group consisting of a Den1 viral envelope protein, a Den2 viral envelope protein, a Den3 viral envelope protein and a Den4 viral envelope protein.

In an additional embodiment, the invention is a fusion protein comprising at least a portion of at least one pathogen-associated molecular pattern and at least a portion of at least one viral protein selected from the group consisting of a West Nile viral protein, a Langat viral protein, a Kunjin viral protein, a Murray Valley encephalitis viral protein, a Japanese encephalitis viral protein, a Tick-borne encephalitis viral protein, a Yellow fever viral protein and a hepatitis C viral protein. The hepatitis C viral protein for use in the compositions, fusion proteins and polypeptides of the invention can include a polypeptide of at least one member selected from the group consisting of SEQ ID NO: 64 (FIG. 22) and SEQ ID NO: 65 (FIG. 23), which are encoded by SEQ ID NOS: 66 (FIG. 24) and 67 (FIG. 25), respectively.

In another embodiment, the invention is a fusion protein comprising at least a portion of at least one pathogen-associated molecular pattern and at least a portion of at least one member selected from the group consisting of a Den1 viral envelope protein, a Den2 viral envelope protein, a Den3 viral envelope protein and a Den4 viral envelope protein.

Fusion proteins of the invention can further include a linker between the pathogen-associated molecular pattern and the viral protein. The linker can be an amino acid linker. The amino acid linker can include synthetic or naturally occurring amino acid residues. The amino acid linker employed in the fusion proteins of the invention can include at least one member selected from the group consisting of a lysine residue, a glutamic acid residue, a serine residue, a cysteine residue and an arginine residue. "Amino acid linker," as used herein, is also referred to as a "peptide linker." The amino acid linker can include at least one member selected from the group consisting of a peptide of KGNSKLEGQLEFPRTS (SEQ ID NO: 26); EFCRYPAQWRPL (SEQ ID NO: 28); EFSRY-
PAQWRPL (SEQ ID NO: 60); KGNSKLEGQLEF- PRTSPVWWNSADIQHSGGRQCDGYLQNSPLRPL (SEQ ID NO: 62); EFSRYPAQWRPL (SEQ ID NO: 75); which are encoded by AAGGGCAATTCGAAGCTTGAAGGTCAATTGGAATTCCCTAGGACTAGT (SEQ ID NO: 25); GAATTCTGCAGATATCCAGCACAGTGGCGGCCGCTC (SEQ ID NO: 27); GAATTCTCTAGATATCCAGCACAGTGGCGGCCGCTC (SEQ ID NO: 61); AAGGGCAATTCGAAGCTTGAAGGTCAATTGGAATTCCCTAGGACTAGTCCA GTGTGGTGGAATTCTGCAGATATCCAGCACAGTGGCGGCCGCCAGTGTGAT GGATATCTGCAGAATTCGCCCTTGCGGCCGCTC (SEQ ID NO: 63); and GAATTCTCTAGATATCCAGCACAGTGGCGGCCGCT ((SEQ ID NO: 74).

The fusion proteins of the invention can further include a linker between at least one component of the fusion protein (e.g., Pam3Cys, Pam2Cys, flagellin, PAMP) and at least one other component of the fusion protein (e.g., at least a portion of an antigen, at least a portion of a viral protein) of the composition, a linker between at least two of similar components of the fusion protein (e.g., Pam3Cys, Pam2Cys, flagellin, PAMP, at least a portion of an antigen, at least a portion of a viral protein) or any combination thereof.

"Linker," as used herein in reference to a fusion protein of the invention, refers to a connector between components of the fusion protein in a manner that the components of the fusion protein are not directly joined. For example, one component of the fusion protein (e.g., Pam3Cys, Pam2Cys, PAMP) can be linked to a distinct component (e.g., at least a portion of an antigen, at least a portion of a viral protein) of the fusion protein. Likewise, at least two or more similar or like components of the fusion protein can be linked (e.g., two PAMPs can further include a linker between each PAMP, or two antigens can further include a linker between each antigen, or two viral proteins can further include a linker between each viral protein).

Additionally or alternatively, the fusion proteins of the invention can include a combination of a linker between distinct components of the fusion protein and similar or like components of the fusion protein. For example, a fusion protein can comprise at least two PAMPs, Pam3Cys and/or Pam2Cys components that further includes a linker between, for example, two or more PAMPs; at least two antigens or at least two viral proteins that further include a linker between them; a linker between one component of the fusion protein (e.g., PAMP) and another distinct component of the fusion protein (e.g., at least a portion of an antigen, at least a portion of a viral protein), or any combination thereof. Thus, the fusion proteins of the invention can further include a linker between at least two pathogen-associated molecular patterns, a linker between at least two antigens, a linker between at least two viral proteins, or any combination thereof.

The pathogen-associated molecular pattern of the fusion proteins of the invention can be fused to a carboxy-terminus, an amino-terminus or both a carboxy- and an amino-terminus of an antigen or at least a portion of a viral protein (e.g., a flavivirus viral protein, such as at least a portion of domain III of the West Nile envelope protein, referred to as "EII," at least a portion of domain III of Dengue1 envelope protein) referred to as "Den1 III." "Fused to," as used herein, means covalently or noncovalently linked or recombinantly produced together.

The fusion proteins of the invention can include at least one pathogen-associated molecular pattern between at least two antigens or at least two viral proteins, which can, optionally, include a linker between the pathogen-associate molecular pattern and the antigen or the viral protein. The fusion proteins of the invention can include a pathogen-associated molecular pattern fused between at least two viral proteins (e.g., designated as "viral protein.PAMP.viral protein"). The fusion proteins of the invention can include an antigen or a viral protein fused between at least two pathogen-associated molecular patterns (e.g., designated as "PAMP.viral protein.PAMP").

The pathogen-associated molecular pattern of the fusion proteins of the invention can be a TLR5 agonist, such as a flagellin. The antigen or viral protein of the fusion proteins of the invention can be fused to the flagellin in a region of the flagellin that lacks at least a portion of a hinge region of the flagellin. For example, at least a portion of the hinge region of the fljB/STF2 flagellin of SEQ ID NO: 1 (FIG. 1) can be deleted and an antigen or a viral protein can be fused to the flagellin in the region of the deletion.

The antigen or viral protein of the fusion proteins of the invention can be fused to the flagellin in a region of the flagellin that contains a hinge region of the flagellin. For example, an antigen or viral protein can be fused to the fljB/STF2 flagellin of SEQ ID NO: 1 (FIG. 1) at any place in the hinge region, for example, at any place with amino acids 176-415 of SEQ ID NO: 1.

The antigen or viral protein of the fusion proteins of the invention can be fused to the flagellin in a region of the flagellin that lacks a hinge region of the flagellin, wherein the hinge region has been replaced with an artificial hinge region, such as an amino acid linker. For example, an antigen or viral protein can be fused to the fljB/STF2Δ flagellin of SEQ ID NO: 3 (FIG. 3) by placing an amino acid linker (also referred to herein as an "artificial hinge" or "an artifical hinge region" or "an artificial hypervariable region"), as depicted, for example, with the placement of an amino acid linker (HGAPVDPASPW, SEQ ID NO: 183) between amino acids 175 to 186 of SEQ ID NO: 3.

In another embodiment, the invention is a fusion protein comprising at least a portion of at least one member selected from the group consisting of fljB/STF2, an *E. coli* fliC, and a *S. muenchen* fliC and at least a portion of at least one member selected from the group consisting of a Den1 viral envelope protein, a Den2 viral envelope protein, a Den3 viral envelope protein and a Den4 viral envelope protein. The portion of the envelope protein can be at least a portion of at least one member selected from the group consisting of domain I, domain II and domain III of the envelope protein.

In still another embodiment, the invention includes a polypeptide that includes SEQ ID NOS: 71, 72, 30, 32, 34, 36, 38, 55, 76, 6, 80, 82, 84, 86 and 159 and a polypeptide encoded by SEQ ID NOS: 70, 73, 29, 31, 33, 35, 37, 54, 77, 5, 81, 83, 85, 87 and 158.

In an additional embodiment, the invention includes a polypeptide having at least about 70%, at least about 75%, at least about 80%, at least about 85%, at least about 90%, at least about 95%, at least about 98% and at least about 99% sequence identity to the polypeptides of SEQ ID NOS: 71, 72, 30, 32, 34, 36, 38, 55, 75, 6, 80, 82, 84, 86 and 159 and the nucleic acids of SEQ ID NOS: 70, 73, 29, 31, 33, 35, 37, 54, 77, 5, 81, 83, 85, 87 and 158.

In a further embodiment, the invention includes compositions, fusion proteins and polypeptides that include a polypeptide having a flagellin that includes polypeptides having at least about 70%, at least about 75%, at least about 80%, at least about 85%, at least about 90%, at least about 95%, at least about 98% and at least about 99% sequence identity to the polypeptides of SEQ ID NOS: 1, 3, 58 and 68 and the nucleic acids of 2, 4, 59 and 69.

The percent identity of two amino acid sequences (or two nucleic acid sequences) can be determined by aligning the sequences for optimal comparison purposes (e.g., gaps can be introduced in the sequence of a first sequence). The amino acid sequence or nucleic acid sequences at corresponding positions are then compared, and the percent identity between the two sequences is a function of the number of identical positions shared by the sequences (i.e., % identity=# of identical positions/total # of positions×100). The length of the protein or nucleic acid encoding a PAMP, at least a portion of a fusion protein, a viral protein, or a polypeptide of the invention aligned for comparison purposes is at least 30%, preferably, at least 40%, more preferably, at least 60%, and even more preferably, at least 70%, 75%, 80%, 85%, 90%, 95%, 98%, 99% or 100%, of the length of the reference sequence, for example, the nucleic acid sequence of a PAMP, at least a portion of a viral protein, or a polypeptide or fusion protein, for example, as depicted in SEQ ID NOS: 71, 72, 30, 32, 34, 36, 38, 55, 75, 6, 80, 82, 84, 86 and 159.

The actual comparison of the two sequences can be accomplished by well-known methods, for example, using a mathematical algorithm. A preferred, non-limiting example of such a mathematical algorithm is described in Karlin et al. (*Proc. Natl. Acad. Sci. USA*, 90:5873-5877 (1993), the teachings of which are hereby incorporated by reference in its entirety). Such an algorithm is incorporated into the BLASTN and BLASTX programs (version 2.2) as described in Schaffer et al. (*Nucleic Acids Res.*, 29:2994-3005 (2001), the teachings of which are hereby incorporated by reference in its entirety). When utilizing BLAST and Gapped BLAST programs, the default parameters of the respective programs (e.g., BLASTN; available at the Internet site for the National Center for Biotechnology Information) can be used. In one embodiment, the database searched is a non-redundant (NR) database, and parameters for sequence comparison can be set at: no filters; Expect value of 10; Word Size of 3; the Matrix is BLOSUM62; and Gap Costs have an Existence of 11 and an Extension of 1.

Another mathematical algorithm employed for the comparison of sequences is the algorithm of Myers and Miller, CABIOS (1989), the teachings of which are hereby incorporated by reference in its entirety. Such an algorithm is incorporated into the ALIGN program (version 2.0), which is part of the GCG (Accelrys, San Diego, Calif.) sequence alignment software package. When utilizing the ALIGN program for comparing amino acid sequences, a PAM120 weight residue table, a gap length penalty of 12, and a gap penalty of 4 is used. Additional algorithms for sequence analysis are known in the art and include ADVANCE and ADAM as described in Torellis and Robotti (Comput. Appl. Biosci., 10: 3-5 (1994), the teachings of which are hereby incorporated by reference in its entirety); and FASTA described in Pearson and Lipman (*Proc. Natl. Acad. Sci USA*, 85: 2444-2448 (1988), the teachings of which are hereby incorporated by reference in its entirety).

The percent identity between two amino acid sequences can also be accomplished using the GAP program in the GCG software package (Accelrys, San Diego, Calif.) using either a Blossom 63 matrix or a PAM250 matrix, and a gap weight of 12, 10, 8, 6, or 4 and a length weight of 2, 3, or 4. In yet another embodiment, the percent identity between two nucleic acid sequences can be accomplished using the GAP program in the GCG software package (Accelrys, San Diego, Calif.), using a gap weight of 50 and a length weight of 3.

The nucleic acid sequence encoding a PAMP, at least a portion of a viral protein, fusion proteins of the invention and polypeptides of the invention can include nucleic acid sequences that hybridize to, for example, a fljB/STF2 (e.g., SEQ ID NOS: 2, 4), a fliC (e.g., SEQ ID NOs: 59, 69), at least a portion of a viral protein (e.g., SEQ ID NOS: 39, 160, 162, 164, 166 and 177 and fusion proteins of the invention (e.g., SEQ ID NOS: 71, 72, 30, 32, 34, 36, 38, 55, 75, 6, 80, 82, 84 and 86) under selective hybridization conditions (e.g., highly stringent hybridization conditions). As used herein, the terms "hybridizes under low stringency," "hybridizes under medium stringency," "hybridizes under high stringency," or "hybridizes under very high stringency conditions," describe conditions for hybridization and washing of the nucleic acid sequences. Guidance for performing hybridization reactions, which can include aqueous and nonaqueous methods, can be found in Aubusel, F. M., et al., Current Protocols in Molecular Biology, John Wiley & Sons, N.Y. (2001), the teachings of which are hereby incorporated herein in its entirety.

For applications that require high selectivity, relatively high stringency conditions to form hybrids can be employed. In solutions used for some membrane based hybridizations, addition of an organic solvent, such as formamide, allows the reaction to occur at a lower temperature. High stringency conditions are, for example, relatively low salt and/or high temperature conditions. High stringency are provided by about 0.02 M to about 0.10 M NaCl at temperatures of about 50° C. to about 70° C. High stringency conditions allow for limited numbers of mismatches between the two sequences. In order to achieve less stringent conditions, the salt concentration may be increased and/or the temperature may be decreased. Medium stringency conditions are achieved at a salt concentration of about 0.1 to 0.25 M NaCl and a temperature of about 37° C. to about 55° C., while low stringency conditions are achieved at a salt concentration of about 0.15 M to about 0.9 M NaCl, and a temperature ranging from about 20° C. to about 55° C. Selection of components and conditions for hybridization are well known to those skilled in the art and are reviewed in Ausubel et al. (1997, Short Protocols in Molecular Biology, John Wiley & Sons, New York N.Y., Units 2.8-2.11, 3.18-3.19 and 4-64.9).

In yet another embodiment, the invention is a composition comprising at least one Pam3Cys and at least a portion of at least one flavivirus protein (e.g., at least one member selected from the group consisting of a West Nile viral protein, a Dengue viral protein, a Langat viral protein, a Kunjin viral protein, a Murray Valley encephalitis viral protein, a Japanese encephalitis viral protein, a Tick-borne encephalitis viral protein, a Yellow fever viral protein and a hepatitis C viral protein). The Dengue viral protein can be at least one member selected from the group consisting of a Den1 viral protein, a Den2 viral protein, a Den3 viral protein and a Den4 viral protein. The Pam3Cys and the flavivirus protein can be components of a fusion protein.

An additional embodiment of the invention is a composition comprising at least one Pam2Cys and at least a portion of at least one flavivirus protein (e.g., at least one member selected from the group consisting of a West Nile viral protein, a Dengue viral protein, a Langat viral protein, a Kunjin viral protein, a Murray Valley encephalitis viral protein, a Japanese encephalitis viral protein, a Tick-borne encephalitis viral protein, a Yellow fever viral protein and a hepatitis C viral protein). The Dengue viral protein can be at least one member selected from the group consisting of a Den1 viral protein, a Den2 viral protein, a Den3 viral protein and a Den4 viral protein. The Pam2Cys and the flavivirus protein can be components of a fusion protein.

In still another embodiment, the invention is a method of stimulating an immune response in a subject, comprising the step of administering to the subject a composition that includes the compositions, fusion proteins and polypeptides of the invention.

"Stimulating an immune response," as used herein, refers to the generation of antibodies to at least a portion of an antigen or a viral protein (e.g., a West Nile viral protein, a Dengue viral protein, a Langat viral protein, a Kunjin viral protein, a Murray Valley encephalitis viral protein, a Japanese encephalitis viral protein, a Tick-borne encephalitis viral protein, a Yellow fever viral protein and a hepatitis C viral protein). Stimulating an immune response in a subject can include the production of humoral and/or cellular immune responses that are reactive against the antigen or viral protein. In stimulating an immune response in the subject, the subject may be protected from infection by the antigen or virus or conditions associated with infection by the antigen or virus that may diminish or be halted as a consequence of stimulating an immune response in the subject.

The compositions, fusion proteins and polypeptides of the invention for use in methods to stimulate immune responses in subjects, can be evaluated for the ability to stimulate an immune response in a subject using well-established methods. Exemplary methods to determine whether the compositions, fusion proteins and polypeptides of the invention stimulate an immune response in a subject, include measuring the production of antibodies specific to the antigen or viral protein (e.g., IgG antibodies) by a suitable technique such as, ELISA assays; the potential to induce antibody-dependent enhancement (ADE) of a secondary infection; macrophage-like assays; neutralization assessed by using the Plaque Reduction Neutralization Test ($PRNT_{80}$); the ability to generate serum antibodies in non-human models (e.g., mice, rabbits, monkeys) (Putnak, et al., *Vaccine* 23:4442-4452 (2005)); the ability to survive a challenge of exposure to an antigen, in particular, a viral antigen employing non-human animals, such as mice and monkeys.

A "subject," as used herein, can be a mammal, such as a primate or rodent (e.g., rat, mouse). In a particular embodiment, the subject is a human.

In a further embodiment, the invention is a method of stimulating an immune response in a subject, comprising the step of administering to the subject a composition that includes at least a portion of at least one pathogen-associated molecular pattern and at least a portion of at least one viral protein selected from the group consisting of a West Nile viral protein, a Langat viral protein, a Kunjin viral protein, a Murray Valley encephalitis viral protein, a Japanese encephalitis viral protein, a Tick-borne encephalitis viral protein, and a Yellow fever virus protein.

In yet another embodiment, the invention is a method of stimulating an immune response in a subject, comprising the step of administering to the subject a composition that includes at least a portion of at least one pathogen-associated molecular pattern and at least a portion of at least one Den2 envelope protein, wherein the Den2 envelope protein is selected from the group consisting of SEQ ID NO: 22, SEQ ID NO: 40 and SEQ ID NO: 97.

In another embodiment, the invention is a method of stimulating an immune response in a subject, comprising the step of administering to the subject a fusion protein that includes at least a portion of at least one pathogen-associated molecular pattern and at least a portion of at least one viral protein selected from the group consisting of a West Nile viral protein, a Langat viral protein, a Kunjin viral protein, a Murray Valley encephalitis viral protein, a Japanese encephalitis viral protein, a Tick-borne encephalitis viral protein and a Yellow fever viral protein.

In still another embodiment, the invention is a method stimulating an immune response in a subject, comprising the step of administering to the subject a composition that includes at least a portion of at least one pathogen-associated molecular pattern and at least a portion of at least one member selected from the group consisting of a Den1 viral envelope protein, a Den2 viral envelope protein, a Den3 viral envelope protein and a Den4 viral envelope protein.

An additional embodiment of the invention is a method stimulating an immune response in a subject, comprising the step of administering to the subject a fusion protein that includes at least a portion of at least one member selected from the group consisting of a fljB/STF2, an *E. coli* fliC, and a *S. muenchen* fliC and at least a portion of at least one member selected from the group consisting of a Den1 viral envelope protein (e.g., KGMSYVMCTGSFKLEKEVAETQHGTVLVQVKYEGTDAPCKIPFSTQDEKGVT QNGRLITANPIVTDKEKPVNIEAEPPFG-ENYIVVGAGEKALKLSWFKK (SEQ ID NOS: 21 and 96)), a Den2 viral envelope protein (e.g., SEQ ID NOS: 22, 40 and KGMSYSMCTGKFKVVKEIAETQHG-TIVIRVQYEGDGSPCKTPFEIMDLEKRHVL GRLT-TVNPIVTEKDSPVNIEAEPPFGDSYII-IGVEPGQLKLDWFKK (SEQ ID NO: 97)), a Den3 viral envelope protein (e.g., SEQ ID NO: 23 and KGMSYAM-CLNTFVLKKEVSETQHGTIL-IKVEYKGEDAPCKIPFSTEDGQKAH NGRLITANPV-VTKKEEPVNIEAEPPFGESNIVIGIGDKALKINWYRK (SEQ ID NO: 98)) and a Den4 viral envelope protein (e.g., SEQ ID NO: 24 and KGMSYTMCSGKFSIDKEMAETQH-GTTVVKVKYEGAGAPCKVPIEIRDVNKEK VVGRI-ISPTPFAENTNSVTNIELER-PLDSYIVIGVGDSALTLHWFRK (SEQ ID NO: 99)).

In a further embodiment, the invention is a method of stimulating an immune response in a subject, comprising the step of administering to the subject a fusion protein that includes at least a portion of at least one pathogen-associated molecular pattern and at least a portion of at least one member selected from the group consisting of a Den1 viral envelope protein, a Den2 viral envelope protein, a Den3 viral envelope protein and a Den4 viral envelope protein.

In yet another embodiment, the invention is a method of stimulating an immune response in a subject, comprising the step of administering to the subject a composition comprising at least a portion of at least one antigen and at least a portion of at least one flagellin, wherein at least one of the flagellins lack at least a portion of a hinge region.

In another embodiment, the invention is a method of stimulating an immune response in a subject, comprising the step of administering to the subject a fusion protein comprising at least a portion of at least one antigen and at least a portion of at least one flagellin, wherein at least one of the flaggelins lack at least a portion of a hinge region.

In another embodiment, the invention is a method of stimulating an immune response in a subject, comprising the step of administering to the subject a fusion protein comprising at least a portion of at least one antigen and at least a portion of at least one flagellin, wherein at least one of the flagellins lack at least a portion of the hinge region.

In another embodiment, the invention is a method of stimulating protective immunity in a subject, comprising the step of administering to the subject a composition that includes at least a portion of at least one pathogen-associated molecular pattern and at least a portion of at least one viral protein selected from the group consisting of a West Nile viral protein, a Langat viral protein, a Kunjin viral protein, a Murray Valley encephalitis viral protein, a Japanese encephalitis viral protein, a Tick-borne encephalitis viral protein, and a Yellow fever virus protein.

In a further embodiment, the invention is a method of stimulating protective immunity in a subject, comprising the step of administering to the subject a composition that includes at least a portion of at least one pathogen-associated molecular pattern and at least a portion of at least one Den2 envelope protein, wherein the Den2 envelope protein is at least one member selected from the group consisting of SEQ ID NO: 22, SEQ ID NO: 40 and SEQ ID NO: 97.

In still another embodiment, the invention is a method of stimulating protective immunity in a subject, comprising the step of administering to the subject a fusion protein that includes at least a portion of at least one pathogen-associated molecular pattern and at least a portion of at least one viral protein selected from the group consisting of a West Nile viral protein, a Langat viral protein, a Kunjin viral protein, a Murray Valley encephalitis viral protein, a Japanese encephalitis viral protein, a Tick-borne encephalitis viral protein and a Yellow fever viral protein.

In an additional embodiment, the invention is a method of stimulating protective immunity in a subject, comprising the step of administering to the subject a composition that includes at least a portion of at least one pathogen-associated molecular pattern and at least a portion of at least one member selected from the group consisting of a Den1 viral envelope protein, a Den2 viral envelope protein, a Den3 viral envelope protein and a Den4 viral envelope protein.

In another embodiment, the invention is a method of stimulating protective immunity in a subject, comprising the step of administering to the subject a fusion protein that includes at least a portion of at least one member selected from the group consisting of a *Salmonella typhimurium* flagellin type 2 (fljB/STF2), an *E. coli* fliC, and a *S. muenchen* fliC and at least a portion of at least one member selected from the group consisting of a Den1 viral envelope protein, a Den2 viral envelope protein, a Den3 viral envelope protein and a Den4 viral envelope protein.

In a further embodiment, the invention is a method of stimulating protective immunity in a subject, comprising the step of administering to the subject a fusion protein that includes at least a portion of at least one pathogen-associated molecular pattern and at least a portion of at least one member selected from the group consisting of a Den1 viral envelope protein, a Den2 viral envelope protein, a Den3 viral envelope protein and a Den4 viral envelope protein.

In yet another embodiment, the invention is a method of stimulating protective immunity in a subject, comprising the step of administering to the subject a composition comprising at least a portion of at least one antigen and at least a portion of at least one flagellin, wherein at least one of the flagellins lacks at least a portion of a hinge region.

In yet another embodiment, the invention is a method of stimulating protective immunity in a subject, comprising the step of administering to the subject a fusion protein comprising at least a portion of at least one antigen and at least a portion of at least one flagellin, wherein at least one of the flagellins lacks at least a portion of a hinge region.

"Stimulates a protective immune response," as used herein, means administration of the compositions of the invention, such as the fusion proteins (e.g., fusion proteins that include a TLR agonist and at least a portion of a flavivirus), results in production of antibodies to the protein to thereby cause a subject to survive challenge by an otherwise lethal dose of a viral protein, such as a flavivirus. Techniques to determine a lethal dose of a virus (e.g., a flavivirus) are known to one of skill in the art (see, for example, Harmon, M. W., et al., *J. Clin. Microbiol.* 26:333-337 (1988); Reed, L. J., et al., *Am. J. Hyg.* 27:493-497 (1938); Rose, T., et al., *J. Clin. Microbiol.* 37:937-943 (1999); Walls, H. H. et al., *J. Clin. Microbiol.* 23:240-245 (1986); Current Protocols in Immunology, 19.11.1-19.11.32, Cottey, R., et al., John Wiley & Sons, Inc (2001)). Exemplary techniques for determining a lethal dose can include administration of varying doses of virus and a determination of the percent of subjects that survive following administration of the dose of virus (e.g., $LD_{10}$, $LD_{20}$, $LD_{40}$, $LD_{50}$, $LD_{60}$, $LD_{70}$, $LD_{80}$, $LD_{90}$). For example, a lethal dose of a virus that results in the death of 50% of a population of subjects is referred to as an "$LD_{50}$"; a lethal dose of a virus that results in the death of 80% of a population of subjects is referred to herein as "$LD_{80}$"; a lethal dose of a virus that results in death of 90% of a population of subjects is referred to herein as "$LD_{90}$."

For example, determination of the $LD_{90}$ can be conducted in subjects (e.g., mice) by administering intranasally or intrapentoneally varying doses (e.g., dilutions, such as log and half-log dilutions of plague forming units (pfu) (e.g., 10 pfu) followed by an assessment of the survival of the subjects about 14 days to about 21 days after infection with the virus. Protective immunity can be assessed by physical appearance of the subject, general demeanor (active), weight (initial loss of weight followed by return to a weight about the weight of the subject prior to infection with the virus) and survival after about 14 to about 21 days following infection with the flavivirus.

Assessment of stimulation of protective immunity can also be made by employing assays that assess the ability of the antibodies produced in response to the compositions of the invention (e.g., a portion of a flavivirus, such as a protein portion of West Nile virus, JE virus or Dengue virus) to result in survival of the subject (see, for example, Current Protocols in Immunonology, 19.11.1-19.11.32, Cottey, R., et al., John Wiley & Sons, Inc (2001)).

In another embodiment, the invention is a method of making fusion proteins or components of fusion proteins (e.g., TLR agonists, at least a portion of a flavivirus) described herein. Methods for making fusion proteins and the components of fusion proteins can include production of fusion proteins in host cells (e.g., eukaroytic host cells, prokaryotic host cells) by, for example, transfecting or transforming host cells with nucleic acid constructs encoding the fusion proteins or components of the fusion proteins.

The methods of making a protein that stimulates an immune response or stimulates a protective immune response in a subject can further include the step of deleting at least one glycosylation site in the nucleic acid sequence encoding the PAMP, TRL agonist or antigen (e.g., flavivirus). The glycosylation site that is deleted can include an N-glycosylation site or an O-glycosylation site.

The host cell employed in the methods described herein can be a prokaryotic host cell. The prokaryotic host cell can be at least one member selected from the group consisting of an *E. coli* prokaryotic host cell, a *Pseudomonas* prokaryotic host cell, a *Bacillus* prokaryotic host cell, a *Salmonella* prokaryotic host cell and a *P. fluorescens* prokaryotic host cell.

The eukaryotic host cells employed in the methods of the invention can include a *Saccharomyces* eukaryotic host cell, an insect eukaryotic host cell (e.g., at least one member selected from the group consisting of a *Baculovirus* infected insect cell, such as *Spodoptera frugiperda* (Sf9) or *Trichhoplusia ni* (High5) cells; and a *Drosophila* insect cell, such as Dme12 cells), a fungal eukaryotic host cell, a parasite eukaryotic host cell (e.g., a *Leishmania tarentolae* eukaryotic host cell), CHO cells, yeast cells (e.g., *Pichia*) and a *Kluyveromyces lactis* host cell.

Suitable eukaryotic host cells and vectors can also include plant cells (e.g., tomato; chloroplast; mono- and dicotyledonous plant cells; *Arabidopsis thaliana; Hordeum vulgare, Zea mays*, potato, such as *Solanum tuberosum*; carrot, such as *Daucus carota* L.; and tobacco, such as *Nicotiana tabacum, Nicotiana benthamiana* (Gils, M., et al., *Plant Biotechnol J.* 3:613-20 (2005); He, D. M., et al., *Colloids Surf B Biointerfaces*, (2006); Huang, Z., et al., *Vaccine* 19:2163-71 (2001); Khandelwal, A., et al., *Virology.* 308:207-15 (2003); Marquet-Blouin, E., et al., *Plant Mol Biol* 51:459-69 (2003); Sudarshana, M. R., et al. *Plant Biotechnol J.* 4:551-9 (2006); Varsani, A., et al., *Virus Res,* 120:91-6 (2006); Kamarajugadda S., et al., *Expert Rev Vaccines* 5:839-49 (2006); Koya V, et al., *Infect Immun.* 73:8266-74 (2005); Zhang, X., et al., *Plant Biotechnol J.* 4:419-32 (2006)).

The proteins made by the methods of the invention and the compositions of the invention can be purified and characterized employing well-known methods (e.g., gel chromatography, cation exchange chromatography, SDS-PAGE), as described herein.

In a further embodiment, the invention is the host cells and vectors that include the nucleic acid sequences of the invention or encoded fusion proteins of the invention.

An "effective amount," when referring to the amount of a composition, fusion protein or a polypeptide of the invention, refers to that amount or dose of the composition, fusion protein, or a polypeptide, that, when administered to the subject is an amount sufficient for therapeutic efficacy (e.g., an amount sufficient to stimulate an immune response in the subject). The compositions, fusion proteins, or polypeptides of the invention can be administered in a single dose or in multiple doses.

The methods of the present invention can be accomplished by the administration of the compositions, fusion proteins or polypeptides of the invention by enteral or parenteral means. Specifically, the route of administration is by oral ingestion (e.g., drink, tablet, capsule form) or intramuscular injection of the composition, fusion protein or polypeptide. Other routes of administration as also encompassed by the present invention including intravenous, intradermal, intraarterial, intraperitoneal, or subcutaneous routes, and nasal administration. Suppositories or transdermal patches can also be employed.

The compositions, fusion proteins or polypeptides of the invention can be administered ex vivo to a subject's autologous dendritic cells. Following exposure of the dendritic cells to the composition, fusion protein or polypeptide of the invention, the dendritic cells can be administered to the subject.

The compositions, fusion proteins or polypeptides of the invention can be administered alone or can be coadministered to the patient. Coadminstration is meant to include simultaneous or sequential administration of the composition, fusion protein or polypeptide of the invention individually or in combination. Where the composition, fusion protein or polypeptide are administered individually, the mode of administration can be conducted sufficiently close in time to each other (for example, administration of the composition close in time to administration of the fusion protein) so that the effects on stimulating an immune response in a subject are maximal. It is also envisioned that multiple routes of administration (e.g., intramuscular, oral, transdermal) can be used to administer the compositions and fusion proteins of the invention.

The compositions, fusion proteins or polypeptide of the invention can be administered alone or as admixtures with conventional excipients, for example, pharmaceutically, or physiologically, acceptable organic, or inorganic carrier substances suitable for enteral or parenteral application which do not deleteriously react with the extract. Suitable pharmaceutically acceptable carriers include water, salt solutions (such as Ringer's solution), alcohols, oils, gelatins and carbohydrates such as lactose, amylose or starch, fatty acid esters, hydroxymethycellulose, and polyvinyl pyrolidine. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like which do not deleteriously react with the compositions, fusion proteins or polypeptides of the invention. The preparations can also be combined, when desired, with other active substances to reduce metabolic degradation. The compositions, fusion proteins or polypeptides of the invention can be administered by is oral administration, such as a drink, intramuscular or intraperitoneal injection. The compositions, fusion proteins, or polypeptides alone, or when combined with an admixture, can be administered in a single or in more than one dose over a period of time to confer the desired effect (e.g., alleviate prevent flavivirus infection, to alleviate symptoms of flavivirus infection).

When parenteral application is needed or desired, particularly suitable admixtures for the compositions, fusion proteins or polypeptides are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampules are convenient unit dosages. The compositions, fusion proteins or polypeptides can also be incorporated into liposomes or administered via transdermal pumps or patches. Pharmaceutical admixtures suitable for use in the present invention are well-known to those of skill in the art and are described, for example, in Pharmaceutical Sciences (17th Ed., Mack Pub. Co., Easton, Pa.) and WO 96/05309 the teachings of which are hereby incorporated by reference.

The compositions, fusion proteins and polypeptides of the invention can be administered to a subject on a presenting carrier. "Presenting carrier," as used herein, means any composition that presents the compositions, fusion proteins and polypeptides of the invention to the immune system of the subject to generate an immune response in the subject. The presentation of the compositions, fusion proteins and polypeptides of the invention would preferably include exposure of antigenic portions of the viral protein to generate antibodies. The components (e.g., PAMP and a viral protein) of the compositions, fusion proteins and polypeptides of the invention are in close physical proximity to one another on the presenting carrier. The compositions, fusion proteins and polypeptides of the invention can be attached to the presenting carrier by covalent or noncovalent attachment. Preferably, the presenting carrier is biocompatible. "Biocompatible," as used herein, means that the presenting carrier does not generate an immune response in the subject (e.g., the production of antibodies). The presenting carrier can be a biodegradable substrate presenting carrier, such as a polymer bead or a liposome. The presenting carrier can further include alum or other suitable adjuvants. The presenting carrier can be a virus (e.g., adenovirus, poxvirus, alphavirus), bacteria (e.g., *Salmonella*) or a nucleic acid (e.g., plasmid DNA).

The compositions and methods of the invention can further include a carrier. "Carrier," as used herein, refers to a molecule (e.g., protein, peptide) that can enhance stimulation of a protective immune response. Carriers can be physically attached (e.g., linked by recombinant technology, peptide synthesis, chemical conjugation or chemical reaction) to a composition (e.g., a protein portion of a naturally occurring viral hemagglutinin) or admixed with the composition.

Carriers for use in the methods and compositions described herein can include, for example, at least one member selected from the group consisting of Tetanus toxoid (TT), *Vibrio cholerae* toxoid, Diphtheria toxoid (DT), a cross-reactive mutant (CRM) of diphtheria toxoid, *E. coli* enterotoxin, *E. coli* B subunit of heat labile enterotoxin (LTB), Tobacco mosaic virus (TMV) coat protein, protein Rabies virus (RV) envelope protein (glycoprotein), thyroglobulin (Thy), heat shock protein HSP 60 Kda, Keyhole limpet hemocyamin (KLH), an early secreted antigen tuberculosis-6 (ESAT-6), exotoxin A, choleragenoid, hepatitis B core antigen, and the outer membrane protein complex of *N. meningiditis* (OMPC) (see, for example, Schneerson, R., et al., *Prog Clin Biol Res* 47:77-94 (1980); Schneerson, R., et al., *J Exp Med* 152:361-76 (1980); Chu, C., et al., *Infect Immun* 40: 245-56 (1983); Anderson, P., *Infect Immun* 39:233-238 (1983); Anderson, P., et al., *J Clin Invest* 76:52-59 (1985); Fenwick, B. W., et al., 54: 583-586 (1986); Que, J. U., et al. *Infect Immun* 56:2645-9 (1988); Que, J. U., et al. *Infect Immun* 56:2645-9 (1988); (Que, J. U., et al. *Infect Immun* 56:2645-9 (1988); Murray, K., et al., *Biol Chem* 380:277-283 (1999); Fingerut, E., et al., *Vet Immunol Immunopathol* 112:253-263 (2006); and Granoff, D. M., et al., *Vaccine* 11:Suppl 1:S46-51 (1993)).

Exemplary carrier proteins for use in the methods and compositions described herein can include at least one member selected from the group consisting of SEQ ID NOS: 275-282:

```
Cross-reactive mutant (CRM) of diphtheria toxin
including, CRM197
                                        (SEQ ID NO: 275)
GADDVVDSSKSFVMENFSSYHGTKPGYVDSIQKGIQKPKSGTQGNYDDDW

KGFYSTDNKYDAAGYSVDNENPLSGKAGGVVKVTYPGLTKVLALKVDNAE

TIKKELGLSLTEPLMEQVGTEEFIKRFGDGASRVVLSLPFAEGSSSVEYI

NNWEQAKALSVELETNFETRGKRGQDAMYEYMAQACAGNRVRRSVGSSLS

CINLDWDVIRDKTKTKIESLKEHGPIKNKMSESPNKTVSEEKAKQYLEEF

HQTALEHPELSELKTVTGTNPVFAGANYAAWAVNVAQVIDSETADNLEKT

TAALSILPGIGSVMGIADGAVHHNTEEIVAQSIALSSLMVAQAIPLVGEL

VDIGFAAYNFVESIINLFQVVHNSYNRPAYSPGHKTQPFLHDGYAVSWNT

VEDSIIRTGFQGESGHDIKITAENTPLPIAGVLLPTIPGKLDVNKSKTHI

SVNGRKIRMRCRAIDGDVTFCRPKSPVYVGNGVHANLHVAFHRSSSEKIH

SNEISSDSIGVLGYQKTVDHTKVNSKLSLFFEIKS

Coat protein of Tobacco mosaic virus (TMV) coat
protein
                                        (SEQ ID NO: 276)
MMAYSIPTPSQLVYFTENYADYIPFVNRLINARSNSFQTQSGRDELREIL

IKSQVSVVSPISRFPAEPAYYIYLRDPSISTVYTALLQSTDTRNRVIEVE

NSTNVTTAEQLNAVRRTDDASTAIHNNLEQLLSLLTNGTGVFNRTSFESA

SGLTWLVTTTPRTA

Coat protein of alfalfa mosaic virus (AMV)
                                        (SEQ ID NO: 277)
MSSSQKKAGGKAGKPTKRSQNYAALRKAQLPKPPALKVPVAKPTNTILPQ

TGCVWQSLGTPLSLSSSNGLGARFLYSFLKDFAAPRILEEDLIFRMVFSI
```

-continued

```
TPSHAGSFCLTDDVTTEDGRAVAHGNPMQEFPHGAFHANEKFGFELVFTA

PTHAGMQNQNFKHSYAVALCLDFDALPEGSRNPSYRFNEVWVERKAFPRA

GPLRSLITVGLFDDADDLDRQ

Coat protein of Potato virus X
                                        (SEQ ID NO: 278)
MTTPANTTQATGSTTSTTTKTAGATPATTSGLFTIPDGEFFSTARAIVAS

NAVATNEDLSKIEAIWKDMKVPTDTMAQAAWDLVRHCADVGSSAQTEMID

TGPYSNGISRARLAAAIKEVCTLRQFCMKYAPVVWNWMLTNNSPPANWQA

QGFKPEHKFAAFDFFNGVTNPAAIMPKEGLIRPPSEAEMNAAQTAAFVKI

TKARAQSNDFASLDAAVTRGRITGTTTAEAVVTLPPP

Porins from Neisseria sp, e.g., class I outer
membrane protein of Neisseria meningitides
                                        (SEQ ID NO: 279)
MRKKLTALVLSALPLAAVADVSLYGEIKAGVEGRNYQLQLTEAQAANGGA

SGQVKVTKVTKAKSRIRTKISDFGSFIGFKGSEDLGEGLKAVWQLEQDVS

VAGGGATQWGNRESFIGLAGEFGTLRAGRVANQFDDASQAIDPWDSNNDV

ASQLGIFKRHDDMPVSVRYDSPEFSGFSGSVQFVPAQNSKSAYKPAYWTT

VNTGSATTTTFVPAVVGKPGSDVYYAGLNYKNGGFAGNYAFKYARHANVG

RDAFELFLLGSGSDQAKGTDPLKNHQVHRLTGGYEEGGLNLALAAQLDLS

ENGDKTKNSTTEIAATASYRFGNAVPRISYAHGFDFIERGKKGENTSYDQ

IIAGVDYDFSKRTSAIVSGAWLKRNTGIGNYTQINAASVGLRHKF

Major fimbrial subunit protein type I (Fimbrillin)
                                        (SEQ ID NO: 280)
MVLKTSNSNRAFGVGDDESKVAKLTVMVYNGEQQEAIKSAENATKVEDIK

CSAGQRTLVVMANTGAMELVGKTLAEVKALTTELTAENQEAAGLIMTAEP

KTIVLKAGKNYIGYSGTGEGNHIENDPLKIKRVHARMAFTEIKVQMSAAY

DNIYTFVPEKIYGLIAKKQSNLFGATLVNADANYLTGSLTTFNGAYTPAN

YANVPWLSRNYVAPAADAPQGFYVLENDYSANGGTIHPTILCVYGKLQKN

GADLAGADLAAAQAANWVDAEGKTYYPVLVNFNSNNYTYDSNYTPKNKIE

RNHKYDIKLTITGPGTNNPENPITESAHLNVQCTVAEWVLVGQNATW

Mycoplasma fermentans macrophage activating
lipopeptide (MALP-2)
                                        (SEQ ID NO: 281)
MKKSKKILLGLSPIAAVLPAVAVSCGNNDESNISFKEKDISKYTTTNANG

KQVVKNAELLKLKPVLITDEGKIDDKSFNQSAFEALKAINKQTGIEINSV

EPSSNFESAYNSALSAGHKIWVLNGFKHQQSIKQYIDAHREELERNQIKI

IGIDFDIETEYKWFYSLQFNIKESAFTTGYAIASWLSEQDESKRVVASFG

VGAFPGVTTFNEGFAKGILYYNQKHKSSKIYHTSPVKLDSGFTAGEKMNT

VINNVLSSTPADVKYNPHVILSVAGPATFETVRLANKGQYVIGVDSDQGM

IQDKDRILTSVLKHIKQAVYETLLDLILEKEEGYKPYVVKDKKADKKWSH

FGTQKEKWIGVAENHFSNTEEQAKINNKIKEAIKMFKELPEDFVKYINSD

KALKDGNKIDNVSERLEAIISAINKAAK p19 protein of Mycobacterium tuberculosis
                                        (SEQ ID NO: 282)
ATTLPVQRHPRSLFPEFSELFAAFPSFAGLRPTFDTRLMRLEDEMKEGRY

EVRAELPGVDPDKDVDIMVRDGQLTIKAERTEQKDFDGRSEFAYGSFVRT

VSLPVGADEDDIKATYDKGILTVSVAVSEGKPTEKHIQIRSTN
```

The compositions of the invention can further include at least one adjuvant. Adjuvants contain agents that can enhance the immune response against substances that are poorly immunogenic on their own (see, for example, Immunology Methods Manual, vol. 2, I. Lefkovits, ed., Academic Press, San Diego, Calif., 1997, ch. 13). Immunology Methods Manual is available as a four volume set, (Product Code Z37,435-0); on CD-ROM, (Product Code Z37,436-9); or both, (Product Code Z37,437-7). Adjuvants can be, for example, mixtures of natural or synthetic compounds that, when administered with compositions of the invention, such as proteins that stimulate a protective immune response made by the methods described herein, further enhance the immune response to the protein. Compositions that further include adjuvants may further increase the protective immune response stimulated by compositions of the invention by, for example, stimulating a cellular and/or a humoral response (i.e., protection from disease versus antibody production). Adjuvants can act by enhancing protein uptake and localization, extend or prolong protein release, macrophage activation, and T and B cell stimulation. Adjuvants for use in the methods and compositions described herein can be mineral salts, oil emulsions, mycobacterial products, saponins, synthetic products and cytokines. Adjuvants can be physically attached (e.g., linked by recombinant technology, by peptide synthesis or chemical reaction) to a composition described herein or admixed with the compositions described herein.

The dosage and frequency (single or multiple doses) administered to a subject can vary depending upon a variety of factors, including prior exposure to an antigen, a viral protein, the duration of viral infection, prior treatment of the viral infection, the route of administration of the composition, fusion protein or polypeptide; size, age, sex, health, body weight, body mass index, and diet of the subject; nature and extent of symptoms of flavivirus exposure, flavivirus infection and the particular flavivirus responsible for the infection (e.g., a West Nile flavivirus, a Dengue flavivirus, a Langat flavivirus, a Kunjin flavivirus, a Murray Valley encephalitis flavivirus, a Japanese encephalitis flavivirus, a Tick-borne encephalitis flavivirus, a Yellow fever flavivirus and a hepatitis C flavivirus), kind of concurrent treatment, complications from the flavivirus exposure, flavivirus infection or other health-related problems. Other therapeutic regimens or agents can be used in conjunction with the methods and compositions, fusion proteins or polypeptides of the present invention. For example, the administration of the compositions, fusion proteins or polypeptides can be accompanied by other viral therapeutics or use of agents to treat the symptoms of the flavivirus infection (e.g., high fever, numbness, DHF, meningoencephalitis). Adjustment and manipulation of established dosages (e.g., frequency and duration) are well within the ability of those skilled in the art.

The teachings of all of the references cited herein are hereby incorporated by reference in their entirety.

The present invention is further illustrated by the following examples, which are not intended to be limited in any way.

EXEMPLIFICATION

Example 1

Materials and Methods

PCR Amplification and DNA primers

All PCR amplifications were performed using Pfu Ultra Hotstart PCR Master Mix (Catalog number 600630) from Stratagene (La Jolla, Calif.) according to the manufacturer's recommendations. DNA primers were purchased from Sigma Genosys and are described below.

```
STF28BGF-1:
                                        (SEQ ID NO: 41)
CTCGGGAGATCTGCACAAGTAATCAACACTAACAGTCT

STF28MCR-1:
                                        (SEQ ID NO: 42)
CCATGGGCTAGCAGGATCCACCGGCGCTCCCTGCACGTTCA

STF28MCF-2:
                                        (SEQ ID NO: 43)
GGAGCGCCGGTGGATCCTGCTAGCCCATGGACCGAAAACCCG

STF28ECR-2:
                                        (SEQ ID NO: 44)
TCTGCAGAATTCACGTAACAGAGACAGCACGTTCTGCGGGACGTCCCGCA

GAACGTGCTGTCTCTGTTACGTGAATTCTGCAGA pET24AR: 5
                                        (SEQ ID NO: 45)
TCCGGCGTAGAGGATCGAGA

STF2-E3R3:
                                        (SEQ ID NO: 46)
CAATTGACCTTCAAGCTTCGAATTGCCCTTACGTAACAGAGACAGCACGT

TCTG

AX-E3F3:
                                        (SEQ ID NO: 47)
AAGCTTGAAGGTCAATTGGAATTCCCTAGGACTAGTATGGAAAAATTGCA

GTTGAAG pET24AF:
                                        (SEQ ID NO: 48)
GCTTAATGCGCCGCTACAGG

5'WNE28:
                                        (SEQ ID NO: 49)
GCGGCCGCTCATGGAAAAATTGCAGTTGAAGGGAACAACC

3'WNE28:
                                        (SEQ ID NO: 50)
CCGCGGTTTGCCAATGCTGCTTCCAGACTTGT

NdeI-STF2:
                                        (SEQ ID NO: 51)
CCGGCATGCCATATGGCACAAGTAATCAACACTAACAGTCTGTCGCTGC

BlpI-EdIII:
                                        (SEQ ID NO: 52)
GCATGCTCAGCTTATTAAGGGTTTGCCAATGCTGCTTCCCAGACTTGTG

JE EIII primer:
                                        (SEQ ID NO: 53)
TACGTGAATTCAGCAGATATCCAGCAC
```

Cloning of pET/STF2Δ.EIII

Full length flagellin of *Salmonella typhimurium* fljb (flagellin phase 2) (also referred to herein as "STF2") is encoded by a 1.5 kb gene. A truncated version of the STF2 (STF2Δ, SEQ ID NO: 3, encoded by SEQ ID NO: 4) was generated by deleting the hyper-variable region that spans amino acids 170 to 415 of SEQ ID NO: 1. The deleted region was replaced with a short flexible linker (GAPVDPASPW, SEQ ID NO: 56) designed to facilitate interactions of the NH2 and COOH termini sequences necessary for TLR5 signaling. To generate this construct, a two-step PCR was used. In the first reaction, STF2.OVA ((FIG. 61) SEQ ID NO: 152 encoding amino acid sequence SEQ ID NO: 153 of FIG. 62) served as the DNA template and STF28BGF-1 and STF28MCR-1 were used as primer pairs. In a separate reaction, the same DNA template was combined with primers STF28MCF-2 and STF28ECR-2.

The PCR amplification reactions generated about 500 bp and about 270 bp fragments, respectively. These PCR products were combined in a final PCR reaction using STF28BGF-1 and STF28ECR-2 as primers. The amplified DNA product from this reaction (about 0.77 kb) was digested with BglII and EcoRI restriction enzymes and ligated into pMTBiP/V5-His B (Invitrogen, Carlsbad, Calif.) that had previously been digested with BglII and EcoRI and treated with alkaline phosphatase. An aliquot of the ligation mix was used to transform TOP 10 cells (InVitrogen, Carlsbad, Calif.). PCR screening was performed using vector specific primers, pMTFOR (methionine promoter) (CATCTCAGTGCAAC-TAAA, SEQ ID NO: 156) and BGHREV (bovine growth hormone poly A) (TAGAAGGCACAGTCGAGG, SEQ ID NO: 157), to identify several positive clones. All positive clones were further analyzed by restriction mapping analysis and confirmed by DNA sequencing. The resultant construct pMT/STF2Δ was used to generate pMT/STF2Δ.EIII+.

The domain III of the West Nile virus envelope protein (FIGS. 45 and 46) of pET/STF2Δ.EIII+ (SEQ ID NOS: 70, 71) was derived from the *Drosophila* expression plasmid pMT/STF2.E. This plasmid contains full-length STF2 (amino acids 1-506, SEQ ID NO: 1) fused to the West Nile Virus envelope protein (amino acids 1-406, SEQ ID NO:39, FIG. 45). The pMT/STF2.E (SEQ ID NO: 158) clone AX-1 was used as a DNA template and 5'WNE28 (SEQ ID NO: 49) and 3'WNE28 (SEQ ID NO: 50) served as primers for PCR amplification. In order to facilitate restriction analysis and subsequent cloning steps, the 5' primer encoded a novel NotI site (New England Biolabls, Beverly, Mass.) and the 3' primer contained a unique SacII site. The amplified EIII+ DNA fragment (345 bp; SEQ ID NO: 178 that encodes amino acids 292-406 of SEQ ID NO: 39) was subcloned into pCR-Blunt II-TOPO cloning vector (InVitrogen, Carlsbad, Calif.) to generate plasmid TOPOEIII. A stop codon was subsequently introduced downstream of the EIII+ sequence by blunting the SacII and SpeI restriction sites using T4 DNA polymerase.

To generate pMT/STF2Δ.EIII+ (SEQ ID NOS: 70, 71), the EIII+ fragment was isolated from TOPOEIII+ using NotI and BamHI restriction sites and ligated into the NotI and SacII restriction sites in pMT/STF2Δ. The BamHI site of the EIII+ DNA fragment and the SacII site of pMTSTF2Δ were blunted with T4 DNA polymerase prior to ligation. The STF2Δ.EIII+ sequence (SEQ ID NOS: 70, 71) from pMT/STF2Δ.EIII+ was isolated by PCR amplification using the primers NdeI-STF2 and BlpI-EdIII. To generate pET/STF2Δ.EIII+ (SEQ ID NO: 71), the PCR product was digested with NdeI and BlpI and ligated into pET24a plasmid that had been predigested with NdeI and BlpI. The ligation mix was transformed into Mach-1 cells (InVitrogen, Carlsbad, Calif.) and the cells were grown on LB supplemented with 50 µg/ml kanamycin. Several colonies were screened by restriction mapping and were verified by DNA sequencing.

Cloning of pET/STF2.EIII+

The West Nile virus EIII+ sequence of pET/STF2.EIII+ (SEQ ID NOS: 54, 55) was derived from pETSTF2.E (SEQ ID NOS: 158, 159). This *E. coli* expression plasmid contains full-length STF2 (amino acids 1-506) fused to the West Nile Virus envelope protein (amino acids 292-406 of SEQ ID NO: 39, which is SEQ ID NO: 7). In two independent PCR reactions, pET/STF2.E was used as the DNA template. One reaction used the primers pET24AR:5 (SEQ ID NO: 45) and STF2-E3R3: (SEQ ID NO: 46) and the other used AX-E3F3 (SEQ ID NO: 47) and pET24AF (SEQ ID NO: 48). These PCR reactions generated a 1.5 kb fragment that consisted of full-length STF2 and a 340 bp fragment that comprised the EIII domain plus additional amino acids that extended into domain I of the envelope protein. Aliquots of these PCR amplification reactions were combined, and the two products served as templates for a PCR reaction with the external primers pET24AR (SEQ ID NO: 45) and pET24AF (SEQ ID NO: 48). This resulted in the generation of about a 1.8 kb DNA fragment that fused EIII+ sequence (SEQ ID NO: 178, a nucleic acid sequence encoding amino acids 292-406 of SEQ ID NO: 39, which is SEQ ID NO: 7) to STF2. The PCR product was digested with NdeI and BlpI and gel purified and ligated by compatible ends to a pET24a vector that had previously been digested with compatible enzymes and de-phosphorylated. The ligation mix was transformed into Mach-1 cells (InVitrogen, Carlsbad, Calif.) as described for pET/STF2Δ.EIII+. Several colonies were screened by restriction mapping and two clones were verified by DNA sequencing.

Cloning of pET/STF2Δ.JEIII+

A portion of the envelope protein of a Japanese encephalitis virus (JEV) (strain SA-14-14-2 (Jai, L., et al., *Chin Med J (Eng)* 116:941-943 (2003)); currently employed in a JEV vaccine encoded by domain III was custom synthesized by DNA 2. Inc (Menlo Park, Calif.). The portion of domain III was excised from the pJ2:G01510 using NotI and Blp I site that flank the insert. The DNA insert was gel isolated and cloned by compatible ends to pET24A/STF2Δ.EIII+ (SEQ ID NOS: 70, 71) that had previously been digested with the appropriate enzymes to release the West Nile virus EIII+ insert. The deleted vector was then gel purified and ligated to an aliquot of JE EIII+. The ligation mix was used to transform TOP-10 cells (InVitrogen, Carlsbad, Calif.) and the cells were grown on LB supplemented with 50 µg/ml kanamycin. Several colonies were screened by restriction mapping and were verified by DNA sequencing.

The resulting construct, pET24A/STF2Δ.JEIII (SEQ ID NOS: 5, 6) was BLR (DE3) strain (Novagen) and expression was monitored in several clones using Commassie Blue staining which was confirmed by Western blot using anti-flagellin antibodies. Using, pET24A/STF2Δ.JEIII+ as the DNA template and the JE EIII+ oligonucleotide as primer (SEQ ID NO: 53) the cysteine residue in the linker region between STF2Δ and JEIII+ was changed to a serine residue using QuikChange Site Directed Mutagenesis Kit (Stratagene, LaJolla, Calif.) according to the manufacturer's instructions. The clone was verified by sequencing and assayed for expression as described for pET24A/STF2Δ.JEIII+ above.

When a cysteine residue in a linker in change to a serine residue the fusion protein in also referred to herein by inclusion of an "s" in the designation of the fusion protein. For example, "STF2Δ.EIII+" includes a cysteine residue in the linker (FIG. 29, SEQ ID NO: 71), whereas "STF2Δ.EIIIs+" include a serine residue substituted for the cysteine residue in the linker (FIG. 30, SEQ ID NO: 72).

Cloning the EIII Domain of Each Dengue Virus Fused to the C-Terminal End of Flagellin (STF2Δ)

Initially, obtaining biologically active material from the fusion of the entire envelope protein of West Nile virus was difficult, perhaps due to the presence of multiple cysteines residues (12 cysteines) in the envelope protein (see SEQ ID NO: 39, FIG. 45). However, when the region encoding domain III (EIII) of the protein was sub-cloned, the fusion protein was abundantly expressed in *E. coli* and was highly efficacious in mice. Although there is an overall sequence dissimilarity among the 4 distinct DEN viruses (Den1, Den2, Den3, Den4, SEQ ID NOS: 160-167, FIGS. 67-74) the three-dimensional structures within domain III of the envelope protein are similar among the flaviviruses. This domain in DEN and other flaviviruses encodes the majority of the type-specific contiguous critical/dominant neutralizing epitopes.

Domain III of the dengue viruses (Den1, Den2, Den3 and Den4) has been expressed in bacteria and shown to be immunogenic, capable of inducing neutralizing antibodies in experimental animals (Simmons, M., et al., *Am. J. Trop. Med Hyg* 65:159 (2001)). Domain III corresponding to residues about 295 to about 399 (exact numbering depends on the particular DEN virus, for example, of SEQ ID NOS: 160, 162, 164, 166) of the four different DEN viruses have been codon-optimized for expression in *E. coli*. The synthetic gene was amplified by using PCR and sub-cloned into the NotI site of the vector pET/STF2Δ generating pET/STF2Δ.DEN1EIII, pET/STF2Δ.DEN2EIII, pET/STF2Δ.DEN3EIII and pET/STF2Δ.DEN4EIII (SEQ ID NOS: 80, 82, 84 AND 86).

*E. coli* Production of STF2.EIII+, STF2Δ.EIII+, STF2Δ.EIIIs+ and STF2Δ.JEIII+

Cell cultures (6 L) of BLR(DE3) pLysS that harbor pETSTF2.EIII+ (SEQ ID NOS: 54, 55), pETSTF2Δ.EIII+ (SEQ ID NOS: 70, 71), pETSTF2Δ.EIIIs+ (SEQ ID NOS: 72, 73) or pETSTF2Δ.JEIII+ SEQ ID NOS: 5, 6) were grown in LB medium containing 15 μg/ml kanamycin, 12.5 μg/ml tetracycline and 24 μg/ml chloramphenicol. At an $OD_{600}$ of about 0.6 protein expression was induced with 1 mM IPTG for about 3 h at about 37° C. Following induction, cells were harvested by centrifugation (7000 rpm×7 minutes in a Sorvall RC5C centrifuge) and resuspended in 2×PBS, 1% glycerol, DNAse, 1 mM PMSF, protease inhibitor cocktail and 1 mg/ml lysozyme. The suspension was passed through a microfluidizer to lyse the cells and the lysate was centrifuged (45,000 g for one hour in a Beckman Optima L ultracentrifuge) to separate the soluble fraction from inclusion bodies. Under these growth and induction conditions, STF2.EIII+ was expressed as a soluble protein and STF2Δ.EIII+ (SEQ ID NOS: 70, 71), STF2Δ.EIIIs+ (SEQ ID NOS: 72, 73) and STF2Δ.JEIII+ (SEQ ID NOS: 5, 6) formed inclusion bodies.

Purification of STF2.EIII+

Cell lysate containing soluble STF2.EIII+ (SEQ ID NOS: 54, 55) was applied to Sepharose Q resin (Amersham Biosciences, Piscataway, N.J.) in the presence of 0.5 M NaCl to reduce DNA, endotoxin, and other contaminants. The flow-through fraction was collected and the conductivity adjusted by a 10-fold dilution with buffer A (Buffer A: 100 mM Tris-Cl, pH 8.0). The diluted material was re-loaded onto Q Sepharose and bound protein was eluted with a linear gradient from 20% to 60% Buffer B (Buffer B: 100 mM Tris-Cl, 1 M NaCl, pH 8.0). Fractions containing STF2.EIII+ were pooled and further processed by Superdex-200 gel (SD200) filtration chromatography in the presence of Na-deoxycholate to remove residual endotoxin (running buffer: 1% Na-deoxycholate, 100 mM NaCl, 100 mM Tris-HCl, 1% glycerol, pH 8.0). Following SD200 chromatography, the eluted protein was loaded directly onto Q Sepharose and washed extensively with buffer A to remove detergent. Bound protein was again eluted with a linear gradient from 20% to 60% Buffer B. In one preparation (Batch 057), this step was substituted with a detergent removal procedure using Extract-D detergent removal gel (Pierce Biotechnology, Rockford, Ill.). The purified protein was dialyzed against buffer containing 50 mM Tris, 100 mM NaCl and 1% glycerol and stored at −80° C.

Purification of STF2Δ.EIII+

STF2Δ.EIII+ inclusion bodies were collected by low-speed centrifugation (7000 rpm×7 minutes in a Sorvall RC5C centrifuge) and solubilized with buffer containing 8 M urea, 100 mM Tris-HCl, 5 mM EDTA, pH 8.0. The urea concentration of the solubilized protein was adjusted to 1 M and the sample was loaded onto Q Sepharose. The bound protein was eluted using a linear gradient from 0% to 100% Buffer B. (Buffer A: 100 mM Tris-HCl, 5 mM EDTA, 1 M urea, pH 8.0. Buffer B: 100 mM Tris-Cl, 5 mM EDTA, 1 M NaCl, 1 M urea, pH 8.0). Due to the formation of protein aggregates following elution, the urea concentration of the Q Sepharose material was adjusted to 8 M. The protein was further purified by gel filtration chromatography using SD200. The column was pre-equilibrated with 100 mM Tris-HCl, pH 8.0, 100 mM NaCl, 1% glycerol, 8 M urea plus 1% Na-deoxycholate. The eluted protein was subjected to a second IEX chromatography step using Source Q to remove 1% Na-deoxycholate. Bound protein was eluted with a linear gradient from 20% to 60% Buffer B. (Buffer A: 100 mM Tris-Cl, pH 8.0, 8 M urea, 5 mM EDTA. Buffer B: 100 mM Tris-HCl, pH 8.0, 5 mM EDTA, 8 M urea, 1 M NaCl). Final polishing of the protein was completed by gel filtration chromatography using SD200 (Running Buffer: 100 mM Tris-HCl, pH 8.0, 8 M urea, 100 mM NaCl and 1% glycerol). Reducing agent was added to the SD200 fraction (2.5 mM DTT) and the protein was refolded by step-wise dialysis against decreasing concentrations of urea. The urea concentration was reduced sequentially against buffers that contained 100 mM Tris-HCl, pH 8.0, 100 mM NaCl, 1% glycerol and 6 M, 4 M, 2 M or no urea.

Refolding and Purification of STF2Δ.EIII+ Trimer

STF2Δ.EIII+ (SEQ ID NOS: 70, 71) from urea-solubilized inclusion bodies was efficiently refolded to form trimer product by simple dialysis as described above the trimer (3 of thes STFΔ.EIII fusion proteins) was deduced based on molecular weight in SDS-PAGE. Following dialysis, endotoxin was removed by multiple extractions with Triton X-114. The trimer was purified and separated from monomer and aggregates by S200 size exclusion chromatography. The final product migrated as a single band with an apparent molecular weight of about 130 kDa on SDS-PAGE.

Refolding and Purification of STF2Δ.EIII+ Monomer

The monomeric form of STF2Δ.EIII+ (SEQ ID NOS: 70, 71) was produced consistently and efficiently by refolding using rapid dilution, which prevented individual STF2Δ.EIII+ fusion proteins from interacting with one another to form meutimers, such as trimers (supra). STF2Δ.EIII+ solubilized from inclusion bodies in 4M urea was raised to 8M urea without reductant. The protein was then rapidly diluted in Tris/NaCl/glycerol buffer, pH 8.0, to about 0.1 mg/ml and a final urea concentration of 0.1M at room temperature. The monomer was further purified and separated from aggregates by S200 size exclusion chromatography. The final product migrated as a single band with an apparent molecular weight of about 43 kDa on SDS-PAGE.

Purification of STF2Δ.EIIIs+ (Serine Substitution of the Linker Between STF2Δ and EIII+, SEQ ID NO: 72)

STF2Δ.EIIIs+ (SEQ ID NOS: 72, 73) from solubilized inclusion bodies was refolded using a rapid dilution method similar to that used to refold the STF2Δ.EIII+ monomer. The refolded protein was captured on a butyl sepharose column and eluted while removing most of the endotoxin contamination. Eluate from the butyl sepharose purification was concentrated and put through 4 cycles of Triton X-114 extractions to reduce endotoxin levels down to about <0.1 EU/μg before a final purification step over SD200 gel filtration. The final pooled product migrated as a single band with an apparent molecular weight of about 43 kDa on SDS-PAGE and contained a trace amount of Triton X-114 (about 0.000015%).

Purification of STF2Δ.JEIII+ (SEQ ID NOS: 5, 6)

Protein was isolated from inclusion bodies under denaturing conditions. Inclusion bodies were washed with detergent (0.5% Triton X 100) and solubilized in 8 M urea, resulting in partial purification of the target protein. For endotoxin removal, protein was applied on a Source S cation exchange column at low pH (about 3.5) and eluted with a salt gradient (0 to about 1M NaCl). The protein was refolded using rapid dilution as described for STF2Δ.EIII+ monomer. The protein was then concentrated and further purified using SD200 to separate the monomeric form of the protein from aggregates. The purified material migrated with an apparent molecular weight of about 43 kDa on SDS PAGE and contained acceptable levels of endotoxin (about 0.03 EU/ug).

Fed Batch Production of Fusion Proteins

STF2Δ.EIIIs+ was produced in an aerobic bioreactor using a fed batch process. Three control loops were placed to control pH by acid (2 N HCl) or base (3 N $NH_4OH$) addition, temperature by heating (heating blanket) or cooling (time cycled cooling loop), and dissolved oxygen by compressed air flow (manually controlled), agitation (mixing speed) and $O_2$ flow (timed cycled) in cascade. Cells [BLR(DE3) pLysS that harbor the STF2Δ.EIIIs+ were adapted to and banked in MRSF media (see infra), and frozen in 25% glycerol. Cells were scaled up for the bioreactor by adding 1 mL of banked cells to 1 L of MRSF media and agitating at about 37° C. for about 15.5 to about 16.5 hours. Cells from the scale up process were added in a about 1:10 ratio to MRSF or MRBR synthetic media at about 37° C. and about 0.5 vvm air flow.

The process was run in batch mode at about 37° C. until the cells oxygen consumption was such that the compressed air flow is about 1.5 vvm and the agitation is at the maximum, about 6 hours, when the temperature is dropped to between about 25° C. and about 33° C. The feed can be started before the culture is induced, or up to about 1 and about ½ hours after. The feed rate can be kept constant, or adjusted based on process variables (dissolved oxygen, glucose concentration). The culture was induced with IPTG upon batch glucose exhaustion. The culture was maintained for a minimum of about 2 hours and a maximum of about 20 hours.

| | g/L |
|---|---|
| MRBR Media Composition | |
| Glucose | 20 |
| $KH_2PO_4$ | 2.2 |
| $(NH_4)_2SO_4$ | 4.5 |
| Citric Acid | 1.0 |
| $MgSO_4(7H_20)$ | 1.0 |
| $CaCl_2$ | 0.04 |
| Trace Metals | 1 ml |
| Thiamine HCl | 0.01 |
| Antifoam | 0.05 |
| MRSF Media Composition | |
| Glucose | 10 (20 in bioreactor) |
| $KH_2PO_4$ | 7.8 |
| $(NH_4)_2SO4$ | 2.33 |
| Citric Acid | 1.0 |
| $MgSO_4(7H_20)$ | 1.0 |
| $CaCl_2$ | 0.04 |
| Trace Metals | 1 ml |
| Thiamine HCl | 0.01 |
| Kanamycin | 0.0075 (shake flask only) |
| Trace Metal Solution 1000x Component | |
| EDTA, disodium | 5 |
| $FeSO_4(7H_2O)$ | 10 |
| $ZnSO_4(7H_2O)$ | 2 |
| $MnSO_4(H_2O)$ | 2 |
| $CoC1_2(6H_2O)$ | 0.2 |
| $CuSO_4(5H_2O)$ | 0.1 |
| $Na_2MoO_4(2H_2O)$ | 0.2 |

-continued

| | g/L |
|---|---|
| $H_3BO_3$ | 0.1 |
| Feed Media Composition | |
| NaC1 | 0.5 |
| $FeSO_4(7H_2O)$ | 2 |
| $CaC1_2$ | 3.5 |
| $MgSO_4(7H_2O)$ | 12 |
| Thiamine HC1 | 1 |
| Trace Metals | 1 ml |
| Glucose | 100 |

STF2Δ.EIIIs+ was produced as inclusion bodies. Upon harvest, the cells were separated from the conditioned media by centrifugation (Beckman Avanti J-20 XP, JLA 8.1000 rotor, 10 kxg for about 20 minutes at about 4° C.) and resuspended in equal volume of 50 mM Tris, 100 mM NaCl, 1 mM EDTA, pH 8.0. The centrifugation was repeated under the same conditions, with the cells resuspended in a minimum volume of the same buffer. The suspension was passed through a homogenizer (APV-1000) at >10,000 psi for at least two passes.

The solids can be separated and the STF2Δ.EIIIs solubilized by one of three methods; centrifugation, filtration, or fluidized bed chromatography.

Method 1

Solids are separated by centrifugation (Beckman Avanti J-20 XP, JA 20 rotor, 20 kxg for 20 minutes at 4° C.) and resuspended in 50 mM tris, 1 m NaCl, 1 mM EDTA, 1% glycerol, 0.5% Triton X-100, pH 8.0. This process was repeated up to 6 times (total) at increasing speeds and times (to a maximum of about 40 kxg for about 20 minutes). After the final pellet recovery, the pellet was resuspended in 50 mM Tris, 0.1M NaCl, 1 mM EDTA, pH 8.0 and clarified by centrifugation (Beckman Avanti J-20 XP, JA 20 rotor, 40 kxg for about 20 minutes at about 4° C.) The pellet was resuspended and dissolved in 50 mM Tris, 0.1M NaCl, 1 mM EDTA, 4 M urea, pH 8.0. Insolubles were removed by centrifugation (Beckman Avanti J-20 XP, JA 20 rotor, 40 kxg for about 50 minutes at about 4° C.), the supernatant retained for further processing.

After the multiple washes described above, STF2Δ.EIIIs can also be dissolved in 50 mM acetate, 10 mM NaCl, 8M urea, pH about 4.1 to about 5.3 and clarified by centrifugation (Beckman Avanti J-20 XP, JA 20 rotor, 20 kxg for about 20 minutes).

Method 2

After homogenization, the lysate was captured in body feed and STF2Δ.EIIIs+ extracted with urea containing buffer. Body feed is a filter aid designed to trap particles in a cake above a depth filter. The body feed (Advanced Minerals Corporation CelPure 65) is a diatomite (silica powder) with a high surface area and low permeability, retaining <0.2 μm particles. The filter aid was pre-mixed with the lysate and pumped over a depth filter (Ertel 703), building up a cake containing both body feed and lysate particles. The suspension creates a depth filter as the particles settle on the filter pad. A 50 mM Tris, 100 mM NaCl pH 8.0 wash was performed to remove soluble proteins and nucleic acids. A subsequent wash with 50 mM Tris, 100 mM NaCl, 4 M urea, pH 8 solubilizes and removes the STF2Δ.EIIIs from the body feed for further processing.

Method 3

After the cells were initially resuspended in buffer, they were resuspended in sodium chloride and urea containing buffer at pH about 6 to about 8 and homogenized. The lysate was applied on a Streamline CST fluidized bed column (GE Healthcare) where the STF2Δ.EIIIs+ binds to the resin and the particulates flow through. STF2Δ.EIIIs+ may be eluted in low salt conditions at a pH greater than the load pH, in the presence or absence of detergents such as Triton X-100 or polysorbate 80.

SDS-PAGE

Proteins (typically about 5 μg) were diluted in SDS-PAGE sample buffer with and without β-mercaptoethanol. The samples were boiled for 5 minutes and loaded onto a 4-20% SDS polyacrylamide gel. Following electrophoresis, gels were stained with coomassie blue to visualize protein bands.

Endotoxin Assay

Endotoxin levels were measured using the QCL-1000 Quantitative Chromogenic LAL test kit (BioWhittaker #50-648U, Walkersville, Md.), following the manufacturer's instructions for the microplate method.

Protein Assay

Protein concentrations were determined by the MicroBCA Protein Assay Reagent Kit in a 96-well format using BSA as a standard (Pierce Biotechnology, Rockford, Ill.).

TLR5 Bioactivity Assay

HEK293 cells (ATCC, Catalog No. CRL-1573 Manassas, Va.) constitutively express TLR5, and secrete several soluble factors, including IL-8, in response to TLR5 signaling. Cells were seeded in 96-well microplates (about 50,000 cells/well), fusion proteins added and incubated overnight. The next day, the conditioned medium was harvested, transferred to a clean 96-well microplate, and frozen at −20° C. After thawing, the conditioned medium was assayed for the presence of IL-8 in a sandwich ELISA using an anti-human IL-8 matched antibody pair (Pierce, #M801E and #M802B, Rockford, Ill.) following the manufacturer's instructions. Optical density was measured using a microplate spectrophotometer (FARCyte, Amersham Biosciences, Piscataway, N.J.).

Plaque Reduction Neutralization Test (PRNT)

PRNT was performed according to Wang, et al., *J. Immunol.* 167:5273-5277 (2001). Briefly, serum samples were heat inactivated by incubation in a 56° C. water bath for about 30 min and were serially diluted in PBS with 5% gelatin from $\frac{1}{10}$ to $\frac{1}{2560}$. West Nile virus was diluted in PBS with 5% gelatin so that the final concentration was about 100 PFU/well. Virus was mixed with about 75 μl serum in a 96-well plate at about 37° C. for about 1 h. Aliquots of serum-virus mixture were inoculated onto confluent monolayers of Vero cells in a six-well tissue culture plate. The cells were incubated at about 37° C. for 1 h, and the plates were shaken every 15 min. The agarose overlay was then added. The overlay was prepared by mixing equal volumes of a solution consisting of 100 ml 2×MEM (Life Technologies) with sterile 2% agarose. Both solutions were placed in a 40° C. water bath for 1 h before adding the overlay. The cells were incubated for 4 days at 37° C. in a humidified 5% $CO_2$-air mixture. A second overlay with an additional 4% neutral red was added on day 5. Virus plaques were counted about 12 h later.

Antigenicity of STF2Δ-Fusion Proteins

ELISA plates (96-well) were coated overnight at 4° C. with serial dilutions (100 μl/well) of purified STF2Δ-fusion proteins (SEQ ID NOS: 158, 159, 54, 55, 70, 71) in PBS (about 2 μg/ml). Plates were blocked with 200 μl/well of Assay Diluent Buffer (ADB; BD Pharmingen) for one hour at room temperature. The plates were washed 3× in PBS-Tween, and then incubated with antibodies reactive with flagellin or the E domain of the construct. The expression of flagellin was detected using the mAb 6H11 (Intotek), while the antigenicity of WNV-E was monitored using a panel of mAb (5C5, 7H2, 5H10, 3A3, and 3D9) (Beasley, D. W., et al., *J. Virol.* 76:13097-13100 (2002)) were purchased from Bioreliance (Road Rockville, Md.). Antibodies diluted in ADB (about 100 μl/well) were incubated overnight at 4° C. The plates were washed 3× with PBS-T. HRP-labeled goat anti-mouse IgG antibodies (Jackson Immunochemical, West Grove, Pa.) diluted in ADB were added (100 μl/well) and the plates were incubated at room temperature for 1 hour. The plates were washed 3× with PBS-T. After adding TMB (3,3',5,5'-tetramentylbenzidine) Ultra substrate (Pierce Biotechnology, Rockford, Ill.) and monitoring color development, $A_{450}$ was measured on a Tecan Farcyte microspectrophotometer.

Immunization of Mice

C3H/HeN mice (10 per group) were immunized intraperitoneally or subcutaneously with the indicated concentrations of fusion proteins or synthetic peptides on days 0, 14 and 28. On days 21 and 35, immunized animals were bled by retro-orbital puncture. Sera were harvested by clotting and centrifugation of the heparin-free blood samples. On day 35, mice were challenged with a lethal dose of WNV strain 2741 (Wang, T., et al., *J. Immunol* 167:5273-5277 (2001)). Survival was monitored for 21 days post-challenge.

Serum Antibody Determination

West Nile envelope protein specific IgG levels were determined by ELISA. ELISA plates (96-wells) were coated overnight at about 4° C. with 100 μl/well of West Nile E protein mAb 5C5, 7H2, 5H10, 3A3, and 3D9 (Beasley, D. W., et al., *J. Viro.* 76:13097-13100 (2002)) (Bioreliance, Road Rockville, Md.) in PBS at a concentration of 2 μg/ml. Plates were blocked with 200 μl/well of Assay Diluent Buffer (ADB; BD Pharmingen, San Diego Calif.) for one hour at room temperature. The plates were washed 3× in PBS-T. Dilutions of the sera in ADB were added (100 μl/well) and the plates were incubated overnight at 4° C. The plates were washed 3× with PBS-T. HRP-labeled goat anti-mouse IgG antibodies (Jackson Immunochemical, West Grove, Pa.) diluted in ADB were added (100 μl/well) and the plates were incubated at room temperature for 1 hour. The plates were washed 3× with PBS-T. After adding TMB (3,3',5,5'-tetramentylbenzidine) Ultra substrate (Pierce Biotechnology, Rockford, Ill.) and monitoring color development, $A_{450}$ was measured on a Tecan Farcyte microspectrophotometer.

Production of Pam3Cys.WNV001 Peptide Synthesis

Pam3Cys.WNV001 was synthesized by Bachem Bioscience, Inc. (King of Prussia, Pa.). WNV001 is a 20 amino acid peptide (SEQ ID NO: 168) of the West Nile virus envelope protein chemically coupled to a tri-palmitoylcysteine (Pam3Cys) moiety through the amino terminal serine residue of the peptide. The chemical name for Pam3Cys.WNV001 is [Palmitoyl-Cys((RS)-2,3-di(palmitoyloxy)-propyl)-LTS-GHLKCRVKMEKLQLKGT (SEQ ID NO: 168) acetate salt]. The molecular mass of Pam3Cys.WNV001 is 3163.3 daltons. The peptide was synthesized by Bachem using solid phase synthesis methodologies and FMOC chemistry. The amino acid sequence of Pam3Cys.WNV001 was assembled on an H-Pro-2-chlorotrityl chloride resin by solid phase peptide synthesis. The peptide chain was elongated by successive coupling of the amino acid derivatives. Each coupling step was preceded by an Fmoc-deprotection step and were accompanied by repeated washing of the resin. After coupling of the last amino acid derivative, the final Fmoc-deprotection step was performed. Finally, the peptide resin was washed and dried under reduced pressure. During solid phase peptide synthesis color indicator tests were performed for each step to monitor the completion of the Fmoc-cleavage and the subsequent coupling of the amino acid derivatives. To couple Pam3Cys-OH to the elongated peptide, the lipid moiety was pre-activated with N,N'-dicyclohexyl-carbodiimide (DCCI) in the presence of 1-hydroxybenzotriazole (HOBt). The resulting solution was filtered and added to the peptide resin. At the end of the reaction time the peptide resin was washed and dried under reduced pressure. Color indicator tests were performed to control the coupling of Pam3Cys-OH. The completed peptide was cleaved from the resin by incubating with trifluroacetic acid (TFA). The liberated product (crude peptide material) was precipitated from the reaction mixture and lyophilized. The crude product was used for initial immunogenicity studies.

Synthesis of WNV-E Peptide Arrays

Peptide arrays (FIGS. 57 and 60) were synthesized by Sigma Genosys (Woodlands, Tex.).

Results:

West Nile Fusion Protein

West Nile virus (WNV) has emerged in recent years in temperate regions of Europe and North America, presenting a threat to public and animal health. The most serious manifestation of WNV infection is fatal encephalitis (inflammation of the brain) in humans and horses, as well as mortality in certain domestic and wild birds. WNV has also been a significant cause of human illness in the United States. The envelope glycoprotein of West Nile (WNV-E) and other flaviviruses may generate neutralizing and protective antibodies. By linking this antigen to a Toll-like receptor ligand, the compositions, fusion proteins and polypeptides described herein may target appropriate antigen presenting cells without the need for adjuvant or other immune modulator formulations.

As described herein, several strategies have been implemented to facilitate production of West Nile virus envelope (WNV-E) fusion proteins in E. coli. One approach is to engineer a smaller WNV-E antigen by fusing domain III (EIII) and, optionally, with amino acids of domain II of the WNV-E protein to full-length STF2 (e.g., STF2.E, STF2.EIII+). Domain III is responsible for virus-host interactions and retains many West Nile virus neutralizing antibody epitopes. It also contains only 2 of the 12 cysteine residues present within the full length envelope protein, making expression in E. coli more feasible. A second approach has been to delete the hyper-variable hinge region of flagellin (e.g., STF2Δ) thereby creating a smaller fusion protein (STF2Δ.EIII+) The hyper-variable region of flagellin is not required for TLR5 signaling and its removal may also reduce the immunogenic potential of flagellin. Both STF2.EIII+ and STF2Δ.EIII+ have been expressed in E. coli and purified. The purified proteins have been characterized for TLR5 signaling activity in bioassays and for E epitope display in ELISA assays using a panel of WNV-E polyclonal and neutralizing monoclonal antibodies. Results from these studies indicate that STF2Δ.EIII+ has higher PAMP activity and more conformation-sensitive neutralizing WNV-E epitopes than STF2.EIII+.

Purity of STF2.EIII+ and STF2Δ.EIII+

Several lots of STF2.EIII+ and STF2Δ.EIII+ have been produced in E. coli and purified (Table 1). STF2.EIII+ was expressed as a soluble protein and purified under non-denaturing conditions using a 4-step process, as described above, that included anion exchange chromatography and gel filtration. Final yields from 6 L cultures ranged from about 0.9 mg to about 3.8 mg and all preparations contained low levels of endotoxin as measured by standard LAL procedures (about <0.1 EU/μg protein, see supra). In contrast, STF2Δ.EIII+ formed inclusion bodies in E. coli, and was purified under denaturing conditions. All chromatography steps used to purify STF2Δ.EIII+ required the use of 8M urea. Following purification, the denatured protein was refolded by step-wise dialysis to allow for gradual urea removal. Refolding was typically carried out at protein concentrations of about 0.3 mg/ml without any loss due to protein precipitation. Two preparations of STF2Δ.EIII+ from a single 6 L culture yielded about 1.2 and about 6.7 mg of protein, both of which had acceptable endotoxin levels. As expected, purified STF2.EIII+ and STF2Δ.EIII+ migrated on SDS PAGE under reducing conditions as about 65 kDa and about 43 kDa proteins, respectively. Notably, STF2Δ.EIII+ migrated slightly faster under non-reducing conditions. This altered migration may be due to disulfide bond formation involving the two cysteines residues in domain III of the envelope protein. As well, a larger species of STF2Δ.EIII+ was detected by Western blot analysis whose molecular weight is consistent with a trimer form of the protein ("(STF2Δ.EIII+)×3 or 3 units of STF2Δ.EIII+").

TABLE 1

Endotoxin levels and TLR-5 activity for STF2.EIII+ (SEQ ID NO: 55) and STF2Δ.EIII+ (SEQ ID NO: 71) fusion proteins.

| Batch Number | Protein | Yield (mg) | Endotoxin Levels (EU/μg) | TLR-5 $EC_{50}$ |
|---|---|---|---|---|
| 052 | STF2.EIII+ | 3.8 | 0.03 | >5000.00 ng/ml |
| 054 | STF2.EIII+ | 0.9 | 0.02 | 1195.00 ng/ml |
| 057 | STF2.EIII+ | 1.6 | 0.07 | 197.92 ng/ml |
| 044 | STF2Δ.EIII+ | 1.2 | 0.07 | 1.13 ng/ml |
| 045 | STF2Δ.EIII+ | 6.7 | 0.07 | 4.34 ng/ml |

TLR5 Activity in the HEK293 IL-8 Assay

To compare the PAMP activity of both fusion proteins, a TLR5 bioassay was performed. HEK293 IL-8 cells were treated with serial dilutions of two independent protein batches (FIGS. 47A and 47B). Cultures were incubated for a 24 hour period and conditioned media were harvested and assayed for IL-8 production by ELISA. As shown in FIG. 47A, STF2Δ.EIII+ showed potent TLR-5 activity. Regression analysis of the titration curve determined the $EC_{50}$ of batches 2004-044 and 2004-045 to be 1.13 ng/ml and 4.34 ng/ml, respectively (Table 1, supra). In both cases, the TLR5 specific-activity was at least about 10-fold higher than the control protein STF2.OVA. In contrast, 2 preparations of STF2.EIII+ showed significantly weaker TLR5 activity than STF2.OVA. The $EC_{50}$ of STF2.EIII+ batches 054 and 057 were about 1195.00 ng/ml and about 197.92 ng/ml.

Antigenicity of STF2.EIII+ and STF2Δ.EIII+

The antigenicity of STF2.EIII+ and STF2Δ.EIII+ was examined by direct ELISA using a flagellin monoclonal antibody specific for the N-terminal region of STF2 (6H11, Inotek Pharmaceuticals, Beverly, Mass.) and a panel of WNV-E-specific antibodies (5C5, 5H10, 3A3, 7H2 and 3D9, Bioreliance, Road Rockville, Md.) previously shown to neutralize West Nile virus in vitro. As shown in FIG. 48, a comparison of the reactivity of full length West Nile virus envelope protein with STF2Δ.EIII+ revealed that West Nile virus monoclonal antibodies 5C5, 5H10, 3A3 and 7H2, but not 3D9 recognize the fusion protein. This pattern of reactivity is consistent with the proposed location of 5C5, 5H10, 3A3 and 7H2 epitopes within EIII. The epitope for 3D9 lies outside of domain III of the West Nile virus envelope protein. As expected, all West Nile virus monoclonal antibodies reacted with full length West Nile virus envelope protein and the flagellin monoclonal only reacted with STF2Δ.EIII+. Both proteins reacted with a polyclonal West Nile virus envelope antiserum, but STF2Δ.EIII+ reactivity was somewhat reduced, perhaps due to the reduced number of potential epitopes present in the smaller domain.

Using 5C5 and 7H10 WNV monoclonal antibodies, a direct antigenic comparison was made between STF2.EIII+ and STF2Δ.EIII+ (FIGS. 49A, 49B, 49C and 49D). In these studies, plates were coated with the indicated proteins and then detected with polyclonal rabbit anti-E, or mouse monoclonal antibodies as described. As shown in FIGS. 49A, 49B, 49C and 49D, both STF2.EIII+ and STF2Δ.EIII+ were readily detected with the flagellin monoclonal antibody with no significant differences in reactivity. However, distinct reactivity with the anti-envelope monoclonal antibodies was observed. The reactivity of STF2Δ.EIII+ with either 5C5 or 7H2 was significantly greater than that observed with STF2.EIII+. Collectively, these results indicate that the flagellin 6H11 epitope of STF2Δ.EIII+ is uncompromised and is comparable to the flagellin sequence of STF2.EIII+. They also highlight distinct differences in the antigenicity of the EIII domains of these proteins and indicate that STF2Δ.EIII+ contains more of the critical conformation dependent neutralizing epitopes than STF2.EIII+.

Efficacy and Immunogenicity

Several efficacy studies designed to examine the protective efficacy our candidates in C3H/HeN mice following challenge with West Nile virus have been completed. Studies typically consisted of 5 groups of mice (10 mice per group) immunized intraperitoneally (i.p.) or subcutaneously (s.c.) on days 0, 14 and 28. On days 21 and 35, sera were harvested and tested for West Nile virus envelope protein—IgG antibody (ELISA) and the ability to neutralize West Nile virus in vitro (PRNT assay). On day 35, mice were challenged with a lethal dose of West Nile virus strain 2741. Survival was monitored for 21 days post-challenge.

Mice were immunized with PBS, Drosophila conditioned medium containing STF2.E (CM, positive control), 25 μg of STF2Δ.EIII+i.p., 25 μg STF2Δ.EIII+ s.c., 25 μg STF2.EIII+ i.p. and 25 μg STF2.EIII+ s.c. The West Nile virus envelope protein antibody responses and survival data are shown FIGS. 50 and 51. By day 35 all groups that received STF2Δ.EIII+ had significant levels of West Nile virus envelope protein IgG. In contrast, mice that received STF2.EIII+ had no measurable West Nile virus envelope protein antibody response. Administration of STF2Δ.EIII+ i.p. or s.c led to 100% survival following West Nile virus challenge. Consistent with the poor immunogenicity of STF2.EIII+, little to no protection was provided by this candidate when compared to the PBS control. The poor immunogenicity and efficacy of STF2.EIII+ in this study are attributed to the reduced TLR5 activity and/or the weak EIII epitope reactivity of this protein.

Plaque Reduction Neutralization Titers

To further evaluate the West Nile virus envelope protein antibody response elicited by STF2Δ.EIII+ and potentially correlate protective efficacy with neutralizing antibody titers, the plaque reduction neutralization test (PRNT) was performed. Day 35 serum samples from efficacy studies described above were tested for their ability to block West Nile virus infection in cultured Vero cells. Briefly, pooled mouse serum samples were heat-inactivated and serially diluted two-fold in PBS with 0.5% gelatin. Dilutions starting with 1:10 were incubated with about 100 pfu of the West Nile virus strain 2741. The virus/serum mixture was incubated at about 37° C. for 1 h and then inoculated onto confluent monolayers of Vero cells (ATCC, Catalog Number CCL-81, Manassas, Va.) in duplicate wells of 6-well tissue culture plates. The virus was allowed to adsorb to the cell monolayer prior to adding a 1% agarose overlay. Infected cell cultures were incubated for 4 days at 37° C. followed by a second agarose overlay containing 4% neutral red. Virus plaques were counted 12 h later. Serum titers that led to 80% reduction in viral plaque numbers (PRNT$_{80}$) were recorded.

A summary of the PRNT$_{80}$ data from efficacy studies concerning STF2.EIII+ and STF2Δ.EIII+ is presented in Table 2 below. In two independent studies involving STF2.EIII+ where survival of about 50% or less was reported, pooled sera failed to inhibit plaque formation. This finding is not surprising given the weak antibody response elicited by this construct. In three efficacy studies involving STF2Δ.EIII+ where survival was about 70% or greater, pooled sera had neutralization titers of 1:40 or better. Neutralization titers of 1:40 or greater typically correlate with protection in vivo.

TABLE 2

Survival and PRNT$_{80}$ Results for STF2.EIII+ (SEQ ID NO: 55), STF2Δ.EIII+ (SEQ ID NO: 71) and STF2.E (SEQ ID NO: 159) CM (Control Media) Fusion Proteins

| Batch | Candidate | Route | Study # | Survival (%) | PRNT$_{80}$ (dilution) |
|---|---|---|---|---|---|
| 054 | STF2.EIII+ | i.p. | 3 | 50 | Negative |
| 057 | STF2.EIII+ | i.p. | 4 | 11 | Negative |
| 057 | STF2.EIII+ | s.c. | 4 | 20 | negative |
| 044 | STF2Δ.EIII+ | i.p. | 2 | 70 | 1:40 |
| 045 | STF2Δ.EIII+ | i.p. | 3 | 90 | 1:40 |
| 045 | STF2Δ.EIII+ | s.c. | 3 | 100 | 1:160 |
| 045 | STF2Δ.EIII+ | i.p. | 4 | 100 | 1:80 |
| 045 | STF2Δ.EIII+ | s.c. | 4 | 100 | 1:40 |
| — | STF2.E CM | i.p. | 3 | 90 | 1:640 |
| — | STF2.E CM | i.p. | 4 | — | 1:1280 |

STF2Δ.EIIIs+ a Modified Version of STF2Δ.EIII+

Protein preparations of STF2Δ.EIII+ tested in the mouse efficacy studies described above were purified by anion-exchange and size-exclusion chromatography steps carried out under denaturing conditions followed by refolding using step-wise dialysis. With this process, two predominant species that correspond to the monomeric and trimeric forms of STF2Δ.EIII+ were generated and present as a mixture in the final product. To minimize the heterogeneity of the final product, new refolding and purification methods have been developed that favor the production of either monomer or trimer. Because it is unclear which form of STF2Δ.EIII+ is the active component or if both are equally potent, both species have been produced in milligram quantities and tested for efficacy in mice.

It was initially unclear as to why STF2Δ.EIII+ refolding resulted in the formation of a trimeric species. However, when the sequence of the STF2Δ.EIII+ expression construct was re-examined, we identified a cysteine residue within the linker sequence that separates STF2Δ from EIII+. The presence of this cysteine would likely interfere with the formation of the appropriate disulfide bond during refolding and might account for the trimeric form of STF2Δ.EIII+. This unnecessary cysteine was changed to a serine using site-directed mutagenesis and the modified protein (STF2Δ.EIIIs+) was produced and purified. It should be noted that refolding the serine-substituted construct yielded only monomeric protein.

Protective efficacy of STF2Δ.EIII+ (monomer) and STF2Δ.EIIIs+ (trimer) were evaluated in C3H/HeN mice following challenge with West Nile virus. Five groups of mice (10 per group) were immunized with about 25 ug of protein s.c. on days 0, 14 and 28. On days 21 and 35, sera were harvested and tested for WNV-E IgG antibody (ELISA). On day 38, mice were challenged with a lethal dose of WNV strain 2741 and survival was monitored for 21 days. ELISA results from boost 2 (day 35, FIG. 52) and survival data (FIG. 53) indicate that all constructs elicited significant levels of WNV-E reactive IgG prior to viral challenge and provided about 90% to about 100% protection against the lethal infection. These findings indicate that monomeric or multimeric (e.g., trimers) forms of STFΔ.EIII+ are efficacious and removal of the additional cysteine from the construct does not appreciably impact potency. Removal of the cysteine within the linker sequence may simplify purification of the protein by reducing heterogeneity following protein refolding.

Conclusion

Two recombinant fusion proteins containing the *Salmonella typhimurium* flagellin (STF2) fused to EIII+ domain of West Nile virus envelope protein have been generated. One includes the full length STF2 sequence (STF2.EIII+) and the other a modified version of STF2 that lacks the internal hypervariable region of STF2 (STF2Δ.EIII+). Both proteins have been expressed in *E. coli* and purified by conventional means using anion exchange chromatography and gel filtration. STF2.EIII+ was produced as a soluble protein and was purified under non-denaturing conditions. In contrast, STF2Δ.EIII+ was expressed as an insoluble protein and was purified under denaturing conditions and refolded by stepwise dialysis to remove urea. In HEK293 IL8 assays, preparations of STF2Δ.EIII+ showed greater TLR-5 activity than STF2.EIII+.

In envelope protein epitope display analysis using ELISA assays and West Nile virus envelope protein antibodies, STF2Δ.EIII+ displayed more of the critical conformation dependent neutralizing epitopes. Consistent with the potent TLR-5 activity and envelope protein epitope antigenicity observed with STF2Δ.EIII+, STF2Δ.EIII+ was highly immunogenic and efficacious in mice challenged with a lethal dose of West Nile virus. Because monomeric and trimeric species of STF2Δ.EIII+ were generated during the purification process of this protein, a cysteine within the linker sequence of the expression construct was changed to a serine. Removal of this cysteine eliminated the production of trimeric forms of the protein during refolding and resulted in the generation of monomeric product that displayed potent efficacy in vivo.

Japanese Encephalitis Fusion Protein

JE virus is localized in Asia and northern Australia (about 50,000 cases with about 10,000 deaths annually). An approved inactivated virus vaccine was recently associated with a case of acute disseminated encephalomyelitis, prompting the Japanese Ministry of Health, Labor and Welfare to recommend the nationwide suspension of the vaccine. Given the complexities of producing inactivated viruses in infected mouse brains or even in cell culture, and the potential for adverse events associated with inactivated viruses, the opportunity for recombinant-based JE vaccine is appealing.

A STF2Δ.JEIII+ fusion construct was constructed. The JE EIII+ DNA fragment was generated synthetically and codon optimized for expression in *E. coli*. The sequence was ligated into pET24STF2Δ to generate pETSTF2Δ.JEIII+. Expression constructs have been screened by restriction analysis and for expression in *E. coli* BLR(DE3) by IPTG induction. The DNA sequence of each construct has been confirmed, and production of the protein has been scaled up. A batch of material has been generated. A total of about 24 mg of material was purified. This material has potent TLR5 activity, acceptable levels of endotoxin (about 0.03 EU/μg) and a A280/A260 ratio of about 1.3.

Flavivirus Peptides

Identification of WNV-E Specific Antibody Epitopes

To identify linear epitopes within the West Nile virus envelope protein that are recognized by antisera from STF-Δ.EIIIs+ immunized mice, several synthetic peptide arrays were generated. One array consisted of overlapping peptides of 20 amino acids in length that spanned the entire West Nile virus domain III and parts of domain II (FIG. 60). ELISA results with this array identified a highly reactive 20 amino acid sequence that mapped to the N-terminal region of domain III and included part of the domain I domain CRVK-MEKLQLKGTTYGVCSK (SEQ ID NO: 125). To fine map this epitope, additional arrays were generated that focused on the domain I and II junctions (FIGS. 57 and 60). These arrays included an alanine substitution scan to identify amino acids critical for antibody binding (FIG. 60). As shown in FIGS. 54 and 55, antisera from STF2Δ.EIII (monomer and trimer) and STF2Δ.EIIIs+ immunized mice reacted with peptides that spanned the EI/EIII junction (peptides E-30 to E-42) and included the E2-21 peptide CRVKMEKLQLKGT-TYGVCSK (SEQ ID NO: 125). This reactivity was severely reduced when specific amino acids (E6, K7, L10 and K11) were changed to alanines (FIG. 56). Although it is not known if the antibodies that recognize this epitope are neutralizing, efforts are underway to design and test a peptide vaccine based on this region of WNV-E.

Immunogenicity of Pam3Cys.WNV001 Peptide Vaccine

A lipidated West Nile virus envelope protein fused to Pam3Cys on the N-terminal end was synthesized using the 20 amino acid sequence LTSGHLKCRVKMEKLQLKGT (SEQ ID NO:169) (Putnak, R., et al, *Vaccine* 23:4442-4452 (2005)). The immunogenicity of this peptide was tested in C3H/HeN mice and compared to peptide without Pam3Cys (FIG. 58). The reactivity of antisera from immunized animals was tested by direct ELISA as described in the legend and the results indicate that the Pam3Cys.WNV001 peptide is significantly more immunogenic than the peptide without the TLR2 modification. The antisera from these studies will be tested in virus neutralization assays (PRNT) to determine if the antibodies elicited will neutralize West Nile virus in vitro. The lipidated peptide will also be tested in the West Nile virus challenge model to assess protective efficacy against a lethal virus challenge.

Assay Development

Competition ELISA Assay Development

To assess the neutralizing potential of antisera derived from immunized mice, a competition ELISA assay was developed using well-characterized monoclonal antibody (7H2) that neutralizes West Nile virus in culture and reacts with a conformation-sensitive epitope within the EIII domain of the West Nile virus envelope protein antigen. The assay was designed as a capture ELISA that measures the ability of sera from immunized animals to prevent 7H2 from binding West Nile virus envelope protein. Serial dilutions ranging from 1:10 to 1:5000 of day 35 mouse antisera from efficacy study 4 (FIGS. 50 and 51, Table 2) were incubated with biotinylated West Nile virus envelope protein and then added to ELISA plates pre-coated with 7H2 monoclonal antibody (Bioreliance, Road Rockville, Md.). Following several washes to remove unbound material, bound West Nile virus envelope protein was detected using avidin-HRP. Results from a representative experiment are shown in FIG. 54. At dilutions of 1:25, a measurable loss of West Nile virus envelope protein binding to 7H2-coated plates was observed when antisera derived from animals immunized with STF2Δ.EIIIs where tested. No competition was detected with antisera derived from mock immunized animals that received PBS in place of antigen. These initial results demonstrate that antibodies elicited by STF2Δ.EIII+ compete with 7H2 for binding Wests Nile virus envelope protein. These findings are consistent with the protection from WNV infection observed in animals immunized with STF2Δ.EIII+ and help establish a correlation between antibody epitope reactivity in vitro and efficacy in vivo.

Example 2

Materials and Methods

Cloning and Expression of Fusion Proteins

STF2Δ.EIIIs+ (SEQ ID NO: 72) and STF2Δ.JEIIIs+ (SEQ ID NO: 76) were cloned and expressed as described above.

Protein Purification

Fusion protein (STF2Δ.EIIIs+ (SEQ ID NO: 72) was purified as described above. The fusion protein STF2Δ.JEIIIs+ (SEQ ID NO: 76) was purified as described above for STF2Δ.JEIII+ (SEQ ID NOS: 5, 6). STF2Δ (SEQ ID NO: 3) and EIII+ (SEQ ID NO: 7) proteins were purified using conventional chromatography as described herein and, if expressed in E. coli, required refolding steps due to low solubility in E. coli. Under standard growth and induction conditions described in materials and methods, STF2Δ (SEQ ID NO: 3) and EIII+ (SEQ ID NO: 7) proteins were expressed as insoluble proteins and formed inclusion bodies (IBs). STF2Δ (SEQ ID NO: 3) inclusion bodies were solubilized in 8 M urea in 50 mM Na Acetate, pH 4.0. The solubilized protein was captured on SP fast flow Sepharose® under denaturing conditions and selectively eluted with 8 M urea, 50 mM Na Acetate, pH 4.0 buffer containing 0.2 M NaCl. The eluted material was pooled, dialyzed against 50 mM Tris-HCl, pH 8.0, and refolded by rapid dilution of about 1:10 into 50 mM Tris-HCl, pH 8.0, to a final protein concentration of about 0.1 mg/ml. The refolded SP pool was loaded directly on Q high performance Sepharose® and bound protein eluted with about 20 column volumes of a linear gradient from 0 to about 0.5 M NaCl in 50 mM Tris-HCl, pH8.0.

EIII+ (SEQ ID NO: 7) inclusion bodies were solubilized with 8 M urea in 50 mM Na Acetate, pH 6.3. The protein was applied to SP fast flow Sepharose® (GE/Amersham Biosciences). Bound protein was eluted with 50 mM Na Acetate, pH 6.3, 8 M urea containing 0.2 M NaCl. SP peak fractions were pooled and dialyzed against 50 mM Tris-HCl, pH 8.5. To refold the protein, the dialyzed sample was diluted about 1:10 (final protein concentration of about 0.1 mg/ml) in 50 mM Tris-HCl, pH 8.5. The refolded SP pool was loaded directly on Q high performance Sepharose® (GE/Amersham). Under these conditions, the majority of EIII+ (SEQ ID 7) did not bind Q and eluted with the flow-through fraction. The Q HP FT was concentrated to about 2 mg/ml (Amicon™ Ultra-15, 5K MW cutoff, Millipore) and applied to size exclusion chromatography (SEC) (SD200, GE/Amersham) pre-equilibrated in Tris-buffered saline (TBS) (25 mM Tris-HCl, pH 7.4, 0.13 M NaCl, 2.7 mM KCl).

For use as ELISA reagents, WNV E (SEQ ID NO: 39) and JE E (SEQ ID NO: 171) proteins were produced in stable Drosophila Dmel-2 cells with a six amino acid histidine repeat fused to the c-terminus of the polypeptide according to manufacturer's directions (Invitrogen, Carlsbad, Calif.). Stable Drosophila cell pools were expanded as adherent cultures and adapted to suspension growth in selection media (Drosophila SFM, 18 mM L-glutamine, 1× penicillin/streptomycin, and 25 μg/mL blasticidin). Protein expression was induced with 0.5 mM $CuSO_4$ and E protein was purified by affinity chromatography using nickel NTA according to the manufacturer's directions (Sigma, St. Louis, Mo.).

Efficacy of STF2Δ.JEIIIs+ (SEQ ID NO: 76)

Three groups of C57BL/6 mice (20 mice per group) received three intramuscular (i.m.) immunizations with PBS, 2.5 μg of STF2Δ.JEIIIs+_(SEQ ID NO: 76) fusion protein in 1× Tris-buffered saline (TBS) or about one-third (⅓) the human dose of JE vaccine (about 0.3 ml of reconstituted lyophilized killed virus distributed by Sanofi Pasteur, manufactured by BIKEN).

Seven days after each immunization, mice were bled and sera examined by ELISA for antibodies to JE E protein. Antigen-specific IgG responses to JE E and STF2 were determined by ELISA. ELISA plates (96 well) (Costar, Catalog No: 9018, Corning, N.Y.) were coated overnight at about 4° C. with about 100 μl/well of recombinant JE E protein expressed in Drosophila and placed in PBS (5 μg/ml). Plates were blocked with 200 μl/well of Assay Diluent Buffer (ADB; BD Pharmingen, Catalog No: 555213, San Diego, Calif.) for about one hour at room temperature. The plates were washed three times in PBS buffer containing 0.05% (v/v) Tween 20 (PBS-T). Dilutions of immune sera in ADB were added (about 100 μl/well) and the plates were incubated overnight at about 4° C. The plates were washed three times with PBS-T. HRP-labeled goat anti-mouse IgG antibodies (Jackson Immunochemical, Catalog No: 115-035-146, West Grove, Pa.) diluted in ADB were added (about 100 μl/well) and the plates were incubated at room temperature for about 1 hour. The plates were washed three times with PBS-T. After adding TMB Ultra substrate (Pierce, Catalog No: 34028, Rockford, Ill.) and monitoring color development, A450 was measured on a Tecan Farcyte (Durham, N.C.) microplate spectrophotometer.

Following the third immunization, mice were challenged with the P3 JE strain (Ni, H., etal., J. Gen Virol. 77:1449-1455 (1996) of JE virus intraperitoneally (i.p.) with an amount of virus equal to ten times the dose needed to cause death in 50% of the mice (10×$LD_{50}$; one $LD_{50}$ about 10 plaque forming units (pfu).

Results

The immunogenicity of STF2Δ.EIIIs+ (SEQ ID NO: 72) was compared with an equimolar amount of STF2Δ (SEQ ID NO: 3) and EIII+ (SEQ ID NO: 7) formulated as a protein cocktail. As shown in FIGS. 81A and 81B, STF2Δ.EIIIs+ (SEQ ID NO: 72) elicited measurable WNV-E-specific antibodies, whereas, the STF2Δ (SEQ ID NO: 3)+EIII+ (SEQ ID NO: 7) mixture did not elicit an E-specific response even though flagellin antibodies were readily detectable in these immunized animals. This pattern of antibody response was also observed following the first boost (days 14) suggesting that a prime and single boost regimen is sufficient to induce a significant antibody response.

Immunizing with EIII+ alone did not elicit E-specific antibodies demonstrating the poor immunogencity of this purified antigen as described herein. The efficacy of STF2Δ.EIIIs+ (SEQ ID NO: 72) was demonstrated by challenging mice with WNV as described herein. As shown in FIG. 82, mice immunized with STF2Δ.EIIIs+ (SEQ ID NO: 72) were 100% protected. In contrast, no protective advantage over PBS was observed in mice that received STF2Δ (SEQ ID NO: 3) or EIII+ (SEQ ID NO: 7) as separate immunogens or as a protein mixture. These data show that both flagellin and EIII+ (SEQ ID NO: 7) are required for protection.

Immunogenicity was also examined in TLR5-deficient mice in a C57BL/6 background (Feuillet, V., et al., Proc Natl Acad Sci USA, 103(33): 12487-92 (2006)). Mice were immunized as described above (see FIGS. 83A and 83B), and sera from immunized mice were collected and analyzed for WNV E-specific IgG antibodies. Following immunization with STF2Δ.EIIIs+ (SEQ ID NO: 72), TLR5-deficient animals exhibited markedly lower WNV-E and flagellin IgG responses when compared to wild-type mice (FIGS. 83A and 83B) These studies demonstrate that TLR5 can be required to elicit a significant antigen-specific immune response.

Immunogenicity and Efficacy of STF2Δ.JEIIIs+ (SEQ ID NO: 76)

The immunogenicity and efficacy of STF2Δ.JEIIIs+ has been demonstrated in mice. To compare the potency of the fusion protein to an approved vaccine and demonstrate non-inferiority (potency that is equal to or better than a vaccine currently in use), an efficacy and immunogenicity study was performed using a JE vaccine (JE Vax, distributed by Sanofi Pasteur, manufactured by BIKEN) approved for use within the US. Three groups of C57BL/6 mice were immunized three times as described above and sera were collected following each immunization and analyzed for JE E protein-specific IgG antibodies. As shown in FIGS. 84A, 84B and 84C, mice immunized with the STF2Δ.JEIIIs+ (SEQ ID NO: 76) fusion protein developed higher JE E protein-specific antibody titers (about 10-fold) than mice immunized with JE Vax (FIGS. 84A, 84B and 84C). These results suggest that the fusion protein is more immunogenic with regard to the E protein than the JE Vax under these conditions. Once immunized, mice were challenged with a lethal dose of JE virus and the survival results 19 days post-challenge are shown (FIG. 85). When challenged with virus delivered ip, STF2Δ.JEIIIs+ (SEQ ID NO: 76) provided comparable protection (100% efficacy) from a lethal challenge when compared to the JE Vax vaccine. Thus, these data indicate that the fusion proteins described herein that include JE are not inferior to an approved JE vaccine with regard to efficacy following ip challenge.

Discussion

The presence of a functional TLR5 and the physical association of EIII+ (SEQ ID NO: 7) domain to flagellin (STF2Δ (SEQ ID NO: 3)) can generate a protective immune response. When administered to TLR5 knockout mice as a fusion protein (STF2Δ. EIII+), reduced E-specific antibody response was observed and when delivered to wild type animals as separate protein components, no E antigen-specific antibody responses were evident. When administered to wild-type mice followed by a challenged with WNV, only animals that received the EIII+ (SEQ ID NO: 7) fused to flagellin (STF2Δ (SEQ ID NO: 3)) survived a lethal West Nile viral dose. In addition, flagellin-JE fusion protein (STF2Δ.JEIIIs+ (e.g., SEQ ID NO: 76) similar in design to STF2Δ.EIIIs+ (SEQ ID NO: 72) is both immunogenic and efficacious in mice challenged with a lethal dose of Japanese encephalitis virus (JEV). Importantly, the efficacy of this recombinant protein vaccine is not inferior to the approved JE vaccine (JE Vax), which is currently in use within the US and abroad.

EQUIVALENTS

While this invention has been particularly shown and described with references to preferred embodiments thereof, it will be understood by those skilled in the art that various changes in form and details may be made therein without departing from the scope of the invention encompassed by the appended claims.

What is claimed is:

1. A non-glycosylated fusion protein comprising a portion of at least one flagellin selected from the group consisting of a *Salmonella typhimurium* flagellin type 2 (fljB/STF2), an *E. coli* fliC, and a *S. muenchen* fliC and at least a portion of at least one Dengue viral envelope protein selected from the group consisting of a Den1 viral envelope protein, a Den2 viral envelope protein, a Den3 viral envelope protein and a Den4 viral envelope protein, wherein the portion of the flagellin is a Toll-like Receptor 5 agonist, the portion of the Dengue viral envelope protein is an antigen, and wherein the fusion protein activates Toll-like Receptor 5 and induces antibodies that neutralize a Dengue virus.

2. The fusion protein of claim 1, wherein the flagellin is the *Salmonella typhimurium* type 2 flagellin.

3. The fusion protein of claim 2, wherein the flagellin includes the amino acid sequence as set forth in SEQ ID NO: 1.

4. The fusion protein of claim 1, wherein the Dengue viral envelope protein is the Den2 viral envelope protein.

5. The fusion protein of claim 4, wherein the Den2 viral envelope protein includes the amino acid sequence as set forth in SEQ ID NO: 162.

6. The fusion protein of claim 1, wherein the Dengue viral envelope protein is the Den1 viral envelope protein.

7. The fusion protein of claim 1, wherein the Dengue viral envelope protein is the Den3 viral envelope protein.

8. The fusion protein of claim 1, wherein the Dengue viral envelope protein is the Den4 viral envelope protein.

9. The fusion protein of claim 1, wherein the antigen is at least one member selected from the group consisting of an EIII protein and an EII protein.

10. The fusion protein of claim 1, wherein the flagellin lacks at least a portion of a hinge region.

11. The fusion protein of claim 10, wherein the antigen is fused to the flagellin in a the portion of the flagellin that lacks the hinge region.

12. The fusion protein of claim 1, wherein the flagellin is fused to a carboxy-terminus of the antigen.

13. The fusion protein of claim 1, wherein the flagellin is fused to an amino-terminus of the antigen.

14. The fusion protein of claim 1, wherein the fljB/STF2 flagellin includes SEQ ID NO: 1.

15. The fusion protein of claim 1, wherein the fusion protein is a recombinant fusion protein.

16. A non-glycosylated, recombinant fusion protein comprising a portion of at least one flagellin selected from the group consisting of a *Salmonella typhimurium* flagellin type 2 (fljB/STF2), an *E. coli* fliC, and a *S. muenchen* fliC and at least a portion of at least one Dengue viral envelope protein selected from the group consisting of a Den1 viral envelope protein, a Den2 viral envelope protein, a Den3 viral envelope protein and a Den4 viral envelope protein, wherein the portion of the flagellin is a Toll-like Receptor 5 agonist, the portion of the viral envelope protein is an antigen and wherein the fusion protein activates Toll-like Receptor 5 and induces antibodies that neutralize a Dengue virus.

17. The fusion protein of claim 16, wherein the antigen is at least one member selected from the group consisting of an EIII protein and an EII protein.

18. The fusion protein of claim 16, wherein the flagellin lacks at least a portion of a hinge region.

19. The fusion protein of claim 18, wherein the antigen is fused to the flagellin in a the portion of the flagellin that lacks the hinge region.

* * * * *

UNITED STATES PATENT AND TRADEMARK OFFICE
CERTIFICATE OF CORRECTION

PATENT NO. : 8,574,588 B2  Page 1 of 1
APPLICATION NO. : 11/879695
DATED : November 5, 2013
INVENTOR(S) : Thomas J. Powell et al.

It is certified that error appears in the above-identified patent and that said Letters Patent is hereby corrected as shown below:

On the title page in the Assignee field, please delete:

"VanInnate Corporation, Cranbury, NJ"

and insert:

-- VaxInnate Corporation, Cranbury, NJ --

Signed and Sealed this
Fourteenth Day of January, 2014

Michelle K. Lee
*Deputy Director of the United States Patent and Trademark Office*

SEQUENCE LISTING

```
<160> NUMBER OF SEQ ID NOS: 282

<210> SEQ ID NO 1
<211> LENGTH: 506
<212> TYPE: PRT
<213> ORGANISM: s. typhimurium

<400> SEQUENCE: 1

Met Ala Gln Val Ile Asn Thr Asn Ser Leu Ser Leu Leu Thr Gln Asn
1               5                   10                  15

Asn Leu Asn Lys Ser Gln Ser Ala Leu Gly Thr Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ala Asn Ile Lys Gly Leu Thr Gln Ala
    50                  55                  60

Ser Arg Asn Ala Asn Asp Gly Ile Ser Ile Ala Gln Thr Thr Glu Gly
65                  70                  75                  80

Ala Leu Asn Glu Ile Asn Asn Asn Leu Gln Arg Val Arg Glu Leu Ala
                85                  90                  95

Val Gln Ser Ala Asn Ser Thr Asn Ser Gln Ser Asp Leu Asp Ser Ile
            100                 105                 110

Gln Ala Glu Ile Thr Gln Arg Leu Asn Glu Ile Asp Arg Val Ser Gly
        115                 120                 125

Gln Thr Gln Phe Asn Gly Val Lys Val Leu Ala Gln Asp Asn Thr Leu
    130                 135                 140

Thr Ile Gln Val Gly Ala Asn Asp Gly Glu Thr Ile Asp Ile Asp Leu
145                 150                 155                 160

Lys Gln Ile Asn Ser Gln Thr Leu Gly Leu Asp Ser Leu Asn Val Gln
                165                 170                 175
```

```
Lys Ala Tyr Asp Val Lys Asp Thr Ala Val Thr Thr Lys Ala Tyr Ala
            180                 185                 190

Asn Asn Gly Thr Thr Leu Asp Val Ser Gly Leu Asp Asp Ala Ala Ile
        195                 200                 205

Lys Ala Ala Thr Gly Gly Thr Asn Gly Thr Ala Ser Val Thr Gly Gly
210                 215                 220

Ala Val Lys Phe Asp Ala Asp Asn Asn Lys Tyr Phe Val Thr Ile Gly
225                 230                 235                 240

Gly Phe Thr Gly Ala Asp Ala Ala Lys Asn Gly Asp Tyr Glu Val Asn
                245                 250                 255

Val Ala Thr Asp Gly Thr Val Thr Leu Ala Ala Gly Ala Thr Lys Thr
            260                 265                 270

Thr Met Pro Ala Gly Ala Thr Thr Lys Thr Glu Val Gln Glu Leu Lys
        275                 280                 285

Asp Thr Pro Ala Val Val Ser Ala Asp Ala Lys Asn Ala Leu Ile Ala
    290                 295                 300

Gly Gly Val Asp Ala Thr Asp Ala Asn Gly Ala Glu Leu Val Lys Met
305                 310                 315                 320

Ser Tyr Thr Asp Lys Asn Gly Lys Thr Ile Glu Gly Gly Tyr Ala Leu
                325                 330                 335

Lys Ala Gly Asp Lys Tyr Tyr Ala Ala Asp Tyr Asp Glu Ala Thr Gly
            340                 345                 350

Ala Ile Lys Ala Lys Thr Thr Ser Tyr Thr Ala Ala Asp Gly Thr Thr
        355                 360                 365

Lys Thr Ala Ala Asn Gln Leu Gly Gly Val Asp Gly Lys Thr Glu Val
    370                 375                 380

Val Thr Ile Asp Gly Lys Thr Tyr Asn Ala Ser Lys Ala Ala Gly His
385                 390                 395                 400

Asp Phe Lys Ala Gln Pro Glu Leu Ala Glu Ala Ala Lys Thr Thr
                405                 410                 415

Glu Asn Pro Leu Gln Lys Ile Asp Ala Ala Leu Ala Gln Val Asp Ala
            420                 425                 430

Leu Arg Ser Asp Leu Gly Ala Val Gln Asn Arg Phe Asn Ser Ala Ile
        435                 440                 445

Thr Asn Leu Gly Asn Thr Val Asn Asn Leu Ser Glu Ala Arg Ser Arg
    450                 455                 460

Ile Glu Asp Ser Asp Tyr Ala Thr Glu Val Ser Asn Met Ser Arg Ala
465                 470                 475                 480

Gln Ile Leu Gln Gln Ala Gly Thr Ser Val Leu Ala Gln Ala Asn Gln
                485                 490                 495

Val Pro Gln Asn Val Leu Ser Leu Leu Arg
            500                 505

<210> SEQ ID NO 2
<211> LENGTH: 1518
<212> TYPE: DNA
<213> ORGANISM: s. typhimurium

<400> SEQUENCE: 2 atggcacaag

```
gcgctgaacg aaatcaacaa caacctgcag cgtgtgcgtg aactggcggt tcagtctgct    300
aacagcacca actcccagtc tgacctcgac tccatccagg ctgaaatcac ccagcgcctg    360
aacgaaatcg accgtgtatc cggccagact cagttcaacg gcgtgaaagt cctggcgcag    420
gacaacaccc tgaccatcca ggttggcgcc aacgacggtg aaactatcga tatcgatctg    480
aagcagatca actctcagac cctgggtctg gactcactga acgtgcagaa agcgtatgat    540
gtgaaagata cagcagtaac aacgaaagct tatgccaata atggtactac actggatgta    600
tcgggtcttg atgatgcagc tattaaagcg gctacgggtg gtacgaatgg tacggcttct    660
gtaaccggtg gtgcggttaa atttgacgca gataataaca agtactttgt tactattggt    720
ggctttactg gtgctgatgc cgccaaaaat ggcgattatg aagttaacgt tgctactgac    780
ggtacagtaa cccttgcggc tggcgcaact aaaaccacaa tgcctgctgg tgcgacaact    840
aaaacagaag tacaggagtt aaaagataca ccggcagttg tttcagcaga tgctaaaaat    900
gccttaattg ctggcggcgt tgacgctacc gatgctaatg cgctgagtt ggtcaaaatg    960 tcttataccg ataaaaatgg taagacaatt gaaggcggtt atgcgcttaa agctggcgat    1020
aagtattacg ccgcagatta cgatgaagcg acaggagcaa ttaaagctaa aactacaagt    1080
tatactgctg ctgacggcac taccaaaaca gcggctaacc aactgggtgg cgtagacggt    1140
aaaaccgaag tcgttactat cgacggtaaa acctacaatg ccagcaaagc cgctggtcat    1200
gatttcaaag cacaaccaga gctggcggaa gcagccgcta aaccaccga aacccgctg    1260 cagaaaattg atgccgcgct ggcgcaggtg atgcgctgc gctctgatct gggtgcggta    1320
caaaaccgtt tcaactctgc tatcaccaac ctgggcaata ccgtaaacaa tctgtctgaa    1380
gcgcgtagcc gtatcgaaga ttccgactac gcgaccgaag tttccaacat gtctcgcgcg    1440
cagattctgc agcaggccgg tacttccgtt ctggcgcagg ctaaccaggt cccgcagaac    1500
gtgctgtctc tgttacgt                                                 1518
```

<210> SEQ ID NO 3  
<211> LENGTH: 277  
<212> TYPE: PRT  
<213> ORGANISM: s. typhimurium

<400> SEQUENCE: 3

```
Met Ala Gln Val Ile Asn Thr Asn Ser Leu Ser Leu Leu Thr Gln Asn
  1               5                  10                  15

Asn Leu Asn Lys Ser Gln Ser Ala Leu Gly Thr Ala Ile Glu Arg Leu
             20                  25                  30

Ser Ser Gly Leu Arg Ile Asn Ser Ala Lys Asp Asp Ala Ala Gly Gln
         35                  40                  45

Ala Ile Ala Asn Arg Phe Thr Ala Asn Ile Lys Gly Leu Thr Gln Ala
     50                  55                  60

Ser Arg Asn Ala Asn Asp Gly Ile Ser Ile Ala Gln Thr Thr Glu Gly
 65                  70                  75                  80

Ala Leu Asn Glu Ile Asn Asn Asn Leu Gln Arg Val Arg Glu Leu Ala
                 85                  90                  95

Val Gln Ser Ala Asn Ser Thr Asn Ser Gln Ser Asp Leu Asp Ser Ile
            100                 105                 110

Gln Ala Glu Ile Thr Gln Arg Leu Asn Glu Ile Asp Arg Val Ser Gly
        115                 120                 125

Gln Thr Gln Phe Asn Gly Val Lys Val Leu Ala Gln Asp Asn Thr Leu
    130                 135                 140

Thr Ile Gln Val Gly Ala Asn Asp Gly Glu Thr Ile Asp Ile Asp Leu
```

|  |  |  | 145 |  |  |  | 150 |  |  |  | 155 |  |  |  | 160 |

Lys Gln Ile Asn Ser Gln Thr Leu Gly Leu Asp Ser Leu Asn Val His
            165                 170                 175

Gly Ala Pro Val Asp Pro Ala Ser Pro Trp Thr Glu Asn Pro Leu Gln
            180                 185                 190

Lys Ile Asp Ala Ala Leu Ala Gln Val Asp Ala Leu Arg Ser Asp Leu
        195                 200                 205

Gly Ala Val Gln Asn Arg Phe Asn Ser Ala Ile Thr Asn Leu Gly Asn
        210                 215                 220

Thr Val Asn Asn Leu Ser Glu Ala Arg Ser Arg Ile Glu Asp Ser Asp
225                 230                 235                 240

Tyr Ala Thr Glu Val Ser Asn Met Ser Arg Ala Gln Ile Leu Gln Gln
                245                 250                 255

Ala Gly Thr Ser Val Leu Ala Gln Ala Asn Gln Val Pro Gln Asn Val
            260                 265                 270

Leu Ser Leu Leu Arg
        275

<210> SEQ ID NO 4
<211> LENGTH: 832
<212> TYPE: DNA
<213> ORGANISM: s. typhimurium

<400> SEQUENCE: 4

```
atggcacaag taatcaacac taacagtctg tcgctgctga cccagaataa cctgaacaaa      60
tcccagtccg cactgggcac cgctatcgag cgtctgtctt ctggtctgcg tatcaacagc     120
gcgaaagacg atgcggcagg tcaggcgatt gctaaccgtt tcaccgcgaa catcaaaggt     180
ctgactcagg cttcccgtaa cgctaacgac ggtatctcca ttgcgcagac cactgaaggc     240
gcgctgaacg aaatcaacaa caacctgcag cgtgtgcgtg aactggcggt tcagtctgct     300
aacagcacca actcccagtc tgacctcgac tccatccagg ctgaaatcac ccagcgcctg     360
aacgaaatcg accgtgtatc cggccagact cagttcaacg gcgtgaaagt cctggcgcag     420
gacaacaccc tgaccatcca ggttggcgcc aacgacggtg aaactatcga tatcgatctg     480
aagcagatca actctcagac cctgggtctg gactcactga acgtgcatgg agcgccggtg     540
gatcctgcta gcccatggac cgaaaacccg ctgcagaaaa ttgatgccgc gctggcgcag     600
gtggatgcgc tgcgctctga tctgggtgcg gtacaaaacc gtttcaactc tgctatcacc     660
aacctgggca ataccgtaaa caatctgtct gaagcgcgta gccgtatcga agattccgac     720
tacgcgaccg aagtttccaa catgtctcgc gcgcagattt tgcagcaggc cggtacttcc     780
gttctggcgc aggctaacca ggtcccgcag aacgtgctgt ctctgttacg tg            832
```

<210> SEQ ID NO 5
<211> LENGTH: 1215
<212> TYPE: DNA
<213> ORGANISM: Artificial Sequence
<220> FEATURE:
<223> OTHER INFORMATION: pET/STF2delta.JEIII+

<400> SEQUENCE: 5

```
atggcacaag taatcaacac taacagtctg tcgctgctga cccagaataa cctgaacaaa      60
tcccagtccg cactgggcac cgctatcgag cgtctgtctt ctggtctgcg tatcaacagc     120
gcgaaagacg atgcggcagg tcaggcgatt gctaaccgtt tcaccgcgaa catcaaaggt     180
ctgactcagg cttcccgtaa cgctaacgac ggtatctcca ttgcgcagac cactgaaggc     240
```

```
gcgctgaacg aaatcaacaa caacctgcag cgtgtgcgtg aactggcggt tcagtctgct    300
aacagcacca actcccagtc tgacctcgac tccatccagg ctgaaatcac ccagcgcctg    360
aacgaaatcg accgtgtatc cggccagact cagttcaacg gcgtgaaagt cctggcgcag    420
gacaacaccc tgaccatcca ggttggcgcc aacgacggtg aaactatcga tatcgatctg    480
aagcagatca actctcagac cctgggtctg gactcactga acgtgcatgg agcgccggtg    540
gatcctgcta gcccatggac cgaaaacccg ctgcagaaaa ttgatgccgc gctggcgcag    600
gtggatgcgc tgcgctctga tctgggtgcg gtacaaaacc gtttcaactc tgctatcacc    660
aacctgggca ataccgtaaa caatctgtct gaagcgcgta ccgtatcga agattccgac    720 tacgcgaccg aagtttccaa catgtctcgc gcgcagattt tgcagcaggc cggtacttcc    780
gttctggcgc aggctaacca ggtcccgcag aacgtgctgt ctctgttacg tgaattctgc    840
agatatccag cacagtggcg gccgctcatg acaaactgg ctctgaaagg cacaacctat    900
ggcatgtgta cagaaaaatt ctcgttcgcg aaaaatccgg tggacactgg tcacggaaca    960
gttgtcattg aactctccta ctctgggagt gatggcccct gcaaaattcc gattgtttcc   1020
gttgcgagcc tcaatgacat gacccccgtt gggcggctgg tgacagtgaa ccccttcgtc   1080
gcgacttcca gtgccaactc aaaggtgctg gtcgagatgg aaccccccctt cggagactcc   1140 tacatcgtag ttggaagggg agacaagcag atcaaccacc attggcacaa agctggaagc   1200
acgctgggca aggcc                                                    1215
```

<210> SEQ ID NO 6
<211> LENGTH: 405
<212> TYPE: PRT
<213> ORGANISM: Artificial Sequence
<220> FEATURE:
<223> OTHER INFORMATION: pET/STF2delta.JEIII+

<400> SEQUENCE: 6

```
Met Ala Gln Val Ile Asn Thr Asn Ser Leu Ser Leu Leu Thr Gln Asn
  1               5                  10                  15

Asn Leu Asn Lys Ser Gln Ser Ala Leu Gly Thr Ala Ile Glu Arg Leu
             20                  25                  30

Ser Ser Gly Leu Arg Ile Asn Ser Ala Lys Asp Asp Ala Ala Gly Gln
         35                  40                  45

Ala Ile Ala Asn Arg Phe Thr Ala Asn Ile Lys Gly Leu Thr Gln Ala
     50                  55                  60

Ser Arg Asn Ala Asn Asp Gly Ile Ser Ile Ala Gln Thr Thr Glu Gly
 65                  70                  75                  80

Ala Leu Asn Glu Ile Asn Asn Asn Leu Gln Arg Val Arg Glu Leu Ala
                 85                  90                  95

Val Gln Ser Ala Asn Ser Thr Asn Ser Gln Ser Asp Leu Asp Ser Ile
            100                 105                 110

Gln Ala Glu Ile Thr Gln Arg Leu Asn Glu Ile Asp Arg Val Ser Gly
        115                 120                 125

Gln Thr Gln Phe Asn Gly Val Lys Val Leu Ala Gln Asp Asn Thr Leu
    130                 135                 140

Thr Ile Gln Val Gly Ala Asn Asp Gly Glu Thr Ile Asp Ile Asp Leu
145                 150                 155                 160

Lys Gln Ile Asn Ser Gln Thr Leu Gly Leu Asp Ser Leu Asn Val His
                165                 170                 175

Gly Ala Pro Val Asp Pro Ala Ser Pro Trp Thr Glu Asn Pro Leu Gln
            180                 185                 190
```

```
Lys Ile Asp Ala Ala Leu Ala Gln Val Asp Ala Leu Arg Ser Asp Leu
        195                 200                 205

Gly Ala Val Gln Asn Arg Phe Asn Ser Ala Ile Thr Asn Leu Gly Asn
    210                 215                 220
Thr Val Asn Asn Leu Ser Glu Ala Arg Ser Arg Ile Glu Asp Ser Asp
225                 230                 235                 240
Tyr Ala Thr Glu Val Ser Asn Met Ser Arg Ala Gln Ile Leu Gln Gln
                245                 250                 255

Ala Gly Thr Ser Val Leu Ala Gln Ala Asn Gln Val Pro Gln Asn Val
            260                 265                 270
Leu Ser Leu Leu Arg Glu Phe Cys Arg Tyr Pro Ala Gln Trp Arg Pro
        275                 280                 285

Leu Met Asp Lys Leu Ala Leu Lys Gly Thr Thr Tyr Gly Met Cys Thr
    290                 295                 300
Glu Lys Phe Ser Phe Ala Lys Asn Pro Val Asp Thr Gly His Gly Thr
305                 310                 315                 320
Val Val Ile Glu Leu Ser Tyr Ser Gly Ser Asp Gly Pro Cys Lys Ile
                325                 330                 335

Pro Ile Val Ser Val Ala Ser Leu Asn Asp Met Thr Pro Val Gly Arg
            340                 345                 350
Leu Val Thr Val Asn Pro Phe Val Ala Thr Ser Ser Ala Asn Ser Lys
        355                 360                 365

Val Leu Val Glu Met Glu Pro Pro Phe Gly Asp Ser Tyr Ile Val Val
    370                 375                 380
Gly Arg Gly Asp Lys Gln Ile Asn His His Trp His Lys Ala Gly Ser
385                 390                 395                 400
Thr Leu Gly Lys Ala
                405

<210> SEQ ID NO 7
<211> LENGTH: 115
<212> TYPE: PRT
<213> ORGANISM: Artificial Sequence
<220> FEATURE:
<223> OTHER INFORMATION: West Nile domain III

<400> SEQUENCE: 7

Met Glu Lys Leu Gln Leu Lys Gly Thr Thr Tyr Gly Val Cys Ser Lys
 1               5                  10                  15

Ala Phe Lys Phe Leu Gly Thr Pro Ala Asp Thr Gly His Gly Thr Val
            20                  25                  30

Val Leu Glu Leu Gln Tyr Thr Gly Thr Asp Gly Pro Cys Lys Val Pro
        35                  40                  45

Ile Ser Ser Val Ala Ser Leu Asn Asp Leu Thr Pro Val Gly Arg Leu
    50                  55                  60

Val Thr Val Asn Pro Phe Val Ser Val Ala Thr Ala Asn Ala Lys Val
65                  70                  75                  80

Leu Ile Glu Leu Glu Pro Pro Phe Gly Asp Ser Tyr Ile Val Val Gly
                85                  90                  95

Arg Gly Glu Gln Gln Ile Asn His His Trp His Lys Ser Gly Ser Ser
            100                 105                 110

Ile Gly Lys
        115

<210> SEQ ID NO 8
<211> LENGTH: 103
<212> TYPE: PRT
```

```
<213> ORGANISM: Artificial Sequence
<220> FEATURE:
<223> OTHER INFORMATION: West Nile domain III

<400> SEQUENCE: 8

Gly Thr Thr Tyr Gly Val Cys Ser Lys Ala Phe Lys Phe Ala Arg Thr
1               5                   10                  15

Pro Ala Asp Thr Gly His Gly Thr Val Val Leu Glu Leu Gln Tyr Thr
            20                  25                  30

Gly Lys Asp Gly Pro Cys Lys Val Pro Ile Ser Ser Val Ala Ser Leu
        35                  40                  45

Asn Asp Leu Thr Pro Val Gly Arg Leu Val Thr Val Asn Pro Phe Val
    50                  55                  60

Ser Val Ala Thr Ala Asn Ser Lys Val Leu Ile Glu Leu Glu Pro Pro
65                  70                  75                  80

Phe Gly Asp Ser Tyr Ile Val Val Gly Arg Gly Glu Gln Gln Ile Asn
                85                  90                  95

His His Trp His Lys Ser Gly
            100

<210> SEQ ID NO 9
<211> LENGTH: 102
<212> TYPE: PRT
<213> ORGANISM: Artificial Sequence
<220> FEATURE:
<223> OTHER INFORMATION: West Nile domain III

<400> SEQUENCE: 9

Gly Thr Thr Tyr Gly Val Cys Ser Lys Ala Phe Lys Phe Leu Gly Thr
1               5                   10                  15

Pro Ala Asp Thr Gly His Gly Thr Val Val Leu Glu Leu Gln Tyr Thr
            20                  25                  30

Gly Thr Asp Gly Pro Cys Lys Val Pro Ile Ser Ser Val Ala Ser Leu
        35                  40                  45

Asn Asp Leu Thr Pro Val Gly Arg Leu Val Thr Val Asn Pro Phe Val
    50                  55                  60

Ser Val Ala Thr Ala Asn Ala Lys Val Leu Ile Glu Leu Glu Pro Pro
65                  70                  75                  80

Phe Gly Asp Ser Tyr Val Val Gly Arg Gly Glu Gln Gln Ile Asn His
                85                  90                  95

His Trp His Lys Ser Gly
            100

<210> SEQ ID NO 10
<211> LENGTH: 27
<212> TYPE: PRT
<213> ORGANISM: Artificial Sequence
<220> FEATURE:
<223> OTHER INFORMATION: West Nile domain III

<400> SEQUENCE: 10

Glu Leu Glu Pro Pro Phe Gly Asp Ser Tyr Ile Val Val Gly Arg Gly
1               5                   10                  15

Glu Gln Gln Ile Asn His His Trp His Lys Ser
            20                  25

<210> SEQ ID NO 11
<211> LENGTH: 345
<212> TYPE: DNA
<213> ORGANISM: Artificial Sequence
<220> FEATURE:
```

-continued

<223> OTHER INFORMATION: West Nile domain III

<400> SEQUENCE: 11

```
atggaaaaat tgcagttgaa gggaacaacc tatggcgtct gttcaaaggc tttcaagttt      60
cttgggactc ccgcagacac aggtcacggc actgtggtgt tggaattgca gtacactggc     120
acggatggac cttgcaaagt tcctatctcg tcagtggctt cattgaacga cctaacgcca     180
gtgggcagat tggtcactgt caacccttt gtttcagtgg ccacggccaa cgctaaggtc      240
ctgattgaat tggaaccacc ctttggagac tcatacatag tggtgggcag aggagaacaa     300
cagatcaatc accattggca caagtctgga agcagcattg gcaaa                    345
```

<210> SEQ ID NO 12
<211> LENGTH: 96
<212> TYPE: PRT
<213> ORGANISM: Artificial Sequence
<220> FEATURE:
<223> OTHER INFORMATION: Langat virus

<400> SEQUENCE: 12

```
Gly Leu Thr Tyr Thr Val Cys Asp Lys Thr Lys Phe Thr Trp Lys Arg
 1               5                  10                  15
Ala Pro Thr Asp Ser Gly His Asp Thr Val Val Met Glu Val Gly Phe
            20                  25                  30
Ser Gly Thr Arg Pro Cys Arg Ile Pro Val Arg Ala Val Ala His Gly
        35                  40                  45
Val Pro Glu Val Asn Val Ala Met Leu Ile Thr Pro Asn Pro Thr Met
    50                  55                  60
Glu Asn Asn Gly Gly Gly Phe Ile Glu Met Gln Leu Pro Pro Gly Asp
65                  70                  75                  80
Asn Ile Ile Tyr Val Gly Asp Leu Asn His Gln Trp Phe Gln Lys Gly
                85                  90                  95
```

<210> SEQ ID NO 13
<211> LENGTH: 103
<212> TYPE: PRT
<213> ORGANISM: Artificial Sequence
<220> FEATURE:
<223> OTHER INFORMATION: Kunjin virus

<400> SEQUENCE: 13

```
Gly Thr Thr Tyr Gly Val Cys Ser Lys Ala Phe Arg Phe Leu Gly Thr
 1               5                  10                  15
Pro Ala Asp Thr Gly His Gly Thr Val Val Leu Glu Leu Gln Tyr Thr
            20                  25                  30
Gly Thr Asp Gly Pro Cys Lys Ile Pro Ile Ser Ser Val Ala Ser Leu
        35                  40                  45
Asn Asp Leu Thr Pro Val Gly Arg Leu Val Thr Val Asn Pro Phe Val
    50                  55                  60
Ser Val Ser Thr Ala Asn Ala Lys Val Leu Ile Glu Leu Glu Pro Pro
65                  70                  75                  80
Phe Gly Asp Ser Tyr Ile Val Val Gly Arg Gly Glu Gln Gln Ile Asn
                85                  90                  95
His His Trp His Lys Ser Gly
            100
```

<210> SEQ ID NO 14
<211> LENGTH: 103
<212> TYPE: PRT
<213> ORGANISM: Artificial Sequence -continued

```
<220> FEATURE:
<223> OTHER INFORMATION: Murray Valley virus

<400> SEQUENCE: 14

Gly Thr Thr Tyr Gly Met Cys Thr Glu Lys Phe Thr Phe Ser Lys Asn
  1               5                  10                  15

Pro Ala Asp Thr Gly His Gly Thr Val Val Leu Glu Leu Gln Tyr Thr
             20                  25                  30

Gly Ser Asp Gly Pro Cys Lys Ile Pro Ile Ser Ser Val Ala Ser Leu
         35                  40                  45

Asn Asp Met Thr Pro Val Gly Arg Met Val Thr Ala Asn Pro Tyr Val
     50                  55                  60

Ala Ser Ser Thr Ala Asn Ala Lys Val Leu Val Glu Ile Glu Pro Pro
 65                  70                  75                  80

Phe Gly Asp Ser Tyr Ile Val Val Gly Arg Gly Asp Lys Gln Ile Asn
                 85                  90                  95

His His Trp His Lys Glu Gly
            100

<210> SEQ ID NO 15
<211> LENGTH: 103
<212> TYPE: PRT
<213> ORGANISM: Artificial Sequence
<220> FEATURE:
<223> OTHER INFORMATION: Japanese encephalitis virus

<400> SEQUENCE: 15

Gly Thr Thr Tyr Gly Met Cys Thr Glu Lys Phe Ser Phe Ala Lys Asn
  1               5                  10                  15

Pro Ala Asp Thr Gly His Gly Thr Val Val Ile Glu Leu Ser Tyr Ser
             20                  25                  30

Gly Ser Asp Gly Pro Cys Lys Ile Pro Ile Val Ser Val Ala Ser Leu
         35                  40                  45

Asn Asp Met Thr Pro Val Gly Arg Leu Val Thr Val Asn Pro Phe Val
     50                  55                  60

Ala Thr Ser Ser Ala Asn Ser Lys Val Leu Val Glu Met Glu Pro Pro
 65                  70                  75                  80

Phe Gly Ser Asp Tyr Ile Val Val Gly Met Gly Asp Lys Gln Ile Asn
                 85                  90                  95

His His Trp His Lys Ala Gly
            100

<210> SEQ ID NO 16
<211> LENGTH: 26
<212> TYPE: PRT
<213> ORGANISM: Artificial Sequence
<220> FEATURE:
<223> OTHER INFORMATION: Japanese encephalitis virus

<400> SEQUENCE: 16

Glu Met Glu Pro Pro Phe Gly Asp Ser Tyr Ile Val Val Met Gly Asp
  1               5                  10                  15

Lys Gln Ile Asn His His Trp His Lys Ala
             20                  25

<210> SEQ ID NO 17
<211> LENGTH: 95
<212> TYPE: PRT
<213> ORGANISM: Artificial Sequence
<220> FEATURE:
<223> OTHER INFORMATION: Tick-borne encephalitis virus
```

```
<400> SEQUENCE: 17

Gly Leu Thr Tyr Thr Met Cys Asp Lys Thr Lys Phe Thr Trp Lys Arg
1               5                   10                  15

Ala Pro Thr Asp Ser Gly His Asp Thr Val Val Met Glu Val Thr Phe
            20                  25                  30

Ser Gly Thr Lys Pro Cys Arg Ile Pro Val Arg Ala Val Ala His Gly
        35                  40                  45

Ser Pro Asp Val Asn Val Ala Met Leu Ile Thr Pro Asn Pro Thr Ile
50                  55                  60

Glu Asn Asn Gly Gly Gly Phe Ile Glu Met Gln Leu Pro Pro Gly Asp
65                  70                  75                  80

Asn Ile Ile Tyr Val Gly Glu Leu Ser His Gln Trp Phe Gln Lys
                85                  90                  95

<210> SEQ ID NO 18
<211> LENGTH: 94
<212> TYPE: PRT
<213> ORGANISM: Artificial Sequence
<220> FEATURE:
<223> OTHER INFORMATION: Yellow fever virus

<400> SEQUENCE: 18

Gly Leu Thr Tyr Thr Met Cys Asp Lys Thr Phe Thr Trp Lys Arg Ala
1               5                   10                  15

Pro Thr Asp Ser Gly His Asp Thr Val Val Met Glu Val Thr Phe Ser
            20                  25                  30

Gly Thr Lys Pro Cys Arg Ile Pro Val Arg Ala Val Ala His Gly Ser
        35                  40                  45

Pro Asp Val Asn Val Ala Met Leu Ile Thr Pro Asn Pro Thr Ile Glu
50                  55                  60

Asn Asn Gly Gly Gly Phe Ile Glu Met Gln Leu Pro Pro Gly Asp Asn
65                  70                  75                  80

Ile Ile Tyr Val Gly Glu Leu Ser His Gln Trp Phe Gln Lys
                85                  90

<210> SEQ ID NO 19
<211> LENGTH: 95
<212> TYPE: PRT
<213> ORGANISM: Artificial Sequence
<220> FEATURE:
<223> OTHER INFORMATION: Envelope protein flavivirus

<400> SEQUENCE: 19

Gly Thr Thr Tyr Gly Met Cys Ser Lys Lys Phe Thr Phe Arg Pro Ala
1               5                   10                  15

Asp Thr Gly His Gly Thr Val Val Leu Glu Leu Gln Tyr Ser Gly Asp
            20                  25                  30

Gly Pro Cys Lys Ile Pro Ile Ser Val Ala Ser Lys Asn Asp Leu Thr
        35                  40                  45

Pro Val Gly Arg Leu Val Thr Val Asn Pro Phe Val Ser Ser Thr Ala
50                  55                  60

Asn Ala Lys Val Leu Ile Glu Met Glu Pro Pro Phe Gly Asp Ser Tyr
65                  70                  75                  80

Ile Val Val Gly Gly Glu Gln Ile Asn His His Trp His Lys Gly
                85                  90                  95

<210> SEQ ID NO 20
<211> LENGTH: 27
```

<212> TYPE: PRT
<213> ORGANISM: Artificial Sequence
<220> FEATURE:
<223> OTHER INFORMATION: Dengue virus

<400> SEQUENCE: 20

```
Glu Ala Glu Pro Pro Phe Gly Glu Ser Tyr Ile Val Val Gly Ala Gly
 1               5                  10                  15

Glu Lys Ala Leu Lys Leu Ser Trp Phe Lys Lys
            20                  25
```

<210> SEQ ID NO 21
<211> LENGTH: 27
<212> TYPE: PRT
<213> ORGANISM: Artificial Sequence
<220> FEATURE:
<223> OTHER INFORMATION: Dengue virus

<400> SEQUENCE: 21

```
Glu Thr Glu Pro Pro Phe Gly Glu Ser Tyr Ile Val Val Gly Ala Gly
 1               5                  10                  15

Glu Lys Ala Leu Lys Leu Ser Trp Phe Lys Lys
            20                  25
```

<210> SEQ ID NO 22
<211> LENGTH: 27
<212> TYPE: PRT
<213> ORGANISM: Artificial Sequence
<220> FEATURE:
<223> OTHER INFORMATION: Dengue virus

<400> SEQUENCE: 22

```
Glu Ala Glu Pro Pro Phe Gly Asp Ser Tyr Ile Ile Ile Gly Val Glu
 1               5                  10                  15

Pro Gln Gln Leu Lys Leu Asn Trp Phe Lys Lys
            20                  25
```

<210> SEQ ID NO 23
<211> LENGTH: 27
<212> TYPE: PRT
<213> ORGANISM: Artificial Sequence
<220> FEATURE:
<223> OTHER INFORMATION: Dengue virus

<400> SEQUENCE: 23

```
Glu Ala Glu Pro Pro Phe Gly Glu Ser Asn Ile Val Ile Gly Ile Gly
 1               5                  10                  15

Asp Lys Ala Leu Lys Ile Asn Trp Tyr Lys Lys
            20                  25
```

<210> SEQ ID NO 24
<211> LENGTH: 27
<212> TYPE: PRT
<213> ORGANISM: Artificial Sequence
<220> FEATURE:
<223> OTHER INFORMATION: Dengue virus

<400> SEQUENCE: 24

```
Glu Leu Glu Pro Pro Phe Gly Glu Ser Tyr Ile Val Ile Gly Val Gly
 1               5                  10                  15

Asn Ser Ala Leu Thr Leu His Trp Phe Arg Lys
            20                  25
```

<210> SEQ ID NO 25
<211> LENGTH: 48

```
<212> TYPE: DNA
<213> ORGANISM: Artificial Sequence
<220> FEATURE:
<223> OTHER INFORMATION: Linker

<400> SEQUENCE: 25
aagggcaatt cgaagcttga aggtcaattg gaattcccta ggactagt        48

<210> SEQ ID NO 26
<211> LENGTH: 16
<212> TYPE: PRT
<213> ORGANISM: Artificial Sequence
<220> FEATURE:
<223> OTHER INFORMATION: Linker

<400> SEQUENCE: 26

Lys Gly Asn Ser Lys Leu Glu Gly Gln Leu Glu Phe Pro Arg Thr Ser
 1               5                  10                  15

<210> SEQ ID NO 27
<211> LENGTH: 36
<212> TYPE: DNA
<213> ORGANISM: Artificial Sequence
<220> FEATURE:
<223> OTHER INFORMATION: Linker

<400> SEQUENCE: 27
gaattctgca gatatccagc acagtggcgg ccgctc                     36

<210> SEQ ID NO 28
<211> LENGTH: 12
<212> TYPE: PRT
<213> ORGANISM: Artificial Sequence
<220> FEATURE:
<223> OTHER INFORMATION: Linker

<400> SEQUENCE: 28

Glu Phe Cys Arg Tyr Pro Ala Gln Trp Arg Pro Leu
 1               5                  10

<210> SEQ ID NO 29
<211> LENGTH: 1863
<212> TYPE: DNA
<213> ORGANISM: Artificial Sequence
<220> FEATURE:
<223> OTHER INFORMATION: STF2.EIII+

<400> SEQUENCE: 29
atggcacaag taatcaacac taacagtctg tcgctgctga cccagaataa cctgaacaaa    60
tcccagtccg cactgggcac cgctatcgag cgtctgtctt ctggtctgcg tatcaacagc   120
gcgaaagacg atgcggcagg tcaggcgatt gctaaccgtt tcaccgcgaa catcaaaggt   180
ctgactcagg cttcccgtaa cgctaacgac ggtatctcca ttgcgcagac cactgaaggc   240
gcgctgaacg aaatcaacaa caacctgcag cgtgtgcgtg aactggcggt tcagtctgct   300
aacagcacca actcccagtc tgacctcgac tccatccagg ctgaaatcac ccagcgcctg   360
aacgaaatcg accgtgtatc cggccagact cagttcaacg gcgtgaaagt cctggcgcag   420
gacaacaccc tgaccatcca ggttggcgcc aacgacggtg aaactatcga tatcgatctg   480
aagcagatca actctcagac cctgggtctg gactcactga acgtgcagaa agcgtatgat   540
gtgaaagata cagcagtaac aacgaaagct tatgccaata atggtactac actggatgta   600
tcgggtcttg atgatgcagc tattaaagcg gctacgggtg tacgaatgg tacggcttct   660 gtaaccggtg gtgcggttaa atttgacgca gataataaca gtactttgt tactattggt   720
```

```
ggctttactg gtgctgatgc cgccaaaaat ggcgattatg aagttaacgt tgctactgac    780
ggtacagtaa cccttgcggc tggcgcaact aaaaccacaa tgcctgctgg tgcgacaact    840
aaaacagaag tacaggagtt aaaagataca ccggcagttg tttcagcaga tgctaaaaat    900
gccttaattg ctggcggcgt tgacgctacc gatgctaatg gcgctgagtt ggtcaaaatg    960
tcttataccg ataaaaatgg taagacaatt gaaggcggtt atgcgcttaa agctggcgat   1020
aagtattacg ccgcagatta cgatgaagcg acaggagcaa ttaaagctaa aactacaagt   1080
tatactgctg ctgacggcac taccaaaaca gcggctaacc aactgggtgg cgtagacggt   1140
aaaaccgaag tcgttactat cgacggtaaa acctacaatg ccagcaaagc cgctggtcat   1200
gatttcaaag cacaaccaga gctggcggaa gcagccgcta aaaccaccga aaacccgctg   1260
cagaaaattg atgccgcgct ggcgcaggtg gatgcgctgc gctctgatct gggtgcggta   1320
caaaaccgtt tcaactctgc tatcaccaac ctgggcaata ccgtaaacaa tctgtctgaa   1380
gcgcgtagcc gtatcgaaga ttccgactac gcgaccgaag tttccaacat gtctcgcgcg   1440
cagattctgc agcaggccgg tacttccgtt ctggcgcagg ctaaccaggt cccgcagaac   1500
gtgctgtctc tgttacgtat ggaaaaattg cagttgaagg aacaacccta tggcgtctgt   1560
tcaaaggctt tcaagtttct tgggactccc gcagacacag gtcacggcac tgtggtgttg   1620
gaattgcagt acactggcac ggatggacct tgcaaagttc ctatctcgtc agtggcttca   1680
ttgaacgacc taacgccagt gggcagattg gtcactgtca acccttttgt ttcagtggcc   1740
acggccaacg ctaaggtcct gattgaattg gaaccaccct ttggagactc atacatagtg   1800
gtgggcagag gagaacaaca gatcaatcac cattggcaca agtctggaag cagcattggc   1860
aaa                                                                 1863

<210> SEQ ID NO 30
<211> LENGTH: 621
<212> TYPE: PRT
<213> ORGANISM: Artificial Sequence
<220> FEATURE:
<223> OTHER INFORMATION: STF2.EIII+

<400> SEQUENCE: 30

Met Ala Gln Val Ile Asn Thr Asn Ser Leu Ser Leu Leu Thr Gln Asn
1               5                   10                  15

Asn Leu Asn Lys Ser Gln Ser Ala Leu Gly Thr Ala Ile Glu Arg Leu
                20                  25                  30

Ser Ser Gly Leu Arg Ile Asn Ser Ala Lys Asp Asp Ala Ala Gly Gln
        35                  40                  45

Ala Ile Ala Asn Arg Phe Thr Ala Asn Ile Lys Gly Leu Thr Gln Ala
    50                  55                  60

Ser Arg Asn Ala Asn Asp Gly Ile Ser Ile Ala Gln Thr Thr Glu Gly
65                  70                  75                  80

Ala Leu Asn Glu Ile Asn Asn Asn Leu Gln Arg Val Arg Glu Leu Ala
                85                  90                  95

Val Gln Ser Ala Asn Ser Thr Asn Ser Gln Ser Asp Leu Asp Ser Ile
            100                 105                 110

Gln Ala Glu Ile Thr Gln Arg Leu Asn Glu Ile Asp Arg Val Ser Gly
        115                 120                 125

Gln Thr Gln Phe Asn Gly Val Lys Val Leu Ala Gln Asp Asn Thr Leu
    130                 135                 140

Thr Ile Gln Val Gly Ala Asn Asp Gly Glu Thr Ile Asp Ile Asp Leu
145                 150                 155                 160
```

-continued

```
Lys Gln Ile Asn Ser Gln Thr Leu Gly Leu Asp Ser Leu Asn Val Gln
                165                 170                 175
Lys Ala Tyr Asp Val Lys Asp Thr Ala Val Thr Thr Lys Ala Tyr Ala
            180                 185                 190
Asn Asn Gly Thr Thr Leu Asp Val Ser Gly Leu Asp Asp Ala Ala Ile
        195                 200                 205
Lys Ala Ala Thr Gly Gly Thr Asn Gly Thr Ala Ser Val Thr Gly Gly
210                 215                 220
Ala Val Lys Phe Asp Ala Asp Asn Asn Lys Tyr Phe Val Thr Ile Gly
225                 230                 235                 240
Gly Phe Thr Gly Ala Asp Ala Ala Lys Asn Gly Asp Tyr Glu Val Asn
                245                 250                 255
Val Ala Thr Asp Gly Thr Val Thr Leu Ala Ala Gly Ala Thr Lys Thr
            260                 265                 270
Thr Met Pro Ala Gly Ala Thr Thr Lys Thr Glu Val Gln Glu Leu Lys
        275                 280                 285
Asp Thr Pro Ala Val Val Ser Ala Asp Ala Lys Asn Ala Leu Ile Ala
290                 295                 300
Gly Gly Val Asp Ala Thr Asp Ala Asn Gly Ala Glu Leu Val Lys Met
305                 310                 315                 320
Ser Tyr Thr Asp Lys Asn Gly Lys Thr Ile Glu Gly Gly Tyr Ala Leu
                325                 330                 335
Lys Ala Gly Asp Lys Tyr Tyr Ala Ala Asp Tyr Asp Glu Ala Thr Gly
            340                 345                 350
Ala Ile Lys Ala Lys Thr Thr Ser Tyr Thr Ala Ala Asp Gly Thr Thr
        355                 360                 365
Lys Thr Ala Ala Asn Gln Leu Gly Gly Val Asp Gly Lys Thr Glu Val
370                 375                 380
Val Thr Ile Asp Gly Lys Thr Tyr Asn Ala Ser Lys Ala Ala Gly His
385                 390                 395                 400
Asp Phe Lys Ala Gln Pro Glu Leu Ala Glu Ala Ala Lys Thr Thr
                405                 410                 415
Glu Asn Pro Leu Gln Lys Ile Asp Ala Ala Leu Ala Gln Val Asp Ala
            420                 425                 430
Leu Arg Ser Asp Leu Gly Ala Val Gln Asn Arg Phe Asn Ser Ala Ile
        435                 440                 445
Thr Asn Leu Gly Asn Thr Val Asn Asn Leu Ser Glu Ala Arg Ser Arg
450                 455                 460
Ile Glu Asp Ser Asp Tyr Ala Thr Glu Val Ser Asn Met Ser Arg Ala
465                 470                 475                 480
Gln Ile Leu Gln Gln Ala Gly Thr Ser Val Leu Ala Gln Ala Asn Gln
                485                 490                 495
Val Pro Gln Asn Val Leu Ser Leu Leu Arg Met Glu Lys Leu Gln Leu
            500                 505                 510
Lys Gly Thr Thr Tyr Gly Val Cys Ser Lys Ala Phe Lys Phe Leu Gly
        515                 520                 525
Thr Pro Ala Asp Thr Gly His Gly Thr Val Leu Glu Leu Gln Tyr
        530                 535                 540
Thr Gly Asp Gly Pro Cys Lys Val Pro Ile Ser Ser Val Ala Ser
545                 550                 555                 560
Leu Asn Asp Leu Thr Pro Val Gly Arg Leu Val Thr Val Asn Pro Phe
                565                 570                 575
Val Ser Val Ala Thr Ala Asn Ala Lys Val Leu Ile Glu Leu Glu Pro
```

```
                580             585             590
Pro Phe Gly Asp Ser Tyr Ile Val Val Gly Arg Gly Glu Gln Gln Ile
            595                 600                 605

Asn His His Trp His Lys Ser Gly Ser Ser Ile Gly Lys
    610                 615                 620

<210> SEQ ID NO 31
<211> LENGTH: 1176
<212> TYPE: DNA
<213> ORGANISM: Artificial Sequence
<220> FEATURE:
<223> OTHER INFORMATION: STF2delta.EIII+

<400> SEQUENCE: 31
atggcacaag taatcaacac taacagtctg tcgctgctga cccagaataa cctgaacaaa        60
tcccagtccg cactgggcac cgctatcgag cgtctgtctt ctggtctgcg tatcaacagc       120
gcgaaagacg atgcggcagg tcaggcgatt gctaaccgtt tcaccgcgaa catcaaaggt       180
ctgactcagg cttcccgtaa cgctaacgac ggtatctcca ttgcgcagac cactgaaggc       240
gcgctgaacg aaatcaacaa caacctgcag cgtgtgcgtg aactggcggt tcagtctgct       300
aacagcacca actcccagtc tgacctcgac tccatccagg ctgaaatcac ccagcgcctg       360
aacgaaatcg accgtgtatc cggccagact cagttcaacg gcgtgaaagt cctggcgcag       420
gacaacaccc tgaccatcca ggttggcgcc aacgacggtg aaactatcga tatcgatctg       480
aagcagatca actctcagac cctgggtctg gactcactga cgtgcatgga gcgccggtg        540 gatcctgcta gcccatggac cgaaaacccg ctgcagaaaa ttgatgccgc gctggcgcag       600
gtggatgcgc tgcgctctga tctgggtgcg gtacaaaacc gtttcaactc tgctatcacc       660
aacctgggca ataccgtaaa caatctgtct gaagcgcgta gccgtatcga agattccgac       720
tacgcgaccg aagtttccaa catgtctcgc gcgcagattt tgcagcaggc cggtacttcc       780
gttctggcgc aggctaacca ggtcccgcag aacgtgctgt ctctgttacg tatggaaaaa       840
ttgcagttga agggaacaac ctatgccgtc tgttcaaagg cttttcaagtt tcttgggact      900 cccgcagaca caggtcacgg cactgtggtg ttggaattgc agtacactgg cacggatgga       960
ccttgcaaag ttcctatctc gtcagtggct tcattgaacg acctaacgcc agtgggcaga      1020
ttggtcactg tcaacccttt tgtttcagtg gccacggcca acgctaaggt cctgattgaa      1080
ttggaaccac cctttggaga ctcatacata gtggtgggca gaggagaaca acagatcaat      1140
caccattggc acaagtctgg aagcagcatt ggcaaa                                1176

<210> SEQ ID NO 32
<211> LENGTH: 392
<212> TYPE: PRT
<213> ORGANISM: Artificial Sequence
<220> FEATURE:
<223> OTHER INFORMATION: STF2delta.EIII+

<400> SEQUENCE: 32

Met Ala Gln Val Ile Asn Thr Asn Ser Leu Ser Leu Leu Thr Gln Asn
  1               5                  10                  15

Asn Leu Asn Lys Ser Gln Ser Ala Leu Gly Thr Ala Ile Glu Arg Leu
             20                  25                  30

Ser Ser Gly Leu Arg Ile Asn Ser Ala Lys Asp Asp Ala Ala Gly Gln
         35                  40                  45

Ala Ile Ala Asn Arg Phe Thr Ala Asn Ile Lys Gly Leu Thr Gln Ala
     50                  55                  60
```

Ser Arg Asn Ala Asn Asp Gly Ile Ser Ile Ala Gln Thr Thr Glu Gly
65                  70                  75                  80

Ala Leu Asn Glu Ile Asn Asn Asn Leu Gln Arg Val Arg Glu Leu Ala
                85                  90                  95

Val Gln Ser Ala Asn Ser Thr Asn Ser Gln Ser Asp Leu Asp Ser Ile
            100                 105                 110

Gln Ala Glu Ile Thr Gln Arg Leu Asn Glu Ile Asp Arg Val Ser Gly
        115                 120                 125

Gln Thr Gln Phe Asn Gly Val Lys Val Leu Ala Gln Asp Asn Thr Leu
    130                 135                 140

Thr Ile Gln Val Gly Ala Asn Asp Gly Glu Thr Ile Asp Ile Asp Leu
145                 150                 155                 160

Lys Gln Ile Asn Ser Gln Thr Leu Gly Leu Asp Ser Leu Asn Val His
                165                 170                 175

Gly Ala Pro Val Asp Pro Ala Ser Pro Trp Thr Glu Asn Pro Leu Gln
            180                 185                 190

Lys Ile Asp Ala Ala Leu Ala Gln Val Asp Ala Leu Arg Ser Asp Leu
        195                 200                 205

Gly Ala Val Gln Asn Arg Phe Asn Ser Ala Ile Thr Asn Leu Gly Asn
    210                 215                 220

Thr Val Asn Asn Leu Ser Glu Ala Arg Ser Arg Ile Glu Asp Ser Asp
225                 230                 235                 240

Tyr Ala Thr Glu Val Ser Asn Met Ser Arg Ala Gln Ile Leu Gln Gln
                245                 250                 255

Ala Gly Thr Ser Val Leu Ala Gln Ala Asn Gln Val Pro Gln Asn Val
            260                 265                 270

Leu Ser Leu Leu Arg Met Glu Lys Leu Gln Leu Lys Gly Thr Thr Tyr
        275                 280                 285

Gly Val Cys Ser Lys Ala Phe Lys Phe Leu Gly Thr Pro Ala Asp Thr
    290                 295                 300

Gly His Gly Thr Val Val Leu Glu Leu Gln Tyr Thr Gly Thr Asp Gly
305                 310                 315                 320

Pro Cys Lys Val Pro Ile Ser Ser Val Ala Ser Leu Asn Asp Leu Thr
                325                 330                 335

Pro Val Gly Arg Leu Val Thr Val Asn Pro Phe Val Ser Val Ala Thr
            340                 345                 350

Ala Asn Ala Lys Val Leu Ile Glu Leu Glu Pro Pro Phe Gly Asp Ser
        355                 360                 365

Tyr Ile Val Val Gly Arg Gly Glu Gln Gln Ile Asn His His Trp His
    370                 375                 380

Lys Ser Gly Ser Ser Ile Gly Lys
385                 390

<210> SEQ ID NO 33
<211> LENGTH: 1224
<212> TYPE: DNA
<213> ORGANISM: Artificial Sequence
<220> FEATURE:
<223> OTHER INFORMATION: STF2delta.EIII+

<400> SEQUENCE: 33
atggcacaag taatcaacac taacagtctg tcgctgctga cccagaataa cctgaacaaa    60
tcccagtccg cactgggcac cgctatcgag cgtctgtctt ctggtctgcg tatcaacagc   120
gcgaaagacg atgcggcagg tcaggcgatt gctaaccgtt tcaccgcgaa catcaaaggt   180
ctgactcagg cttcccgtaa cgctaacgac ggtatctcca ttgcgcagac cactgaaggc   240

```
gcgctgaacg aaatcaacaa caacctgcag cgtgtgcgtg aactggcggt tcagtctgct      300
aacagcacca actcccagtc tgacctcgac tccatccagg ctgaaatcac ccagcgcctg      360
aacgaaatcg accgtgtatc cggccagact cagttcaacg gcgtgaaagt cctggcgcag      420
gacaacaccc tgaccatcca ggttggcgcc aacgacggtg aaactatcga tatcgatctg      480
aagcagatca actctcagac cctgggtctg gactcactga acgtgcatgg agcgccggtg      540
gatcctgcta gcccatggac cgaaaacccg ctgcagaaaa ttgatgccgc gctggcgcag      600
gtggatgcgc tgcgctctga tctgggtgcg gtacaaaacc gtttcaactc tgctatcacc      660
aacctgggca ataccgtaaa caatctgtct gaagcgcgta gccgtatcga agattccgac      720
tacgcgaccg aagtttccaa catgtctcgc gcgcagattt tgcagcaggc cggtacttcc      780
gttctggcgc aggctaacca ggtcccgcag aacgtgctgt ctctgttacg tgaattctgc      840
agatatccag cacagtggcg gccgctcatg gaaaaattgc agttgaaggg aacaacctat      900
ggcgtctgtt caaaggcttt caagtttctt gggactcccg cagacacagg tcacggcact      960
gtggtgttgg aattgcagta cactggcacg gatggacctt gcaaagttcc tatctcgtca     1020
gtggcttcat tgaacgacct aacgccagtg ggcagattgg tcactgtcaa ccctttttgtt     1080 tcagtggcca cggccaacgc taaggtcctg attgaattgg aaccaccctt tggagactca     1140
tacatagtgg tgggcagagg agaacaacag atcaatcacc attggcacaa gtctggaagc     1200
agcattggca aacccttaat aagc                                           1224
```

<210> SEQ ID NO 34
<211> LENGTH: 408
<212> TYPE: PRT
<213> ORGANISM: Artificial Sequence
<220> FEATURE:
<223> OTHER INFORMATION: STF2delta.EIII+

<400> SEQUENCE: 34

```
Met Ala Gln Val Ile Asn Thr Asn Ser Leu Ser Leu Leu Thr Gln Asn
  1               5                  10                  15

Asn Leu Asn Lys Ser Gln Ser Ala Leu Gly Thr Ala Ile Glu Arg Leu
             20                  25                  30

Ser Ser Gly Leu Arg Ile Asn Ser Ala Lys Asp Asp Ala Ala Gly Gln
         35                  40                  45

Ala Ile Ala Asn Arg Phe Thr Ala Asn Ile Lys Gly Leu Thr Gln Ala
     50                  55                  60

Ser Arg Asn Ala Asn Asp Gly Ile Ser Ile Ala Gln Thr Thr Glu Gly
 65                  70                  75                  80

Ala Leu Asn Glu Ile Asn Asn Asn Leu Gln Arg Val Arg Glu Leu Ala
                 85                  90                  95

Val Gln Ser Ala Asn Ser Thr Asn Ser Gln Ser Asp Leu Asp Ser Ile
            100                 105                 110

Gln Ala Glu Ile Thr Gln Arg Leu Asn Glu Ile Asp Arg Val Ser Gly
        115                 120                 125

Gln Thr Gln Phe Asn Gly Val Lys Val Leu Ala Gln Asp Asn Thr Leu
    130                 135                 140

Thr Ile Gln Val Gly Ala Asn Asp Gly Glu Thr Ile Asp Ile Asp Leu
145                 150                 155                 160

Lys Gln Ile Asn Ser Gln Thr Leu Gly Leu Asp Ser Leu Asn Val His
                165                 170                 175

Gly Ala Pro Val Asp Pro Ala Ser Pro Trp Thr Glu Asn Pro Leu Gln
            180                 185                 190
```

```
Lys Ile Asp Ala Ala Leu Ala Gln Val Asp Ala Leu Arg Ser Asp Leu
            195                 200                 205
Gly Ala Val Gln Asn Arg Phe Asn Ser Ala Ile Thr Asn Leu Gly Asn
        210                 215                 220
Thr Val Asn Asn Leu Ser Glu Ala Arg Ser Arg Ile Glu Asp Ser Asp
225                 230                 235                 240
Tyr Ala Thr Glu Val Ser Asn Met Ser Arg Ala Gln Ile Leu Gln Gln
                245                 250                 255
Ala Gly Thr Ser Val Leu Ala Gln Ala Asn Gln Val Pro Gln Asn Val
            260                 265                 270
Leu Ser Leu Leu Arg Glu Phe Cys Arg Tyr Pro Ala Gln Trp Arg Pro
        275                 280                 285
Leu Met Glu Lys Leu Gln Leu Lys Gly Thr Thr Tyr Gly Val Cys Ser
    290                 295                 300
Lys Ala Phe Lys Phe Leu Gly Thr Pro Ala Asp Thr Gly His Gly Thr
305                 310                 315                 320
Val Val Leu Glu Leu Gln Tyr Thr Gly Thr Asp Gly Pro Cys Lys Val
                325                 330                 335
Pro Ile Ser Ser Val Ala Ser Leu Asn Asp Leu Thr Pro Val Gly Arg
            340                 345                 350
Leu Val Thr Val Asn Pro Phe Val Ser Val Ala Thr Ala Asn Ala Lys
        355                 360                 365
Val Leu Ile Glu Leu Glu Pro Pro Phe Gly Asp Ser Tyr Ile Val Val
    370                 375                 380
Gly Arg Gly Glu Gln Gln Ile Asn His His Trp His Lys Ser Gly Ser
385                 390                 395                 400
Ser Ile Gly Lys Pro Leu Ile Ser
                405
```

<210> SEQ ID NO 35
<211> LENGTH: 1899
<212> TYPE: DNA
<213> ORGANISM: Artificial Sequence
<220> FEATURE:
<223> OTHER INFORMATION: STF2.EIII+

<400> SEQUENCE: 35

```
atggcacaag taatcaacac taacagtctg tcgctgctga cccagaataa cctgaacaaa      60
tcccagtccg cactgggcac cgctatcgag cgtctgtctt ctggtctgcg tatcaacagc     120
gcgaaagacg atgcggcagg tcaggcgatt gctaaccgtt tcaccgcgaa catcaaaggt     180
ctgactcagg cttcccgtaa cgctaacgac ggtatctcca ttgcgcagac cactgaaggc     240
gcgctgaacg aaatcaacaa caacctgcag cgtgtgcgtg aactggcggt tcagtctgct     300
aacagcacca actcccagtc tgacctcgac tccatccagg ctgaaatcac ccagcgcctg     360
aacgaaatcg accgtgtatc cggccagact cagttcaacg gcgtgaaagt cctggcgcag     420
gacaacaccc tgaccatcca ggttggcgcc aacgacggtg aaactatcga tatcgatctg     480
aagcagatca actctcagac cctgggtctg gactcactga cgtgcagaa agcgtatgat     540
gtgaaagata cagcagtaac aacgaaagct tatgccaata atggtactac actggatgta     600
tcgggtcttg atgatgcagc tattaaagcg ctacgggtg tacgaatgg tacggcttct     660
gtaaccggtg gtgcggttaa atttgacgca gataataaca agtactttgt tactattggt     720
ggctttactg gtgctgatgc cgccaaaaat ggcgattatg aagttaacgt tgctactgac     780
ggtacagtaa cccttgcggc tggcgcaact aaaaccacaa tgcctgctgg tgcgacaact     840
```

```
aaaacagaag tacaggagtt aaaagataca ccggcagttg tttcagcaga tgctaaaaat      900
gccttaattg ctggcggcgt tgacgctacc gatgctaatg gcgctgagtt ggtcaaaatg      960
tcttataccg ataaaaatgg taagacaatt gaaggcggtt atgcgcttaa agctggcgat     1020
aagtattacg ccgcagatta cgatgaagcg acaggagcaa ttaaagctaa aactacaagt     1080
tatactgctg ctgacggcac taccaaaaca gcggctaacc aactgggtgg cgtagacggt     1140
aaaaccgaag tcgttactat cgacggtaaa acctacaatg ccagcaaagc cgctggtcat     1200
gatttcaaag cacaaccaga gctggcggaa gcagccgcta aaaccaccga aaacccgctg     1260
cagaaaattg atgccgcgct ggcgcaggtg gatgcgctgc gctctgatct gggtgcggta     1320
caaaaccgtt tcaactctgc tatcaccaac ctgggcaata ccgtaaacaa tctgtctgaa     1380
gcgcgtagcc gtatcgaaga ttccgactac gcgaccgaag tttccaacat gtctcgcgcg     1440
cagattctgc agcaggccgg tacttccgtt ctggcgcagg ctaaccaggt cccgcagaac     1500
gtgctgtctc tgttacgtga attctgcaga tatccagcac agtggcggcc gctcatggaa     1560
aaattgcagt tgaagggaac aacctatggc gtctgttcaa aggctttcaa gtttcttggg     1620
actcccgcag acacaggtca cggcactgtg gtgttggaat tgcagtacac tggcacggat     1680
ggaccttgca aagttcctat ctcgtcagtg gcttcattga acgacctaac gccagtgggc     1740
agattggtca ctgtcaaccc ttttgtttca gtggccacgg ccaacgctaa ggtcctgatt     1800
gaattggaac cacccttttgg agactcatac atagtggtgg cagaggaga acaacagatc     1860 aatcaccatt ggcacaagtc tggaagcagc attggcaaa                            1899
```

<210> SEQ ID NO 36
<211> LENGTH: 633
<212> TYPE: PRT
<213> ORGANISM: Artificial Sequence
<220> FEATURE:
<223> OTHER INFORMATION: STF2.EIII+

<400> SEQUENCE: 36

```
Met Ala Gln Val Ile Asn Thr Asn Ser Leu Ser Leu Leu Thr Gln Asn
  1               5                  10                  15

Asn Leu Asn Lys Ser Gln Ser Ala Leu Gly Thr Ala Ile Glu Arg Leu
                 20                  25                  30

Ser Ser Gly Leu Arg Ile Asn Ser Ala Lys Asp Asp Ala Ala Gly Gln
             35                  40                  45

Ala Ile Ala Asn Arg Phe Thr Ala Asn Ile Lys Gly Leu Thr Gln Ala
         50                  55                  60

Ser Arg Asn Ala Asn Asp Gly Ile Ser Ile Ala Gln Thr Thr Glu Gly
 65                  70                  75                  80

Ala Leu Asn Glu Ile Asn Asn Asn Leu Gln Arg Val Arg Glu Leu Ala
                 85                  90                  95

Val Gln Ser Ala Asn Ser Thr Asn Ser Gln Ser Asp Leu Asp Ser Ile
                100                 105                 110

Gln Ala Glu Ile Thr Gln Arg Leu Asn Glu Ile Asp Arg Val Ser Gly
            115                 120                 125

Gln Thr Gln Phe Asn Gly Val Lys Val Leu Ala Gln Asp Asn Thr Leu
        130                 135                 140

Thr Ile Gln Val Gly Ala Asn Asp Gly Glu Thr Ile Asp Ile Asp Leu
145                 150                 155                 160

Lys Gln Ile Asn Ser Gln Thr Leu Gly Leu Asp Ser Leu Asn Val Gln
                165                 170                 175
```

-continued

```
Lys Ala Tyr Asp Val Lys Asp Thr Ala Val Thr Thr Lys Ala Tyr Ala
            180                 185                 190
Asn Asn Gly Thr Thr Leu Asp Val Ser Gly Leu Asp Ala Ala Ile
        195                 200                 205
Lys Ala Ala Thr Gly Gly Thr Asn Gly Thr Ala Ser Val Thr Gly Gly
210                 215                 220
Ala Val Lys Phe Asp Ala Asp Asn Asn Lys Tyr Phe Val Thr Ile Gly
225                 230                 235                 240
Gly Phe Thr Gly Ala Asp Ala Ala Lys Asn Gly Asp Tyr Glu Val Asn
                245                 250                 255
Val Ala Thr Asp Gly Thr Val Thr Leu Ala Ala Gly Ala Thr Lys Thr
            260                 265                 270
Thr Met Pro Ala Gly Ala Thr Thr Lys Thr Glu Val Gln Glu Leu Lys
        275                 280                 285
Asp Thr Pro Ala Val Val Ser Ala Asp Ala Lys Asn Ala Leu Ile Ala
    290                 295                 300
Gly Gly Val Asp Ala Thr Asp Ala Asn Gly Ala Glu Leu Val Lys Met
305                 310                 315                 320
Ser Tyr Thr Asp Lys Asn Gly Lys Thr Ile Glu Gly Gly Tyr Ala Leu
                325                 330                 335
Lys Ala Gly Asp Lys Tyr Tyr Ala Ala Asp Tyr Asp Glu Ala Thr Gly
            340                 345                 350
Ala Ile Lys Ala Lys Thr Thr Ser Tyr Thr Ala Ala Asp Gly Thr Thr
        355                 360                 365
Lys Thr Ala Ala Asn Gln Leu Gly Gly Val Asp Gly Lys Thr Glu Val
    370                 375                 380
Val Thr Ile Asp Gly Lys Thr Tyr Asn Ala Ser Lys Ala Ala Gly His
385                 390                 395                 400
Asp Phe Lys Ala Gln Pro Glu Leu Ala Glu Ala Ala Lys Thr Thr
                405                 410                 415
Glu Asn Pro Leu Gln Lys Ile Asp Ala Ala Leu Ala Gln Val Asp Ala
            420                 425                 430
Leu Arg Ser Asp Leu Gly Ala Val Gln Asn Arg Phe Asn Ser Ala Ile
        435                 440                 445
Thr Asn Leu Gly Asn Thr Val Asn Asn Leu Ser Glu Ala Arg Ser Arg
    450                 455                 460
Ile Glu Asp Ser Asp Tyr Ala Thr Glu Val Ser Asn Met Ser Arg Ala
465                 470                 475                 480
Gln Ile Leu Gln Gln Ala Gly Thr Ser Val Leu Ala Gln Ala Asn Gln
                485                 490                 495
Val Pro Gln Asn Val Leu Ser Leu Leu Arg Glu Phe Cys Arg Tyr Pro
            500                 505                 510
Ala Gln Trp Arg Pro Leu Met Glu Lys Leu Gln Leu Lys Gly Thr Thr
        515                 520                 525
Tyr Gly Val Cys Ser Lys Ala Phe Lys Phe Leu Gly Thr Pro Ala Asp
    530                 535                 540
Thr Gly His Gly Thr Val Val Leu Glu Leu Gln Tyr Thr Gly Thr Asp
545                 550                 555                 560
Gly Pro Cys Lys Val Pro Ile Ser Ser Val Ala Ser Leu Asn Asp Leu
                565                 570                 575
Thr Pro Val Gly Arg Leu Val Thr Val Asn Pro Phe Val Ser Val Ala
            580                 585                 590
Thr Ala Asn Ala Lys Val Leu Ile Glu Leu Glu Pro Pro Phe Gly Asp
        595                 600                 605
```

```
Ser Tyr Ile Val Val Gly Arg Gly Glu Gln Gln Ile Asn His His Trp
    610                 615                 620
His Lys Ser Gly Ser Ser Ile Gly Lys
625                 630
```

<210> SEQ ID NO 37
<211> LENGTH: 1143
<212> TYPE: DNA
<213> ORGANISM: Artificial Sequence
<220> FEATURE:
<223> OTHER INFORMATION: STF2delta.EIII+

<400> SEQUENCE: 37

```
atggcacaag taatcaacac taacagtctg tcgctgctga cccagaataa cctgaacaaa      60
tcccagtccg cactgggcac cgctatcgag cgtctgtctt ctggtctgcg tatcaacagc     120
gcgaaagacg atgcggcagg tcaggcgatt gctaaccgtt tcaccgcgaa catcaaaggt     180
ctgactcagg cttcccgtaa cgctaacgac ggtatctcca ttgcgcagac cactgaaggc     240
gcgctgaacg aaatcaacaa caacctgcag cgtgtgcgtg aactggcggt tcagtctgct     300
aacagcacca ctcccagtc tgacctcgac tccatccagg ctgaaatcac ccagcgcctg     360
aacgaaatcg accgtgtatc cggccagact cagttcaacg gcgtgaaagt cctggcgcag     420
gacaacaccc tgaccatcca ggttggcgcc aacgacggtg aaactatcga tatcgatctg     480
aagcagatca actctcagac cctgggtctg gactcactga acgtgaccga aacccgctg     540
cagaaaattg atgccgcgct ggcgcaggtg gatgcgctgc gctctgatct gggtgcggta     600
caaaaccgtt tcaactctgc tatcaccaac ctgggcaata ccgtaaacaa tctgtctgaa     660
gcgcgtagcc gtatcgaaga ttccgactac gcgaccgaag tttccaacat gtctcgcgcg     720
cagattctgc agcaggccgg tacttccgtt ctggcgcagg ctaaccaggt cccgcagaac     780
gtgctgtctc tgttacgtat ggaaaaattg cagttgaagg aacaaccta tggcgtctgt     840
tcaaaggctt tcaagtttct tgggactccc gcagacacag gtcacggcac tgtggtgttg     900
gaattgcagt acactggcac ggatggacct tgcaaagttc ctatctcgtc agtggcttca     960
ttgaacgacc taacgccagt gggcagattg gtcactgtca acccttttgt ttcagtggcc    1020
acggccaacg ctaaggtcct gattgaattg gaaccaccct ttggagactc atacatagtg    1080
gtgggcagag gaacaaca gatcaatcac cattggcaca gtctggaag cagcattggc    1140
aaa                                                                  1143
```

<210> SEQ ID NO 38
<211> LENGTH: 381
<212> TYPE: PRT
<213> ORGANISM: Artificial Sequence
<220> FEATURE:
<223> OTHER INFORMATION: STF2delta.EIII+

<400> SEQUENCE: 38

```
Met Ala Gln Val Ile Asn Thr Asn Ser Leu Ser Leu Leu Thr Gln Asn
  1               5                  10                  15
Asn Leu Asn Lys Ser Gln Ser Ala Leu Gly Thr Ala Ile Glu Arg Leu
             20                  25                  30
Ser Ser Gly Leu Arg Ile Asn Ser Ala Lys Asp Asp Ala Ala Gly Gln
         35                  40                  45
Ala Ile Ala Asn Arg Phe Thr Ala Asn Ile Lys Gly Leu Thr Gln Ala
     50                  55                  60
Ser Arg Asn Ala Asn Asp Gly Ile Ser Ile Ala Gln Thr Thr Glu Gly
```

```
                65                  70                  75                  80
Ala Leu Asn Glu Ile Asn Asn Leu Gln Arg Val Arg Glu Leu Ala
                    85                  90                  95

Val Gln Ser Ala Asn Ser Thr Asn Ser Gln Ser Asp Leu Asp Ser Ile
                100                 105                 110

Gln Ala Glu Ile Thr Gln Arg Leu Asn Glu Ile Asp Arg Val Ser Gly
                115                 120                 125

Gln Thr Gln Phe Asn Gly Val Lys Val Leu Ala Gln Asp Asn Thr Leu
            130                 135                 140

Thr Ile Gln Val Gly Ala Asn Asp Gly Glu Thr Ile Asp Ile Asp Leu
145                 150                 155                 160

Lys Gln Ile Asn Ser Gln Thr Leu Gly Leu Asp Ser Leu Asn Val Thr
                165                 170                 175

Glu Asn Pro Leu Gln Lys Ile Asp Ala Ala Leu Ala Gln Val Asp Ala
                180                 185                 190

Leu Arg Ser Asp Leu Gly Ala Val Gln Asn Arg Phe Asn Ser Ala Ile
            195                 200                 205

Thr Asn Leu Gly Asn Thr Val Asn Asn Leu Ser Glu Ala Arg Ser Arg
210                 215                 220

Ile Glu Asp Ser Asp Tyr Ala Thr Glu Val Ser Asn Met Ser Arg Ala
225                 230                 235                 240

Gln Ile Leu Gln Gln Ala Gly Thr Ser Val Leu Ala Gln Ala Asn Gln
                245                 250                 255

Val Pro Gln Asn Val Leu Ser Leu Leu Arg Met Glu Lys Leu Gln Leu
                260                 265                 270

Lys Gly Thr Thr Tyr Gly Val Cys Ser Lys Ala Phe Lys Phe Leu Gly
            275                 280                 285

Thr Pro Ala Asp Thr Gly His Gly Thr Val Val Leu Glu Leu Gln Tyr
            290                 295                 300

Thr Gly Thr Asp Gly Pro Cys Lys Val Pro Ile Ser Ser Val Ala Ser
305                 310                 315                 320

Leu Asn Asp Leu Thr Pro Val Gly Arg Leu Val Thr Val Asn Pro Phe
                325                 330                 335

Val Ser Val Ala Thr Ala Asn Ala Lys Val Leu Ile Glu Leu Glu Pro
                340                 345                 350

Pro Phe Gly Asp Ser Tyr Ile Val Val Gly Arg Gly Glu Gln Gln Ile
            355                 360                 365

Asn His His Trp His Lys Ser Gly Ser Ser Ile Gly Lys
            370                 375                 380

<210> SEQ ID NO 39
<211> LENGTH: 406
<212> TYPE: PRT
<213> ORGANISM: Artificial Sequence
<220> FEATURE:
<223> OTHER INFORMATION: West Nile virus envelope

<400> SEQUENCE: 39

Phe Asn Cys Leu Gly Met Ser Asn Arg Asp Phe Leu Glu Gly Val Ser
 1               5                  10                  15

Gly Ala Thr Trp Val Asp Leu Val Leu Glu Gly Asp Ser Cys Val Thr
                20                  25                  30

Ile Met Ser Lys Asp Lys Pro Thr Ile Asp Val Lys Met Met Asn Met
            35                  40                  45

Glu Ala Ala Asn Leu Ala Glu Val Arg Ser Tyr Cys Tyr Leu Ala Thr
        50                  55                  60
```

Val Ser Asp Leu Ser Thr Lys Ala Ala Cys Pro Thr Met Gly Glu Ala
65                  70                  75                  80

His Asn Asp Lys Arg Ala Asp Pro Ala Phe Val Cys Arg Gln Gly Val
                85                  90                  95

Val Asp Arg Gly Trp Gly Asn Gly Cys Gly Leu Phe Gly Lys Gly Ser
            100                 105                 110

Ile Asp Thr Cys Ala Lys Phe Ala Cys Ser Thr Lys Ala Ile Gly Arg
        115                 120                 125

Thr Ile Leu Lys Glu Asn Ile Lys Tyr Glu Val Ala Ile Phe Val His
    130                 135                 140

Gly Pro Thr Thr Val Glu Ser His Gly Asn Tyr Ser Thr Gln Val Gly
145                 150                 155                 160

Ala Thr Gln Ala Gly Arg Phe Ser Ile Thr Pro Ala Ala Pro Ser Tyr
                165                 170                 175

Thr Leu Lys Leu Gly Glu Tyr Gly Glu Val Thr Val Asp Cys Glu Pro
            180                 185                 190

Arg Ser Gly Ile Asp Thr Asn Ala Tyr Tyr Val Met Thr Val Gly Thr
        195                 200                 205

Lys Thr Phe Leu Val His Arg Glu Trp Phe Met Asp Leu Asn Leu Pro
    210                 215                 220

Trp Ser Ser Ala Gly Ser Thr Val Trp Arg Asn Arg Glu Thr Leu Met
225                 230                 235                 240

Glu Phe Glu Glu Pro His Ala Thr Lys Gln Ser Val Ile Ala Leu Gly
                245                 250                 255

Ser Gln Glu Gly Ala Leu His Gln Ala Leu Ala Gly Ala Ile Pro Val
            260                 265                 270

Glu Phe Ser Ser Asn Thr Val Lys Leu Thr Ser Gly His Leu Lys Cys
        275                 280                 285

Arg Val Lys Met Glu Lys Leu Gln Leu Lys Gly Thr Thr Tyr Gly Val
    290                 295                 300

Cys Ser Lys Ala Phe Lys Phe Leu Gly Thr Pro Ala Asp Thr Gly His
305                 310                 315                 320

Gly Thr Val Val Leu Glu Leu Gln Tyr Thr Gly Thr Asp Gly Pro Cys
                325                 330                 335

Lys Val Pro Ile Ser Ser Val Ala Ser Leu Asn Asp Leu Thr Pro Val
            340                 345                 350

Gly Arg Leu Val Thr Val Asn Pro Phe Val Ser Val Ala Thr Ala Asn
        355                 360                 365

Ala Lys Val Leu Ile Glu Leu Glu Pro Pro Phe Gly Asp Ser Tyr Ile
    370                 375                 380

Val Val Gly Arg Gly Glu Gln Gln Ile Asn His His Trp His Lys Ser
385                 390                 395                 400

Gly Ser Ser Ile Gly Lys
                405

<210> SEQ ID NO 40
<211> LENGTH: 99
<212> TYPE: PRT
<213> ORGANISM: Artificial Sequence
<220> FEATURE:
<223> OTHER INFORMATION: flavivirus

<400> SEQUENCE: 40

Gly Met Ser Tyr Ser Met Cys Thr Gly Lys Phe Lys Val Val Lys Glu
1               5                   10                  15

```
Ile Ala Glu Thr Gln His Gly Thr Ile Val Ile Arg Val Gln Tyr Glu
         20                  25                  30

Gly Asp Gly Ser Pro Cys Lys Ile Pro Phe Glu Ile Met Asp Leu Glu
             35                  40                  45

Lys Arg His Val Leu Gly Arg Leu Ile Thr Val Asn Pro Ile Val Thr
 50                  55                  60

Glu Lys Asp Ser Pro Val Asn Ile Glu Ala Gly Pro Pro Phe Gly Asp
 65                  70                  75                  80

Ser Tyr Ile Ile Ile Gly Val Glu Pro Gly Gln Leu Lys Leu Asn Trp
                 85                  90                  95

Phe Lys Lys

<210> SEQ ID NO 41
<211> LENGTH: 38
<212> TYPE: DNA
<213> ORGANISM: Artificial Sequence
<220> FEATURE:
<223> OTHER INFORMATION: primer

<400> SEQUENCE: 41
ctcgggagat ctgcacaagt aatcaacact aacagtct                          38

<210> SEQ ID NO 42
<211> LENGTH: 41
<212> TYPE: DNA
<213> ORGANISM: Artificial Sequence
<220> FEATURE:
<223> OTHER INFORMATION: primer

<400> SEQUENCE: 42
ccatgggcta gcaggatcca ccggcgctcc ctgcacgttc a                      41

<210> SEQ ID NO 43
<211> LENGTH: 42
<212> TYPE: DNA
<213> ORGANISM: Artificial Sequence
<220> FEATURE:
<223> OTHER INFORMATION: primer

<400> SEQUENCE: 43
ggagcgccgg tggatcctgc tagcccatgg accgaaaacc cg                     42

<210> SEQ ID NO 44
<211> LENGTH: 84
<212> TYPE: DNA
<213> ORGANISM: Artificial Sequence
<220> FEATURE:
<223> OTHER INFORMATION: primer

<400> SEQUENCE: 44
tctgcagaat tcacgtaaca gagacagcac gttctgcggg acgtcccgca gaacgtgctg  60
tctctgttac gtgaattctg caga                                        84

<210> SEQ ID NO 45
<211> LENGTH: 20
<212> TYPE: DNA
<213> ORGANISM: Artificial Sequence
<220> FEATURE:
<223> OTHER INFORMATION: primer

<400> SEQUENCE: 45
tccggcgtag aggatcgaga                                              20
```

```
<210> SEQ ID NO 46
<211> LENGTH: 54
<212> TYPE: DNA
<213> ORGANISM: Artificial Sequence
<220> FEATURE:
<223> OTHER INFORMATION: primer

<400> SEQUENCE: 46
caattgacct tcaagcttcg aattgccctt acgtaacaga gacagcacgt tctg         54

<210> SEQ ID NO 47
<211> LENGTH: 57
<212> TYPE: DNA
<213> ORGANISM: Artificial Sequence
<220> FEATURE:
<223> OTHER INFORMATION: primer

<400> SEQUENCE: 47
aagcttgaag gtcaattgga attccctagg actagtatgg aaaaattgca gttgaag      57

<210> SEQ ID NO 48
<211> LENGTH: 20
<212> TYPE: DNA
<213> ORGANISM: Artificial Sequence
<220> FEATURE:
<223> OTHER INFORMATION: primer

<400> SEQUENCE: 48
gcttaatgcg ccgctacagg                                               20

<210> SEQ ID NO 49
<211> LENGTH: 40
<212> TYPE: DNA
<213> ORGANISM: Artificial Sequence
<220> FEATURE:
<223> OTHER INFORMATION: primer

<400> SEQUENCE: 49
gcggccgctc atgaaaaat tgcagttgaa gggaacaacc                          40

<210> SEQ ID NO 50
<211> LENGTH: 32
<212> TYPE: DNA
<213> ORGANISM: Artificial Sequence
<220> FEATURE:
<223> OTHER INFORMATION: primer

<400> SEQUENCE: 50
ccgcggtttg ccaatgctgc ttccagactt gt                                 32

<210> SEQ ID NO 51
<211> LENGTH: 49
<212> TYPE: DNA
<213> ORGANISM: Artificial Sequence
<220> FEATURE:
<223> OTHER INFORMATION: primer

<400> SEQUENCE: 51
ccggcatgcc atatggcaca agtaatcaac actaacagtc tgtcgctgc               49

<210> SEQ ID NO 52
<211> LENGTH: 49
<212> TYPE: DNA
<213> ORGANISM: Artificial Sequence
<220> FEATURE:
<223> OTHER INFORMATION: primer

<400> SEQUENCE: 52
```

```
gcatgctcag cttattaagg gtttgccaat gctgcttccc agacttgtg        49
```

<210> SEQ ID NO 53
<211> LENGTH: 27
<212> TYPE: DNA
<213> ORGANISM: Artificial Sequence
<220> FEATURE:
<223> OTHER INFORMATION: primer

<400> SEQUENCE: 53

```
tacgtgaatt cagcagatat ccagcac                                27
```

<210> SEQ ID NO 54
<211> LENGTH: 1911
<212> TYPE: DNA
<213> ORGANISM: Artificial Sequence
<220> FEATURE:
<223> OTHER INFORMATION: STF2.EIII+

<400> SEQUENCE: 54

```
atggcacaag taatcaacac taacagtctg tcgctgctga cccagaataa cctgaacaaa     60
tcccagtccg cactgggcac cgctatcgag cgtctgtctt ctggtctgcg tatcaacagc    120
gcgaaagacg atgcggcagg tcaggcgatt gctaaccgtt tcaccgcgaa catcaaaggt    180
ctgactcagg cttcccgtaa cgctaacgac ggtatctcca ttgcgcagac cactgaaggc    240
gcgctgaacg aaatcaacaa caacctgcag cgtgtgcgtg aactggcggt tcagtctgct    300
aacagcacca actcccagtc tgacctcgac tccatccagg ctgaaatcac ccagcgcctg    360
aacgaaatcg accgtgtatc cggccagact cagttcaacg gcgtgaaagt cctggcgcag    420
gacaacaccc tgaccatcca ggttggcgcc aacgacggtg aaactatcga tatcgatctg    480
aagcagatca actctcagac cctgggtctg gactcactga acgtgcagaa agcgtatgat    540
gtgaaagata cagcagtaac aacgaaagct tatgccaata atggtactac actggatgta    600
tcgggtcttg atgatgcagc tattaaagcg ctacgggtg gtacgaatgg tacggcttct    660
gtaaccggtg gtgcggttaa atttgacgca gataataaca agtactttgt tactattggt    720
ggctttactg gtgctgatgc cgccaaaaat ggcgattatg aagttaacgt tgctactgac    780
ggtacagtaa cccttgcggc tggcgcaact aaaaccacaa tgcctgctgg tgcgacaact    840
aaaacagaag tacaggagtt aaaagataca ccggcagttg tttcagcaga tgctaaaaat    900
gccttaattg ctggcggcgt tgacgctacc gatgctaatg cgctgagtt ggtcaaaatg    960
tcttataccg ataaaaatgg taagacaatt gaaggcggtt atgcgcttaa agctggcgat   1020
aagtattacg ccgcagatta cgatgaagcg acaggagcaa ttaaagctaa actacaagt    1080
tatactgctg ctgacggcac taccaaaaca gcggctaacc aactgggtgg cgtagacggt   1140
aaaaccgaag tcgttactat cgacggtaaa acctacaatg ccagcaaagc cgctggtcat   1200
gatttcaaag cacaaccaga gctggcggaa gcagccgcta aaaccaccga aaacccgctg   1260
cagaaaattg atgccgcgct ggcgcaggtg gatgcgctgc gctctgatct gggtgcggta   1320
caaaaccgtt tcaactctgc tatcaccaac ctgggcaata ccgtaaacaa tctgtctgaa   1380
gcgcgtagcc gtatcgaaga ttccgactac gcgaccgaag tttccaacat gtctcgcgcg   1440
cagattctgc agcaggccgg tacttccgtt ctggcgcagg ctaaccaggt cccgcagaac   1500
gtgctgtctc tgttacgtaa gggcaattcg aagcttgaag gtcaattgga attccctagg   1560
actagtatgg aaaaattgca gttgaaggga acaacctatg cgtctgttc aaaggctttc   1620
aagtttcttg ggactcccgc agacacaggt cacggcactg tggtgttgga attgcagtac   1680
```

```
actggcacgg atggaccttg caaagttcct atctcgtcag tggcttcatt gaacgaccta      1740
acgccagtgg gcagattggt cactgtcaac ccttttgttt cagtggccac ggccaacgct      1800
aaggtcctga ttgaattgga accacccttt ggagactcat acatagtggt gggcagagga      1860
gaacaacaga tcaatcacca ttggcacaag tctggaagca gcattggcaa a              1911
```

<210> SEQ ID NO 55
<211> LENGTH: 637
<212> TYPE: PRT
<213> ORGANISM: Artificial Sequence
<220> FEATURE:
<223> OTHER INFORMATION: STF2.EIII+

<400> SEQUENCE: 55

```
Met Ala Gln Val Ile Asn Thr Asn Ser Leu Ser Leu Leu Thr Gln Asn
 1               5                  10                  15

Asn Leu Asn Lys Ser Gln Ser Ala Leu Gly Thr Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ala Asn Ile Lys Gly Leu Thr Gln Ala
    50                  55                  60

Ser Arg Asn Ala Asn Asp Gly Ile Ser Ile Ala Gln Thr Thr Glu Gly
65                  70                  75                  80

Ala Leu Asn Glu Ile Asn Asn Asn Leu Gln Arg Val Arg Glu Leu Ala
                85                  90                  95

Val Gln Ser Ala Asn Ser Thr Asn Ser Gln Ser Asp Leu Asp Ser Ile
            100                 105                 110

Gln Ala Glu Ile Thr Gln Arg Leu Asn Glu Ile Asp Arg Val Ser Gly
        115                 120                 125

Gln Thr Gln Phe Asn Gly Val Lys Val Leu Ala Gln Asp Asn Thr Leu
    130                 135                 140

Thr Ile Gln Val Gly Ala Asn Asp Gly Glu Thr Ile Asp Ile Asp Leu
145                 150                 155                 160

Lys Gln Ile Asn Ser Gln Thr Leu Gly Leu Asp Ser Leu Asn Val Gln
                165                 170                 175

Lys Ala Tyr Asp Val Lys Asp Thr Ala Val Thr Thr Lys Ala Tyr Ala
            180                 185                 190

Asn Asn Gly Thr Thr Leu Asp Val Ser Gly Leu Asp Asp Ala Ala Ile
        195                 200                 205

Lys Ala Ala Thr Gly Gly Thr Asn Gly Thr Ala Ser Val Thr Gly Gly
    210                 215                 220

Ala Val Lys Phe Asp Ala Asp Asn Asn Lys Tyr Phe Val Thr Ile Gly
225                 230                 235                 240

Gly Phe Thr Gly Ala Asp Ala Ala Lys Asn Gly Asp Tyr Glu Val Asn
                245                 250                 255

Val Ala Thr Asp Gly Thr Val Thr Leu Ala Ala Gly Ala Thr Lys Thr
            260                 265                 270

Thr Met Pro Ala Gly Ala Thr Thr Lys Thr Glu Val Gln Glu Leu Lys
        275                 280                 285

Asp Thr Pro Ala Val Val Ser Ala Asp Ala Lys Asn Ala Leu Ile Ala
    290                 295                 300

Gly Gly Val Asp Ala Thr Asp Ala Asn Gly Ala Glu Leu Val Lys Met
305                 310                 315                 320

Ser Tyr Thr Asp Lys Asn Gly Lys Thr Ile Glu Gly Gly Tyr Ala Leu
```

325                 330                 335
Lys Ala Gly Asp Lys Tyr Tyr Ala Ala Asp Tyr Asp Glu Ala Thr Gly
                340                 345                 350
Ala Ile Lys Ala Lys Thr Thr Ser Tyr Thr Ala Ala Asp Gly Thr Thr
                355                 360                 365
Lys Thr Ala Ala Asn Gln Leu Gly Gly Val Asp Gly Lys Thr Glu Val
                370                 375                 380
Val Thr Ile Asp Gly Lys Thr Tyr Asn Ala Ser Lys Ala Ala Gly His
385                 390                 395                 400
Asp Phe Lys Ala Gln Pro Glu Leu Ala Glu Ala Ala Lys Thr Thr
                405                 410                 415
Glu Asn Pro Leu Gln Lys Ile Asp Ala Ala Leu Ala Gln Val Asp Ala
                420                 425                 430
Leu Arg Ser Asp Leu Gly Ala Val Gln Asn Arg Phe Asn Ser Ala Ile
                435                 440                 445
Thr Asn Leu Gly Asn Thr Val Asn Asn Leu Ser Glu Ala Arg Ser Arg
                450                 455                 460
Ile Glu Asp Ser Asp Tyr Ala Thr Glu Val Ser Asn Met Ser Arg Ala
465                 470                 475                 480
Gln Ile Leu Gln Gln Ala Gly Thr Ser Val Leu Ala Gln Ala Asn Gln
                485                 490                 495
Val Pro Gln Asn Val Leu Ser Leu Leu Arg Lys Gly Asn Ser Lys Leu
                500                 505                 510
Glu Gly Gln Leu Glu Phe Pro Arg Thr Ser Met Glu Lys Leu Gln Leu
                515                 520                 525
Lys Gly Thr Thr Tyr Gly Val Cys Ser Lys Ala Phe Lys Phe Leu Gly
                530                 535                 540
Thr Pro Ala Asp Thr Gly His Gly Thr Val Val Leu Glu Leu Gln Tyr
545                 550                 555                 560
Thr Gly Thr Asp Gly Pro Cys Lys Val Pro Ile Ser Ser Val Ala Ser
                565                 570                 575
Leu Asn Asp Leu Thr Pro Val Gly Arg Leu Val Thr Val Asn Pro Phe
                580                 585                 590
Val Ser Val Ala Thr Ala Asn Ala Lys Val Leu Ile Glu Leu Glu Pro
                595                 600                 605
Pro Phe Gly Asp Ser Tyr Ile Val Val Gly Arg Gly Glu Gln Gln Ile
                610                 615                 620
Asn His His Trp His Lys Ser Gly Ser Ser Ile Gly Lys
625                 630                 635

<210> SEQ ID NO 56
<211> LENGTH: 10
<212> TYPE: PRT
<213> ORGANISM: Artificial Sequence
<220> FEATURE:
<223> OTHER INFORMATION: Linker

<400> SEQUENCE: 56

Gly Ala Pro Val Asp Pro Ala Ser Pro Trp
 1               5                  10

<210> SEQ ID NO 57
<211> LENGTH: 1218
<212> TYPE: DNA
<213> ORGANISM: Artificial Sequence
<220> FEATURE:
<223> OTHER INFORMATION: West Nile virus envelope protein

<400> SEQUENCE: 57

```
ttcaactgcc ttggaatgag caacagagac ttcttggaag gagtgtctgg agcaacatgg      60
gtggatttgg ttctcgaagg cgacagctgc gtgactatca tgtctaagga caagcctacc     120
atcgatgtga agatgatgaa tatggaggcg gccaacctgg cagaggtccg cagttattgc     180
tatttggcta ccgtcagcga tctctccacc aaagctgcgt gcccgaccat gggagaagct     240
cacaatgaca aacgtgctga cccagctttt gtgtgcagac aaggagtggt ggacaggggc     300
tggggcaacg gctgcggact atttggcaaa ggaagcattg acacatgcgc caaatttgcc     360
tgctctacca aggcaatagg aagaaccatc ttgaaagaga atatcaagta cgaagtggcc     420
attttgtcc atggaccaac tactgtggag tcgcacggaa actactccac acaggttgga     480
gccactcagg cagggagatt cagcatcact cctgcagcgc ttcatacac actaaagctt      540
ggagaatatg gagaggtgac agtggactgt gaaccacggt cagggattga caccaatgca     600
tactacgtga tgactgttgg aacaaagacg ttcttggtcc atcgtgagtg gttcatggac     660
ctcaacctcc cttggagcag tgctggaagt actgtgtgga ggaacagaga gacgttaatg     720
gagtttgagg aaccacacgc cacgaagcag tctgtgatag cattgggctc acaagaggga     780
gctctgcatc aagctttggc tggagccatt cctgtggaat tttcaagcaa cactgtcaag     840
ttgacgtcgg tcatttgaa gtgtagagtg aagatgaaa aattgcagtt gaagggaaca      900
acctatggcg tctgttcaaa ggcttttcaag tttcttggga ctcccgcaga cacaggtcac     960
ggcactgtgg tgttggaatt gcagtacact ggcacggatg gaccttgcaa agttcctatc    1020
tcgtcagtgg cttcattgaa cgacctaacg ccagtgggca gattggtcac tgtcaaccct    1080
tttgttcag tggccacggc caacgctaag gtcctgattg aattggaacc accctttgga    1140
gactcataca tagtggtggg cagaggagaa caacagatca atcaccattg gcacaagtct    1200
ggaagcagca ttggcaaa                                                  1218
```

<210> SEQ ID NO 58
<211> LENGTH: 506
<212> TYPE: PRT
<213> ORGANISM: S. muenchen

<400> SEQUENCE: 58

```
Met Ala Gln Val Ile Asn Thr Asn Ser Leu Ser Leu Leu Thr Gln Asn
 1               5                  10                  15

Asn Leu Asn Lys Ser Gln Ser Ala Leu Gly Thr Ala Ile Glu Arg Leu
             20                  25                  30

Ser Ser Gly Leu Arg Ile Asn Ser Ala Lys Asp Asp Ala Ala Gly Gln
         35                  40                  45

Ala Ile Ala Asn Arg Phe Thr Ala Asn Ile Lys Gly Leu Thr Gln Ala
     50                  55                  60

Ser Arg Asn Ala Asn Asp Gly Ile Ser Ile Ala Gln Thr Thr Glu Gly
 65                  70                  75                  80

Ala Leu Asn Glu Ile Asn Asn Asn Leu Gln Arg Val Arg Glu Leu Ala
                 85                  90                  95

Val Gln Ser Ala Asn Gly Thr Asn Ser Gln Ser Asp Leu Asp Ser Ile
            100                 105                 110

Gln Ala Glu Ile Thr Gln Arg Leu Asn Glu Ile Asp Arg Val Ser Gly
        115                 120                 125

Gln Thr Gln Phe Asn Gly Val Lys Val Leu Ala Gln Asp Asn Thr Leu
    130                 135                 140

Thr Ile Gln Val Gly Ala Asn Asp Gly Glu Thr Ile Asp Ile Asp Leu
```

```
          145                 150                 155                 160
Lys Glu Ile Ser Ser Lys Thr Leu Gly Leu Asp Lys Leu Asn Val Gln
                165                 170                 175

Asp Ala Tyr Thr Pro Lys Glu Thr Ala Val Thr Val Asp Lys Thr Thr
            180                 185                 190

Tyr Lys Asn Gly Thr Asp Thr Ile Ala Gln Ser Asn Thr Asp Ile
        195                 200                 205

Gln Thr Ala Ile Gly Gly Ala Thr Gly Val Thr Gly Ala Asp Ile
    210                 215                 220

Lys Phe Lys Asp Gly Gln Tyr Tyr Leu Asp Val Lys Gly Gly Ala Ser
225                 230                 235                 240

Ala Gly Val Tyr Lys Ala Thr Tyr Asp Glu Thr Thr Lys Lys Val Asn
                245                 250                 255

Ile Asp Thr Thr Asp Lys Thr Pro Leu Ala Thr Ala Glu Ala Thr Ala
            260                 265                 270

Ile Arg Gly Thr Ala Thr Ile Thr His Asn Gln Ile Ala Glu Val Thr
        275                 280                 285

Lys Glu Gly Val Asp Thr Thr Thr Val Ala Ala Gln Leu Ala Ala Ala
    290                 295                 300

Gly Val Thr Gly Ala Asp Lys Asp Asn Thr Ser Leu Val Lys Leu Ser
305                 310                 315                 320

Phe Glu Asp Lys Asn Gly Lys Val Ile Asp Gly Gly Tyr Ala Val Lys
                325                 330                 335

Met Gly Asp Asp Phe Tyr Ala Ala Thr Tyr Asp Glu Lys Thr Gly Thr
            340                 345                 350

Ile Thr Ala Lys Thr Thr Thr Tyr Thr Asp Gly Ala Gly Val Ala Gln
        355                 360                 365

Thr Gly Ala Val Lys Phe Gly Gly Ala Asn Gly Lys Ser Glu Val Val
    370                 375                 380

Thr Ala Thr Asp Gly Lys Thr Tyr Leu Ala Ser Asp Leu Asp Lys His
385                 390                 395                 400

Asn Phe Arg Thr Gly Gly Glu Leu Lys Glu Val Asn Thr Asp Lys Thr
                405                 410                 415

Glu Asn Pro Leu Gln Lys Ile Asp Ala Ala Leu Ala Gln Val Asp Thr
            420                 425                 430

Leu Arg Ser Asp Leu Gly Ala Val Gln Asn Arg Phe Asn Ser Ala Ile
        435                 440                 445

Thr Asn Leu Gly Asn Thr Val Asn Asn Leu Ser Ser Ala Arg Ser Arg
    450                 455                 460

Ile Glu Asp Ser Asp Tyr Ala Thr Glu Val Ser Asn Met Ser Arg Ala
465                 470                 475                 480

Gln Ile Leu Gln Gln Ala Gly Thr Ser Val Leu Ala Gln Ala Asn Gln
                485                 490                 495

Val Pro Gln Asn Val Leu Ser Leu Leu Arg
            500                 505

<210> SEQ ID NO 59
<211> LENGTH: 1521
<212> TYPE: DNA
<213> ORGANISM: S. muenchen

<400> SEQUENCE: 59
atggcacaag tcattaatac aaacagcctg tcgctgttga cccagaataa cctgaacaaa      60
tcccagtccg ctctgggcac cgctatcgag cgtctgtctt ccggtctgcg tatcaacagc     120
```

-continued

| | |
|---|---|
| gcgaaagacg atgcggcagg tcaggcgatt gctaaccgtt tcaccgcgaa catcaaaggt | 180 |
| ctgactcagg cttcccgtaa cgctaacgac ggtatctcca ttgcgcagac cactgaaggc | 240 |
| gcgctgaacg aaatcaacaa caacctgcag cgtgtgcgtg aactggcggt tcagtctgct | 300 |
| aacggtacta actcccagtc tgaccttgac tctatccagg ctgaaatcac ccagcgtctg | 360 |
| aacgaaatcg accgtgtatc cggtcagact cagttcaacg gcgtgaaagt cctggcgcag | 420 |
| gacaacaccc tgaccatcca ggttggtgcc aacgacggtg aaactattga tattgattta | 480 |
| aaagaaatta gctctaaaac actgggactt gataagctta atgtccagga tgcctacacc | 540 |
| ccgaaagaaa ctgctgtaac cgttgataaa actacctata aaaatggtac agatactatt | 600 |
| acagcccaga gcaatactga tatccaaact gcaattggcg gtggtgcaac ggggggttact | 660 |
| ggggctgata tcaaatttaa agatggtcaa tactatttag atgttaaagg cggtgcttct | 720 |
| gctggtgttt ataaagccac ttatgatgaa actcaaagaa agttaatat tgatacgact | 780 |
| gataaaactc cgttagcaac tgcggaagct acagctattc ggggaacggc cactataacc | 840 |
| cacaaccaaa ttgctgaagt aacaaagag ggtgttgata cgaccacagt tgcggctcaa | 900 |
| cttgctgctg caggggttac tggtgccgat aaggacaata ctagccttgt aaaactatcg | 960 |
| tttgaggata aaacggtaa ggttattgat ggtggctatg cagtgaaaat gggcgacgat | 1020 |
| ttctatgccg ctacatatga tgagaaaaca ggtacaatta ctgctaaaac aaccacttat | 1080 |
| acagatggtg ctggcgttgc tcaaactgga gctgtgaaat tggtggcgc aaatggtaaa | 1140 |
| tctgaagttg ttactgctac cgatggtaaa acttacttag caagcgacct tgacaaacat | 1200 |
| aacttcagaa caggcggtga gcttaaagag gttaatacag ataagactga aaacccactg | 1260 |
| cagaaaattg atgctgcctt ggcacaggtt gatacacttc gttctgacct gggtgcggta | 1320 |
| cagaaccgtt tcaactccgc tatcaccaac ctgggcaata ccgtaaataa cctgtcttct | 1380 |
| gcccgtagcc gtatcgaaga ttccgactac gcgaccgaag tctccaacat gtctcgcgcg | 1440 |
| cagattctgc agcaggccgg tacctccgtt ctggcgcagg ctaaccaggt tccgcaaaac | 1500 |
| gtcctctctt tactgcgtta a | 1521 |

<210> SEQ ID NO 60
<211> LENGTH: 12
<212> TYPE: PRT
<213> ORGANISM: Artificial Sequence
<220> FEATURE:
<223> OTHER INFORMATION: Linker

<400> SEQUENCE: 60

Glu Phe Ser Arg Tyr Pro Ala Gln Trp Arg Pro Leu
1               5                   10

<210> SEQ ID NO 61
<211> LENGTH: 36
<212> TYPE: DNA
<213> ORGANISM: Artificial Sequence
<220> FEATURE:
<223> OTHER INFORMATION: Linker

<400> SEQUENCE: 61
gaattctcta gatatccagc acagtggcgg ccgctc         36

<210> SEQ ID NO 62
<211> LENGTH: 45
<212> TYPE: PRT
<213> ORGANISM: Artificial Sequence
<220> FEATURE:
<223> OTHER INFORMATION: Linker

<400> SEQUENCE: 62

Lys Gly Asn Ser Lys Leu Glu Gly Gln Leu Glu Phe Pro Arg Thr Ser
1               5                   10                  15

Pro Val Trp Trp Asn Ser Ala Asp Ile Gln His Ser Gly Gly Arg Gln
            20                  25                  30

Cys Asp Gly Tyr Leu Gln Asn Ser Pro Leu Arg Pro Leu
        35                  40                  45

<210> SEQ ID NO 63
<211> LENGTH: 135
<212> TYPE: DNA
<213> ORGANISM: Artificial Sequence
<220> FEATURE:
<223> OTHER INFORMATION: Linker

<400> SEQUENCE: 63
aagggcaatt cgaagcttga aggtcaattg gaattcccta ggactagtcc agtgtggtgg     60
aattctgcag atatccagca cagtggcggc cgccagtgtg atggatatct gcagaattcg    120
cccttgcggc cgctc                                                    135

<210> SEQ ID NO 64
<211> LENGTH: 192
<212> TYPE: PRT
<213> ORGANISM: Artificial Sequence
<220> FEATURE:
<223> OTHER INFORMATION: Hepatitis C E1

<400> SEQUENCE: 64

Tyr Gln Val Arg Asn Ser Thr Gly Leu Tyr His Val Thr Asn Asp Cys
1               5                   10                  15

Pro Asn Ser Ser Ile Val Tyr Glu Ala Ala Asp Ala Ile Leu His Thr
            20                  25                  30

Pro Gly Cys Val Pro Cys Val Arg Glu Gly Asn Ala Ser Arg Cys Trp
        35                  40                  45

Val Ala Met Thr Pro Thr Val Ala Thr Arg Asp Gly Lys Leu Pro Ala
    50                  55                  60

Thr Gln Leu Arg Arg His Ile Asp Leu Leu Val Gly Ser Ala Thr Leu
65                  70                  75                  80

Cys Ser Ala Leu Tyr Val Gly Asp Leu Cys Gly Ser Val Phe Leu Val
                85                  90                  95

Gly Gln Leu Phe Thr Phe Ser Pro Arg Arg His Trp Thr Thr Gln Gly
            100                 105                 110

Cys Asn Cys Ser Ile Tyr Pro Gly His Ile Thr Gly His Arg Met Ala
        115                 120                 125

Trp Asp Met Met Met Asn Trp Ser Pro Thr Thr Ala Leu Val Met Ala
    130                 135                 140

Gln Leu Leu Arg Ile Pro Gln Ala Ile Leu Asp Met Ile Ala Gly Ala
145                 150                 155                 160

His Trp Gly Val Leu Ala Gly Ile Ala Tyr Phe Ser Met Val Gly Asn
                165                 170                 175

Trp Ala Lys Val Leu Val Val Leu Leu Leu Phe Ala Gly Val Asp Ala
            180                 185                 190

<210> SEQ ID NO 65
<211> LENGTH: 363
<212> TYPE: PRT
<213> ORGANISM: Artificial Sequence
<220> FEATURE:

<223> OTHER INFORMATION: Hepatitis C E2

<400> SEQUENCE: 65

| | | | | | | | | | | | | | | |
|---|---|---|---|---|---|---|---|---|---|---|---|---|---|---|
| Glu | Thr | His | Val | Thr | Gly | Gly | Ser | Ala | Gly | His | Thr | Val | Ser | Gly | Phe |
| 1 | | | | 5 | | | | | 10 | | | | | 15 | |
| Val | Ser | Leu | Leu | Ala | Pro | Gly | Ala | Lys | Gln | Asn | Val | Gln | Leu | Ile | Asn |
| | | | 20 | | | | | 25 | | | | | 30 | | |
| Thr | Asn | Gly | Ser | Trp | His | Leu | Asn | Ser | Thr | Ala | Leu | Asn | Cys | Asn | Asp |
| | | 35 | | | | | 40 | | | | | 45 | | | |
| Ser | Leu | Asn | Thr | Gly | Trp | Leu | Ala | Gly | Leu | Phe | Tyr | His | His | Lys | Phe |
| 50 | | | | | 55 | | | | | 60 | | | | | |
| Asn | Ser | Ser | Gly | Cys | Pro | Glu | Arg | Leu | Ala | Ser | Cys | Arg | Pro | Leu | Thr |
| 65 | | | | | 70 | | | | | 75 | | | | | 80 |
| Asp | Phe | Asp | Gln | Gly | Trp | Gly | Pro | Ile | Ser | Tyr | Ala | Asn | Gly | Ser | Gly |
| | | | | 85 | | | | | 90 | | | | | 95 | |
| Pro | Asp | Gln | Arg | Pro | Tyr | Cys | Trp | His | Tyr | Pro | Pro | Lys | Pro | Cys | Gly |
| | | | 100 | | | | | 105 | | | | | 110 | | |
| Ile | Val | Pro | Ala | Lys | Ser | Val | Cys | Gly | Pro | Val | Tyr | Cys | Phe | Thr | Pro |
| | | | 115 | | | | | 120 | | | | | 125 | | |
| Ser | Pro | Val | Val | Val | Gly | Thr | Thr | Asp | Arg | Ser | Gly | Ala | Pro | Thr | Tyr |
| | | 130 | | | | | 135 | | | | | 140 | | | |
| Ser | Trp | Gly | Glu | Asn | Asp | Thr | Asp | Val | Phe | Val | Leu | Asn | Asn | Thr | Arg |
| 145 | | | | | 150 | | | | | 155 | | | | | 160 |
| Pro | Pro | Leu | Gly | Asn | Trp | Phe | Gly | Cys | Thr | Trp | Met | Asn | Ser | Thr | Gly |
| | | | | 165 | | | | | 170 | | | | | 175 | |
| Phe | Thr | Lys | Val | Cys | Gly | Ala | Pro | Pro | Cys | Val | Ile | Gly | Gly | Ala | Gly |
| | | | 180 | | | | | 185 | | | | | 190 | | |
| Asn | Asn | Thr | Leu | His | Cys | Pro | Thr | Asp | Cys | Phe | Arg | Lys | His | Pro | Asp |
| | | | 195 | | | | | 200 | | | | | 205 | | |
| Ala | Thr | Tyr | Ser | Arg | Cys | Gly | Ser | Gly | Pro | Trp | Ile | Thr | Pro | Arg | Cys |
| | | 210 | | | | | 215 | | | | | 220 | | | |
| Leu | Val | Asp | Tyr | Pro | Tyr | Arg | Leu | Trp | His | Tyr | Pro | Cys | Thr | Ile | Asn |
| 225 | | | | | 230 | | | | | 235 | | | | | 240 |
| Tyr | Thr | Ile | Phe | Lys | Ile | Arg | Met | Tyr | Val | Gly | Gly | Val | Glu | His | Arg |
| | | | | 245 | | | | | 250 | | | | | 255 | |
| Leu | Glu | Ala | Ala | Cys | Asn | Trp | Thr | Arg | Gly | Glu | Arg | Cys | Asp | Leu | Glu |
| | | | 260 | | | | | 265 | | | | | 270 | | |
| Asp | Arg | Asp | Arg | Ser | Glu | Leu | Ser | Pro | Leu | Leu | Leu | Thr | Thr | Thr | Gln |
| | | | 275 | | | | | 280 | | | | | 285 | | |
| Trp | Gln | Val | Leu | Pro | Cys | Ser | Phe | Thr | Thr | Leu | Pro | Ala | Leu | Ser | Thr |
| | | 290 | | | | | 295 | | | | | 300 | | | |
| Gly | Leu | Ile | His | Leu | His | Gln | Asn | Ile | Val | Asp | Val | Gln | Tyr | Leu | Tyr |
| 305 | | | | | 310 | | | | | 315 | | | | | 320 |
| Gly | Val | Gly | Ser | Ser | Ile | Ala | Ser | Trp | Ala | Ile | Lys | Trp | Glu | Tyr | Val |
| | | | | 325 | | | | | 330 | | | | | 335 | |
| Val | Leu | Leu | Phe | Leu | Leu | Leu | Ala | Asp | Ala | Arg | Val | Cys | Ser | Cys | Leu |
| | | | 340 | | | | | 345 | | | | | 350 | | |
| Trp | Met | Met | Leu | Leu | Ile | Ser | Gln | Ala | Glu | Ala | | | | | |
| | | | | 355 | | | | | 360 | | | | | | |

<210> SEQ ID NO 66
<211> LENGTH: 576
<212> TYPE: DNA
<213> ORGANISM: Artificial Sequence
<220> FEATURE:
<223> OTHER INFORMATION: Hepatitis C E1

<400> SEQUENCE: 66

```
taccaagtgc gcaactccac ggggctctac cacgtcacca atgattgccc taactcgagt      60
attgtgtacg aggcggccga tgccatcctg cacactccgg ggtgcgtccc ttgcgttcgc     120
gagggcaacg cctcgaggtg ttgggtggcg atgacccta cggtggccac cagggatggc      180
aaactccccg cgacgcagct tcgacgtcac atcgatctgc ttgtcgggag cgccaccctc     240
tgttcggccc tctacgtggg ggacctgtgc gggtctgtct ttcttgtcgg ccaactgttt     300
accttctctc ccaggcgcca ctggacgacg caaggttgca attgctctat ctatcccggc     360
catataacgg gtcaccgcat ggcatgggat atgatgatga actggtcccc tacgacggcg     420
ttggtaatgg ctcagctgct ccggatccca caagccatct tggacatgat cgctggtgct     480
cactggggag tcctggcggg catagcgtat ttctccatgg tggggaactg ggcgaaggtc     540
ctggtagtgc tgctgctatt tgccggcgtc gacgcg                                576
```

<210> SEQ ID NO 67
<211> LENGTH: 1089
<212> TYPE: DNA
<213> ORGANISM: Artificial Sequence
<220> FEATURE:
<223> OTHER INFORMATION: Hepatitis C E2

<400> SEQUENCE: 67

```
gaaacccacg tcaccggggg aagtgccggc cacactgtgt ctggatttgt tagcctcctc      60
gcaccaggcg ccaagcagaa cgtccagctg atcaacacca acggcagttg gcacctcaat     120
agcacggccc tgaactgcaa tgatagcctc aacaccggct ggttggcagg cttttctat      180
caccacaagt tcaactcttc aggctgtcct gagaggctag ccagctgccg acccttacc      240
gattttgacc agggctgggg ccctatcagt tatgccaacg gaagcggccc cgaccagcgc     300
ccctactgct ggcactaccc cccaaaaacct tgcggtattg tgcccgcgaa gagtgtgtgt     360
ggtccggtat attgcttcac tcccagcccc gtggtggtgg aacgaccga caggtcgggc     420
gcgcccacct acagctgggg tgaaaatgat acggacgtct cgtccttaa caataccagg     480
ccaccgctgg gcaattggtt cggttgtacc tggatgaact caactggatt caccaaagtg     540
tgcggagcgc ctccttgtgt catcggaggg gcggcaaca acaccctgca ctgccccact     600
gattgcttcc gcaagcatcc ggacgccaca tactctcggt gcggctccgg tcctggatc     660
acacccaggt gcctggtcga ctaccctat aggctttggc attatccttg taccatcaac     720
tacactatat ttaaaatcag gatgtacgtg ggaggggtcg agcacaggct ggaagctgcc     780
tgcaactgga cgcggggcga acgttgcgat ctggaagata gggacaggtc cgagctcagc     840
ccgttactgc tgaccactac acagtggcag gtcctcccgt gttccttcac aaccctgcca     900
gccttgtcca ccggcctcat ccacctccac cagaacattg tggacgtgca gtacttgtac     960
ggggtggggt caagcatcgc gtcctgggcc attaagtggg agtacgtcgt cctcctgttc    1020
cttctgcttg cagacgcgcg cgtctgctcc tgcttgtgga tgatgctact catatcccaa    1080
gcggaagcg                                                             1089
```

<210> SEQ ID NO 68
<211> LENGTH: 595
<212> TYPE: PRT
<213> ORGANISM: E. coli

<400> SEQUENCE: 68

Met Ala Gln Val Ile Asn Thr Asn Ser Leu Ser Leu Ile Thr Gln Asn

-continued

```
                1               5                  10                  15
Asn Ile Asn Lys Asn Gln Ser Ala Leu Ser Ser Ser Ile Glu Arg Leu
                20                  25                  30

Ser Ser Gly Leu Arg Ile Asn Ser Ala Lys Asp Asp Ala Ala Gly Gln
            35                  40                  45

Ala Ile Ala Asn Arg Phe Thr Ser Asn Ile Lys Gly Leu Thr Gln Ala
 50                  55                  60

Ala Arg Asn Ala Asn Asp Gly Ile Ser Val Ala Gln Thr Thr Glu Gly
 65                  70                  75                  80

Ala Leu Ser Glu Ile Asn Asn Leu Gln Arg Ile Arg Glu Leu Thr
                85                  90                  95

Val Gln Ala Ser Thr Gly Thr Asn Ser Asp Ser Asp Leu Asp Ser Ile
            100                 105                 110

Gln Asp Glu Ile Lys Ser Arg Leu Asp Glu Ile Asp Arg Val Ser Gly
            115                 120                 125

Gln Thr Gln Phe Asn Gly Val Asn Val Leu Ala Lys Asp Gly Ser Met
            130                 135                 140

Lys Ile Gln Val Gly Ala Asn Asp Gly Gln Thr Ile Thr Ile Asp Leu
145                 150                 155                 160

Lys Lys Ile Asp Ser Asp Thr Leu Gly Leu Asn Gly Phe Asn Val Asn
                165                 170                 175

Gly Ser Gly Thr Ile Ala Asn Lys Ala Ala Thr Ile Ser Asp Leu Thr
            180                 185                 190

Ala Ala Lys Met Asp Ala Ala Thr Asn Thr Ile Thr Thr Thr Asn Asn
            195                 200                 205

Ala Leu Thr Ala Ser Lys Ala Leu Asp Gln Leu Lys Asp Gly Asp Thr
 210                 215                 220

Val Thr Ile Lys Ala Asp Ala Ala Gln Thr Ala Thr Val Tyr Thr Tyr
225                 230                 235                 240

Asn Ala Ser Ala Gly Asn Phe Ser Phe Ser Asn Val Ser Asn Asn Thr
                245                 250                 255

Ser Ala Lys Ala Gly Asp Val Ala Ala Ser Leu Leu Pro Pro Ala Gly
            260                 265                 270

Gln Thr Ala Ser Gly Val Tyr Lys Ala Ala Ser Gly Glu Val Asn Phe
            275                 280                 285

Asp Val Asp Ala Asn Gly Lys Ile Thr Ile Gly Gly Gln Lys Ala Tyr
            290                 295                 300

Leu Thr Ser Asp Gly Asn Leu Thr Thr Asn Asp Ala Gly Gly Ala Thr
305                 310                 315                 320

Ala Ala Thr Leu Asp Gly Leu Phe Lys Lys Ala Gly Asp Gly Gln Ser
                325                 330                 335

Ile Gly Phe Lys Lys Thr Ala Ser Val Thr Met Gly Gly Thr Thr Tyr
            340                 345                 350

Asn Phe Lys Thr Gly Ala Asp Ala Ala Thr Ala Asn Ala Gly
            355                 360                 365

Val Ser Phe Thr Asp Thr Ala Ser Lys Glu Thr Val Leu Asn Lys Val
            370                 375                 380

Ala Thr Ala Lys Gln Gly Lys Ala Val Ala Asp Gly Asp Thr Ser
385                 390                 395                 400

Ala Thr Ile Thr Tyr Lys Ser Gly Val Gln Thr Tyr Gln Ala Val Phe
                405                 410                 415

Ala Ala Gly Asp Gly Thr Ala Ser Ala Lys Tyr Ala Asp Lys Ala Asp
            420                 425                 430
```

```
Val Ser Asn Ala Thr Ala Thr Tyr Thr Asp Ala Asp Gly Glu Met Thr
            435                 440                 445
Thr Ile Gly Ser Tyr Thr Thr Lys Tyr Ser Ile Asp Ala Asn Asn Gly
450                 455                 460
Lys Val Thr Val Asp Ser Gly Thr Gly Thr Lys Tyr Ala Pro Lys
465                 470                 475                 480
Val Gly Ala Glu Val Tyr Val Ser Ala Asn Gly Thr Leu Thr Thr Asp
                485                 490                 495
Ala Thr Ser Glu Gly Thr Val Thr Lys Asp Pro Leu Lys Ala Leu Asp
            500                 505                 510
Glu Ala Ile Ser Ser Ile Asp Lys Phe Arg Ser Leu Gly Ala Ile
            515                 520                 525
Gln Asn Arg Leu Asp Ser Ala Val Thr Asn Leu Asn Asn Thr Thr Thr
            530                 535                 540
Asn Leu Ser Glu Ala Gln Ser Arg Ile Gln Asp Ala Asp Tyr Ala Thr
545                 550                 555                 560
Glu Val Ser Asn Met Ser Lys Ala Gln Ile Ile Gln Ala Gly Asn
                565                 570                 575
Ser Val Leu Ala Lys Ala Asn Gln Val Pro Gln Gln Val Leu Ser Leu
            580                 585                 590
Leu Gln Gly
        595

<210> SEQ ID NO 69
<211> LENGTH: 1788
<212> TYPE: DNA
<213> ORGANISM: E. coli

<400> SEQUENCE: 69
atggcacaag tcattaatac caacagcctc tcgctgatca ctcaaaataa tatcaacaag     60
aaccagtctg cgctgtcgag ttctatcgag cgtctgtctt ctggcttgcg tattaacagc    120
gcgaaggatg acgcagcggg tcaggcgatt gctaaccgtt tcacctctaa cattaaaggc    180
ctgactcagg cggcccgtaa cgccaacgac ggtatctccg ttgcgcagac caccgaaggc    240
gcgctgtccg aaatcaacaa caacttacag cgtatccgtg aactgacggt tcaggcttct    300
accgggacta actccgattc ggatctggac tccattcagg acgaaatcaa atcccgtctg    360
gacgaaattg accgcgtatc tggccagacc cagttcaacg gcgtgaacgt actggcgaaa    420
gacggttcaa tgaaaattca ggttggtgcg aatgacggcc agactatcac gattgatctg    480
aagaaaattg actcagatac gctggggctg aatggtttta cgtgaatgg ttccggtacg     540 atagccaata aagcggcgac cattagcgac ctgacagcag cgaaaatgga tgctgcaact    600
aatactataa ctacaacaaa taatgcgctg actgcatcaa aggcgcttga tcaactgaaa    660
gatggtgaca ctgttactat caaagcagat gctgctcaaa ctgccacggt ttatacatac    720
aatgcatcag ctggtaactt ctcattcagt aatgtatcga ataatacttc agcaaaagca    780
ggtgatgtag cagctagcct tctcccgccg gctgggcaaa ctgctagtgg tgttatataaa  840 gcagcaagcg gtgaagtgaa cttgatgtt gatgcgaatg gtaaaatcac aatcggagga    900
cagaaagcat attaactag tgatggtaac ttaactacaa cgatgctgg tggtgcgact     960 gcggctacgc ttgatggttt attcaagaaa gctggtgatg tcaatcaat cgggtttaag   1020 aagactgcat cagtcacgat gggggaaca acttataact ttaaaacggg tgctgatgct   1080
gatgctgcaa ctgctaacgc aggggtatcg ttcactgata cagctagcaa agaaccgtt   1140 ttaaataaag tggctacagc taaacaaggc aaagcagttg cagctgacgg tgatacatcc   1200
```

```
gcaacaatta ccctataaatc tggcgttcag acgtatcagg ctgtatttgc cgcaggtgac    1260
ggtactgcta gcgcaaaata tgccgataaa gctgacgttt ctaatgcaac agcaacatac    1320
actgatgctg atggtgaaat gactacaatt ggttcataca ccacgaagta ttcaatcgat    1380
gctaacaacg gcaaggtaac tgttgattct ggaactggta cgggtaaata tgcgccgaaa    1440
gtaggggctg aagtatatgt tagtgctaat ggtactttaa caacagatgc aactagcgaa    1500
ggcacagtaa caaaagatcc actgaaagct ctggatgaag ctatcagctc catcgacaaa    1560
ttccgttctt ccctgggtgc tatccagaac cgtctggatt ccgcagtcac caacctgaac    1620
aacaccacta ccaacctgtc cgaagcgcag tcccgtattc aggacgccga ctatgcgacc    1680
gaagtgtcca acatgtcgaa agcgcagatc attcagcagg ccggtaactc cgtgctggca    1740
aaagccaacc aggtaccgca gcaggttctg tctctgctgc agggttaa                 1788
```

<210> SEQ ID NO 70
<211> LENGTH: 1224
<212> TYPE: DNA
<213> ORGANISM: Artificial Sequence
<220> FEATURE:
<223> OTHER INFORMATION: STF2delta.EIII+

<400> SEQUENCE: 70

```
atggcacaag taatcaacac taacagtctg tcgctgctga cccagaataa cctgaacaaa      60
tcccagtccg cactgggcac cgctatcgag cgtctgtctt ctggtctgcg tatcaacagc     120
gcgaaagacg atgcggcagg tcaggcgatt gctaaccgtt tcaccgcgaa catcaaaggt     180
ctgactcagg cttcccgtaa cgctaacgac ggtatctcca ttgcgcagac cactgaaggc     240
gcgctgaacg aaatcaacaa caacctgcag cgtgtgcgtg aactggcggt tcagtctgct     300
aacagcacca actcccagtc tgacctcgac tccatccagg ctgaaatcac ccagcgcctg     360
aacgaaatcg accgtgtatc cggccagact cagttcaacg gcgtgaaagt cctggcgcag     420
gacaacaccc tgaccatcca ggttggcgcc aacgacggtg aaactatcga tatcgatctg     480
aagcagatca actctcagac cctgggtctg gactcactga cgtgcatgg agcgccggtg     540 gatcctgcta gcccatggac cgaaaacccg ctgcagaaaa ttgatgccgc gctggcgcag     600
gtggatgcgc tgcgctctga tctgggtgcg gtacaaaacc gtttcaactc tgctatcacc     660
aacctgggca ataccgtaaa caatctgtct gaagcgcgta gccgtatcga agattccgac     720
tacgcgaccg aagtttccaa catgtctcgc gcgcagattt tgcagcaggc cggtacttcc     780
gttctggcgc aggctaacca ggtcccgcag aacgtgctgt ctctgttacg tgaattctgc     840
agatatccag cacagtggcg gccgctcatg gaaaaattgc agttgaaggg aacaaccatt     900
ggcgtctgtt caaaggcttt caagtttctt gggactcccg cagacacagg tcacggcact     960
gtggtgttgg aattgcagta cactggcacg gatggacctt gcaaagttcc tatctcgtca    1020
gtggcttcat tgaacgacct aacgccagtg ggcagattgg tcactgtcaa cccttttgtt    1080
tcagtggcca cggccaacgc taaggtcctg attgaattgg aaccaccctt tggagactca    1140
tacatagtgg tgggcagagg agaacaacag atcaatcacc attggcacaa gtctggaagc    1200
agcattggca acccttaat aagc                                            1224
```

<210> SEQ ID NO 71
<211> LENGTH: 408
<212> TYPE: PRT
<213> ORGANISM: Artificial Sequence
<220> FEATURE:
<223> OTHER INFORMATION: STF2delta.EIII+

<400> SEQUENCE: 71

```
Met Ala Gln Val Ile Asn Thr Asn Ser Leu Ser Leu Leu Thr Gln Asn
1               5                   10                  15

Asn Leu Asn Lys Ser Gln Ser Ala Leu Gly Thr Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ala Asn Ile Lys Gly Leu Thr Gln Ala
    50                  55                  60

Ser Arg Asn Ala Asn Asp Gly Ile Ser Ile Ala Gln Thr Thr Glu Gly
65                  70                  75                  80

Ala Leu Asn Glu Ile Asn Asn Leu Gln Arg Val Arg Glu Leu Ala
                85                  90                  95

Val Gln Ser Ala Asn Ser Thr Asn Ser Gln Ser Asp Leu Asp Ser Ile
            100                 105                 110

Gln Ala Glu Ile Thr Gln Arg Leu Asn Glu Ile Asp Arg Val Ser Gly
        115                 120                 125

Gln Thr Gln Phe Asn Gly Val Lys Val Leu Ala Gln Asp Asn Thr Leu
    130                 135                 140

Thr Ile Gln Val Gly Ala Asn Asp Gly Glu Thr Ile Asp Ile Asp Leu
145                 150                 155                 160

Lys Gln Ile Asn Ser Gln Thr Leu Gly Leu Asp Ser Leu Asn Val His
                165                 170                 175

Gly Ala Pro Val Asp Pro Ala Ser Pro Trp Thr Glu Asn Pro Leu Gln
            180                 185                 190

Lys Ile Asp Ala Ala Leu Ala Gln Val Asp Ala Leu Arg Ser Asp Leu
        195                 200                 205

Gly Ala Val Gln Asn Arg Phe Asn Ser Ala Ile Thr Asn Leu Gly Asn
    210                 215                 220

Thr Val Asn Asn Leu Ser Glu Ala Arg Ser Arg Ile Glu Asp Ser Asp
225                 230                 235                 240

Tyr Ala Thr Glu Val Ser Asn Met Ser Arg Ala Gln Ile Leu Gln Gln
                245                 250                 255

Ala Gly Thr Ser Val Leu Ala Gln Ala Asn Gln Val Pro Gln Asn Val
            260                 265                 270

Leu Ser Leu Leu Arg Glu Phe Cys Arg Tyr Pro Ala Gln Trp Arg Pro
        275                 280                 285

Leu Met Glu Lys Leu Gln Leu Lys Gly Thr Thr Tyr Gly Val Cys Ser
    290                 295                 300

Lys Ala Phe Lys Phe Leu Gly Thr Pro Ala Asp Thr Gly His Gly Thr
305                 310                 315                 320

Val Val Leu Glu Leu Gln Tyr Thr Gly Thr Asp Gly Pro Cys Lys Val
                325                 330                 335

Pro Ile Ser Ser Val Ala Ser Leu Asn Asp Leu Thr Pro Val Gly Arg
            340                 345                 350

Leu Val Thr Val Asn Pro Phe Val Ser Val Ala Thr Ala Asn Ala Lys
        355                 360                 365

Val Leu Ile Glu Leu Glu Pro Pro Phe Gly Asp Ser Tyr Ile Val Val
    370                 375                 380

Gly Arg Gly Glu Gln Gln Ile Asn His His Trp His Lys Ser Gly Ser
385                 390                 395                 400

Ser Ile Gly Lys Pro Leu Ile Ser
                405
```

<210> SEQ ID NO 72
<211> LENGTH: 408
<212> TYPE: PRT
<213> ORGANISM: Artificial Sequence
<220> FEATURE:
<223> OTHER INFORMATION: STF2delta.EIII+

<400> SEQUENCE: 72

```
Met Ala Gln Val Ile Asn Thr Asn Ser Leu Ser Leu Leu Thr Gln Asn
 1               5                  10                  15

Asn Leu Asn Lys Ser Gln Ser Ala Leu Gly Thr Ala Ile Glu Arg Leu
             20                  25                  30

Ser Ser Gly Leu Arg Ile Asn Ser Ala Lys Asp Asp Ala Ala Gly Gln
         35                  40                  45

Ala Ile Ala Asn Arg Phe Thr Ala Asn Ile Lys Gly Leu Thr Gln Ala
     50                  55                  60

Ser Arg Asn Ala Asn Asp Gly Ile Ser Ile Ala Gln Thr Thr Glu Gly
 65                  70                  75                  80

Ala Leu Asn Glu Ile Asn Asn Asn Leu Gln Arg Val Arg Glu Leu Ala
                 85                  90                  95

Val Gln Ser Ala Asn Ser Thr Asn Ser Gln Ser Asp Leu Asp Ser Ile
            100                 105                 110

Gln Ala Glu Ile Thr Gln Arg Leu Asn Glu Ile Asp Arg Val Ser Gly
        115                 120                 125

Gln Thr Gln Phe Asn Gly Val Lys Val Leu Ala Gln Asp Asn Thr Leu
    130                 135                 140

Thr Ile Gln Val Gly Ala Asn Asp Gly Glu Thr Ile Asp Ile Asp Leu
145                 150                 155                 160

Lys Gln Ile Asn Ser Gln Thr Leu Gly Leu Asp Ser Leu Asn Val His
                165                 170                 175

Gly Ala Pro Val Asp Pro Ala Ser Pro Trp Thr Glu Asn Pro Leu Gln
            180                 185                 190

Lys Ile Asp Ala Ala Leu Ala Gln Val Asp Ala Leu Arg Ser Asp Leu
        195                 200                 205

Gly Ala Val Gln Asn Arg Phe Asn Ser Ala Ile Thr Asn Leu Gly Asn
    210                 215                 220

Thr Val Asn Asn Leu Ser Glu Ala Arg Ser Arg Ile Glu Asp Ser Asp
225                 230                 235                 240

Tyr Ala Thr Glu Val Ser Asn Met Ser Arg Ala Gln Ile Leu Gln Gln
                245                 250                 255

Ala Gly Thr Ser Val Leu Ala Gln Ala Asn Gln Val Pro Gln Asn Val
            260                 265                 270

Leu Ser Leu Leu Arg Glu Phe Ser Arg Tyr Pro Ala Gln Trp Arg Pro
        275                 280                 285

Leu Met Glu Lys Leu Gln Leu Lys Gly Thr Thr Tyr Gly Val Cys Ser
    290                 295                 300

Lys Ala Phe Lys Phe Leu Gly Thr Pro Ala Asp Thr Gly His Gly Thr
305                 310                 315                 320

Val Val Leu Glu Leu Gln Tyr Thr Gly Thr Asp Gly Pro Cys Lys Val
                325                 330                 335

Pro Ile Ser Ser Val Ala Ser Leu Asn Asp Leu Thr Pro Val Gly Arg
            340                 345                 350

Leu Val Thr Val Asn Pro Phe Val Ser Val Ala Thr Ala Asn Ala Lys
        355                 360                 365
```

Val Leu Ile Glu Leu Glu Pro Pro Phe Gly Asp Ser Tyr Ile Val Val
             370                 375                 380

Gly Arg Gly Glu Gln Gln Ile Asn His His Trp His Lys Ser Gly Ser
385                 390                 395                 400

Ser Ile Gly Lys Pro Leu Ile Ser
            405

<210> SEQ ID NO 73
<211> LENGTH: 1227
<212> TYPE: DNA
<213> ORGANISM: Artificial Sequence
<220> FEATURE:
<223> OTHER INFORMATION: STF2delta.EIII+

<400> SEQUENCE: 73

| | | | | |
|---|---|---|---|---|
| atggcacaag | taatcaacac | taacagtctg | tcgctgctga | cccagaataa | cctgaacaaa |    60 |
| tcccagtccg | cactgggcac | cgctatcgag | cgtctgtctt | ctggtctgcg | tatcaacagc |   120 |
| gcgaaagaca | tgcgggcagg | tcaggcgatt | gctaaccgtt | tcaccgcgaa | catcaaaggt |   180 |
| ctgactcagg | cttcccgtaa | cgctaacgac | ggtatctcca | ttgcgcagac | cactgaaggc |   240 |
| gcgctgaacg | aaatcaacaa | caacctgcag | cgtgtgcgtg | aactggcggt | tcagtctgct |   300 |
| aacagcacca | actcccagtc | tgacctcgac | tccatccagg | ctgaaatcac | ccagcgcctg |   360 |
| aacgaaatcg | accgtgtatc | cggccagact | cagttcaacg | gcgtgaaagt | cctggcgcag |   420 |
| gacaacaccc | tgaccatcca | ggttggcgcc | aacgacggtg | aaactatcga | tatcgatctg |   480 |
| aagcagatca | actctcagac | cctgggtctg | gactcactga | acgtgcatgg | agcgccggtg |   540 |
| gatcctgcta | gcccatggac | cgaaaaccog | ctgcagaaaa | ttgatgccgc | gctggcgcag |   600 |
| gtggatgcgc | tgcgctctga | tctgggtgcg | gtacaaaacc | gtttcaactc | tgctatcacc |   660 |
| aacctgggca | ataccgtaaa | caatctgtct | gaagcgcgta | gccgtatcga | agattccgac |   720 |
| tacgcgaccg | aagtttccaa | catgtctcgc | gcgcagattt | tgcagcaggc | cggtacttcc |   780 |
| gttctggcgc | aggctaacca | ggtcccgcag | aacgtgctgt | ctctgttacg | tgaattctct |   840 |
| agatatccag | cacagtggcg | gccgctcatg | gaaaaattgc | agttgaaggg | aacaacctat |   900 |
| ggcgtctgtt | caaaggcttt | caagtttctt | gggactcccg | cagacacagg | tcacggcact |   960 |
| gtggtgttgg | aattgcagta | cactggcacg | gatggacctt | gcaaagttcc | tatctcgtca |  1020 |
| gtggcttcat | tgaacgacct | aacgccagtg | ggcagattgg | tcactgtcaa | ccctttttgtt |  1080 |
| tcagtggcca | cggccaacgc | taaggtcctg | attgaattgg | aaccacccht | tggagactca |  1140 |
| tacatagtgg | tgggcagagg | agaacaacag | atcaatcacc | attggcacaa | gtctggaagc |  1200 |
| agcattggca | aacccttaat | aagctga | | | | 1227 |

<210> SEQ ID NO 74
<211> LENGTH: 35
<212> TYPE: DNA
<213> ORGANISM: Artificial Sequence
<220> FEATURE:
<223> OTHER INFORMATION: Linker

<400> SEQUENCE: 74
gaattctcta gatatccagc acagtggcgg ccgct          35

<210> SEQ ID NO 75
<211> LENGTH: 12
<212> TYPE: PRT
<213> ORGANISM: Artificial Sequence
<220> FEATURE:
<223> OTHER INFORMATION: Linker -continued

```
<400> SEQUENCE: 75

Glu Phe Ser Arg Tyr Pro Ala Gln Trp Arg Pro Leu
1               5                   10

<210> SEQ ID NO 76
<211> LENGTH: 405
<212> TYPE: PRT
<213> ORGANISM: Artificial Sequence
<220> FEATURE:
<223> OTHER INFORMATION: pET/STF2delta.JEIII+

<400> SEQUENCE: 76

Met Ala Gln Val Ile Asn Thr Asn Ser Leu Ser Leu Leu Thr Gln Asn
1               5                   10                  15

Asn Leu Asn Lys Ser Gln Ser Ala Leu Gly Thr Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ala Asn Ile Lys Gly Leu Thr Gln Ala
    50                  55                  60

Ser Arg Asn Ala Asn Asp Gly Ile Ser Ile Ala Gln Thr Thr Glu Gly
65                  70                  75                  80

Ala Leu Asn Glu Ile Asn Asn Asn Leu Gln Arg Val Arg Glu Leu Ala
                85                  90                  95

Val Gln Ser Ala Asn Ser Thr Asn Ser Gln Ser Asp Leu Asp Ser Ile
            100                 105                 110

Gln Ala Glu Ile Thr Gln Arg Leu Asn Glu Ile Asp Arg Val Ser Gly
        115                 120                 125

Gln Thr Gln Phe Asn Gly Val Lys Val Leu Ala Gln Asp Asn Thr Leu
    130                 135                 140

Thr Ile Gln Val Gly Ala Asn Asp Gly Glu Thr Ile Asp Ile Asp Leu
145                 150                 155                 160

Lys Gln Ile Asn Ser Gln Thr Leu Gly Leu Asp Ser Leu Asn Val His
                165                 170                 175

Gly Ala Pro Val Asp Pro Ala Ser Pro Trp Thr Glu Asn Pro Leu Gln
            180                 185                 190

Lys Ile Asp Ala Ala Leu Ala Gln Val Asp Ala Leu Arg Ser Asp Leu
        195                 200                 205

Gly Ala Val Gln Asn Arg Phe Asn Ser Ala Ile Thr Asn Leu Gly Asn
    210                 215                 220

Thr Val Asn Asn Leu Ser Glu Ala Arg Ser Arg Ile Glu Asp Ser Asp
225                 230                 235                 240

Tyr Ala Thr Glu Val Ser Asn Met Ser Arg Ala Gln Ile Leu Gln Gln
                245                 250                 255

Ala Gly Thr Ser Val Leu Ala Gln Ala Asn Gln Val Pro Gln Asn Val
            260                 265                 270

Leu Ser Leu Leu Arg Glu Phe Ser Arg Tyr Pro Ala Gln Trp Arg Pro
        275                 280                 285

Leu Met Asp Lys Leu Ala Leu Lys Gly Thr Thr Tyr Gly Met Cys Thr
    290                 295                 300

Glu Lys Phe Ser Phe Ala Lys Asn Pro Val Asp Thr Gly His Gly Thr
305                 310                 315                 320

Val Val Ile Glu Leu Ser Tyr Ser Gly Ser Asp Gly Pro Cys Lys Ile
                325                 330                 335

Pro Ile Val Ser Val Ala Ser Leu Asn Asp Met Thr Pro Val Gly Arg
```

```
                        340                 345                 350
Leu Val Thr Val Asn Pro Phe Val Ala Thr Ser Ser Ala Asn Ser Lys
                355                 360                 365
Val Leu Val Glu Met Glu Pro Pro Phe Gly Asp Ser Tyr Ile Val Val
        370                 375                 380
Gly Arg Gly Asp Lys Gln Ile Asn His His Trp His Lys Ala Gly Ser
385                 390                 395                 400
Thr Leu Gly Lys Ala
            405

<210> SEQ ID NO 77
<211> LENGTH: 1215
<212> TYPE: DNA
<213> ORGANISM: Artificial Sequence
<220> FEATURE:
<223> OTHER INFORMATION: pET/STF2delta.JEIII+

<400> SEQUENCE: 77
atggcacaag taatcaacac taacagtctg tcgctgctga cccagaataa cctgaacaaa        60
tcccagtccg cactgggcac cgctatcgag cgtctgtctt ctggtctgcg tatcaacagc       120
gcgaaagacg atgcggcagg tcaggcgatt gctaaccgtt tcaccgcgaa catcaaaggt       180
ctgactcagg cttcccgtaa cgctaacgac ggtatctcca ttgcgcagac cactgaaggc       240
gcgctgaacg aaatcaacaa caacctgcag cgtgtgcgtg aactggcggt tcagtctgct       300
aacagcacca actcccagtc tgacctcgac tccatccagg ctgaaatcac ccagcgcctg       360
aacgaaatcg accgtgtatc cggccagact cagttcaacg gcgtgaaagt cctggcgcag       420
gacaacaccc tgaccatcca ggttggcgcc aacgacggtg aaactatcga tatcgatctg       480
aagcagatca actctcagac cctgggtctg gactcactga acgtgcatgg agcgccggtg       540
gatcctgcta gcccatggac cgaaaacccg ctgcagaaaa ttgatgccgc gctggcgcag       600
gtggatgcgc tgcgctctga tctgggtgcg gtacaaaacc gtttcaactc tgctatcacc       660
aacctgggca ataccgtaaa caatctgtct gaagcgcgta gccgtatcga agattccgac       720
tacgcgaccg aagtttccaa catgtctcgc gcgcagattt gcagcaggc cggtacttcc        780 gttctggcgc aggctaacca ggtcccgcag aacgtgctgt ctctgttacg tgaattcagc       840
agatatccag cacagtggcg gccgctcatg acaaactgg ctctgaaagg cacaacctat        900
ggcatgtgta cagaaaaatt ctcgttcgcg aaaaatccgg tggacactgg tcacggaaca       960
gttgtcattg aactctccta ctctgggagt gatggcccct gcaaaattcc gattgtttcc      1020
gttgcgagcc tcaatgacat gaccccgtt gggcggctgg tgacagtgaa cccttcgtc       1080 gcgacttcca gtgccaactc aaaggtgctg gtcgagatgg aaccccctt cggagactcc      1140 tacatcgtag ttggaagggg agacaagcag atcaaccacc attggcacaa agctggaagc       1200
acgctgggca aggcc                                                      1215

<210> SEQ ID NO 78
<211> LENGTH: 348
<212> TYPE: DNA
<213> ORGANISM: Artificial Sequence
<220> FEATURE:
<223> OTHER INFORMATION: JEIII+

<400> SEQUENCE: 78
atggacaaac tggctctgaa aggcacaacc tatggcatgt gtacagaaaa attctcgttc        60
gcgaaaaatc cggtggacac tggtcacgga acagttgtca ttgaactctc ctactctggg       120
```

```
agtgatggcc cctgcaaaat tccgattgtt tccgttgcga gcctcaatga catgaccccc    180
gttgggcggc tggtgacagt gaacccctcc gtcgcgactt ccagtgccaa ctcaaaggtg    240
ctggtcgaga tggaaccccc cttcggagac tcctacatcg tagttggaag gggagacaag    300
cagatcaacc accattggca caaagctgga agcacgctgg gcaaggcc                348
```

<210> SEQ ID NO 79
<211> LENGTH: 116
<212> TYPE: PRT
<213> ORGANISM: Artificial Sequence
<220> FEATURE:
<223> OTHER INFORMATION: JEIII+

<400> SEQUENCE: 79

```
Met Asp Lys Leu Ala Leu Lys Gly Thr Thr Tyr Gly Met Cys Thr Glu
  1               5                  10                  15

Lys Phe Ser Phe Ala Lys Asn Pro Val Asp Thr Gly His Gly Thr Val
             20                  25                  30

Val Ile Glu Leu Ser Tyr Ser Gly Ser Asp Gly Pro Cys Lys Ile Pro
         35                  40                  45

Ile Val Ser Val Ala Ser Leu Asn Asp Met Thr Pro Val Gly Arg Leu
     50                  55                  60

Val Thr Val Asn Pro Phe Val Ala Thr Ser Ser Ala Asn Ser Lys Val
 65                  70                  75                  80

Leu Val Glu Met Glu Pro Pro Phe Gly Asp Ser Tyr Ile Val Val Gly
                 85                  90                  95

Arg Gly Asp Lys Gln Ile Asn His His Trp His Lys Ala Gly Ser Thr
            100                 105                 110

Leu Gly Lys Ala
        115
```

<210> SEQ ID NO 80
<211> LENGTH: 389
<212> TYPE: PRT
<213> ORGANISM: Artificial Sequence
<220> FEATURE:
<223> OTHER INFORMATION: pET/STF2delta.Den1 EIII

<400

```
                    145                 150                 155                 160
Lys Gln Ile Asn Ser Gln Thr Leu Gly Leu Asp Ser Leu Asn Val His
                165                 170                 175
Gly Ala Pro Val Asp Pro Ala Ser Pro Trp Thr Glu Asn Pro Leu Gln
                180                 185                 190
Lys Ile Asp Ala Ala Leu Ala Gln Val Asp Ala Leu Arg Ser Asp Leu
                195                 200                 205
Gly Ala Val Gln Asn Arg Phe Asn Ser Ala Ile Thr Asn Leu Gly Asn
                210                 215                 220
Thr Val Asn Asn Leu Ser Glu Ala Arg Ser Arg Ile Glu Asp Ser Asp
225                 230                 235                 240
Tyr Ala Thr Glu Val Ser Asn Met Ser Arg Ala Gln Ile Leu Gln Gln
                245                 250                 255
Ala Gly Thr Ser Val Leu Ala Gln Ala Asn Gln Val Pro Gln Asn Val
                260                 265                 270
Leu Ser Leu Leu Arg Glu Phe Ser Arg Tyr Pro Ala Gln Trp Arg Pro
                275                 280                 285
Leu Lys Gly Met Ser Tyr Val Met Cys Thr Gly Ser Phe Lys Leu Glu
                290                 295                 300
Lys Glu Val Ala Glu Thr Gln His Gly Thr Val Leu Val Gln Val Lys
305                 310                 315                 320
Tyr Glu Gly Thr Asp Ala Pro Cys Lys Ile Pro Phe Ser Thr Gln Asp
                325                 330                 335
Glu Lys Gly Val Thr Gln Asn Gly Arg Leu Ile Thr Ala Asn Pro Ile
                340                 345                 350
Val Thr Asp Lys Glu Lys Pro Val Asn Ile Glu Ala Glu Pro Pro Phe
                355                 360                 365
Gly Glu Asn Tyr Ile Val Val Gly Ala Gly Glu Lys Ala Leu Lys Leu
                370                 375                 380
Ser Trp Phe Lys Lys
385

<210> SEQ ID NO 81
<211> LENGTH: 1185
<212> TYPE: DNA
<213> ORGANISM: Artificial Sequence
<220> FEATURE:
<223> OTHER INFORMATION: pET/STF2delta.Den1 EIII

<400> SEQUENCE: 81
atggcacaag taatcaacac taacagtctg tcgctgctga cccagaataa cctgaacaaa      60
tcccagtccg cactgggcac cgctatcgag cgtctgtctt ctggtctgcg tatcaacagc     120
gcgaaagacg atgcggcagg tcaggcgatt gctaaccgtt tcaccgcgaa catcaaaggt     180
ctgactcagg cttcccgtaa cgctaacgac ggtatctcca ttgcgcagac cactgaaggc     240
gcgctgaacg aaatcaacaa caacctgcag cgtgtgcgtg aactggcggt tcagtctgct     300
aacagcacca actcccagtc tgacctcgac tccatccagg ctgaaatcac ccagcgcctg     360
aacgaaatcg accgtgtatc cggccagact cagttcaacg gcgtgaaagt cctggcgcag     420
gacaacaccc tgaccatcca ggttggcgcc aacgacggtg aaactatcga tatcgatctg     480
aagcagatca actctcagac cctggtctct gactcactga cgtgcatgg agcgccggtg     540 gatcctgcta gcccatggac cgaaaacccg ctgcagaaaa ttgatgccgc gctggcgcag     600
gtggatgcgc tgcgctctga tctgggtgcg gtacaaaacc gtttcaactc tgctatcacc     660
aacctgggca ataccgtaaa caatctgtct gaagcgcgta gccgtatcga agattccgac     720
```

```
tacgcgaccg aagtttccaa catgtctcgc gcgcagattt tgcagcaggc cggtacttcc      780
gttctggcgc aggctaacca ggtcccgcag aacgtgctgt ctctgttacg tgaattcagc      840
agatatccag cacagtggcg gccgctcaaa ggaatgtctt acgtaatgtg cacaggcagt      900
ttcaagctgg aaaagaagt tgccgaaaca cagcatggca cggtactagt ccaagtgaaa       960
tatgagggaa cagacgcgcc atgtaagata ccatttccca ctcaagatga gaaaggggcg      1020
actcagaacg gaagattgat aaccgcaaat cctatcgtaa ccgacaagga aaagcccgtg      1080
aatattgagg cagagcctcc gtttggggag tcgtatatcg tcgttggtgc tggtgaaaag      1140
gctttaaagc tcagttggtt caaaaagggg tcaagcattg gtaaa                     1185
```

<210> SEQ ID NO 82
<211> LENGTH: 389
<212> TYPE: PRT
<213> ORGANISM: Artificial Sequence
<220> FEATURE:
<223> OTHER INFORMATION: pET/STF2delta.Den2 EIII

<400> SEQUENCE: 82

```
Met Ala Gln Val Ile Asn Thr Asn Ser Leu Ser Leu Leu Thr Gln Asn
 1               5                  10                  15

Asn Leu Asn Lys Ser Gln Ser Ala Leu Gly Thr Ala Ile Glu Arg Leu
            20                  25                  30

Ser Ser Gly Leu Arg Ile Asn Ser Ala Lys Asp As

```
Leu Lys Gly Met Ser Tyr Ser Met Cys Thr Gly Lys Phe Lys Val Val
    290             295                 300
Lys Glu Ile Ala Glu Thr Gln His Gly Thr Ile Val Ile Arg Val Gln
305             310                 315                 320
Tyr Glu Gly Asp Gly Ser Pro Cys Lys Thr Pro Phe Glu Ile Met Asp
                325                 330                 335
Leu Glu Lys Arg His Val Leu Gly Arg Leu Thr Thr Val Asn Pro Ile
            340                 345                 350
Val Thr Glu Lys Asp Ser Pro Val Asn Ile Glu Ala Glu Pro Pro Phe
        355                 360                 365
Gly Asp Ser Tyr Ile Ile Ile Gly Val Glu Pro Gly Gln Leu Lys Leu
    370                 375                 380
Asp Trp Phe Lys Lys
385

<210> SEQ ID NO 83
<211> LENGTH: 1185
<212> TYPE: DNA
<213> ORGANISM: Artificial Sequence
<220> FEATURE:
<223> OTHER INFORMATION: pET/STF2delta.Den2 EIII

<400> SEQUENCE: 83
atggcacaag taatcaacac taacagtctg tcgctgctga cccagaataa cctgaacaaa     60
tcccagtccg cactgggcac cgctatcgag cgtctgtctt ctggtctgcg tatcaacagc    120
gcgaaagacg atgcggcagg tcaggcgatt gctaaccgtt tcaccgcgaa catcaaaggt    180
ctgactcagg cttcccgtaa cgctaacgac ggtatctcca ttgcgcagac cactgaaggc    240
gcgctgaacg aaatcaacaa caacctgcag cgtgtgcgtg aactggcggt tcagtctgct    300
aacagcacca actcccagtc tgacctcgac tccatccagg ctgaaatcac ccagcgcctg    360
aacgaaatcg accgtgtatc cggccagact cagttcaacg gcgtgaaagt cctggcgcag    420
gacaacaccc tgaccatcca ggttggcgcc aacgacggtg aaactatcga tatcgatctg    480
aagcagatca actctcagac cctgggtctg gactcactga cgtgcatgg agcgccggtg    540 gatcctgcta gcccatggac cgaaaacccg ctgcagaaaa ttgatgccgc gctggcgcag    600
gtggatgcgc tgcgctctga tctgggtgcg gtacaaaacc gtttcaactc tgctatcacc    660
aacctgggca taccgtaaa caatctgtct gaagcgcgta gccgtatcga agattccgac    720
tacgcgaccg aagtttccaa catgtctcgc gcgcagattt gcagcaggc cggtacttcc    780 gttctggcgc aggctaacca ggtcccgcag aacgtgctgt ctctgttacg tgaattcagc    840
agatatccag cacagtggcg gccgctcaaa ggtatgagct atagcatgtg taccggtaaa    900
tttaaagttg ttaaagaaat tgcggaaacc cagcatggta ccattgttat cgtgttcag    960 tatgaaggtg atggtagccc gtgtaaaatt ccgtttgaaa ttatggatct ggaaaaacgt   1020
catgttctgg gtcgtctgat accgttaat ccgattgtta ccgaaaaaga tagcccggtt   1080
aatattgaag cggaaccgcc gtttggtgat agctatatta ttattggtgt tgaaccgggt   1140
cagctgaaac tgaattggtt taaaaaggt agcagcattg gtcag                   1185

<210> SEQ ID NO 84
<211> LENGTH: 389
<212> TYPE: PRT
<213> ORGANISM: Artificial Sequence
<220> FEATURE:
<223> OTHER INFORMATION: pET/STF2delta.Den3 EIII
```

<400> SEQUENCE: 84

```
Met Ala Gln Val Ile Asn Thr Asn Ser Leu Ser Leu Leu Thr Gln Asn
 1               5                  10                  15

Asn Leu Asn Lys Ser Gln Ser Ala Leu Gly Thr Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ala Asn Ile Lys Gly Leu Thr Gln Ala
    50                  55                  60

Ser Arg Asn Ala Asn Asp Gly Ile Ser Ile Ala Gln Thr Thr Glu Gly
65                  70                  75                  80

Ala Leu Asn Glu Ile Asn Asn Asn Leu Gln Arg Val Arg Glu Leu Ala
                85                  90                  95

Val Gln Ser Ala Asn Ser Thr Asn Ser Gln Ser Asp Leu Asp Ser Ile
            100                 105                 110

Gln Ala Glu Ile Thr Gln Arg Leu Asn Glu Ile Asp Arg Val Ser Gly
        115                 120                 125

Gln Thr Gln Phe Asn Gly Val Lys Val Leu Ala Gln Asp Asn Thr Leu
    130                 135                 140

Thr Ile Gln Val Gly Ala Asn Asp Gly Glu Thr Ile Asp Ile Asp Leu
145                 150                 155                 160

Lys Gln Ile Asn Ser Gln Thr Leu Gly Leu Asp Ser Leu Asn Val His
                165                 170                 175

Gly Ala Pro Val Asp Pro Ala Ser Pro Trp Thr Glu Asn Pro Leu Gln
            180                 185                 190

Lys Ile Asp Ala Ala Leu Ala Gln Val Asp Ala Leu Arg Ser Asp Leu
        195                 200                 205

Gly Ala Val Gln Asn Arg Phe Asn Ser Ala Ile Thr Asn Leu Gly Asn
    210                 215                 220

Thr Val Asn Asn Leu Ser Glu Ala Arg Ser Arg Ile Glu Asp Ser Asp
225                 230                 235                 240

Tyr Ala Thr Glu Val Ser Asn Met Ser Arg Ala Gln Ile Leu Gln Gln
                245                 250                 255

Ala Gly Thr Ser Val Leu Ala Gln Ala Asn Gln Val Pro Gln Asn Val
            260                 265                 270

Leu Ser Leu Leu Arg Glu Phe Ser Arg Tyr Pro Ala Gln Trp Arg Pro
        275                 280                 285

Leu Lys Gly Met Ser Tyr Ala Met Cys Leu Asn Thr Phe Val Leu Lys
    290                 295                 300

Lys Glu Val Ser Glu Thr Gln His Gly Thr Ile Leu Ile Lys Val Glu
305                 310                 315                 320

Tyr Lys Gly Glu Asp Ala Pro Cys Lys Ile Pro Phe Ser Thr Glu Asp
                325                 330                 335

Gly Gln Gly Lys Ala His Asn Gly Arg Leu Ile Thr Ala Asn Pro Val
            340                 345                 350

Val Thr Lys Lys Glu Glu Pro Val Asn Ile Glu Ala Glu Pro Pro Phe
        355                 360                 365

Gly Glu Ser Asn Ile Val Ile Gly Ile Gly Asp Lys Ala Leu Lys Ile
    370                 375                 380

Asn Trp Tyr Arg Lys
385
```

<210> SEQ ID NO 85
<211> LENGTH: 1185

<212> TYPE: DNA
<213> ORGANISM: Artificial Sequence
<220> FEATURE:
<223> OTHER INFORMATION: pET/STF2delta.Den3 EIII

<400> SEQUENCE: 85

```
atggcacaag taatcaacac taacagtctg tcgctgctga cccagaataa cctgaacaaa      60
tcccagtccg cactgggcac cgctatcgag cgtctgtctt ctggtctgcg tatcaacagc     120
gcgaaagacg atgcggcagg tcaggcgatt gctaaccgtt tcaccgcgaa catcaaaggt     180
ctgactcagg cttcccgtaa cgctaacgac ggtatctcca ttgcgcagac cactgaaggc     240
gcgctgaacg aaatcaacaa caacctgcag cgtgtgcgtg aactgg

```
Gln Thr Gln Phe Asn Gly Val Lys Val Leu Ala Gln Asp Asn Thr Leu
    130                 135                 140

Thr Ile Gln Val Gly Ala Asn Asp Gly Glu Thr Ile Asp Ile Asp Leu
145                 150                 155                 160

Lys Gln Ile Asn Ser Gln Thr Leu Gly Leu Asp Ser Leu Asn Val His
                165                 170                 175

Gly Ala Pro Val Asp Pro Ala Ser Pro Trp Thr Glu Asn Pro Leu Gln
            180                 185                 190

Lys Ile Asp Ala Ala Leu Ala Gln Val Asp Ala Leu Arg Ser Asp Leu
        195                 200                 205

Gly Ala Val Gln Asn Arg Phe Asn Ser Ala Ile Thr Asn Leu Gly Asn
    210                 215                 220

Thr Val Asn Asn Leu Ser Glu Ala Arg Ser Arg Ile Glu Asp Ser Asp
225                 230                 235                 240

Tyr Ala Thr Glu Val Ser Asn Met Ser Arg Ala Gln Ile Leu Gln Gln
                245                 250                 255

Ala Gly Thr Ser Val Leu Ala Gln Ala Asn Gln Val Pro Gln Asn Val
            260                 265                 270

Leu Ser Leu Leu Arg Glu Phe Ser Arg Tyr Pro Ala Gln Trp Arg Pro
        275                 280                 285

Leu Lys Gly Met Ser Tyr Thr Met Cys Ser Gly Lys Phe Ser Ile Asp
    290                 295                 300

Lys Glu Met Ala Glu Thr Gln His Gly Thr Thr Val Val Lys Val Lys
305                 310                 315                 320

Tyr Glu Gly Ala Gly Ala Pro Cys Lys Val Pro Ile Glu Ile Arg Asp
                325                 330                 335

Val Asn Lys Glu Lys Val Val Gly Arg Ile Ile Ser Pro Thr Pro Phe
            340                 345                 350

Ala Glu Asn Thr Asn Ser Val Thr Asn Ile Glu Leu Glu Arg Pro Leu
        355                 360                 365

Asp Ser Tyr Ile Val Ile Gly Val Gly Asp Ser Ala Leu Thr Leu His
    370                 375                 380

Trp Phe Arg Lys
385

<210> SEQ ID NO 87
<211> LENGTH: 1185
<212> TYPE: DNA
<213> ORGANISM: Artificial Sequence
<220> FEATURE:
<223> OTHER INFORMATION: PET/STF2delta.Den4 EIII

<400> SEQUENCE: 87
atggcacaag taatcaacac taacagtctg tcgctgctga cccagaataa cctgaacaaa      60
tcccagtccg cactgggcac cgctatcgag cgtctgtctt ctggtctgcg tatcaacagc     120
gcgaaagacg atgcggcagg tcaggcgatt gctaaccgtt tcaccgcgaa catcaaaggt     180
ctgactcagg cttcccgtaa cgctaacgac ggtatctcca ttgcgcagac cactgaaggc     240
gcgctgaacg aaatcaacaa caacctgcag cgtgtgcgtg aactggcggt tcagtctgct     300
aacagcacca actcccagtc tgacctcgac tccatccagg ctgaaatcac ccagcgcctg     360
aacgaaatcg accgtgtatc cggccagact cagttcaacg gcgtgaaagt cctggcgcag     420
gacaacaccc tgaccatcca ggttggcgcc aacgacggtg aaactatcga tatcgatctg     480
aagcagatca actctcagac cctgggtctg gactcactga acgtgcatgg agcgccggtg     540
```

```
gatcctgcta gcccatggac cgaaaacccg ctgcagaaaa ttgatgccgc gctggcgcag    600
gtggatgcgc tgcgctctga tctgggtgcg gtacaaaacc gtttcaactc tgctatcacc    660
aacctgggca ataccgtaaa caatctgtct gaagcgcgta gccgtatcga agattccgac    720
tacgcgaccg aagtttccaa catgtctcgc gcgcagattt tgcagcaggc cggtacttcc    780
gttctggcgc aggctaacca ggtcccgcag aacgtgctgt ctctgttacg tgaattcagc    840
agatatccag cacagtggcg gccgctcaag ggaatgtcat acacgatgtg tagtggtaaa    900
ttctctatag acaaagagat ggcagagaca caacacggga caaccgtcgt gaaggttaag    960
tatgaaggag ctggcgcacc gtgcaaagta cccatcgaaa ttagggatgt aaacaaagag   1020
aaggtcgttg gcgtatcat tagctcaacc ccacttgcgg aaaatactaa ttctgtaacg   1080
aacatagagt tggaaccacc ttttggtgat agctatatag ttattggtgt gggcaatagt   1140
gccttaactc tacattggtt tagaaaagga tcctcgatcg ggaaa                   1185

<210> SEQ ID NO 88
<211> LENGTH: 27
<212> TYPE: PRT
<213> ORGANISM: Artificial Sequence
<220> FEATURE:
<223> OTHER INFORMATION: West Nile virus

<400> SEQUENCE: 88

Leu Thr Ser Gly His Leu Lys Cys Arg Val Lys Met Glu Lys Leu Gln
 1               5                  10                  15

Leu Lys Gly Thr Thr Tyr Gly Val Cys Ser Lys
            20                  25

<210> SEQ ID NO 89
<211> LENGTH: 27
<212> TYPE: PRT
<213> ORGANISM: Artificial Sequence
<220> FEATURE:
<223> OTHER INFORMATION: Japanese encephalitis virus

<400> SEQUENCE: 89

Leu Thr Ser Gly His Leu Lys Cys Arg Leu Lys Met Asp Lys Leu Ala
 1               5                  10                  15

Leu Lys Gly Thr Thr Tyr Gly Met Cys Thr Glu
            20                  25

<210> SEQ ID NO 90
<211> LENGTH: 27
<212> TYPE: PRT
<213> ORGANISM: Artificial Sequence
<220> FEATURE:
<223> OTHER INFORMATION: Dengue virus

<400> SEQUENCE: 90

Ile Phe Ala Gly His Leu Lys Cys Arg Leu Lys Met Asp Lys Leu Thr
 1               5                  10                  15

Leu Lys Gly Met Ser Tyr Val Met Cys Thr Gly
            20                  25

<210> SEQ ID NO 91
<211> LENGTH: 27
<212> TYPE: PRT
<213> ORGANISM: Artificial Sequence
<220> FEATURE:
<223> OTHER INFORMATION: Dengue virus

<400> SEQUENCE: 91
```

```
Leu Phe Thr Gly His Leu Lys Cys Arg Leu Arg Met Asp Lys Leu Gln
1               5                   10                  15

Leu Lys Gly Met Ser Tyr Ser Met Cys Thr Gly
            20                  25

<210> SEQ ID NO 92
<211> LENGTH: 27
<212> TYPE: PRT
<213> ORGANISM: Artificial Sequence
<220> FEATURE:
<223> OTHER INFORMATION: Dengue virus

<400> SEQUENCE: 92

Ile Phe Ala Gly His Leu Lys Cys Arg Leu Lys Met Asp Lys Leu Lys
1               5                   10                  15

Leu Lys Gly Met Ser Tyr Ala Met Cys Leu Asn
            20                  25

<210> SEQ ID NO 93
<211> LENGTH: 27
<212> TYPE: PRT
<213> ORGANISM: Artificial Sequence
<220> FEATURE:
<223> OTHER INFORMATION: Dengue virus

<400> SEQUENCE: 93

Met Phe Ala Gly His Leu Lys Cys Lys Val Arg Met Glu Lys Leu Arg
1               5                   10                  15

Ile Lys Gly Met Ser Tyr Thr Met Cys Ser Gly
            20                  25

<210> SEQ ID NO 94
<211> LENGTH: 27
<212> TYPE: PRT
<213> ORGANISM: Artificial Sequence
<220> FEATURE:
<223> OTHER INFORMATION: Flavivirus envelope protein
<220> FEATURE:
<223> OTHER INFORMATION: X=any amino acid
<220> FEATURE:
<221> NAME/KEY: VARIANT
<222> LOCATION: 1, 2, 3, 10, 11, 13, 16, 20, 21, 23, 24, 26, 27
<223> OTHER INFORMATION: Xaa = Any Amino Acid

<400> SEQUENCE: 94

Xaa Xaa Xaa Gly His Leu Lys Cys Arg Xaa Xaa Met Xaa Lys Leu Xaa
1               5                   10                  15

Leu Lys Gly Xaa Xaa Tyr Xaa Xaa Cys Xaa Xaa
            20                  25

<210> SEQ ID NO 95
<211> LENGTH: 14
<212> TYPE: PRT
<213> ORGANISM: Artificial Sequence
<220> FEATURE:
<223> OTHER INFORMATION: Flavivirus envelope protein

<400> SEQUENCE: 95

Gly His Leu Lys Cys Arg Met Lys Leu Leu Lys Gly Tyr Cys
1               5                   10

<210> SEQ ID NO 96
<211> LENGTH: 100
<212> TYPE: PRT
<213> ORGANISM: Artificial Sequence
<220> FEATURE:
<223> OTHER INFORMATION: Dengue virus
```

<400> SEQUENCE: 96

Lys Gly Met Ser Tyr Val Met Cys Thr Gly Ser Phe Lys Leu Glu Lys
1 5 10 15

Glu Val Ala Glu Thr Gln His Gly Thr Val Leu Val Gln Val Lys Tyr
20 25 30

Glu Gly Thr Asp Ala Pro Cys Lys Ile Pro Phe Ser Thr Gln Asp Glu
35 40 45

Lys Gly Val Thr Gln Asn Gly Arg Leu Ile Thr Ala Asn Pro Ile Val
50 55 60

Thr Asp Lys Glu Lys Pro Val Asn Ile Glu Ala Glu Pro Pro Phe Gly
65 70 75 80

Glu Asn Tyr Ile Val Val Gly Ala Gly Glu Lys Ala Leu Lys Leu Ser
85 90 95

Trp Phe Lys Lys
100

<210> SEQ ID NO 97
<211> LENGTH: 100
<212> TYPE: PRT
<213> ORGANISM: Artificial Sequence
<220> FEATURE:
<223> OTHER INFORMATION: Dengue virus

<400> SEQUENCE: 97

Lys Gly Met Ser Tyr Ser Met Cys Thr Gly Lys Phe Lys Val Val Lys
1 5 10 15

Glu Ile Ala Glu Thr Gln His Gly Thr Ile Val Ile Arg Val Gln Tyr
20 25 30

Glu Gly Asp Gly Ser Pro Cys Lys Thr Pro Phe Glu Ile Met Asp Leu
35 40 45

Glu Lys Arg His Val Leu Gly Arg Leu Thr Thr Val Asn Pro Ile Val
50 55 60

Thr Glu Lys Asp Ser Pro Val Asn Ile Glu Ala Glu Pro Pro Phe Gly
65 70 75 80

Asp Ser Tyr Ile Ile Ile Gly Val Glu Pro Gly Gln Leu Lys Leu Asp
85 90 95

Trp Phe Lys Lys
100

<210> SEQ ID NO 98
<211> LENGTH: 100
<212> TYPE: PRT
<213> ORGANISM: Artificial Sequence
<220> FEATURE:
<223> OTHER INFORMATION: Dengue virus

<400> SEQUENCE: 98

Lys Gly Met Ser Tyr Ala Met Cys Leu Asn Thr Phe Val Leu Lys Lys
1 5 10 15

Glu Val Ser Glu Thr Gln His Gly Thr Ile Leu Ile Lys Val Glu Tyr
20 25 30

Lys Gly Glu Asp Ala Pro Cys Lys Ile Pro Phe Ser Thr Glu Asp Gly
35 40 45

Gln Gly Lys Ala His Asn Gly Arg Leu Ile Thr Ala Asn Pro Val Val
50 55 60

Thr Lys Lys Glu Glu Pro Val Asn Ile Glu Ala Glu Pro Pro Phe Gly
65 70 75 80

Glu Ser Asn Ile Val Ile Gly Ile Gly Asp Lys Ala Leu Lys Ile Asn
            85                  90                  95

Trp Tyr Arg Lys
        100

<210> SEQ ID NO 99
<211> LENGTH: 99
<212> TYPE: PRT
<213> ORGANISM: Artificial Sequence
<220> FEATURE:
<223> OTHER INFORMATION: Dengue virus

<400> SEQUENCE: 99

Lys Gly Met Ser Tyr Thr Met Cys Ser Gly Lys Phe Ser Ile Asp Lys
1               5                   10                  15

Glu Met Ala Glu Thr Gln His Gly Thr Thr Val Val Lys Val Lys Tyr
            20                  25                  30

Glu Gly Ala Gly Ala Pro Cys Lys Val Pro Ile Glu Ile Arg Asp Val
        35                  40                  45

Asn Lys Glu Lys Val Val Gly Arg Ile Ile Ser Pro Thr Pro Phe Ala
    50                  55                  60

Glu Asn Thr Asn Ser Val Thr Asn Ile Glu Leu Glu Arg Pro Leu Asp
65                  70                  75                  80

Ser Tyr Ile Val Ile Gly Val Gly Asp Ser Ala Leu Thr Leu His Trp
                85                  90                  95

Phe Arg Lys

<210> SEQ ID NO 100
<211> LENGTH: 20
<212> TYPE: PRT
<213> ORGANISM: Artificial Sequence
<220> FEATURE:
<223> OTHER INFORMATION: Flavivirus envelope protein

<400> SEQUENCE: 100

Cys Arg Val Lys Met Glu Lys Leu Gln Leu Lys Gly Thr Thr Tyr Gly
1               5                   10                  15

Val Cys Ser Lys
            20

<210> SEQ ID NO 101
<211> LENGTH: 20
<212> TYPE: PRT
<213> ORGANISM: Artificial Sequence
<220> FEATURE:
<223> OTHER INFORMATION: Flavivirus envelope protein

<400> SEQUENCE: 101

Ser Arg Val Lys Met Glu Lys Leu Gln Leu Lys Gly Thr Thr Tyr Gly
1               5                   10                  15

Val Cys Ser Lys
            20

<210> SEQ ID NO 102
<211> LENGTH: 20
<212> TYPE: PRT
<213> ORGANISM: Artificial Sequence
<220> FEATURE:
<223> OTHER INFORMATION: Flavivirus envelope protein

<400> SEQUENCE: 102

Cys Arg Val Lys Met Glu Lys Leu Gln Leu Lys Gly Thr Thr Tyr Gly
1               5                   10                  15

Val Ser Ser Lys
            20

<210> SEQ ID NO 103
<211> LENGTH: 20
<212> TYPE: PRT
<213> ORGANISM: Artificial Sequence
<220> FEATURE:
<223> OTHER INFORMATION: Flavivirus envelope protein

<400> SEQUENCE: 103

Ser Arg Val Lys Met Glu Lys Leu Gln Leu Lys Gly Thr Thr Tyr Gly
 1               5                  10                  15

Val Ser Ser Lys
            20

<210> SEQ ID NO 104
<211> LENGTH: 20
<212> TYPE: PRT
<213> ORGANISM: Artificial Sequence
<220> FEATURE:
<223> OTHER INFORMATION: Flavivirus envelope protein

<400> SEQUENCE: 104

Cys Arg Val Lys Met Glu Lys Leu Gln Leu Lys Gly Thr Thr Tyr Gly
 1               5                  10                  15

Val Cys Ser Lys
            20

<210> SEQ ID NO 105
<211> LENGTH: 20
<212> TYPE: PRT
<213> ORGANISM: Artificial Sequence
<220> FEATURE:
<223> OTHER INFORMATION: Flavivirus envelope protein

<400> SEQUENCE: 105

Ala Arg Val Lys Met Glu Lys Leu Gln Leu Lys Gly Thr Thr Tyr Gly
 1               5                  10                  15

Val Cys Ser Lys
            20

<210> SEQ ID NO 106
<211> LENGTH: 20
<212> TYPE: PRT
<213> ORGANISM: Artificial Sequence
<220> FEATURE:
<223> OTHER INFORMATION: Flavivirus envelope protein

<400> SEQUENCE: 106

Cys Ala Val Lys Met Glu Lys Leu Gln Leu Lys Gly Thr Thr Tyr Gly
 1               5                  10                  15

Val Cys Ser Lys
            20

<210> SEQ ID NO 107
<211> LENGTH: 20
<212> TYPE: PRT
<213> ORGANISM: Artificial Sequence
<220> FEATURE:
<223> OTHER INFORMATION: Flavivirus envelope protein

<400> SEQUENCE: 107

Cys Arg Ala Lys Met Glu Lys Leu Gln Leu Lys Gly Thr Thr Tyr Gly
 1               5                  10                  15

Val Cys Ser Lys
            20

<210> SEQ ID NO 108
<211> LENGTH: 20
<212> TYPE: PRT
<213> ORGANISM: Artificial Sequence
<220> FEATURE:
<223> OTHER INFORMATION: Flavivirus envelope protein

<400> SEQUENCE: 108

Cys Arg Val Ala Met Glu Lys Leu Gln Leu Lys Gly Thr Thr Tyr Gly
 1               5                  10                  15

Val Cys Ser Lys
            20

<210> SEQ ID NO 109
<211> LENGTH: 20
<212> TYPE: PRT
<213> ORGANISM: Artificial Sequence
<220> FEATURE:
<223> OTHER INFORMATION: Flavivirus envelope protein

<400> SEQUENCE: 109

Cys Arg Val Lys Ala Glu Lys Leu Gln Leu Lys Gly Thr Thr Tyr Gly
 1               5                  10                  15

Val Cys Ser Lys
            20

<210> SEQ ID NO 110
<211> LENGTH: 20
<212> TYPE: PRT
<213> ORGANISM: Artificial Sequence
<220> FEATURE:
<223> OTHER INFORMATION: Flavivirus envelope protein

<400> SEQUENCE: 110

Cys Arg Val Lys Met Ala Lys Leu Gln Leu Lys Gly Thr Thr Tyr Gly
 1               5                  10                  15

Val Cys Ser Lys
            20

<210> SEQ ID NO 111
<211> LENGTH: 20
<212> TYPE: PRT
<213> ORGANISM: Artificial Sequence
<220> FEATURE:
<223> OTHER INFORMATION: Flavivirus envelope protein

<400> SEQUENCE: 111

Cys Arg Val Lys Met Glu Ala Leu Gln Leu Lys Gly Thr Thr Tyr Gly
 1               5                  10                  15

Val Cys Ser Lys
            20

<210> SEQ ID NO 112
<211> LENGTH: 20
<212> TYPE: PRT
<213> ORGANISM: Artificial Sequence
<220> FEATURE:
<223> OTHER INFORMATION: Flavivirus envelope protein

<400> SEQUENCE: 112

Cys Arg Val Lys Met Glu Lys Ala Gln Leu Lys Gly Thr Thr Tyr Gly
 1               5                  10                  15

Val Cys Ser Lys
            20

<210> SEQ ID NO 113
<211> LENGTH: 20
<212> TYPE: PRT
<213> ORGANISM: Artificial Sequence
<220> FEATURE:
<223> OTHER INFORMATION: Flavivirus envelope protein

<400> SEQUENCE: 113

Cys Arg Val Lys Met Glu Lys Leu Ala Leu Lys Gly Thr Thr Tyr Gly
1               5                   10                  15

Val Cys Ser Lys
            20

<210> SEQ ID NO 114
<211> LENGTH: 20
<212> TYPE: PRT
<213> ORGANISM: Artificial Sequence
<220> FEATURE:
<223> OTHER INFORMATION: Flavivirus envelope protein

<400> SEQUENCE: 114

Cys Arg Val Lys Met Glu Lys Leu Gln Ala Lys Gly Thr Thr Tyr Gly
1               5                   10                  15

Val Cys Ser Lys
            20

<210> SEQ ID NO 115
<211> LENGTH: 20
<212> TYPE: PRT
<213> ORGANISM: Artificial Sequence
<220> FEATURE:
<223> OTHER INFORMATION: Flavivirus envelope protein

<400> SEQUENCE: 115

Cys Arg Val Lys Met Glu Lys Leu Gln Leu Ala Gly Thr Thr Tyr Gly
1               5                   10                  15

Val Cys Ser Lys
            20

<210> SEQ ID NO 116
<211> LENGTH: 20
<212> TYPE: PRT
<213> ORGANISM: Artificial Sequence
<220> FEATURE:
<223> OTHER INFORMATION: Flavivirus envelope protein

<400> SEQUENCE: 116

Cys Arg Val Lys Met Glu Lys Leu Gln Leu Lys Ala Thr Thr Tyr Gly
1               5                   10                  15

Val Cys Ser Lys
            20

<210> SEQ ID NO 117
<211> LENGTH: 20
<212> TYPE: PRT
<213> ORGANISM: Artificial Sequence
<220> FEATURE:
<223> OTHER INFORMATION: Flavivirus envelope protein

<400> SEQUENCE: 117

Cys Arg Val Lys Met Glu Lys Leu Gln Leu Lys Gly Ala Thr Tyr Gly
1               5                   10                  15

Val Cys Ser Lys
            20

<210> SEQ ID NO 118
<211> LENGTH: 20
<212> TYPE: PRT
<213> ORGANISM: Artificial Sequence
<220> FEATURE:
<223> OTHER INFORMATION: Flavivirus envelope protein

<400> SEQUENCE: 118

Cys Arg Val Lys Met Glu Lys Leu Gln Leu Lys Gly Thr Ala Tyr Gly
1               5                   10                  15

Val Cys Ser Lys
            20

<210> SEQ ID NO 119
<211> LENGTH: 20
<212> TYPE: PRT
<213> ORGANISM: Artificial Sequence
<220> FEATURE:
<223> OTHER INFORMATION: Flavivirus envelope protein

<400> SEQUENCE: 119

Cys Arg Val Lys Met Glu Lys Leu Gln Leu Lys Gly Thr Thr Ala Gly
1               5                   10                  15

Val Cys Ser Lys
            20

<210> SEQ ID NO 120
<211> LENGTH: 20
<212> TYPE: PRT
<213> ORGANISM: Artificial Sequence
<220> FEATURE:
<223> OTHER INFORMATION: Flavivirus envelope protein

<400> SEQUENCE: 120

Cys Arg Val Lys Met Glu Lys Leu Gln Leu Lys Gly Thr Thr Tyr Ala
1               5                   10                  15

Val Cys Ser Lys
            20

<210> SEQ ID NO 121
<211> LENGTH: 20
<212> TYPE: PRT
<213> ORGANISM: Artificial Sequence
<220> FEATURE:
<223> OTHER INFORMATION: Flavivirus envelope protein

<400> SEQUENCE: 121

Cys Arg Val Lys Met Glu Lys Leu Gln Leu Lys Gly Thr Thr Tyr Gly
1               5                   10                  15

Ala Cys Ser Lys
            20

<210> SEQ ID NO 122
<211> LENGTH: 20
<212> TYPE: PRT
<213> ORGANISM: Artificial Sequence
<220> FEATURE:
<223> OTHER INFORMATION: Flavivirus envelope protein

<400> SEQUENCE: 122

Cys Arg Val Lys Met Glu Lys Leu Gln Leu Lys Gly Thr Thr Tyr Gly
1               5                   10                  15

Val Ala Ser Lys
            20

<210> SEQ ID NO 123
<211> LENGTH: 20
<212> TYPE: PRT
<213> ORGANISM: Artificial Sequence
<220> FEATURE:
<223> OTHER INFORMATION: Flavivirus envelope protein

<400> SEQUENCE: 123

Cys Arg Val Lys Met Glu Lys Leu Gln Leu Lys Gly Thr Thr Tyr Gly
1               5                   10                  15

Val Cys Ala Lys
            20

<210> SEQ ID NO 124
<211> LENGTH: 20
<212> TYPE: PRT
<213> ORGANISM: Artificial Sequence
<220> FEATURE:
<223> OTHER INFORMATION: Flavivirus envelope protein

<400> SEQUENCE: 124

Cys Arg Val Lys Met Glu Lys Leu Gln Leu Lys Gly Thr Thr Tyr Gly
1               5                   10                  15

Val Cys Ser Ala
            20

<210> SEQ ID NO 125
<211> LENGTH: 20
<212> TYPE: PRT
<213> ORGANISM: Artificial Sequence
<220> FEATURE:
<223> OTHER INFORMATION: Flavivirus envelope protein

<400> SEQUENCE: 125

Cys Arg Val Lys Met Glu Lys Leu Gln Leu Lys Gly Thr Thr Tyr Gly
1               5                   10                  15

Val Cys Ser Lys
            20

<210> SEQ ID NO 126
<211> LENGTH: 20
<212> TYPE: PRT
<213> ORGANISM: Artificial Sequence
<220> FEATURE:
<223> OTHER INFORMATION: Flavivirus envelope protein

<400> SEQUENCE: 126

Ser Asn Thr Val Lys Leu Thr Ser Gly His Leu Lys Cys Arg Val Lys
1               5                   10                  15

Met Glu Lys Leu
            20

<210> SEQ ID NO 127
<211> LENGTH: 20
<212> TYPE: PRT
<213> ORGANISM: Artificial Sequence
<220> FEATURE:
<223> OTHER INFORMATION: Flavivirus envelope protein

<400> SEQUENCE: 127

Asn Thr Val Lys Leu Thr Ser Gly His Leu Lys Cys Arg Val Lys Met
1               5                   10                  15

Glu Lys Leu Gln
           20

<210> SEQ ID NO 128
<211> LENGTH: 20
<212> TYPE: PRT
<213> ORGANISM: Artificial Sequence
<220> FEATURE:
<223> OTHER INFORMATION: Flavivirus envelope protein

<400> SEQUENCE: 128

Thr Val Lys Leu Thr Ser Gly His Leu Lys Cys Arg Val Lys Met Glu
 1               5                  10                  15

Lys Leu Gln Leu
           20

<210> SEQ ID NO 129
<211> LENGTH: 20
<212> TYPE: PRT
<213> ORGANISM: Artificial Sequence
<220> FEATURE:
<223> OTHER INFORMATION: Flavivirus envelope protein

<400> SEQUENCE: 129

Val Lys Leu Thr Ser Gly His Leu Lys Cys Arg Val Lys Met Glu Lys
 1               5                  10                  15

Leu Gln Leu Lys
           20

<210> SEQ ID NO 130
<211> LENGTH: 20
<212> TYPE: PRT
<213> ORGANISM: Artificial Sequence
<220> FEATURE:
<223> OTHER INFORMATION: Flavivirus envelope protein

<400> SEQUENCE: 130

Lys Leu Thr Ser Gly His Leu Lys Cys Arg Val Lys Met Glu Lys Leu
 1               5                  10                  15

Gln Leu Lys Gly
           20

<210> SEQ ID NO 131
<211> LENGTH: 20
<212> TYPE: PRT
<213> ORGANISM: Artificial Sequence
<220> FEATURE:
<223> OTHER INFORMATION: Flavivirus envelope protein

<400> SEQUENCE: 131

Leu Thr Ser Gly His Leu Lys Cys Arg Val Lys Met Glu Lys Leu Gln
 1               5                  10                  15

Leu Lys Gly Thr
           20

<210> SEQ ID NO 132
<211> LENGTH: 20
<212> TYPE: PRT
<213> ORGANISM: Artificial Sequence
<220> FEATURE:
<223> OTHER INFORMATION: Flavivirus envelope protein

<400> SEQUENCE: 132

Thr Ser Gly His Leu Lys Cys Arg Val Lys Met Glu Lys Leu Gln Leu
 1               5                  10                  15

Lys Gly Thr Thr
        20

<210> SEQ ID NO 133
<211> LENGTH: 20
<212> TYPE: PRT
<213> ORGANISM: Artificial Sequence
<220> FEATURE:
<223> OTHER INFORMATION: Flavivirus envelope protein

<400> SEQUENCE: 133

Ser Gly His Leu Lys Cys Arg Val Lys Met Glu Lys Leu Gln Leu Lys
1               5                   10                  15

Gly Thr Thr Tyr
        20

<210> SEQ ID NO 134
<211> LENGTH: 20
<212> TYPE: PRT
<213> ORGANISM: Artificial Sequence
<220> FEATURE:
<223> OTHER INFORMATION: Flavivirus envelope protein

<400> SEQUENCE: 134

Gly His Leu Lys Cys Arg Val Lys Met Glu Lys Leu Gln Leu Lys Gly
1               5                   10                  15

Thr Thr Tyr Gly
        20

<210> SEQ ID NO 135
<211> LENGTH: 20
<212> TYPE: PRT
<213> ORGANISM: Artificial Sequence
<220> FEATURE:
<223> OTHER INFORMATION: Flavivirus envelope protein

<400> SEQUENCE: 135

His Leu Lys Cys Arg Val Lys Met Glu Lys Leu Gln Leu Lys Gly Thr
1               5                   10                  15

Thr Tyr Gly Val
        20

<210> SEQ ID NO 136
<211> LENGTH: 20
<212> TYPE: PRT
<213> ORGANISM: Artificial Sequence
<220> FEATURE:
<223> OTHER INFORMATION: Flavivirus envelope protein

<400> SEQUENCE: 136

Leu Lys Cys Arg Val Lys Met Glu Lys Leu Gln Leu Lys Gly Thr Thr
1               5                   10                  15

Tyr Gly Val Cys
        20

<210> SEQ ID NO 137
<211> LENGTH: 20
<212> TYPE: PRT
<213> ORGANISM: Artificial Sequence
<220> FEATURE:
<223> OTHER INFORMATION: Flavivirus envelope protein

<400> SEQUENCE: 137

Lys Cys Arg Val Lys Met Glu Lys Leu Gln Leu Lys Gly Thr Thr Tyr
1               5                   10                  15

```
Gly Val Cys Ser
        20

<210> SEQ ID NO 138
<211> LENGTH: 20
<212> TYPE: PRT
<213> ORGANISM: Artificial Sequence
<220> FEATURE:
<223> OTHER INFORMATION: Flavivirus envelope protein

<400> SEQUENCE: 138

Cys Arg Val Lys Met Glu Lys Leu Gln Leu Lys Gly Thr Thr Tyr Gly
1               5                   10                  15

Val Cys Ser Lys
        20

<210> SEQ ID NO 139
<211> LENGTH: 20
<212> TYPE: PRT
<213> ORGANISM: Artificial Sequence
<220> FEATURE:
<223> OTHER INFORMATION: Flavivirus envelope protein

<400> SEQUENCE: 139

Arg Val Lys Met Glu Lys Leu Gln Leu Lys Gly Thr Thr Tyr Gly Val
1               5                   10                  15

Cys Ser Lys Ala
        20

<210> SEQ ID NO 140
<211> LENGTH: 20
<212> TYPE: PRT
<213> ORGANISM: Artificial Sequence
<220> FEATURE:
<223> OTHER INFORMATION: Flavivirus envelope protein

<400> SEQUENCE: 140

Val Lys Met Glu Lys Leu Gln Leu Lys Gly Thr Thr Tyr Gly Val Cys
1               5                   10                  15

Ser Lys Ala Phe
        20

<210> SEQ ID NO 141
<211> LENGTH: 20
<212> TYPE: PRT
<213> ORGANISM: Artificial Sequence
<220> FEATURE:
<223> OTHER INFORMATION: Flavivirus envelope protein

<400> SEQUENCE: 141

Lys Met Glu Lys Leu Gln Leu Lys Gly Thr Thr Tyr Gly Val Cys Ser
1               5                   10                  15

Lys Ala Phe Lys
        20

<210> SEQ ID NO 142
<211> LENGTH: 20
<212> TYPE: PRT
<213> ORGANISM: Artificial Sequence
<220> FEATURE:
<223> OTHER INFORMATION: Flavivirus envelope protein

<400> SEQUENCE: 142

Met Glu Lys Leu Gln Leu Lys Gly Thr Thr Tyr Gly Val Cys Ser Lys
1               5                   10                  15
```

Ala Phe Lys Phe
            20

<210> SEQ ID NO 143
<211> LENGTH: 20
<212> TYPE: PRT
<213> ORGANISM: Artificial Sequence
<220> FEATURE:
<223> OTHER INFORMATION: Flavivirus envelope protein

<400> SEQUENCE: 143

Glu Lys Leu Gln Leu Lys Gly Thr Thr Tyr Gly Val Cys Ser Lys Ala
1               5                   10                  15

Phe Lys Phe Leu
            20

<210> SEQ ID NO 144
<211> LENGTH: 20
<212> TYPE: PRT
<213> ORGANISM: Artificial Sequence
<220> FEATURE:
<223> OTHER INFORMATION: Flavivirus envelope protein

<400> SEQUENCE: 144

Lys Leu Gln Leu Lys Gly Thr Thr Tyr Gly Val Cys Ser Lys Ala Phe
1               5                   10                  15

Lys Phe Leu Gly
            20

<210> SEQ ID NO 145
<211> LENGTH: 20
<212> TYPE: PRT
<213> ORGANISM: Artificial Sequence
<220> FEATURE:
<223> OTHER INFORMATION: Flavivirus envelope protein

<400> SEQUENCE: 145

Leu Gln Leu Lys Gly Thr Thr Tyr Gly Val Cys Ser Lys Ala Phe Lys
1               5                   10                  15

Phe Leu Gly Thr
            20

<210> SEQ ID NO 146
<211> LENGTH: 20
<212> TYPE: PRT
<213> ORGANISM: Artificial Sequence
<220> FEATURE:
<223> OTHER INFORMATION: Flavivirus envelope protein

<400> SEQUENCE: 146

Gln Leu Lys Gly Thr Thr Tyr Gly Val Cys Ser Lys Ala Phe Lys Phe
1               5                   10                  15

Leu Gly Thr Pro
            20

<210> SEQ ID NO 147
<211> LENGTH: 20
<212> TYPE: PRT
<213> ORGANISM: Artificial Sequence
<220> FEATURE:
<223> OTHER INFORMATION: Flavivirus envelope protein

<400> SEQUENCE: 147

Leu Lys Gly Thr Thr Tyr Gly Val Cys Ser Lys Ala Phe Lys Phe Leu
1               5                   10                  15

```
Gly Thr Pro Ala
        20

<210> SEQ ID NO 148
<211> LENGTH: 20
<212> TYPE: PRT
<213> ORGANISM: Artificial Sequence
<220> FEATURE:
<223> OTHER INFORMATION: Flavivirus envelope protein

<400> SEQUENCE: 148

Lys Gly Thr Thr Tyr Gly Val Cys Ser Lys Ala Phe Lys Phe Leu Gly
 1               5                  10                  15

Thr Pro Ala Asp
        20

<210> SEQ ID NO 149
<211> LENGTH: 20
<212> TYPE: PRT
<213> ORGANISM: Artificial Sequence
<220> FEATURE:
<223> OTHER INFORMATION: Flavivirus envelope protein

<400> SEQUENCE: 149

Gly Thr Thr Tyr Gly Val Cys Ser Lys Ala Phe Lys Phe Leu Gly Thr
 1               5                  10                  15

Pro Ala Asp Thr
        20

<210> SEQ ID NO 150
<211> LENGTH: 20
<212> TYPE: PRT
<213> ORGANISM: Artificial Sequence
<220> FEATURE:
<223> OTHER INFORMATION: Flavivirus envelope protein

<400> SEQUENCE: 150

Thr Thr Tyr Gly Val Cys Ser Lys Ala Phe Lys Phe Leu Gly Thr Pro
 1               5                  10                  15

Ala Asp Thr Gly
        20

<210> SEQ ID NO 151
<211> LENGTH: 20
<212> TYPE: PRT
<213> ORGANISM: Artificial Sequence
<220> FEATURE:
<223> OTHER INFORMATION: Flavivirus envelope protein

<400> SEQUENCE: 151

Thr Tyr Gly Val Cys Ser Lys Ala Phe Lys Phe Leu Gly Thr Pro Ala
 1               5                  10                  15

Asp Thr Gly His
        20

<210> SEQ ID NO 152
<211> LENGTH: 2760
<212> TYPE: DNA
<213> ORGANISM: Artificial Sequence
<220> FEATURE:
<223> OTHER INFORMATION: STF2.OVA

<400> SEQUENCE: 152
atggcacaag taatcaacac taacagtctg tcgctgctga cccagaataa cctgaacaaa      60
```

```
tcccagtccg cactgggcac cgctatcgag cgtctgtctt ctggtctgcg tatcaacagc      120
gcgaaagacg atgcggcagg tcaggcgatt gctaaccgtt tcaccgcgaa catcaaaggt      180
ctgactcagg cttcccgtaa cgctaacgac ggtatctcca ttgcgcagac cactgaaggc      240
gcgctgaacg aaatcaacaa caacctgcag cgtgtgcgtg aactggcggt tcagtctgct      300
aacagcacca actcccagtc tgacctcgac tccatccagg ctgaaatcac ccagcgcctg      360
aacgaaatcg accgtgtatc cggccagact cagttcaacg gcgtgaaagt cctggcgcag      420
gacaacaccc tgaccatcca ggttggcgcc aacgacggtg aaactatcga tatcgatctg      480
aagcagatca actctcagac cctgggtctg gactcactga acgtgcagaa agcgtatgat      540
gtgaaagata cagcagtaac aacgaaagct tatgccaata atggtactac actggatgta      600
tcgggtcttg atgatgcagc tattaaagcg gctacgggtg gtacgaatgg tacggcttct      660
gtaaccggtg gtgcggttaa atttgacgca gataataaca agtactttgt tactattggt      720
ggctttactg gtgctgatgc cgccaaaaat ggcgattatg aagttaacgt tgctactgac      780
ggtacagtaa cccttgcggc tggcgcaact aaaaccacaa tgcctgctgg tgcgacaact      840
aaaacagaag tacaggagtt aaaagataca ccggcagttg tttcagcaga tgctaaaaat      900
gccttaattg ctggcggcgt tgacgctacc gatgctaatg gcgctgagtt ggtcaaaatg      960
tcttataccg ataaaaatgg taagacaatt gaaggcggtt atgcgcttaa agctggcgat     1020
aagtattacg ccgcagatta cgatgaagcg acaggagcaa ttaaagctaa aaccacaagt     1080
tatactgctg ctgacggcac taccaaaaca gcggctaacc aactgggtgg cgtagacggt     1140
aaaaccgaag tcgttactat cgacggtaaa acctacaatg ccagcaaagc cgctggtcat     1200
gatttcaaag cacaaccaga gctgcggaa gcagccgcta aaaccaccga aaacccgctg     1260
```

```
tctggcatct cctcagcaga gagcctgaag atatctcaag ctgtccatgc agcacatgca    2520
gaaatcaatg aagcaggcag agaggtggta gggtcagcag aggctggagt ggatgctgca    2580
agcgtctctg aagaatttag ggctgaccat ccattcctct tctgtatcaa gcacatcgca    2640
accaacgccg ttctcttctt tggcagatgt gtttcccctt cgaagcttga aggtaagcct    2700
atccctaacc ctctcctcgg tctcgattct acgcgtaccg gtcatcatca ccatcaccat    2760
```

<210> SEQ ID NO 153
<211> LENGTH: 920
<212> TYPE: PRT
<213> ORGANISM: Artificial Sequence
<220> FEATURE:
<223> OTHER INFORMATION: STF2.OVA

<400> SEQUENCE: 153

```
Met Ala Gln Val Ile Asn Thr Asn Ser Leu Ser Leu Leu Thr Gln Asn
 1               5                  10                  15

Asn Leu Asn Lys Ser Gln Ser Ala Leu Gly Thr Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ala Asn Ile Lys Gly Leu Thr Gln Ala
    50                  55                  60

Ser Arg Asn Ala Asn Asp Gly Ile Ser Ile Ala Gln Thr Thr Glu Gly
65                  70                  75                  80

Ala Leu Asn Glu Ile Asn Asn Asn Leu Gln Arg Val Arg Glu Leu Ala
                85                  90                  95

Val Gln Ser Ala Asn Ser Thr Asn Ser Gln Ser Asp Leu Asp Ser Ile
            100                 105                 110

Gln Ala Glu Ile Thr Gln Arg Leu Asn Glu Ile Asp Arg Val Ser Gly
        115                 120                 125

Gln Thr Gln Phe Asn Gly Val Lys Val Leu Ala Gln Asp Asn Thr Leu
    130                 135                 140

Thr Ile Gln Val Gly Ala Asn Asp Gly Glu Thr Ile Asp Ile Asp Leu
145                 150                 155                 160

Lys Gln Ile Asn Ser Gln Thr Leu Gly Leu Asp Ser Leu Asn Val Gln
                165                 170                 175

Lys Ala Tyr Asp Val Lys Asp Thr Ala Val Thr Thr Lys Ala Tyr Ala
            180                 185                 190

Asn Asn Gly Thr Thr Leu Asp Val Ser Gly Leu Asp Asp Ala Ala Ile
        195                 200                 205

Lys Ala Ala Thr Gly Gly Thr Asn Gly Thr Ala Ser Val Thr Gly Gly
    210                 215                 220

Ala Val Lys Phe Asp Ala Asp Asn Asn Lys Tyr Phe Val Thr Ile Gly
225                 230                 235                 240

Gly Phe Thr Gly Ala Asp Ala Ala Lys Asn Gly Asp Tyr Glu Val Asn
                245                 250                 255

Val Ala Thr Asp Gly Thr Val Thr Leu Ala Ala Gly Ala Thr Lys Thr
            260                 265                 270

Thr Met Pro Ala Gly Ala Thr Thr Lys Thr Glu Val Gln Glu Leu Lys
        275                 280                 285

Asp Thr Pro Ala Val Val Ser Ala Asp Ala Lys Asn Ala Leu Ile Ala
    290                 295                 300

Gly Gly Val Asp Ala Thr Asp Ala Asn Gly Ala Glu Leu Val Lys Met
305                 310                 315                 320
```

```
Ser Tyr Thr Asp Lys Asn Gly Lys Thr Ile Glu Gly Tyr Ala Leu
            325                 330                 335

Lys Ala Gly Asp Lys Tyr Tyr Ala Ala Asp Tyr Asp Glu Ala Thr Gly
            340                 345                 350

Ala Ile Lys Ala Lys Thr Thr Ser Tyr Thr Ala Ala Asp Gly Thr Thr
            355                 360                 365

Lys Thr Ala Ala Asn Gln Leu Gly Gly Val Asp Gly Lys Thr Glu Val
370                 375                 380

Val Thr Ile Asp Gly Lys Thr Tyr Asn Ala Ser Lys Ala Ala Gly His
385                 390                 395                 400

Asp Phe Lys Ala Gln Pro Glu Leu Ala Glu Ala Ala Lys Thr Thr
                405                 410                 415

Glu Asn Pro Leu Gln Lys Ile Asp Ala Ala Leu Ala Gln Val Asp Ala
            420                 425                 430

Leu Arg Ser Asp Leu Gly Ala Val Gln Asn Arg Phe Asn Ser Ala Ile
            435                 440                 445

Thr Asn Leu Gly Asn Thr Val Asn Asn Leu Ser Glu Ala Arg Ser Arg
            450                 455                 460

Ile Glu Asp Ser Asp Tyr Ala Thr Glu Val Ser Asn Met Ser Arg Ala
465                 470                 475                 480

Gln Ile Leu Gln Gln Ala Gly Thr Ser Val Leu Ala Gln Ala Asn Gln
                485                 490                 495

Val Pro Gln Asn Val Leu Ser Leu Leu Arg Leu Glu Gly Ser Ile Gly
            500                 505                 510

Ala Ala Ser Met Glu Phe Cys Phe Asp Val Phe Lys Glu Leu Lys Val
            515                 520                 525

His His Ala Asn Glu Asn Ile Phe Tyr Cys Pro Ile Ala Ile Met Ser
530                 535                 540

Ala Leu Ala Met Val Tyr Leu Gly Ala Lys Asp Ser Thr Arg Thr Gln
545                 550                 555                 560

Ile Asn Lys Val Val Arg Phe Asp Lys Leu Pro Gly Phe Gly Asp Ser
                565                 570                 575

Ile Glu Ala Gln Cys Gly Thr Ser Val Asn Val His Ser Ser Leu Arg
            580                 585                 590

Asp Ile Leu Asn Gln Ile Thr Lys Pro Asn Asp Val Tyr Ser Phe Ser
            595                 600                 605

Leu Ala Ser Arg Leu Tyr Ala Glu Glu Arg Tyr Pro Ile Leu Pro Glu
            610                 615                 620

Tyr Leu Gln Cys Val Lys Glu Leu Tyr Arg Gly Gly Leu Glu Pro Ile
625                 630                 635                 640

Asn Phe Gln Thr Ala Ala Asp Gln Ala Arg Glu Leu Ile Asn Ser Trp
                645                 650                 655

Val Glu Ser Gln Thr Asn Gly Ile Ile Arg Asn Val Leu Gln Pro Ser
            660                 665                 670

Ser Val Asp Ser Gln Thr Ala Met Val Leu Val Asn Ala Ile Val Phe
            675                 680                 685

Lys Gly Leu Trp Glu Lys Ala Phe Lys Asp Glu Asp Thr Gln Ala Met
690                 695                 700

Pro Phe Arg Val Thr Glu Gln Glu Ser Lys Pro Val Gln Met Met Tyr
705                 710                 715                 720

Gln Ile Gly Leu Phe Arg Val Ala Ser Met Ala Ser Glu Lys Met Lys
                725                 730                 735

Ile Leu Glu Leu Pro Phe Ala Ser Gly Thr Met Ser Met Leu Val Leu
            740                 745                 750
```

Leu Pro Asp Glu Val Ser Gly Leu Glu Gln Leu Glu Ser Ile Ile Asn
        755                 760                 765

Phe Glu Lys Leu Thr Glu Trp Thr Ser Ser Asn Val Met Glu Glu Arg
    770                 775                 780

Lys Ile Lys Val Tyr Leu Pro Arg Met Lys Met Glu Glu Lys Tyr Asn
785                 790                 795                 800

Leu Thr Ser Val Leu Met Ala Met Gly Ile Thr Asp Val Phe Ser Ser
            805                 810                 815

Ser Ala Asn Leu Ser Gly Ile Ser Ser Ala Glu Ser Leu Lys Ile Ser
            820                 825                 830

Gln Ala Val His Ala Ala His Ala Glu Ile Asn Glu Ala Gly Arg Glu
            835                 840                 845

Val Val Gly Ser Ala Glu Ala Gly Val Asp Ala Ala Ser Val Ser Glu
        850                 855                 860

Glu Phe Arg Ala Asp His Pro Phe Leu Phe Cys Ile Lys His Ile Ala
865                 870                 875                 880

Thr Asn Ala Val Leu Phe Phe Gly Arg Cys Val Ser Pro Ser Lys Leu
                885                 890                 895

Glu Gly Lys Pro Ile Pro Asn Pro Leu Gly Leu Asp Ser Thr Arg
            900                 905                 910

Thr Gly His His His His His His
        915                 920

<210> SEQ ID NO 154
<211> LENGTH: 385
<212> TYPE: PRT
<213> ORGANISM: Artificial Sequence
<220> FEATURE:
<223> OTHER INFORMATION: OVA

<400> SEQUENCE: 154

Gly Ser Ile Gly Ala Ala Ser Met Glu Phe Cys Phe Asp Val Phe Lys
1               5                   10                  15

Glu Leu Lys Val His His Ala Asn Glu Asn Ile Phe Tyr Cys Pro Ile
            20                  25                  30

Ala Ile Met Ser Ala Leu Ala Met Val Tyr Leu Gly Ala Lys Asp Ser
        35                  40                  45

Thr Arg Thr Gln Ile Asn Lys Val Val Arg Phe Asp Lys Leu Pro Gly
    50                  55                  60

Phe Gly Asp Ser Ile Glu Ala Gln Cys Gly Thr Ser Val Asn Val His
65                  70                  75                  80

Ser Ser Leu Arg Asp Ile Leu Asn Gln Ile Thr Lys Pro Asn Asp Val
                85                  90                  95

Tyr Ser Phe Ser Leu Ala Ser Arg Leu Tyr Ala Glu Glu Arg Tyr Pro
            100                 105                 110

Ile Leu Pro Glu Tyr Leu Gln Cys Val Lys Glu Leu Tyr Arg Gly Gly
        115                 120                 125

Leu Glu Pro Ile Asn Phe Gln Thr Ala Ala Asp Gln Ala Arg Glu Leu
    130                 135                 140

Ile Asn Ser Trp Val Glu Ser Gln Thr Asn Gly Ile Ile Arg Asn Val
145                 150                 155                 160

Leu Gln Pro Ser Ser Val Asp Ser Gln Thr Ala Met Val Leu Val Asn
                165                 170                 175

Ala Ile Val Phe Lys Gly Leu Trp Glu Lys Ala Phe Lys Asp Glu Asp
            180                 185                 190

```
Thr Gln Ala Met Pro Phe Arg Val Thr Glu Gln Glu Ser Lys Pro Val
        195                 200                 205
Gln Met Met Tyr Gln Ile Gly Leu Phe Arg Val Ala Ser Met Ala Ser
        210                 215                 220
Glu Lys Met Lys Ile Leu Glu Leu Pro Phe Ala Ser Gly Thr Met Ser
225                 230                 235                 240
Met Leu Val Leu Leu Pro Asp Glu Val Ser Gly Leu Glu Gln Leu Glu
                245                 250                 255
Ser Ile Ile Asn Phe Glu Lys Leu Thr Glu Trp Thr Ser Ser Asn Val
                260                 265                 270
Met Glu Glu Arg Lys Ile Lys Val Tyr Leu Pro Arg Met Lys Met Glu
            275                 280                 285
Glu Lys Tyr Asn Leu Thr Ser Val Leu Met Ala Met Gly Ile Thr Asp
        290                 295                 300
Val Phe Ser Ser Ser Ala Asn Leu Ser Gly Ile Ser Ser Ala Glu Ser
305                 310                 315                 320
Leu Lys Ile Ser Gln Ala Val His Ala Ala His Ala Glu Ile Asn Glu
                325                 330                 335
Ala Gly Arg Glu Val Val Gly Ser Ala Glu Ala Gly Val Asp Ala Ala
            340                 345                 350
Ser Val Ser Glu Glu Phe Arg Ala Asp His Pro Phe Leu Phe Cys Ile
        355                 360                 365
Lys His Ile Ala Thr Asn Ala Val Leu Phe Phe Gly Arg Cys Val Ser
    370                 375                 380
Pro
385

<210> SEQ ID NO 155
<211> LENGTH: 1156
<212> TYPE: DNA
<213> ORGANISM: Artificial Sequence
<220> FEATURE:
<223> OTHER INFORMATION: OVA

<400> SEQUENCE: 155
gggctccatc ggcgcagcaa gcatggaatt tgttttgat gtattcaagg agctcaaagt     60
ccaccatgcc aatgagaaca tcttctactg ccccattgcc atcatgtcag ctctagccat    120
ggtatacctg ggtgcaaaag acagcaccag gacacaaata aataaggttg ttcgctttga    180
taaacttcca ggattcggag acagtattga agctcagtgt ggcacatctg taaacgttca    240
ctcttcactt agagacatcc tcaaccaaat caccaaacca aatgatgttt attcgttcag    300
ccttgccagt agactttatg ctgaagagag atacccaatc ctgccagaat acttgcagtg    360
tgtgaaggaa ctgtatagag aggcttgga  acctatcaac tttcaaacag ctgcagatca    420
agccagagag ctcatcaatt cctgggtaga aagtcagaca aatggaatta tcagaaatgt    480
ccttcagcca agctccgtgg attctcaaac tgcaatggtt ctggttaatg ccattgtctt    540
caaaggactg tgggagaaag catttaagga tgaagacaca caagcaatgc ctttcagagt    600
gactgagcaa gaaagcaaac ctgtgcagat gatgtaccag attggtttat ttagagtggc    660
atcaatggct tctgagaaaa tgaagatcct ggagcttcca tttgccagtg gacaatgag     720
catgttggtg ctgttgcctg atgaagtctc aggccttgag cagcttgaga gtataatcaa    780
ctttgaaaaa ctgactgaat ggaccagttc taatgttatg gaagagagga gatcaaagt     840
gtacttacct cgcatgaaga tggaggaaaa atacaacctc acatctgtct taatggctat    900
gggcattact gacgtgttta gctcttcagc caatctgtct ggcatctcct cagcagagag    960
```

```
cctgaagata tctcaagctg tccatgcagc acatgcagaa atcaatgaag caggcagaga    1020
ggtggtaggg tcagcagagg ctggagtgga tgctgcaagc gtctctgaag aatttagggc    1080
tgaccatcca ttcctcttct gtatcaagca catcgcaacc aacgccgttc tcttctttgg    1140
cagatgtgtt tcccct                                                    1156

<210> SEQ ID NO 156
<211> LENGTH: 18
<212> TYPE: DNA
<213> ORGANISM: Artificial Sequence
<220> FEATURE:
<223> OTHER INFORMATION: Primer

<400> SEQUENCE: 156
catctcagtg caactaaa                                                  18

<210> SEQ ID NO 157
<211> LENGTH: 18
<212> TYPE: DNA
<213> ORGANISM: Artificial Sequence
<220> FEATURE:
<223> OTHER INFORMATION: Primer

<400> SEQUENCE: 157
tagaaggcac agtcgagg                                                  18

<210> SEQ ID NO 158
<211> LENGTH: 2736
<212> TYPE: DNA
<213> ORGANISM: Artificial Sequence
<220> FEATURE:
<223> OTHER INFORMATION: STF2.E

<400> SEQUENCE: 158
atggcacaag taatcaacac taacagtctg tcgctgctga cccagaataa cctgaacaaa    60
tcccagtccg cactgggcac cgctatcgag cgtctgtctt ctggtctgcg tatcaacagc    120
gcgaaagacg atgcggcagg tcaggcgatt gctaaccgtt tcaccgcgaa catcaaaggt    180
ctgactcagg cttcccgtaa cgctaacgac ggtatctcca ttgcgcagac cactgaaggc    240
gcgctgaacg aaatcaacaa caacctgcag cgtgtgcgtg aactggcggt tcagtctgct    300
aacagcacca actcccagtc tgacctcgac tccatccagg ctgaaatcac ccagcgcctg    360
aacgaaatcg accgtgtatc cggccagact cagttcaacg gcgtgaaagt cctggcgcag    420
gacaacaccc tgaccatcca ggttggcgcc aacgacggtg aaactatcga tatcgatctg    480
aagcagatca actctcagac cctgggtctg gactcactga cgtgcagaa agcgtatgat    540 gtgaaagata cagcagtaac aacgaaagct tatgccaata atggtactac actggatgta    600
tcgggtcttg atgatgcagc tattaaagcg ctacgggtg gtacgaatgg tacggcttct    660
gtaaccggtg gtgcggttaa atttgacgca gataataaca agtactttgt tactattggt    720
ggctttactg gtgctgatgc cgccaaaaat ggcgattatg aagttaacgt tgctactgac    780
ggtacagtaa cccttgcggc tggcgcaact aaaaccacaa tgcctgctgg tgcgacaact    840
aaaacagaag tacaggagtt aaaagatacc cggcagttg tttcagcaga tgctaaaaat    900
gccttaattg ctggcggcgt tgacgctacc gatgctaatg gcgctgagtt ggtcaaaatg    960
tcttataccg ataaaaatgg taagacaatt gaaggcggtt atgcgcttaa agctggcgat    1020
aagtattacg ccgcagatta cgatgaagcg acaggagcaa ttaaagctaa aaccacaagt    1080
tatactgctg ctgacggcac taccaaaaca gcggctaacc aactgggtgg cgtagacggt    1140
```

```
aaaaccgaag tcgttactat cgacggtaaa acctacaatg ccagcaaagc cgctggtcat   1200
gatttcaaag cacaaccaga gctggcggaa gcagccgcta aaaccaccga aaacccgctg   1260
cagaaaattg atgccgcgct ggcgcaggtg gatgcgctgc gctctgatct gggtgcggta   1320
caaaaccgtt tcaactctgc tatcaccaac ctgggcaata ccgtaaacaa tctgtctgaa   1380
gcgcgtagcc gtatcgaaga ttccgactac gcgaccgaag tttccaacat gtctcgcgcg   1440
cagattttgc agcaggccgg tacttccgtt ctggcgcagg ctaaccaggt cccgcagaac   1500
gtgctgtctc tgttacgttt caactgcctt ggaatgagca acagagactt cttggaagga   1560
gtgtctggag caacatgggt ggatttggtt ctcgaaggcg acagctgcgt gactatcatg   1620
tctaaggaca agcctaccat cgatgtgaag atgatgaata tggaggcggc caacctggca   1680
gaggtccgca gttattgcta tttggctacc gtcagcgatc tctccaccaa agctgcgtgc   1740
ccgaccatgg gagaagctca caatgacaaa cgtgctgacc cagcttttgt gtgcagacaa   1800
ggagtggtgg acaggggctg gggcaacggc tgcggactat ttggcaaagg aagcattgac   1860
acatgcgcca aatttgcctg ctctaccaag gcaataggaa gaaccatctt gaaagagaat   1920
atcaagtacg aagtggccat ttttgtccat ggaccaacta ctgtggagtc gcacggaaac   1980
tactccacac aggttggagc cactcaggca gggagattca gcatcactcc tgcagcgcct   2040
tcatacacac taaagcttgg agaatatgga gaggtgacag tggactgtga accacggtca   2100
gggattgaca ccaatgcata ctacgtgatg actgttggaa caaagacgtt cttggtccat   2160
cgtgagtggt tcatggacct caacctccct tggagcagtg ctggaagtac tgtgtggagg   2220
aacagagaga cgttaatgga gtttgaggaa ccacacgcca cgaagcagtc tgtgatagca   2280
ttgggctcac aagagggagc tctgcatcaa gctttggctg gagccattcc tgtggaattt   2340
tcaagcaaca ctgtcaagtt gacgtcgggt catttgaagt gtagagtgaa gatggaaaaa   2400
ttgcagttga agggaacaac ctatggcgtc tgttcaaagg ctttcaagtt tcttgggact   2460
cccgcagaca caggtcacgg cactgtggtg ttggaattgc agtacactgg cacggatgga   2520
ccttgcaaag ttcctatctc gtcagtggct tcattgaacg acctaacgcc agtgggcaga   2580
ttggtcactg tcaacccttt tgtttcagtg gccacggcca acgctaaggt cctgattgaa   2640
ttggaaccac cctttggaga ctcatacata gtggtgggca gaggagaaca acagatcaat   2700
caccattggc acaagtctgg aagcagcatt ggcaaa                             2736
```

<210> SEQ ID NO 159  
<211> LENGTH: 912  
<212> TYPE: PRT  
<213> ORGANISM: Artificial Sequence  
<220> FEATURE:  
<223> OTHER INFORMATION: STF2.E

<400> SEQUENCE: 159

```
Met Ala Gln Val Ile Asn Thr Asn Ser Leu Ser Leu Leu Thr Gln Asn
 1               5                  10                  15

Asn Leu Asn Lys Ser Gln Ser Ala Leu Gly Thr Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ala Asn Ile Lys Gly Leu Thr Gln Ala
    50                  55                  60

Ser Arg Asn Ala Asn Asp Gly Ile Ser Ile Ala Gln Thr Thr Glu Gly
65                  70                  75                  80
```

-continued

```
Ala Leu Asn Glu Ile Asn Asn Leu Gln Arg Val Arg Glu Leu Ala
                85                  90                  95

Val Gln Ser Ala Asn Ser Thr Asn Ser Gln Ser Asp Leu Asp Ser Ile
            100                 105                 110

Gln Ala Glu Ile Thr Gln Arg Leu Asn Glu Ile Asp Arg Val Ser Gly
        115                 120                 125

Gln Thr Gln Phe Asn Gly Val Lys Val Leu Ala Gln Asp Asn Thr Leu
    130                 135                 140

Thr Ile Gln Val Gly Ala Asn Asp Gly Glu Thr Ile Asp Ile Asp Leu
145                 150                 155                 160

Lys Gln Ile Asn Ser Gln Thr Leu Gly Leu Asp Ser Leu Asn Val Gln
                165                 170                 175

Lys Ala Tyr Asp Val Lys Asp Thr Ala Val Thr Thr Lys Ala Tyr Ala
            180                 185                 190

Asn Asn Gly Thr Thr Leu Asp Val Ser Gly Leu Asp Asp Ala Ala Ile
        195                 200                 205

Lys Ala Ala Thr Gly Gly Thr Asn Gly Thr Ala Ser Val Thr Gly Gly
    210                 215                 220

Ala Val Lys Phe Asp Ala Asp Asn Asn Lys Tyr Phe Val Thr Ile Gly
225                 230                 235                 240

Gly Phe Thr Gly Ala Asp Ala Ala Lys Asn Gly Asp Tyr Glu Val Asn
                245                 250                 255

Val Ala Thr Asp Gly Thr Val Thr Leu Ala Ala Gly Ala Thr Lys Thr
            260                 265                 270

Thr Met Pro Ala Gly Ala Thr Thr Lys Thr Glu Val Gln Glu Leu Lys
        275                 280                 285

Asp Thr Pro Ala Val Val Ser Ala Asp Ala Lys Asn Ala Leu Ile Ala
    290                 295                 300

Gly Gly Val Asp Ala Thr Asp Ala Asn Gly Ala Glu Leu Val Lys Met
305                 310                 315                 320

Ser Tyr Thr Asp Lys Asn Gly Lys Thr Ile Glu Gly Gly Tyr Ala Leu
                325                 330                 335

Lys Ala Gly Asp Lys Tyr Tyr Ala Ala Asp Tyr Asp Glu Ala Thr Gly
            340                 345                 350

Ala Ile Lys Ala Lys Thr Thr Ser Tyr Thr Ala Ala Asp Gly Thr Thr
        355                 360                 365

Lys Thr Ala Ala Asn Gln Leu Gly Gly Val Asp Gly Lys Thr Glu Val
    370                 375                 380

Val Thr Ile Asp Gly Lys Thr Tyr Asn Ala Ser Lys Ala Ala Gly His
385                 390                 395                 400

Asp Phe Lys Ala Gln Pro Glu Leu Ala Glu Ala Ala Lys Thr Thr
                405                 410                 415

Glu Asn Pro Leu Gln Lys Ile Asp Ala Ala Leu Ala Gln Val Asp Ala
            420                 425                 430

Leu Arg Ser Asp Leu Gly Ala Val Gln Asn Arg Phe Asn Ser Ala Ile
        435                 440                 445

Thr Asn Leu Gly Asn Thr Val Asn Asn Leu Ser Glu Ala Arg Ser Arg
    450                 455                 460

Ile Glu Asp Ser Asp Tyr Ala Thr Glu Val Ser Asn Met Ser Arg Ala
465                 470                 475                 480

Gln Ile Leu Gln Gln Ala Gly Thr Ser Val Leu Ala Gln Ala Asn Gln
                485                 490                 495

Val Pro Gln Asn Val Leu Ser Leu Leu Arg Phe Asn Cys Leu Gly Met
            500                 505                 510
```

Ser Asn Arg Asp Phe Leu Glu Gly Val Ser Gly Ala Thr Trp Val Asp
            515                 520                 525

Leu Val Leu Glu Gly Asp Ser Cys Val Thr Ile Met Ser Lys Asp Lys
        530                 535                 540

Pro Thr Ile Asp Val Lys Met Met Asn Met Glu Ala Ala Asn Leu Ala
545                 550                 555                 560

Glu Val Arg Ser Tyr Cys Tyr Leu Ala Thr Val Ser Asp Leu Ser Thr
                565                 570                 575

Lys Ala Ala Cys Pro Thr Met Gly Glu Ala His Asn Asp Lys Arg Ala
            580                 585                 590

Asp Pro Ala Phe Val Cys Arg Gln Gly Val Val Asp Arg Gly Trp Gly
        595                 600                 605

Asn Gly Cys Gly Leu Phe Gly Lys Gly Ser Ile Asp Thr Cys Ala Lys
            610                 615                 620

Phe Ala Cys Ser Thr Lys Ala Ile Gly Arg Thr Ile Leu Lys Glu Asn
625                 630                 635                 640

Ile Lys Tyr Glu Val Ala Ile Phe Val His Gly Pro Thr Thr Val Glu
                645                 650                 655

Ser His Gly Asn Tyr Ser Thr Gln Val Gly Ala Thr Gln Ala Gly Arg
            660                 665                 670

Phe Ser Ile Thr Pro Ala Ala Pro Ser Tyr Thr Leu Lys Leu Gly Glu
            675                 680                 685

Tyr Gly Glu Val Thr Val Asp Cys Glu Pro Arg Ser Gly Ile Asp Thr
            690                 695                 700

Asn Ala Tyr Tyr Val Met Thr Val Gly Thr Lys Thr Phe Leu Val His
705                 710                 715                 720

Arg Glu Trp Phe Met Asp Leu Asn Leu Pro Trp Ser Ser Ala Gly Ser
            725                 730                 735

Thr Val Trp Arg Asn Arg Glu Thr Leu Met Glu Phe Glu Glu Pro His
            740                 745                 750

Ala Thr Lys Gln Ser Val Ile Ala Leu Gly Ser Gln Glu Gly Ala Leu
            755                 760                 765

His Gln Ala Leu Ala Gly Ala Ile Pro Val Glu Phe Ser Ser Asn Thr
            770                 775                 780

Val Lys Leu Thr Ser Gly His Leu Lys Cys Arg Val Lys Met Glu Lys
785                 790                 795                 800

Leu Gln Leu Lys Gly Thr Thr Tyr Gly Val Cys Ser Lys Ala Phe Lys
                805                 810                 815

Phe Leu Gly Thr Pro Ala Asp Thr Gly His Gly Thr Val Val Leu Glu
            820                 825                 830

Leu Gln Tyr Thr Gly Thr Asp Gly Pro Cys Lys Val Pro Ile Ser Ser
            835                 840                 845

Val Ala Ser Leu Asn Asp Leu Thr Pro Val Gly Arg Leu Val Thr Val
850                 855                 860

Asn Pro Phe Val Ser Val Ala Thr Ala Asn Ala Lys Val Leu Ile Glu
865                 870                 875                 880

Leu Glu Pro Pro Phe Gly Asp Ser Tyr Ile Val Val Gly Arg Gly Glu
                885                 890                 895

Gln Gln Ile Asn His His Trp His Lys Ser Gly Ser Ser Ile Gly Lys
                900                 905                 910

<210> SEQ ID NO 160
<211> LENGTH: 495
<212> TYPE: PRT

```
<213> ORGANISM: Artificial Sequence
<220> FEATURE:
<223> OTHER INFORMATION: Dengue 1

<400> SEQUENCE: 160

Met Arg Cys Val Gly Ile Gly Asn Arg Asp Phe Val Glu Gly Leu Ser
 1               5                  10                  15

Gly Ala Thr Trp Val Asp Val Val Leu Glu His Gly Ser Cys Val Thr
            20                  25                  30

Thr Met Ala Lys Asn Lys Pro Thr Leu Asp Ile Glu Leu Leu Lys Thr
        35                  40                  45

Glu Val Thr Asn Pro Ala Val Leu Arg Lys Leu Cys Ile Glu Ala Lys
    50                  55                  60

Ile Ser Asn Thr Thr Thr Asp Ser Arg Cys Pro Thr Gln Gly Glu Ala
65                  70                  75                  80

Thr Leu Val Glu Glu Gln Asp Ala Asn Phe Val Cys Arg Arg Thr Phe
                85                  90                  95

Val Asp Arg Gly Trp Gly Asn Gly Cys Gly Leu Phe Gly Lys Gly Ser
            100                 105                 110

Leu Ile Thr Cys Ala Lys Phe Lys Cys Val Thr Lys Leu Glu Gly Lys
        115                 120                 125

Ile Ala Gln Tyr Glu Asn Leu Lys Tyr Ser Val Ile Val Thr Val His
    130                 135                 140

Thr Gly Asp Gln His Gln Val Gly Asn Glu Thr Thr Glu His Gly Thr
145                 150                 155                 160

Thr Ala Thr Ile Thr Pro Gln Ala Pro Thr Ser Glu Ile Gln Leu Thr
                165                 170                 175

Asp Tyr Gly Thr Leu Thr Leu Asp Cys Ser Pro Arg Thr Gly Leu Asp
            180                 185                 190

Phe Asn Glu Met Val Leu Leu Thr Met Lys Lys Lys Ser Trp Leu Val
        195                 200                 205

His Lys Gln Trp Phe Leu Asp Leu Pro Leu Pro Trp Thr Ser Gly Ala
    210                 215                 220

Leu Thr Ser Gln Glu Thr Trp Asn Arg Gln Asp Leu Leu Val Thr Phe
225                 230                 235                 240

Lys Thr Ala His Ala Lys Lys Gln Glu Val Val Val Leu Gly Ser Gln
                245                 250                 255

Glu Gly Ala Met His Thr Ala Leu Thr Gly Ala Thr Glu Ile Gln Thr
            260                 265                 270

Ser Gly Thr Thr Thr Ile Phe Ala Gly His Leu Lys Cys Arg Leu Lys
        275                 280                 285

Met Asp Lys Leu Thr Leu Lys Gly Met Ser Tyr Val Met Cys Thr Gly
    290                 295                 300

Ser Phe Lys Leu Glu Lys Glu Val Ala Glu Thr Gln His Gly Thr Val
305                 310                 315                 320

Leu Val Gln Val Lys Tyr Glu Gly Thr Asp Ala Pro Cys Lys Ile Pro
                325                 330                 335

Phe Ser Thr Gln Asp Glu Lys Gly Ala Thr Gln Asn Gly Arg Leu Ile
            340                 345                 350

Thr Ala Asn Pro Ile Val Thr Asp Lys Glu Lys Pro Val Asn Ile Glu
        355                 360                 365

Ala Glu Pro Pro Phe Gly Glu Ser Tyr Ile Val Val Gly Ala Gly Glu
    370                 375                 380

Lys Ala Leu Lys Leu Ser Trp Phe Lys Lys Gly Ser Ser Ile Gly Lys
385                 390                 395                 400
```

-continued

```
Met Phe Glu Ala Thr Ala Arg Gly Ala Arg Arg Met Ala Ile Leu Gly
                405                 410                 415

Asp Thr Ala Trp Asp Phe Gly Ser Ile Gly Gly Val Phe Thr Ser Met
            420                 425                 430

Gly Lys Leu Val His Gln Val Phe Gly Thr Ala Tyr Gly Val Leu Phe
        435                 440                 445

Ser Gly Val Ser Trp Thr Met Lys Ile Gly Ile Gly Ile Leu Leu Thr
    450                 455                 460

Trp Leu Gly Leu Asn Ser Arg Asn Thr Ser Leu Ser Val Met Cys Ile
465                 470                 475                 480

Ala Val Gly Met Val Thr Leu Tyr Leu Gly Val Met Val Gln Ala
                485                 490                 495
```

<210> SEQ ID NO 161
<211> LENGTH: 1485
<212> TYPE: DNA
<213> ORGANISM: Artificial Sequence
<220> FEATURE:
<223> OTHER INFORMATION: Dengue 1

<400> SEQUENCE: 161

```
atgcgatgcg tgggaatagg caacagagac ttcgtggaag gactgtcagg agcaacatgg     60
gtggatgtgg tactggagca tggaagttgc gtcaccacca tggcaaaaaa caaaccaaca    120
ctggacattg aactcttgaa gacggaggtc acaaaccctg cagttctgcg taaattgtgc    180
attgaagcta aaatatcaaa caccaccacc gattcgagat gtccaacaca aggagaagcc    240
acactggtgg aagaacaaga cgcgaacttt gtgtgccgac gaacgttcgt ggacagaggc    300
tggggcaatg gctgtgggct attcggaaaa ggtagtctaa taacgtgtgc caagtttaag    360
tgtgtgacaa actagaagg aaagatagct caatatgaaa acctaaaata ttcagtgata    420
gtcaccgtcc acactggaga tcagcaccag gtgggaaatg agactacaga acatggaaca    480
actgcaacca taacacctca agctcctacg tcggaaatac agctgaccga ctacggaacc    540
cttacattag attgttcacc taggacaggg ctagatttta acgagatggt gttgctgaca    600
atgaaaaaga atcatggct tgtccacaaa cagtggtttc tagacttacc actgccttgg    660
acctctgggg cttaacatc ccaagagact tggaacagac aagatttact ggtcacattt    720
aagacagctc atgcaaagaa gcaggaagta gtcgtactag gatcacaaga aggagcaatg    780
cacactgcgc tgactggagc gacagaaatc caaacgtcag gaacgacaac aattttcgca    840
ggacacctaa aatgcagact aaaaatggac aaactaactt taaagggat gtcatatgtg    900
atgtgcacag gctcattcaa gttagagaaa gaagtggctg agacccagca tggaactgtt    960
ctggtgcagg ttaaatatga aggaacagac gcaccatgca gattcccctt ttcgacccaa   1020
gatgagaaag gagcaaccca gaatgggaga ttaataacag ccaacccat agtcactgac   1080
aaagaaaaac cagtcaatat tgaggcagaa ccaccctttg tgagagcta catcgtggta   1140
ggagcaggtg aaaaagcttt gaaactaagc tggttcaaga aggaagcag catagggaaa   1200
atgtttgaag caactgcccg aggagcacga aggatggcca ttctgggaga caccgcatgg   1260
gacttcggtt ctataggagg agtgttcacg tctatgggaa aactggtaca ccaggttttt   1320
ggaactgcat atggagtttt gtttagcgga gtttcttgga ccatgaaaat aggaataggg   1380
attctgctga catggctagg attaaattca aggaacacgt cccttcggt gatgtgcatc   1440
gcagttggca tggtcacact gtacctagga gtcatggttc aggca                   1485
```

```
<210> SEQ ID NO 162
<211> LENGTH: 495
<212> TYPE: PRT
<213> ORGANISM: Artificial Sequence
<220> FEATURE:
<223> OTHER INFORMATION: Dengue 2

<400> SEQUENCE: 162

Met Arg Cys Ile Gly Met Ser Asn Arg Asp Phe Val Glu Gly Val Ser
 1               5                  10                  15

Gly Gly Ser Trp Val Asp Ile Val Leu Glu His Gly Ser Cys Val Thr
            20                  25                  30

Thr Met Ala Lys Asn Lys Pro Thr Leu Asp Phe Glu Leu Ile Lys Thr
        35                  40                  45

Glu Ala Lys Gln Pro Ala Thr Leu Arg Lys Tyr Cys Ile Glu Ala Lys
    50                  55                  60

Leu Thr Asn Thr Thr Thr Glu Ser Arg Cys Pro Thr Gln Gly Glu Pro
65                  70                  75                  80

Ser Leu Asn Glu Glu Gln Asp Lys Arg Phe Val Cys Lys His Ser Met
                85                  90                  95

Val Asp Arg Gly Trp Gly Asn Gly Cys Gly Leu Phe Gly Lys Gly Gly
            100                 105                 110

Ile Val Thr Cys Ala Met Phe Arg Cys Lys Lys Asn Met Glu Gly Lys
        115                 120                 125

Val Val Gln Pro Glu Asn Leu Glu Tyr Thr Ile Val Ile Thr Pro His
    130                 135                 140

Ser Gly Glu Glu His Ala Val Gly Asn Asp Thr Gly Lys His Gly Lys
145                 150                 155                 160

Glu Ile Lys Ile Thr Pro Gln Ser Ser Thr Thr Glu Ala Glu Leu Thr
                165                 170                 175

Gly Tyr Gly Thr Val Thr Met Glu Cys Ser Pro Arg Thr Gly Leu Asp
            180                 185                 190

Phe Asn Glu Met Val Leu Leu Gln Met Glu Asn Lys Ala Trp Leu Val
        195                 200                 205

His Arg Gln Trp Phe Leu Asp Leu Pro Leu Pro Trp Leu Pro Gly Ala
    210                 215                 220

Asp Thr Gln Gly Ser Asn Trp Ile Gln Lys Glu Thr Leu Val Thr Phe
225                 230                 235                 240

Lys Asn Pro His Ala Lys Lys Gln Asp Val Val Val Leu Gly Ser Gln
                245                 250                 255

Glu Gly Ala Met His Thr Ala Leu Thr Gly Ala Thr Glu Ile Gln Met
            260                 265                 270

Ser Ser Gly Asn Leu Leu Phe Thr Gly His Leu Lys Cys Arg Leu Arg
        275                 280                 285

Met Asp Lys Leu Gln Leu Lys Gly Met Ser Tyr Ser Met Cys Thr Gly
    290                 295                 300

Lys Phe Lys Val Val Lys Glu Ile Ala Glu Thr Gln His Gly Thr Ile
305                 310                 315                 320

Val Ile Arg Val Gln Tyr Glu Gly Asp Gly Ser Pro Cys Lys Ile Pro
                325                 330                 335

Phe Glu Ile Met Asp Leu Glu Lys Arg His Val Leu Gly Arg Leu Ile
            340                 345                 350

Thr Val Asn Pro Ile Val Thr Glu Lys Asp Ser Pro Val Asn Ile Glu
        355                 360                 365

Ala Glu Pro Pro Phe Gly Asp Ser Tyr Ile Ile Ile Gly Val Glu Pro
    370                 375                 380
```

Gly Gln Leu Lys Leu Asn Trp Phe Lys Gly Ser Ser Ile Gly Gln
385                 390                 395                 400

Met Phe Glu Thr Thr Met Arg Gly Ala Lys Arg Met Ala Ile Leu Gly
            405                 410                 415

Asp Thr Ala Trp Asp Phe Gly Ser Leu Gly Gly Val Phe Thr Ser Ile
            420                 425                 430

Gly Lys Ala Leu His Gln Val Phe Gly Ala Ile Tyr Gly Ala Ala Phe
            435                 440                 445

Ser Gly Val Ser Trp Thr Met Lys Ile Leu Ile Gly Val Ile Ile Thr
        450                 455                 460

Trp Ile Gly Met Asn Ser Arg Ser Thr Ser Leu Ser Val Thr Leu Val
465                 470                 475                 480

Leu Val Gly Ile Val Thr Leu Tyr Leu Gly Val Met Val Gln Ala
                485                 490                 495

<210> SEQ ID NO 163
<211> LENGTH: 1485
<212> TYPE: DNA
<213> ORGANISM: Artificial Sequence
<220> FEATURE:
<223> OTHER INFORMATION: Dengue 2

<400> SEQUENCE: 163
atgcgttgca taggaatgtc aaatagagac tttgtggaag gggtttcagg aggaagctgg      60
gttgacatag tcttagaaca tggaagctgt gtgacgacga tggcaaaaaa caaaccaaca     120
ttggattttg aactgataaa aacagaagcc aaacagcctg ccaccctaag gaagtactgt     180
atagaggcaa agctaaccaa cacaacaaca gaatctcgct gcccaacaca agggggaaccc     240 agcctaaatg aagagcagga caaaaggttc gtctgcaaac actccatggt agacagagga     300
tggggaaatg gatgtggact atttggaaag ggaggcattg tgacctgtgc tatgttcaga     360
tgcaaaaaga catggaagg aaaagttgtg caaccagaaa acttggaata caccattgtg     420
ataacacctc actcagggga gagcatgca gtcggaaatg cacaggaaa catggcaag     480 gaaatcaaaa taacaccaca gagttccacc acagaagcag aattgacagg ttatggcact     540
gtcacaatgg agtgctctcc aagaacgggc ctcgacttca tgagatggt gttgctgcag     600 atggaaaata agcttggct ggtgcacagg caatggttcc tagacctgcc gttaccatgg     660 ttgccccggag cggacacaca agggtcaaat tggatacaga agagacatt ggtcactttc     720 aaaaatcccc atgcgaagaa acaggatgtt gttgttttag atccaagaa aggggccatg     780 cacacagcac ttacaggggc cacagaaatc caaatgtcat caggaaactt actcttcaca     840
ggacatctca gtgcaggct gagaatggac aagctacagc tcaaaggaat gtcatactct     900
atgtgcacag gaaagtttaa agttgtgaag gaaatagcag aaacacaaca tggaacaata     960
gttatcagag tgcaatatga gggacggc tctccatgca agatccctt tgagataatg    1020 gatttggaaa aaagacatgt cttaggtcgc ctgattacag tcaacccaat tgtgacagaa    1080
aaagatagcc cagtcaacat agaagcagaa cctccattcg agacagcta catcatcata    1140 ggagtagagc cggacaact gaagctcaac tggtttaaga aggaagttc tatcggccaa    1200 atgtttgaga caacaatgag gggggcgaag agaatggcca ttttaggtga cacagcctgg    1260
gattttggat ccttgggag agtgtttaca tctataggaa aggctctcca ccaagtcttt    1320
ggagcaatct atggagctgc cttcagtggg gtttcatgga ctatgaaaat cctcataggg    1380
gtcattatca catggatagg aatgaattca cgcagcacct cactgtctgt gacactagta    1440
ttggtgggaa ttgtgacact gtatttggga gtcatggtgc aggcc    1485

<210> SEQ ID NO 164
<211> LENGTH: 493
<212> TYPE: PRT
<213> ORGANISM: Artificial Sequence
<220> FEATURE:
<223> OTHER INFORMATION: Dengue 3

<400> SEQUENCE: 164

```
Met Arg Cys Val Gly Val Gly Asn Arg Asp Phe Val Glu Gly Leu Ser
 1               5                  10                  15
Gly Ala Thr Trp Val Asp Val Val Leu Glu His Gly Gly Cys Val Thr
             20                  25                  30
Thr Met Ala Lys Asn Lys Pro Thr Leu Asp Ile Glu Leu Gln Lys Thr
         35                  40                  45
Glu Ala Thr Gln Leu Ala Thr Leu Arg Lys Leu Cys Ile Glu Gly Lys
     50                  55                  60
Ile Thr Asn Ile Thr Thr Asp Ser Arg Cys Pro Thr Gln Gly Glu Ala
 65                  70                  75                  80
Ile Leu Pro Glu Glu Gln Asp Gln Asn Tyr Val Cys Lys His Thr Tyr
                 85                  90                  95
Val Asp Arg Gly Trp Gly Asn Gly Cys Gly Leu Phe Gly Lys Gly Ser
            100                 105                 110
Leu Val Thr Cys Ala Lys Phe Gln Cys Leu Glu Pro Ile Glu Gly Lys
        115                 120                 125
Val Val Gln His Glu Asn Leu Lys Tyr Thr Val Ile Ile Thr Val His
    130                 135                 140
Thr Gly Asp Gln His Gln Val Gly Asn Asp Thr Gln Gly Val Thr Val
145                 150                 155                 160
Glu Ile Thr Pro Gln Ala Ser Thr Val Glu Ala Ile Leu Pro Glu Tyr
                165                 170                 175
Gly Thr Leu Gly Leu Glu Cys Ser Pro Arg Thr Gly Leu Asp Phe Asn
            180                 185                 190
Glu Met Ile Leu Leu Thr Met Lys Asn Lys Ala Trp Met Val His Arg
        195                 200                 205
Gln Trp Phe Phe Asp Leu Pro Leu Pro Trp Thr Ser Gly Ala Thr Thr
    210                 215                 220
Glu Thr Pro Thr Trp Asn Arg Lys Glu Leu Leu Val Thr Phe Lys Asn
225                 230                 235                 240
Ala His Ala Lys Lys Gln Glu Val Val Val Leu Gly Ser Gln Glu Gly
                245                 250                 255
Ala Met His Thr Ala Leu Thr Gly Ala Thr Glu Ile Gln Asn Ser Gly
            260                 265                 270
Gly Thr Ser Ile Phe Ala Gly His Leu Lys Cys Arg Leu Lys Met Asp
        275                 280                 285
Lys Leu Glu Leu Lys Gly Met Ser Tyr Ala Met Cys Leu Asn Thr Phe
    290                 295                 300
Val Leu Lys Lys Glu Val Ser Glu Thr Gln His Gly Thr Ile Leu Ile
305                 310                 315                 320
Lys Val Glu Tyr Lys Gly Glu Asp Ala Pro Cys Lys Ile Pro Phe Ser
                325                 330                 335
Thr Glu Asp Gly Gln Gly Lys Ala His Asn Gly Arg Leu Ile Thr Ala
            340                 345                 350
Asn Pro Val Val Thr Lys Lys Glu Glu Pro Val Asn Ile Glu Ala Glu
        355                 360                 365
```

```
Pro Pro Phe Gly Glu Ser Asn Ile Val Ile Gly Ile Gly Asp Lys Ala
    370                 375                 380

Leu Lys Ile Asn Trp Tyr Lys Lys Gly Ser Ser Ile Gly Lys Met Phe
385                 390                 395                 400

Glu Ala Thr Ala Arg Gly Ala Arg Arg Met Ala Ile Leu Gly Asp Thr
                405                 410                 415

Ala Trp Asp Phe Gly Ser Val Gly Gly Val Leu Asn Ser Leu Gly Lys
            420                 425                 430

Met Val His Gln Ile Phe Gly Ser Ala Tyr Thr Ala Leu Phe Ser Gly
            435                 440                 445

Val Ser Trp Ile Met Lys Ile Gly Ile Gly Val Leu Leu Thr Trp Ile
        450                 455                 460

Gly Leu Asn Ser Lys Asn Thr Ser Met Ser Phe Ser Cys Ile Ala Ile
465                 470                 475                 480

Gly Ile Ile Thr Leu Tyr Leu Gly Ala Val Val Gln Ala
                485                 490
```

<210> SEQ ID NO 165
<211> LENGTH: 1479
<212> TYPE: DNA
<213> ORGANISM: Artificial Sequence
<220> FEATURE:
<223> OTHER INFORMATION: Dengue 3

<400> SEQUENCE: 165

```
atgagatgcg tgggagtagg aaacagagat tttgtggaag gtctgtcggg agctacgtgg    60
gttgatgtgg tgctcgagca cggagggtgt gtgaccacca tggctaagaa caagcctacg   120
ctggacatag agctccagaa gaccgaggcc acccaactgg cgaccctaag aaagttatgc   180
attgagggaa aaattaccaa cataacaact gactcaaggt gtcctaccca gggggaagcg   240
attttacctg aggagcagga ccagaactac gtatgtaagc acacatacgt ggatagaggt   300
tggggaaacg gttgtggttt gtttggaaaa ggaagcttgg tgacatgcgc gaaatttcaa   360
tgtctagaac caatagaggg aaaagtggtg caacatgaga acctcaaata cactgtcatc   420
atcacagtgc acacaggaga ccaacaccag gtgggaaatg acacgcaggg agtcacggtt   480
gagataacac cccaggcatc aaccgttgaa gctatcttgc ctgaatatgg aacccttggg   540
ctagaatgtt caccacggac aggtttggat ttcaacgaaa tgattttatt gacaatgaag   600
aacaaagcat ggatggtaca taggcaatgg ttctttgacc taccectacc atggacatca   660
ggagctacaa cagagacacc aacttggaac aggaaagagc tccttgtgac attcaagaat   720
gcacatgcaa aaaagcaaga agtagttgtc cttggatcgc aagagggagc aatgcacaca   780
gcgctgacag gagctacaga gattcaaaac tcaggaggta caagcatttt tgcggggcac   840
ttgaaatgta gacttaagat ggacaaattg gaactcaagg ggatgagcta tgcaatgtgc   900
ttgaatacct ttgtgttgaa gaagaagtc tctgaaacgc agcatgggac aatactcatc   960
aaggttgagt acaaagggga agatgcacct tgcaagattc ctttctccac agaggatgga   1020
caagggaaag ctcacaatgg tagactgatc acagccaacc cagtggtgac caagaaggag   1080
gagcctgtca acattgaggc tgaacctcct tttgggaaa gtaacatagt gattgggatt   1140
ggagacaaag ccttgaaaat taactggtac aagaaggga gctcgattgg aaagatgttc   1200
gaggctactg ccagaggtgc aaggcgcatg gccatcttgg gagacacagc ctgggatttt   1260
ggttcagtgg gtggtgttct gaattcatta gggaaatgg tacaccaaat attcggaagt   1320
gcttacacag ccctgtttag tggagtctca tggataatga aaattggaat aggtgtcctc   1380
```

```
ttaacctgga tagggttgaa ttcaaaaaac acttccatgt cattttcatg cattgcgata    1440
ggaattatta cactctatct gggagccgtg gtacaagct                           1479
```

<210> SEQ ID NO 166
<211> LENGTH: 491
<212> TYPE: PRT
<213> ORGANISM: Artificial Sequence
<220> FEATURE:
<223> OTHER INFORMATION: Dengue 4

<400> SEQUENCE: 166

```
Met Arg Cys Val Gly Val Gly Asn Arg Asp Phe Val Glu Gly Val Ser
  1               5                  10                  15

Gly Gly Ala Trp Val Asp Leu Val Leu Glu His Gly Gly Cys Val Thr
             20                  25                  30

Thr Met Ala Gln Gly Lys Pro Thr Leu Asp Phe Glu Leu Thr Lys Thr
         35                  40                  45

Thr Ala Lys Glu Val Ala Leu Leu Arg Thr Tyr Cys Ile Glu Ala Ser
     50                  55                  60

Ile Ser Asn Ile Thr Thr Ala Thr Arg Cys Pro Thr Gln Gly Glu Pro
 65                  70                  75                  80

Tyr Leu Lys Glu Glu Gln Asp Gln Gln Tyr Ile Cys Arg Arg Asp Val
                 85                  90                  95

Val Asp Arg Gly Trp Gly Asn Gly Cys Gly Leu Phe Gly Lys Gly Gly
            100                 105                 110

Val Val Thr Cys Ala Lys Phe Ser Cys Ser Gly Lys Ile Thr Gly Asn
        115                 120                 125

Leu Val Arg Ile Glu Asn Leu Glu Tyr Thr Val Val Thr Val His
    130                 135                 140

Asn Gly Asp Thr His Ala Val Gly Asn Asp Thr Ser Asn His Gly Val
145                 150                 155                 160

Thr Ala Met Ile Thr Pro Arg Ser Pro Ser Val Glu Val Lys Leu Pro
                165                 170                 175

Asp Tyr Gly Glu Leu Thr Leu Asp Cys Glu Pro Arg Ser Gly Ile Asp
            180                 185                 190

Phe Asn Glu Met Ile Leu Met Lys Met Lys Lys Thr Trp Leu Val
        195                 200                 205

His Lys Gln Trp Phe Leu Asp Leu Pro Leu Pro Trp Thr Ala Gly Ala
    210                 215                 220

Asp Thr Ser Glu Val His Trp Asn Tyr Lys Glu Arg Met Val Thr Phe
225                 230                 235                 240

Lys Val Pro His Ala Lys Arg Gln Asp Val Thr Val Leu Gly Ser Gln
                245                 250                 255

Glu Gly Ala Met His Ser Ala Leu Ala Gly Ala Thr Glu Val Asp Ser
            260                 265                 270

Gly Asp Gly Asn His Met Phe Ala Gly His Leu Lys Cys Glu Val Arg
        275                 280                 285

Met Glu Lys Leu Arg Ile Lys Gly Met Ser Tyr Thr Met Cys Ser Gly
    290                 295                 300

Lys Phe Ser Ile Asp Lys Glu Met Ala Glu Thr Gln His Gly Thr Thr
305                 310                 315                 320

Val Val Lys Val Lys Tyr Glu Gly Ala Gly Ala Pro Cys Lys Val Pro
                325                 330                 335

Ile Glu Ile Arg Asp Val Asn Lys Glu Lys Val Val Gly Arg Ile Ile
            340                 345                 350
```

```
Ser Ser Thr Pro Leu Ala Glu Asn Thr Asn Ser Val Thr Asn Ile Glu
        355                 360                 365

Leu Glu Pro Pro Phe Gly Asp Ser Tyr Ile Val Ile Gly Val Gly Asn
        370                 375                 380

Ser Ala Leu Thr Leu His Trp Phe Arg Lys Gly Ser Ser Ile Gly Lys
385                 390                 395                 400

Met Phe Glu Ser Thr Tyr Arg Gly Ala Lys Arg Met Ala Ile Leu Gly
                405                 410                 415

Glu Thr Ala Trp Asp Phe Gly Ser Val Gly Gly Leu Phe Thr Ser Leu
            420                 425                 430

Gly Lys Ala Val His Gln Val Phe Gly Ser Val Tyr Thr Thr Met Phe
        435                 440                 445

Gly Gly Val Ser Trp Met Ile Arg Ile Leu Ile Gly Phe Leu Val Leu
    450                 455                 460

Trp Ile Gly Thr Asn Ser Arg Asn Thr Ser Met Ala Met Thr Cys Ile
465                 470                 475                 480

Ala Val Gly Gly Ile Thr Leu Phe Leu Gly Phe
                485                 490

<210> SEQ ID NO 167
<211> LENGTH: 1473
<212> TYPE: DNA
<213> ORGANISM: Artificial Sequence
<220> FEATURE:
<223> OTHER INFORMATION: Dengue 4

<400> SEQUENCE: 167
atgcgatgcg taggagtagg aaacagagac tttgtggaag gagtctcagg tggagcatgg      60
gtcgacctgg tgctagaaca tggaggatgc gtcacaacca tggcccaggg aaaaccaacc     120
ttggattttg aactgaccaa gacaacagcc aaggaagtgg ctctgttaag aacctattgc     180
attgaagcct caatatcaaa cataactacg gcaacaagat gtccaacgca aggagagcct     240
tatctgaaag aggaacagga ccaacagtac atttgccgga gagatgtggt agacagaggg     300
tggggcaatg gctgtggctt gtttggaaaa ggaggagttg tgacatgtgc gaagtttcca     360
tgttcgggga agataacagg caatttggtc cgaattgaga accttgaata cacagtggtg     420
gtaacagtcc acaatggaga cacccatgca gtaggaaatg acacatccaa tcatggagtt     480
acagccatga taccccccag gtcaccatcg gtggaagtca aattgccgga ctatggagaa     540
ctaacactcg attgtgaacc caggtctgga attgacttta tgagatgat tctgatgaaa      600 atgaaaaaga aacatggct cgtgcataag caatggtttt ggatctgcc tcttccatgg      660 acagcaggag cagacacatc agaggttcac tggaattaca agagagaat ggtgacattt      720 aaggttcctc atgccaagag acaggatgtg acagtgctgg atctcagga aggagccatg     780 cattctgccc tcgctggagc cacagaagtg actccggtg atggaaatca catgtttgca     840
ggacatctca gtgcgaagt ccgtatggag aaattgagaa tcaagggaat gtcatacacg      900
atgtgttcag aaagtttttc aattgacaaa gagatggcag aaacagca tgggacaaca      960 gtggtgaaag tcaagtatga aggtgctgga gctccgtgta aagtcccccat agagataaga    1020 gatgtaaaca aggaaaaagt ggttgggcgt atcatctcat ccaccccttt ggctgagaat    1080
accaacagtg taaccaacat agaattagaa ccccccttg gggacagcta catagtgata    1140
ggtgttggaa acagcgcatt aacactccat tggttcagga agggagttc cattggcaag    1200 atgtttgagt ccacatacag aggtgcaaaa cgaatggcca ttctaggtga aacagcttgg    1260
```

-continued

```
gattttggtt ccgttggtgg attgttcaca tcattgggaa aggctgtgca ccaggttttt    1320
ggaagtgtgt atacaaccat gtttggagga gtctcatgga tgattagaat cctaattggg    1380
ttcttagtgt tgtggattgg cacgaactca aggaacactt caatggctat gacgtgcata    1440
gctgttggag gaatcactct gtttctgggc ttc                                 1473
```

<210> SEQ ID NO 168
<211> LENGTH: 20
<212> TYPE: PRT
<213> ORGANISM: Artificial Sequence
<220> FEATURE:
<223> OTHER INFORMATION: West Nile virus

<400> SEQUENCE: 168

```
Leu Thr Ser Gly His Leu Lys Cys Arg Val Lys Met Glu Lys Leu Gln
 1               5                  10                  15

Leu Lys Gly Thr
            20
```

<210> SEQ ID NO 169
<211> LENGTH: 20
<212> TYPE: PRT
<213> ORGANISM: Artificial Sequence
<220> FEATURE:
<223> OTHER INFORMATION: West Nile virus

<400> SEQUENCE: 169

```
Leu Thr Ser Gly His Leu Lys Cys Arg Val Lys Met Glu Lys Leu Gln
 1               5                  10                  15

Leu Lys Gly Thr
            20
```

<210> SEQ ID NO 170
<211> LENGTH: 1217
<212> TYPE: DNA
<213> ORGANISM: Artificial Sequence
<220> FEATURE:
<223> OTHER INFORMATION: Japanese encephalitis

<400> SEQUENCE: 170

```
tttaattgtc tgggaatggg caatcgtgac ttcatagaag gagccagtgg agccgcttgg     60
gtgacttggt gctagaagga gacagctgct tgacaatcat ggcaaacgac aaaccaacat    120
tggacgtccg catgattaac atcgaagcta gccaacttgc tgaggtcaga agttactgct    180
atcatgcttc agtcactgac atctcgacgg tggctcggtg ccccacgact ggagaagccc    240
acaacgagaa gcgagctgat agtagctatg tgtgcaaaca aggcttcact gaccgtgggt    300
ggggcaacgg atgtggattt tcgggaagg aagcattga cacatgtgca aaattctcct    360
gcaccagtaa agcgattggg agaacaatcc agccagaaaa catcaaatac aaagttggca    420
tttttgtgca tggaaccacc acttcggaaa accatgggaa ttattcagcg caagttgggg    480
cgtcccaggc ggcaaagttt acagtaacac ccaatgctcc ttcggtagcc ctcaaacttg    540
gtgactacgg agaagtcaca ctggactgtg agccaaggag tggactgaac actgaagcgt    600
tttacgtcat gaccgtgggg tcaaagtcat ttctggtcca tagggagtgg tttcatgacc    660
tcgctctccc ctggacgtcc ccttcgagca cagcgtggag aaacagagaa ctcctcatgg    720
aatttgaagg ggcgcacgcc acaaaacagt ccgttgttgc tcttgggtca caggaaggag    780
gcctccatca tgcgttggca ggagccatcg tggtggagta ctcaagctca gtgatgttaa    840
catcaggcca cctgaaatgt aggctgaaaa tggacaaact ggctctgaaa ggcacaacct    900
```

```
atggcatgtg tacagaaaaa ttctcgttcg cgaaaaatcc ggtggacact ggtcacggaa      960
cagttgtcat tgaactctcc tactctggga gtgatggccc ctgcaaaatt ccgattgttt     1020
ccgttgcgag cctcaatgac atgaccccccg ttgggcggct ggtgacagtg aaccccttcg     1080
tcgcgacttc cagtgccaac tcaaaggtgc tggtcgagat ggaaccccccc ttcggagact    1140 cctacatcgt agttggaagg ggagacaagc agatcaacca ccattggcac aaagctggaa     1200
gcacgctggg caaggcc                                                    1217
```

<210> SEQ ID NO 171
<211> LENGTH: 406
<212> TYPE: PRT
<213> ORGANISM: Artificial Sequence
<220> FEATURE:
<223> OTHER INFORMATION: Japanese encephalitis

<400> SEQUENCE: 171

```
Phe Asn Cys Leu Gly Met Gly Asn Arg Asp Phe Ile Glu Gly Ala Ser
  1               5                  10                  15

Gly Ala Ala Trp Val Asp Leu Val Leu Glu Gly Asp Ser Cys Leu Thr
             20                  25                  30

Ile Met Ala Asn Asp Lys Pro Thr Leu Asp Val Arg Met Ile Asn Ile
         35                  40                  45

Glu Ala Ser Gln Leu Ala Glu Val Arg Ser Tyr Cys Tyr His Ala Ser
     50                  55                  60

Val Thr Asp Ile Ser Thr Val Ala Arg Cys Pro Thr Thr Gly Glu Ala
 65                  70                  75                  80

His Asn Glu Lys Arg Ala Asp Ser Ser Tyr Val Cys Lys Gln Gly Phe
                 85                  90                  95

Thr Asp Arg Gly Trp Gly Asn Gly Cys Gly Phe Phe Gly Lys Gly Ser
            100                 105                 110

Ile Asp Thr Cys Ala Lys Phe Ser Cys Thr Ser Lys Ala Ile Gly Arg
        115                 120                 125

Thr Ile Gln Pro Glu Asn Ile Lys Tyr Lys Val Gly Ile Phe Val His
    130                 135                 140

Gly Thr Thr Thr Ser Glu Asn His Gly Asn Tyr Ser Ala Gln Val Gly
145                 150                 155                 160

Ala Ser Gln Ala Ala Lys Phe Thr Val Thr Pro Asn Ala Pro Ser Val
                165                 170                 175

Ala Leu Lys Leu Gly Asp Tyr Gly Glu Val Thr Leu Asp Cys Glu Pro
            180                 185                 190

Arg Ser Gly Leu Asn Thr Glu Ala Phe Tyr Val Met Thr Val Gly Ser
        195                 200                 205

Lys Ser Phe Leu Val His Arg Glu Trp Phe His Asp Leu Ala Leu Pro
    210                 215                 220

Trp Thr Ser Pro Ser Ser Thr Ala Trp Arg Asn Arg Glu Leu Leu Met
225                 230                 235                 240

Glu Phe Glu Gly Ala His Ala Thr Lys Gln Ser Val Val Ala Leu Gly
                245                 250                 255

Ser Gln Glu Gly Gly Leu His His Ala Leu Ala Gly Ala Ile Val Val
            260                 265                 270

Glu Tyr Ser Ser Ser Val Met Leu Thr Ser Gly His Leu Lys Cys Arg
        275                 280                 285

Leu Lys Met Asp Lys Leu Ala Leu Lys Gly Thr Thr Tyr Gly Met Cys
    290                 295                 300

Thr Glu Lys Phe Ser Phe Ala Lys Asn Pro Val Asp Thr Gly His Gly
```

```
                    305                 310                 315                 320
Thr Val Val Ile Glu Leu Ser Tyr Ser Gly Ser Asp Gly Pro Cys Lys
                325                 330                 335

Ile Pro Ile Val Ser Val Ala Ser Leu Asn Asp Met Thr Pro Val Gly
                340                 345                 350

Arg Leu Val Thr Val Asn Pro Phe Val Ala Thr Ser Ser Ala Asn Ser
                355                 360                 365

Lys Val Leu Val Glu Met Glu Pro Pro Phe Gly Asp Ser Tyr Ile Val
            370                 375                 380

Val Gly Arg Gly Asp Lys Gln Ile Asn His His Trp His Lys Ala Gly
385                 390                 395                 400

Ser Thr Leu Gly Lys Ala
                405

<210> SEQ ID NO 172
<211> LENGTH: 5
<212> TYPE: PRT
<213> ORGANISM: Artificial Sequence
<220> FEATURE:
<223> OTHER INFORMATION: West Nile virus

<400> SEQUENCE: 172

Met Glu Lys Leu Gln
1               5

<210> SEQ ID NO 173
<211> LENGTH: 6
<212> TYPE: PRT
<213> ORGANISM: Artificial Sequence
<220> FEATURE:
<223> OTHER INFORMATION: West Nile virus

<400> SEQUENCE: 173

Met Asp Lys Leu Ala Leu
1               5

<210> SEQ ID NO 174
<211> LENGTH: 496
<212> TYPE: PRT
<213> ORGANISM: Artificial Sequence
<220> FEATURE:
<223> OTHER INFORMATION: Tick-borne encephalitis

<400> SEQUENCE: 174

Ser Arg Cys Thr His Leu Glu Asn Arg Asp Phe Val Thr Gly Thr Gln
1               5                   10                  15

Gly Thr Thr Arg Val Thr Leu Val Leu Glu Leu Gly Gly Cys Val Thr
                20                  25                  30

Ile Thr Ala Glu Gly Lys Pro Ser Met Asp Val Trp Leu Asp Ser Ile
            35                  40                  45

Tyr Gln Glu Asn Pro Ala Lys Thr Arg Glu Tyr Cys Leu His Ala Lys
        50                  55                  60

Leu Ser Asp Thr Lys Val Ala Ala Arg Cys Pro Thr Met Gly Pro Ala
65                  70                  75                  80

Thr Leu Thr Glu Glu His Gln Ser Gly Thr Val Cys Lys Arg Asp Gln
                85                  90                  95

Ser Asp Arg Gly Trp Gly Asn His Cys Gly Leu Phe Gly Lys Gly Ser
            100                 105                 110

Ile Val Thr Cys Val Lys Val Ala Cys Glu Ala Lys Lys Lys Ala Ile
        115                 120                 125
```

```
Gly His Val Tyr Asp Ala Asn Lys Ile Val Tyr Thr Val Lys Val Glu
        130                 135                 140

Pro His Thr Gly Asp Tyr Val Ala Ala Asn Glu Thr His Ser Gly Arg
145                 150                 155                 160

Lys Thr Ala Ser Phe Thr Val Ser Ser Glu Lys Thr Ile Leu Thr Met
                165                 170                 175

Gly Asp Tyr Gly Asp Val Pro Leu Leu Cys Arg Val Ala Ser Gly Val
                180                 185                 190

Asp Leu Ala Gln Thr Val Ile Leu Glu Leu Asp Lys Thr Leu Glu His
            195                 200                 205

Leu Pro Thr Ala Trp Gln Val His Arg Asp Trp Phe Asn Asp Leu Ala
    210                 215                 220

Leu Pro Trp Lys His Glu Gly Ala Gln Gln Trp Asn Asn Ala Glu Arg
225                 230                 235                 240

Leu Val Glu Phe Gly Ala Pro His Ala Val Lys Met Asp Val Tyr Asn
                245                 250                 255

Leu Gly Asp Gln Thr Gly Val Leu Leu Lys Ser Leu Ala Gly Val Pro
            260                 265                 270

Val Ala His Ile Asp Gly Thr Lys Tyr His Leu Lys Ser Gly His Val
        275                 280                 285

Thr Cys Glu Val Gly Leu Glu Lys Leu Lys Met Lys Gly Leu Thr Tyr
    290                 295                 300

Thr Met Cys Asp Lys Thr Lys Phe Ala Trp Lys Arg Thr Pro Thr Asp
305                 310                 315                 320

Ser Gly His Asp Thr Val Val Met Glu Val Thr Phe Ser Gly Thr Lys
                325                 330                 335

Pro Cys Arg Ile Pro Val Arg Ala Val Ala His Gly Ser Pro Asp Val
            340                 345                 350

Asn Val Ala Met Leu Ile Thr Pro Asn Pro Thr Ile Glu Asn Asn Gly
        355                 360                 365

Gly Gly Phe Ile Glu Met Gln Leu Pro Pro Gly Asp Asn Ile Ile Tyr
    370                 375                 380

Val Gly Glu Leu Ser His Gln Trp Phe Gln Lys Gly Ser Ser Ile Gly
385                 390                 395                 400

Arg Val Phe Gln Lys Thr Arg Lys Gly Ile Glu Arg Leu Thr Val Ile
                405                 410                 415

Gly Glu His Ala Trp Asp Phe Gly Ser Thr Gly Gly Phe Leu Thr Ser
            420                 425                 430

Val Gly Lys Ala Leu His Thr Val Leu Gly Gly Ala Phe Asn Ser Ile
        435                 440                 445

Phe Gly Gly Val Gly Phe Leu Pro Lys Leu Leu Leu Gly Val Ala Leu
    450                 455                 460

Ala Trp Leu Gly Leu Asn Met Arg Asn Pro Thr Met Ser Met Ser Phe
465                 470                 475                 480

Leu Leu Ala Gly Gly Leu Val Leu Ala Met Thr Leu Gly Val Gly Ala
                485                 490                 495

<210> SEQ ID NO 175
<211> LENGTH: 1488
<212> TYPE: DNA
<213> ORGANISM: Artificial Sequence
<220> FEATURE:
<223> OTHER INFORMATION: Tick-borne encephalitis

<400> SEQUENCE: 175
tcgcggtgca cacatttgga gaacagggac tttgtcactg gtactcaggg aaccacgaga    60
```

```
gtgactctgg tgttggagct gggggatgt gtcacgatca ctgctgaggg aagccctca      120 atggatgtgt ggctcgattc catctatcag gagaaccctg ccaagacacg cgagtactgt      180
ctgcatgcca agctgtcgga caccaaagtt gcggccagat gcccaacaat ggggcctgcc      240
actctgactg aggagcatca gagtggtacg gtgtgcaaga gagaccagag tgaccgaggc      300
tggggcaatc actgcggatt gtttggaaag ggcagtattg tgacctgtgt caaggtggct      360
tgtgaggcaa agaagaaggc cattggacat gtgtatgatg ccaacaagat cgtgtacacc      420
gttaaggttg agccacacac gggggactat gttgccgcca atgaaaccca cagtgggagg      480
aagacggcat ccttcacggt ctcctcagaa aagaccatct tgactatggg ggactatgga      540
gatgtgccct tgttgtgcag agtcgccagt ggcgttgact tggctcagac tgtcattctt      600
gagcttgaca agactctgga acaccttcca acagcctggc aggtccatcg tgactggttc      660
aatgatctgg ctctaccgtg gaaacacgaa ggagcgcaac aatggaacaa tgctgagcga      720
ctggttgaat tggagctcc gcatgccgtt aaaatggacg tgtataacct ggagatcaa      780 actggggtgt tgttgaagtc acttgctggg gttcctgtgg cgcacattga tggaacaaag      840
taccacctaa aaagcggcca tgtaacatgc gaggttggac tagaaaagct caaaatgaag      900
ggtctcacat acacaatgtg tgacaaaacg aagttcgcat ggaagcggac tccaacagac      960
agcggacatg acacagtggt catggaggtc acgttctctg gaacaaaacc ttgcaggatc     1020
ccagtgcggg cagtggcaca cggctctcca gatgtaaatg tggccatgct gataacacca     1080
aaccccacca ttgagaacaa tggaggtggc ttcatagaga tgcagctacc cccagggggat     1140 aacatcatct atgttgggga actaagccat cagtggttcc agaaggggag cagcatcgga     1200
agggtgtttc aaaagaccag gaagggcatc gagagactga cagtgatagg agaacacgcc     1260
tgggacttcg gttccactgg aggtttcttg acttcggtag gcaaagcgct gcacacagtc     1320
ctcggcggag ccttcaacag catctttggg ggagtggggt ttctgcccaa gctcctgttg     1380
ggtgtggcct tagcctggtt gggcctgaac atgaggaacc ccaccatgtc catgagtttc     1440
ctcttggctg ggggactggt cctggctatg acacttggag tgggtgct              1488
```

<210> SEQ ID NO 176  
<211> LENGTH: 110  
<212> TYPE: PRT  
<213> ORGANISM: Artificial Sequence  
<220> FEATURE:  
<223> OTHER INFORMATION: Domain III of West Nile virus

<400> SEQUENCE: 176

```
Leu Lys Gly Thr Thr Tyr Gly Val Cys Ser Lys Ala Phe Lys Phe Leu
  1               5                  10                  15

Gly Thr Pro Ala Asp Thr Gly His Gly Thr Val Val Leu Glu Leu Gln
             20                  25                  30

Tyr Thr Gly Thr Asp Gly Pro Cys Lys Val Pro Ile Ser Ser Val Ala
         35                  40                  45

Ser Leu Asn Asp Leu Thr Pro Val Gly Arg Leu Val Thr Val Asn Pro
     50                  55                  60

Phe Val Ser Val Ala Thr Ala Asn Ala Lys Val Leu Ile Glu Leu Glu
 65                  70                  75                  80

Pro Pro Phe Gly Asp Ser Tyr Ile Val Val Gly Arg Gly Glu Gln Gln
                 85                  90                  95

Ile Asn His His Trp His Lys Ser Gly Ser Ser Ile Gly Lys
                100                 105                 110
```

```
<210> SEQ ID NO 177
<211> LENGTH: 110
<212> TYPE: PRT
<213> ORGANISM: Artificial Sequence
<220> FEATURE:
<223> OTHER INFORMATION: Domain III of Japanese encephalitis virus

<400> SEQUENCE: 177
```

Lys Gly Thr Thr Tyr Gly Met Cys Thr Glu Lys Phe Ser Phe Ala Lys
 1               5                  10                  15

Asn Pro Val Asp Thr Gly His Gly Thr Val Val Ile Glu Leu Ser Tyr
            20                  25                  30

Ser Gly Ser Asp Gly Pro Cys Lys Ile Pro Ile Val Ser Val Ala Ser
        35                  40                  45

Leu Asn Asp Met Thr Pro Val Gly Arg Leu Val Thr Val Asn Pro Phe
    50                  55                  60

Val Ala Thr Ser Ser Ala Asn Ser Lys Val Leu Val Glu Met Glu Pro
65                  70                  75                  80

Pro Phe Gly Asp Ser Tyr Ile Val Val Gly Arg Gly Asp Lys Gln Ile
                85                  90                  95

Asn His His Trp His Lys Ala Gly Ser Thr Leu Gly Lys Ala
            100                 105                 110

```
<210> SEQ ID NO 178
<211> LENGTH: 345
<212> TYPE: DNA
<213> ORGANISM: Artificial Sequence
<220> FEATURE:
<223> OTHER INFORMATION: West Nile EIII+

<400> SEQUENCE: 178
atggaaaaat tgcagttgaa gggaacaacc tatggcgtct gttcaaaggc tttcaagttt      60
cttgggactc ccgcagacac aggtcacggc actgtggtgt tggaattgca gtacactggc     120
acggatggac cttgcaaagt tcctatctcg tcagtggctt cattgaacga cctaacgcca     180
gtgggcagat tggtcactgt caaccttttt gtttcagtgg ccacggccaa cgctaaggtc     240
ctgattgaat tggaaccacc ctttggagac tcatacatag tggtgggcag aggagaacaa     300
cagatcaatc accattggca caagtctgga agcagcattg gcaaa                    345

<210> SEQ ID NO 179
<211> LENGTH: 23
<212> TYPE: PRT
<213> ORGANISM: Artificial Sequence
<220> FEATURE:
<223> OTHER INFORMATION: P. aeruginosa

<400> SEQUENCE: 179
```

Met Asn Asn Val Leu Lys Phe Ser Ala Leu Ala Leu Ala Ala Val Leu
 1               5                  10                  15

Ala Thr Gly Cys Ser Ser His
            20

```
<210> SEQ ID NO 180
<211> LENGTH: 72
<212> TYPE: DNA
<213> ORGANISM: Artificial Sequence
<220> FEATURE:
<223> OTHER INFORMATION: P. aeruginosa

<400> SEQUENCE: 180
atgaaagcta ctaaactggt actgggcgcg gtaatcctgg gttctactct gctggcaggt      60
```
tgctccagca ac                                                          72

<210> SEQ ID NO 181
<211> LENGTH: 24
<212> TYPE: PRT
<213> ORGANISM: Artificial Sequence
<220> FEATURE:
<223> OTHER INFORMATION: E. coli

<400> SEQUENCE: 181

Met Lys Ala Thr Lys Leu Val Leu Gly Ala Val Ile Leu Gly Ser Thr
1               5                   10                  15

Leu Leu Ala Gly Cys Ser Ser Asn
            20

<210> SEQ ID NO 182
<211> LENGTH: 72
<212> TYPE: DNA
<213> ORGANISM: Artificial Sequence
<220> FEATURE:
<223> OTHER INFORMATION: E. coli

<400> SEQUENCE: 182
atgaaagcta ctaaactggt actgggcgcg gtaatcctgg gttctactct gctggcaggt    60
tgctccagca ac                                                          72

<210> SEQ ID NO 183
<211> LENGTH: 11
<212> TYPE: PRT
<213> ORGANISM: Artificial Sequence
<220> FEATURE:
<223> OTHER INFORMATION: Linker

<400> SEQUENCE: 183

His Gly Ala Pro Val Asp Pro Ala Ser Pro Trp
1               5                   10

<210> SEQ ID NO 184
<211> LENGTH: 8
<212> TYPE: PRT
<213> ORGANISM: Artificial Sequence
<220> FEATURE:
<223> OTHER INFORMATION: TLR4 ligand

<400> SEQUENCE: 184

Gly Gly Lys Ser Gly Arg Thr Gly
1               5

<210> SEQ ID NO 185
<211> LENGTH: 9
<212> TYPE: PRT
<213> ORGANISM: Artificial Sequence
<220> FEATURE:
<223> OTHER INFORMATION: TLR4 ligand

<400> SEQUENCE: 185

Lys Gly Tyr Asp Trp Leu Val Val Gly
1               5

<210> SEQ ID NO 186
<211> LENGTH: 10
<212> TYPE: PRT
<213> ORGANISM: Artificial Sequence
<220> FEATURE:
<223> OTHER INFORMATION: TLR4 ligand

```
<400> SEQUENCE: 186

Glu Asp Met Val Tyr Arg Ile Gly Val Pro
1               5                   10

<210> SEQ ID NO 187
<211> LENGTH: 6
<212> TYPE: PRT
<213> ORGANISM: Artificial Sequence
<220> FEATURE:
<223> OTHER INFORMATION: TLR4 ligand

<400> SEQUENCE: 187

Val Lys Leu Ser Gly Ser
1               5

<210> SEQ ID NO 188
<211> LENGTH: 8
<212> TYPE: PRT
<213> ORGANISM: Artificial Sequence
<220> FEATURE:
<223> OTHER INFORMATION: TLR4 ligand

<400> SEQUENCE: 188

Gly Met Leu Ser Leu Ala Leu Phe
1               5

<210> SEQ ID NO 189
<211> LENGTH: 7
<212> TYPE: PRT
<213> ORGANISM: Artificial Sequence
<220> FEATURE:
<223> OTHER INFORMATION: TLR4 ligand

<400> SEQUENCE: 189

Cys Val Val Gly Ser Val Arg
1               5

<210> SEQ ID NO 190
<211> LENGTH: 8
<212> TYPE: PRT
<213> ORGANISM: Artificial Sequence
<220> FEATURE:
<223> OTHER INFORMATION: TLR4 ligand

<400> SEQUENCE: 190

Ile Val Arg Gly Cys Leu Gly Trp
1               5

<210> SEQ ID NO 191
<211> LENGTH: 8
<212> TYPE: PRT
<213> ORGANISM: Artificial Sequence
<220> FEATURE:
<223> OTHER INFORMATION: TLR4 ligand

<400> SEQUENCE: 191

Ala Ala Glu Glu Arg Thr Leu Gly
1               5

<210> SEQ ID NO 192
<211> LENGTH: 9
<212> TYPE: PRT
<213> ORGANISM: Artificial Sequence
<220> FEATURE:
<223> OTHER INFORMATION: TLR4 ligand

<400> SEQUENCE: 192
```

```
Trp Ala Arg Val Val Gly Trp Leu Arg
1               5
```

<210> SEQ ID NO 193
<211> LENGTH: 9
<212> TYPE: PRT
<213> ORGANISM: Artificial Sequence
<220> FEATURE:
<223> OTHER INFORMATION: TLR4 ligand

<400> SEQUENCE: 193

```
Ser Glu Gly Tyr Arg Leu Phe Gly Gly
1               5
```

<210> SEQ ID NO 194
<211> LENGTH: 10
<212> TYPE: PRT
<213> ORGANISM: Artificial Sequence
<220> FEATURE:
<223> OTHER INFORMATION: TLR4 ligand

<400> SEQUENCE: 194

```
Leu Val Gly Gly Val Val Arg Arg Gly Ser
1               5                   10
```

<210> SEQ ID NO 195
<211> LENGTH: 10
<212> TYPE: PRT
<213> ORGANISM: Artificial Sequence
<220> FEATURE:
<223> OTHER INFORMATION: TLR4 ligand

<400> SEQUENCE: 195

```
Gly Arg Val Asn Asp Leu Trp Leu Ala Ala
1               5                   10
```

<210> SEQ ID NO 196
<211> LENGTH: 10
<212> TYPE: PRT
<213> ORGANISM: Artificial Sequence
<220> FEATURE:
<223> OTHER INFORMATION: TLR4 ligand

<400> SEQUENCE: 196

```
Ser Gly Trp Met Leu Trp Arg Glu Gly Ser
1               5                   10
```

<210> SEQ ID NO 197
<211> LENGTH: 10
<212> TYPE: PRT
<213> ORGANISM: Artificial Sequence
<220> FEATURE:
<223> OTHER INFORMATION: TLR4 ligand

<400> SEQUENCE: 197

```
Glu Arg Met Glu Asp Arg Gly Gly Asp Leu
1               5                   10
```

<210> SEQ ID NO 198
<211> LENGTH: 9
<212> TYPE: PRT
<213> ORGANISM: Artificial Sequence
<220> FEATURE:
<223> OTHER INFORMATION: TLR4 ligand

<400> SEQUENCE: 198

```
Lys Leu Cys Cys Phe Thr Glu Cys Met
1               5
```

```
<210> SEQ ID NO 199
<211> LENGTH: 10
<212> TYPE: PRT
<213> ORGANISM: Artificial Sequence
<220> FEATURE:
<223> OTHER INFORMATION: TLR4 ligand

<400> SEQUENCE: 199

Ala Val Gly Ser Met Glu Arg Gly Arg Gly
 1               5                  10

<210> SEQ ID NO 200
<211> LENGTH: 9
<212> TYPE: PRT
<213> ORGANISM: Artificial Sequence
<220> FEATURE:
<223> OTHER INFORMATION: TLR4 ligand

<400> SEQUENCE: 200

Arg Asp Trp Val Gly Gly Asp Leu Val
 1               5

<210> SEQ ID NO 201
<211> LENGTH: 10
<212> TYPE: PRT
<213> ORGANISM: Artificial Sequence
<220> FEATURE:
<223> OTHER INFORMATION: TLR4 ligand

<400> SEQUENCE: 201

Phe Phe Glu Val Ala Lys Ile Ser Gln Gln
 1               5                  10

<210> SEQ ID NO 202
<211> LENGTH: 5
<212> TYPE: PRT
<213> ORGANISM: Artificial Sequence
<220> FEATURE:
<223> OTHER INFORMATION: TLR4 ligand

<400> SEQUENCE: 202

Trp Trp Tyr Trp Cys
 1               5

<210> SEQ ID NO 203
<211> LENGTH: 7
<212> TYPE: PRT
<213> ORGANISM: Artificial Sequence
<220> FEATURE:
<223> OTHER INFORMATION: TLR4 ligand

<400> SEQUENCE: 203

Met His Leu Cys Ser His Ala
 1               5

<210> SEQ ID NO 204
<211> LENGTH: 7
<212> TYPE: PRT
<213> ORGANISM: Artificial Sequence
<220> FEATURE:
<223> OTHER INFORMATION: TLR4 ligand

<400> SEQUENCE: 204

Trp Leu Phe Arg Arg Ile Gly
 1               5
```

```
<210> SEQ ID NO 205
<211> LENGTH: 7
<212> TYPE: PRT
<213> ORGANISM: Artificial Sequence
<220> FEATURE:
<223> OTHER INFORMATION: TLR4 ligand

<400> SEQUENCE: 205

Tyr Trp Phe Trp Arg Ile Gly
 1               5

<210> SEQ ID NO 206
<211> LENGTH: 7
<212> TYPE: PRT
<213> ORGANISM: Artificial Sequence
<220> FEATURE:
<223> OTHER INFORMATION: TLR4 ligand

<400> SEQUENCE: 206

Met His Leu Tyr Cys Ile Ala
 1               5

<210> SEQ ID NO 207
<211> LENGTH: 8
<212> TYPE: PRT
<213> ORGANISM: Artificial Sequence
<220> FEATURE:
<223> OTHER INFORMATION: TLR4 ligand

<400> SEQUENCE: 207

Trp Pro Leu Phe Pro Trp Ile Val
 1               5

<210> SEQ ID NO 208
<211> LENGTH: 7
<212> TYPE: PRT
<213> ORGANISM: Artificial Sequence
<220> FEATURE:
<223> OTHER INFORMATION: TLR4 ligand

<400> SEQUENCE: 208

Asp Met Arg Ser His Ala Arg
 1               5

<210> SEQ ID NO 209
<211> LENGTH: 7
<212> TYPE: PRT
<213> ORGANISM: Artificial Sequence
<220> FEATURE:
<223> OTHER INFORMATION: TLR4 ligand

<400> SEQUENCE: 209

Met His Leu Cys Thr His Ala
 1               5

<210> SEQ ID NO 210
<211> LENGTH: 6
<212> TYPE: PRT
<213> ORGANISM: Artificial Sequence
<220> FEATURE:
<223> OTHER INFORMATION: TLR4 ligand

<400> SEQUENCE: 210

Asn Leu Phe Pro Phe Tyr
 1               5

<210> SEQ ID NO 211
<211> LENGTH: 7
```

```
<212> TYPE: PRT
<213> ORGANISM: Artificial Sequence
<220> FEATURE:
<223> OTHER INFORMATION: TLR4 ligand

<400> SEQUENCE: 211

Met His Leu Cys Thr Arg Ala
1               5

<210> SEQ ID NO 212
<211> LENGTH: 7
<212> TYPE: PRT
<213> ORGANISM: Artificial Sequence
<220> FEATURE:
<223> OTHER INFORMATION: TLR4 ligand

<400> SEQUENCE: 212

Arg His Leu Trp Tyr His Ala
1               5

<210> SEQ ID NO 213
<211> LENGTH: 7
<212> TYPE: PRT
<213> ORGANISM: Artificial Sequence
<220> FEATURE:
<223> OTHER INFORMATION: TLR4 ligand

<400> SEQUENCE: 213

Trp Pro Phe Ser Ala Tyr Trp
1               5

<210> SEQ ID NO 214
<211> LENGTH: 6
<212> TYPE: PRT
<213> ORGANISM: Artificial Sequence
<220> FEATURE:
<223> OTHER INFORMATION: TLR4 ligand

<400> SEQUENCE: 214

Trp Tyr Leu Arg Gly Ser
1               5

<210> SEQ ID NO 215
<211> LENGTH: 7
<212> TYPE: PRT
<213> ORGANISM: Artificial Sequence
<220> FEATURE:
<223> OTHER INFORMATION: TLR4 ligand

<400> SEQUENCE: 215

Gly Lys Gly Thr Asp Leu Gly
1               5

<210> SEQ ID NO 216
<211> LENGTH: 6
<212> TYPE: PRT
<213> ORGANISM: Artificial Sequence
<220> FEATURE:
<223> OTHER INFORMATION: TLR4 ligand

<400> SEQUENCE: 216

Ile Phe Val Arg Met Arg
1               5

<210> SEQ ID NO 217
<211> LENGTH: 7
<212> TYPE: PRT
<213> ORGANISM: Artificial Sequence
```

```
<220> FEATURE:
<223> OTHER INFORMATION: TLR4 ligand

<400> SEQUENCE: 217

Trp Leu Phe Arg Pro Val Phe
1               5

<210> SEQ ID NO 218
<211> LENGTH: 7
<212> TYPE: PRT
<213> ORGANISM: Artificial Sequence
<220> FEATURE:
<223> OTHER INFORMATION: TLR4 ligand

<400> SEQUENCE: 218

Phe Leu Gly Trp Leu Met Gly
1               5

<210> SEQ ID NO 219
<211> LENGTH: 7
<212> TYPE: PRT
<213> ORGANISM: Artificial Sequence
<220> FEATURE:
<223> OTHER INFORMATION: TLR4 ligand

<400> SEQUENCE: 219

Met His Leu Trp His His Ala
1               5

<210> SEQ ID NO 220
<211> LENGTH: 7
<212> TYPE: PRT
<213> ORGANISM: Artificial Sequence
<220> FEATURE:
<223> OTHER INFORMATION: TLR4 ligand

<400> SEQUENCE: 220

Trp Trp Phe Pro Trp Lys Ala
1               5

<210> SEQ ID NO 221
<211> LENGTH: 7
<212> TYPE: PRT
<213> ORGANISM: Artificial Sequence
<220> FEATURE:
<223> OTHER INFORMATION: TLR4 ligand

<400> SEQUENCE: 221

Trp Tyr Leu Pro Trp Leu Gly
1               5

<210> SEQ ID NO 222
<211> LENGTH: 7
<212> TYPE: PRT
<213> ORGANISM: Artificial Sequence
<220> FEATURE:
<223> OTHER INFORMATION: TLR4 ligand

<400> SEQUENCE: 222

Trp Pro Phe Pro Arg Thr Phe
1               5

<210> SEQ ID NO 223
<211> LENGTH: 7
<212> TYPE: PRT
<213> ORGANISM: Artificial Sequence
<220> FEATURE:
<223> OTHER INFORMATION: TLR4 ligand
```

```
<400> SEQUENCE: 223

Trp Pro Phe Pro Ala Tyr Trp
1               5

<210> SEQ ID NO 224
<211> LENGTH: 7
<212> TYPE: PRT
<213> ORGANISM: Artificial Sequence
<220> FEATURE:
<223> OTHER INFORMATION: TLR4 ligand

<400> SEQUENCE: 224

Phe Leu Gly Leu Arg Trp Leu
1               5

<210> SEQ ID NO 225
<211> LENGTH: 10
<212> TYPE: PRT
<213> ORGANISM: Artificial Sequence
<220> FEATURE:
<223> OTHER INFORMATION: TLR4 ligand

<400> SEQUENCE: 225

Ser Arg Thr Asp Val Gly Val Leu Glu Val
1               5                   10

<210> SEQ ID NO 226
<211> LENGTH: 10
<212> TYPE: PRT
<213> ORGANISM: Artificial Sequence
<220> FEATURE:
<223> OTHER INFORMATION: TLR4 ligand

<400> SEQUENCE: 226

Arg Glu Lys Val Ser Arg Gly Asp Lys Gly
1               5                   10

<210> SEQ ID NO 227
<211> LENGTH: 10
<212> TYPE: PRT
<213> ORGANISM: Artificial Sequence
<220> FEATURE:
<223> OTHER INFORMATION: TLR4 ligand

<400> SEQUENCE: 227

Asp Trp Asp Ala Val Glu Ser Glu Tyr Met
1               5                   10

<210> SEQ ID NO 228
<211> LENGTH: 10
<212> TYPE: PRT
<213> ORGANISM: Artificial Sequence
<220> FEATURE:
<223> OTHER INFORMATION: TLR4 ligand

<400> SEQUENCE: 228

Val Ser Ser Ala Gln Glu Val Arg Val Pro
1               5                   10

<210> SEQ ID NO 229
<211> LENGTH: 10
<212> TYPE: PRT
<213> ORGANISM: Artificial Sequence
<220> FEATURE:
<223> OTHER INFORMATION: TLR4 ligand

<400> SEQUENCE: 229
```

```
Leu Thr Tyr Gly Gly Leu Glu Ala Leu Gly
 1               5                  10

<210> SEQ ID NO 230
<211> LENGTH: 10
<212> TYPE: PRT
<213> ORGANISM: Artificial Sequence
<220> FEATURE:
<223> OTHER INFORMATION: TLR4 ligand

<400> SEQUENCE: 230

Val Glu Glu Tyr Ser Ser Ser Gly Val Ser
 1               5                  10

<210> SEQ ID NO 231
<211> LENGTH: 10
<212> TYPE: PRT
<213> ORGANISM: Artificial Sequence
<220> FEATURE:
<223> OTHER INFORMATION: TLR4 ligand

<400> SEQUENCE: 231

Val Cys Glu Val Ser Asp Ser Val Met Ala
 1               5                  10

<210> SEQ ID NO 232
<211> LENGTH: 5
<212> TYPE: PRT
<213> ORGANISM: Artificial Sequence
<220> FEATURE:
<223> OTHER INFORMATION: TLR2 ligand

<400> SEQUENCE: 232

Asn Pro Pro Thr Thr
 1               5

<210> SEQ ID NO 233
<211> LENGTH: 5
<212> TYPE: PRT
<213> ORGANISM: Artificial Sequence
<220> FEATURE:
<223> OTHER INFORMATION: TLR2 ligand

<400> SEQUENCE: 233

Met Arg Arg Ile Leu
 1               5

<210> SEQ ID NO 234
<211> LENGTH: 4
<212> TYPE: PRT
<213> ORGANISM: Artificial Sequence
<220> FEATURE:
<223> OTHER INFORMATION: TLR2 ligand

<400> SEQUENCE: 234

Met Ile Ser Ser
 1

<210> SEQ ID NO 235
<211> LENGTH: 5
<212> TYPE: PRT
<213> ORGANISM: Artificial Sequence
<220> FEATURE:
<223> OTHER INFORMATION: TLR2 ligand

<400> SEQUENCE: 235

Arg Gly Gly Ser Lys
```

<210> SEQ ID NO 236
<211> LENGTH: 4
<212> TYPE: PRT
<213> ORGANISM: Artificial Sequence
<220> FEATURE:
<223> OTHER INFORMATION: TLR2 ligand

<400> SEQUENCE: 236

Arg Gly Gly Phe
 1

<210> SEQ ID NO 237
<211> LENGTH: 5
<212> TYPE: PRT
<213> ORGANISM: Artificial Sequence
<220> FEATURE:
<223> OTHER INFORMATION: TLR2 ligand

<400> SEQUENCE: 237

Asn Arg Thr Val Phe
 1               5

<210> SEQ ID NO 238
<211> LENGTH: 5
<212> TYPE: PRT
<213> ORGANISM: Artificial Sequence
<220> FEATURE:
<223> OTHER INFORMATION: TLR2 ligand

<400> SEQUENCE: 238

Asn Arg Phe Gly Leu
 1               5

<210> SEQ ID NO 239
<211> LENGTH: 5
<212> TYPE: PRT
<213> ORGANISM: Artificial Sequence
<220> FEATURE:
<223> OTHER INFORMATION: TLR2 ligand

<400> SEQUENCE: 239

Ser Arg His Gly Arg
 1               5

<210> SEQ ID NO 240
<211> LENGTH: 5
<212> TYPE: PRT
<213> ORGANISM: Artificial Sequence
<220> FEATURE:
<223> OTHER INFORMATION: TLR2 ligand

<400> SEQUENCE: 240

Ile Met Arg His Pro
 1               5

<210> SEQ ID NO 241
<211> LENGTH: 5
<212> TYPE: PRT
<213> ORGANISM: Artificial Sequence
<220> FEATURE:
<223> OTHER INFORMATION: TLR2 ligand

<400> SEQUENCE: 241

Glu Val Cys Ala Pro
 1               5

```
<210> SEQ ID NO 242
<211> LENGTH: 5
<212> TYPE: PRT
<213> ORGANISM: Artificial Sequence
<220> FEATURE:
<223> OTHER INFORMATION: TLR2 ligand

<400> SEQUENCE: 242

Ala Cys Gly Val Tyr
1               5

<210> SEQ ID NO 243
<211> LENGTH: 5
<212> TYPE: PRT
<213> ORGANISM: Artificial Sequence
<220> FEATURE:
<223> OTHER INFORMATION: TLR2 ligand

<400> SEQUENCE: 243

Cys Gly Pro Lys Leu
1               5

<210> SEQ ID NO 244
<211> LENGTH: 5
<212> TYPE: PRT
<213> ORGANISM: Artificial Sequence
<220> FEATURE:
<223> OTHER INFORMATION: TLR2 ligand

<400> SEQUENCE: 244

Ala Gly Cys Phe Ser
1               5

<210> SEQ ID NO 245
<211> LENGTH: 5
<212> TYPE: PRT
<213> ORGANISM: Artificial Sequence
<220> FEATURE:
<223> OTHER INFORMATION: TLR2 ligand

<400> SEQUENCE: 245

Ser Gly Gly Leu Phe
1               5

<210> SEQ ID NO 246
<211> LENGTH: 5
<212> TYPE: PRT
<213> ORGANISM: Artificial Sequence
<220> FEATURE:
<223> OTHER INFORMATION: TLR2 ligand

<400> SEQUENCE: 246

Ala Val Arg Leu Ser
1               5

<210> SEQ ID NO 247
<211> LENGTH: 5
<212> TYPE: PRT
<213> ORGANISM: Artificial Sequence
<220> FEATURE:
<223> OTHER INFORMATION: TLR2 ligand

<400> SEQUENCE: 247

Gly Gly Lys Leu Ser
1               5

<210> SEQ ID NO 248
```

```
<211> LENGTH: 5
<212> TYPE: PRT
<213> ORGANISM: Artificial Sequence
<220> FEATURE:
<223> OTHER INFORMATION: TLR2 ligand

<400> SEQUENCE: 248

Val Ser Glu Gly Val
1               5

<210> SEQ ID NO 249
<211> LENGTH: 5
<212> TYPE: PRT
<213> ORGANISM: Artificial Sequence
<220> FEATURE:
<223> OTHER INFORMATION: TLR2 ligand

<400> SEQUENCE: 249

Lys Cys Gln Ser Phe
1               5

<210> SEQ ID NO 250
<211> LENGTH: 5
<212> TYPE: PRT
<213> ORGANISM: Artificial Sequence
<220> FEATURE:
<223> OTHER INFORMATION: TLR2 ligand

<400> SEQUENCE: 250

Phe Cys Gly Leu Gly
1               5

<210> SEQ ID NO 251
<211> LENGTH: 5
<212> TYPE: PRT
<213> ORGANISM: Artificial Sequence
<220> FEATURE:
<223> OTHER INFORMATION: TLR2 ligand

<400> SEQUENCE: 251

Pro Glu Ser Gly Val
1               5

<210> SEQ ID NO 252
<211> LENGTH: 5
<212> TYPE: PRT
<213> ORGANISM: Artificial Sequence
<220> FEATURE:
<223> OTHER INFORMATION: TLR2 ligand

<400> SEQUENCE: 252

Asp Pro Asp Ser Gly
1               5

<210> SEQ ID NO 253
<211> LENGTH: 5
<212> TYPE: PRT
<213> ORGANISM: Artificial Sequence
<220> FEATURE:
<223> OTHER INFORMATION: TLR2 ligand

<400> SEQUENCE: 253

Ile Gly Arg Phe Arg
1               5

<210> SEQ ID NO 254
<211> LENGTH: 5
<212> TYPE: PRT
```

```
<213> ORGANISM: Artificial Sequence
<220> FEATURE:
<223> OTHER INFORMATION: TLR2 ligand

<400> SEQUENCE: 254

Met Gly Thr Leu Pro
 1               5

<210> SEQ ID NO 255
<211> LENGTH: 5
<212> TYPE: PRT
<213> ORGANISM: Artificial Sequence
<220> FEATURE:
<223> OTHER INFORMATION: TLR2 ligand

<400> SEQUENCE: 255

Ala Asp Thr His Gln
 1               5

<210> SEQ ID NO 256
<211> LENGTH: 5
<212> TYPE: PRT
<213> ORGANISM: Artificial Sequence
<220> FEATURE:
<223> OTHER INFORMATION: TLR2 ligand

<400> SEQUENCE: 256

His Leu Leu Pro Gly
 1               5

<210> SEQ ID NO 257
<211> LENGTH: 5
<212> TYPE: PRT
<213> ORGANISM: Artificial Sequence
<220> FEATURE:
<223> OTHER INFORMATION: TLR2 ligand

<400> SEQUENCE: 257

Gly Pro Leu Leu His
 1               5

<210> SEQ ID NO 258
<211> LENGTH: 5
<212> TYPE: PRT
<213> ORGANISM: Artificial Sequence
<220> FEATURE:
<223> OTHER INFORMATION: TLR2 ligand

<400> SEQUENCE: 258

Asn Tyr Arg Arg Trp
 1               5

<210> SEQ ID NO 259
<211> LENGTH: 5
<212> TYPE: PRT
<213> ORGANISM: Artificial Sequence
<220> FEATURE:
<223> OTHER INFORMATION: TLR2 ligand

<400> SEQUENCE: 259

Leu Arg Gln Gly Arg
 1               5

<210> SEQ ID NO 260
<211> LENGTH: 5
<212> TYPE: PRT
<213> ORGANISM: Artificial Sequence
<220> FEATURE:
```

<223> OTHER INFORMATION: TLR2 ligand

<400> SEQUENCE: 260

Ile Met Trp Phe Pro
1               5

<210> SEQ ID NO 261
<211> LENGTH: 5
<212> TYPE: PRT
<213> ORGANISM: Artificial Sequence
<220> FEATURE:
<223> OTHER INFORMATION: TLR2 ligand

<400> SEQUENCE: 261

Arg Val Val Ala Pro
1               5

<210> SEQ ID NO 262
<211> LENGTH: 5
<212> TYPE: PRT
<213> ORGANISM: Artificial Sequence
<220> FEATURE:
<223> OTHER INFORMATION: TLR2 ligand

<400> SEQUENCE: 262

Ile His Val Val Pro
1               5

<210> SEQ ID NO 263
<211> LENGTH: 5
<212> TYPE: PRT
<213> ORGANISM: Artificial Sequence
<220> FEATURE:
<223> OTHER INFORMATION: TLR2 ligand

<400> SEQUENCE: 263

Met Phe Gly Val Pro
1               5

<210> SEQ ID NO 264
<211> LENGTH: 5
<212> TYPE: PRT
<213> ORGANISM: Artificial Sequence
<220> FEATURE:
<223> OTHER INFORMATION: TLR2 ligand

<400> SEQUENCE: 264

Cys Val Trp Leu Gln
1               5

<210> SEQ ID NO 265
<211> LENGTH: 5
<212> TYPE: PRT
<213> ORGANISM: Artificial Sequence
<220> FEATURE:
<223> OTHER INFORMATION: TLR2 ligand

<400> SEQUENCE: 265

Ile Tyr Lys Leu Ala
1               5

<210> SEQ ID NO 266
<211> LENGTH: 4
<212> TYPE: PRT
<213> ORGANISM: Artificial Sequence
<220> FEATURE:
<223> OTHER INFORMATION: TLR2 ligand

```
<400> SEQUENCE: 266

Lys Gly Trp Phe
1

<210> SEQ ID NO 267
<211> LENGTH: 5
<212> TYPE: PRT
<213> ORGANISM: Artificial Sequence
<220> FEATURE:
<223> OTHER INFORMATION: TLR2 ligand

<400> SEQUENCE: 267

Lys Tyr Met Pro His
1               5

<210> SEQ ID NO 268
<211> LENGTH: 5
<212> TYPE: PRT
<213> ORGANISM: Artificial Sequence
<220> FEATURE:
<223> OTHER INFORMATION: TLR2 ligand

<400> SEQUENCE: 268

Val Gly Lys Asn Asp
1               5

<210> SEQ ID NO 269
<211> LENGTH: 5
<212> TYPE: PRT
<213> ORGANISM: Artificial Sequence
<220> FEATURE:
<223> OTHER INFORMATION: TLR2 ligand

<400> SEQUENCE: 269

Thr His Lys Pro Lys
1               5

<210> SEQ ID NO 270
<211> LENGTH: 5
<212> TYPE: PRT
<213> ORGANISM: Artificial Sequence
<220> FEATURE:
<223> OTHER INFORMATION: TLR2 ligand

<400> SEQUENCE: 270

Ser His Ile Ala Leu
1               5

<210> SEQ ID NO 271
<211> LENGTH: 5
<212> TYPE: PRT
<213> ORGANISM: Artificial Sequence
<220> FEATURE:
<223> OTHER INFORMATION: TLR2 ligand

<400> SEQUENCE: 271

Ala Trp Ala Gly Thr
1               5

<210> SEQ ID NO 272
<211> LENGTH: 20
<212> TYPE: PRT
<213> ORGANISM: Artificial Sequence
<220> FEATURE:
<223> OTHER INFORMATION: TLR2 ligand

<400> SEQUENCE: 272
```

```
Lys Gly Gly Val Gly Pro Val Arg Arg Ser Arg Leu Arg Arg Thr
1               5                   10                  15

Thr Gln Pro Gly
            20

<210> SEQ ID NO 273
<211> LENGTH: 23
<212> TYPE: PRT
<213> ORGANISM: Artificial Sequence
<220> FEATURE:
<223> OTHER INFORMATION: TLR2 ligand

<400> SEQUENCE: 273

Gly Arg Arg Gly Leu Cys Arg Gly Cys Arg Thr Arg Gly Arg Ile Lys
1               5                   10                  15

Gln Leu Gln Ser Ala His Lys
            20

<210> SEQ ID NO 274
<211> LENGTH: 22
<212> TYPE: PRT
<213> ORGANISM: Artificial Sequence
<220> FEATURE:
<223> OTHER INFORMATION: TLR2 ligand

<400> SEQUENCE: 274

Arg Trp Gly Tyr His Leu Arg Asp Arg Lys Tyr Lys Gly Val Arg Ser
1               5                   10                  15

His Lys Gly Val Pro Arg
            20

<210> SEQ ID NO 275
<211> LENGTH: 535
<212> TYPE: PRT
<213> ORGANISM: Artificial Sequence
<220> FEATURE:
<223> OTHER INFORMATION: Cross-reactive Mutant (CRM) of diptheria toxin

<400> SEQUENCE: 275

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
                20                  25                  30

Lys Gly Ile Gln Lys Pro Lys Ser Gly Thr Gln Gly Asn Tyr Asp Asp
            35                  40                  45

Asp Trp Lys Gly Phe Tyr Ser Thr Asp Asn Lys Tyr Asp Ala Ala Gly
        50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175
```

```
Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
            195                 200                 205

Ile Arg Asp Lys Thr Lys Thr Lys Ile Glu Ser Leu Lys Glu His Gly
210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
            245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
            275                 280                 285

Ile Asp Ser Glu Thr Ala Asp Asn Leu Glu Lys Thr Thr Ala Ala Leu
290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
            325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
            355                 360                 365

Gln Val Val His Asn Ser Tyr Asn Arg Pro Ala Tyr Ser Pro Gly His
            370                 375                 380

Lys Thr Gln Pro Phe Leu His Asp Gly Tyr Ala Val Ser Trp Asn Thr
385                 390                 395                 400

Val Glu Asp Ser Ile Ile Arg Thr Gly Phe Gln Gly Glu Ser Gly His
                405                 410                 415

Asp Ile Lys Ile Thr Ala Glu Asn Thr Pro Leu Pro Ile Ala Gly Val
            420                 425                 430

Leu Leu Pro Thr Ile Pro Gly Lys Leu Asp Val Asn Lys Ser Lys Thr
            435                 440                 445

His Ile Ser Val Asn Gly Arg Lys Ile Arg Met Arg Cys Arg Ala Ile
450                 455                 460

Asp Gly Asp Val Thr Phe Cys Arg Pro Lys Ser Pro Val Tyr Val Gly
465                 470                 475                 480

Asn Gly Val His Ala Asn Leu His Val Ala Phe His Arg Ser Ser Ser
            485                 490                 495

Glu Lys Ile His Ser Asn Glu Ile Ser Ser Asp Ser Ile Gly Val Leu
            500                 505                 510

Gly Tyr Gln Lys Thr Val Asp His Thr Lys Val Asn Ser Lys Leu Ser
            515                 520                 525

Leu Phe Phe Glu Ile Lys Ser
            530                 535

<210> SEQ ID NO 276
<211> LENGTH: 164
<212> TYPE: PRT
<213> ORGANISM: Artificial Sequence
<220> FEATURE:
<223> OTHER INFORMATION: Coat protein of Tobacco mosaic virus (TMV)

<400> SEQUENCE: 276
```

```
Met Met Ala Tyr Ser Ile Pro Thr Pro Ser Gln Leu Val Tyr Phe Thr
1               5                   10                  15

Glu Asn Tyr Ala Asp Tyr Ile Pro Phe Val Asn Arg Leu Ile Asn Ala
            20                  25                  30

Arg Ser Asn Ser Phe Gln Thr Gln Ser Gly Arg Asp Glu Leu Arg Glu
        35                  40                  45

Ile Leu Ile Lys Ser Gln Val Ser Val Val Ser Pro Ile Ser Arg Phe
    50                  55                  60

Pro Ala Glu Pro Ala Tyr Tyr Ile Tyr Leu Arg Asp Pro Ser Ile Ser
65                  70                  75                  80

Thr Val Tyr Thr Ala Leu Leu Gln Ser Thr Asp Thr Arg Asn Arg Val
                85                  90                  95

Ile Glu Val Glu Asn Ser Thr Asn Val Thr Thr Ala Glu Gln Leu Asn
            100                 105                 110

Ala Val Arg Arg Thr Asp Asp Ala Ser Thr Ala Ile His Asn Asn Leu
        115                 120                 125

Glu Gln Leu Leu Ser Leu Leu Thr Asn Gly Thr Gly Val Phe Asn Arg
    130                 135                 140

Thr Ser Phe Glu Ser Ala Ser Gly Leu Thr Trp Leu Val Thr Thr Thr
145                 150                 155                 160

Pro Arg Thr Ala

<210> SEQ ID NO 277
<211> LENGTH: 221
<212> TYPE: PRT
<213> ORGANISM: Artificial Sequence
<220> FEATURE:
<223> OTHER INFORMATION: Coat protein of alfalfa mosaic virus

<400> SEQUENCE: 277

Met Ser Ser Ser Gln Lys Lys Ala Gly Gly Lys Ala Gly Lys Pro Thr
1               5                   10                  15

Lys Arg Ser Gln Asn Tyr Ala Ala Leu Arg Lys Ala Gln Leu Pro Lys
            20                  25                  30

Pro Pro Ala Leu Lys Val Pro Val Ala Lys Pro Thr Asn Thr Ile Leu
        35                  40                  45

Pro Gln Thr Gly Cys Val Trp Gln Ser Leu Gly Thr Pro Leu Ser Leu
    50                  55                  60

Ser Ser Ser Asn Gly Leu Gly Ala Arg Phe Leu Tyr Ser Phe Leu Lys
65                  70                  75                  80

Asp Phe Ala Ala Pro Arg Ile Leu Glu Glu Asp Leu Ile Phe Arg Met
                85                  90                  95

Val Phe Ser Ile Thr Pro Ser His Ala Gly Ser Phe Cys Leu Thr Asp
            100                 105                 110

Asp Val Thr Thr Glu Asp Gly Arg Ala Val Ala His Gly Asn Pro Met
        115                 120                 125

Gln Glu Phe Pro His Gly Ala Phe His Ala Asn Glu Lys Phe Gly Phe
    130                 135                 140

Glu Leu Val Phe Thr Ala Pro Thr His Ala Gly Met Gln Asn Gln Asn
145                 150                 155                 160

Phe Lys His Ser Tyr Ala Val Ala Leu Cys Leu Asp Phe Asp Ala Leu
                165                 170                 175

Pro Glu Gly Ser Arg Asn Pro Ser Tyr Arg Phe Asn Glu Val Trp Val
            180                 185                 190

Glu Arg Lys Ala Phe Pro Arg Ala Gly Pro Leu Arg Ser Leu Ile Thr
        195                 200                 205

```
Val Gly Leu Phe Asp Asp Ala Asp Asp Leu Asp Arg Gln
    210                 215                 220
```

<210> SEQ ID NO 278
<211> LENGTH: 237
<212> TYPE: PRT
<213> ORGANISM: Artificial Sequence
<220> FEATURE:
<223> OTHER INFORMATION: Coat protein of Potato virus X

<400> SEQUENCE: 278

```
Met Thr Thr Pro Ala Asn Thr Thr Gln Ala Thr Gly Ser Thr Thr Ser
  1               5                  10                  15

Thr Thr Thr Lys Thr Ala Gly Ala Thr Pro Ala Thr Thr Ser Gly Leu
             20                  25                  30

Phe Thr Ile Pro Asp Gly Glu Phe Phe Ser Thr Ala Arg Ala Ile Val
         35                  40                  45

Ala Ser Asn Ala Val Ala Thr Asn Glu Asp Leu Ser Lys Ile Glu Ala
     50                  55                  60

Ile Trp Lys Asp Met Lys Val Pro Thr Asp Thr Met Ala Gln Ala Ala
 65                  70                  75                  80

Trp Asp Leu Val Arg His Cys Ala Asp Val Gly Ser Ser Ala Gln Thr
                 85                  90                  95

Glu Met Ile Asp Thr Gly Pro Tyr Ser Asn Gly Ile Ser Arg Ala Arg
            100                 105                 110

Leu Ala Ala Ala Ile Lys Glu Val Cys Thr Leu Arg Gln Phe Cys Met
        115                 120                 125

Lys Tyr Ala Pro Val Val Trp Asn Trp Met Leu Thr Asn Asn Ser Pro
    130                 135                 140

Pro Ala Asn Trp Gln Ala Gln Gly Phe Lys Pro Glu His Lys Phe Ala
145                 150                 155                 160

Ala Phe Asp Phe Phe Asn Gly Val Thr Asn Pro Ala Ala Ile Met Pro
                165                 170                 175

Lys Glu Gly Leu Ile Arg Pro Pro Ser Glu Ala Glu Met Asn Ala Ala
            180                 185                 190

Gln Thr Ala Ala Phe Val Lys Ile Thr Lys Ala Arg Ala Gln Ser Asn
        195                 200                 205

Asp Phe Ala Ser Leu Asp Ala Ala Val Thr Arg Gly Arg Ile Thr Gly
    210                 215                 220

Thr Thr Thr Ala Glu Ala Val Val Thr Leu Pro Pro Pro
225                 230                 235
```

<210> SEQ ID NO 279
<211> LENGTH: 395
<212> TYPE: PRT
<213> ORGANISM: Artificial Sequence
<220> FEATURE:
<223> OTHER INFORMATION: class I outer membrane protein of Neisseria meningitides

<400> SEQUENCE: 279

```
Met Arg Lys Lys Leu Thr Ala Leu Val Leu Ser Ala Leu Pro Leu Ala
  1               5                  10                  15

Ala Val Ala Asp Val Ser Leu Tyr Gly Glu Ile Lys Ala Gly Val Glu
             20                  25                  30

Gly Arg Asn Tyr Gln Leu Gln Leu Thr Glu Ala Gln Ala Ala Asn Gly
         35                  40                  45

Gly Ala Ser Gly Gln Val Lys Val Thr Lys Val Thr Lys Ala Lys Ser
```

-continued

```
                50                  55                  60
Arg Ile Arg Thr Lys Ile Ser Asp Phe Gly Ser Phe Ile Gly Phe Lys
65                  70                  75                  80

Gly Ser Glu Asp Leu Gly Glu Gly Leu Lys Ala Val Trp Gln Leu Glu
                85                  90                  95

Gln Asp Val Ser Val Ala Gly Gly Ala Thr Gln Trp Gly Asn Arg
            100                 105                 110

Glu Ser Phe Ile Gly Leu Ala Gly Glu Phe Gly Thr Leu Arg Ala Gly
            115                 120                 125

Arg Val Ala Asn Gln Phe Asp Asp Ala Ser Gln Ala Ile Asp Pro Trp
130                 135                 140

Asp Ser Asn Asn Asp Val Ala Ser Gln Leu Gly Ile Phe Lys Arg His
145                 150                 155                 160

Asp Asp Met Pro Val Ser Val Arg Tyr Asp Ser Pro Glu Phe Ser Gly
                165                 170                 175

Phe Ser Gly Ser Val Gln Phe Val Pro Ala Gln Asn Ser Lys Ser Ala
            180                 185                 190

Tyr Lys Pro Ala Tyr Trp Thr Thr Val Asn Thr Gly Ser Ala Thr Thr
            195                 200                 205

Thr Thr Phe Val Pro Ala Val Val Gly Lys Pro Gly Ser Asp Val Tyr
210                 215                 220

Tyr Ala Gly Leu Asn Tyr Lys Asn Gly Phe Ala Gly Asn Tyr Ala
225                 230                 235                 240

Phe Lys Tyr Ala Arg His Ala Asn Val Gly Arg Asp Ala Phe Glu Leu
                245                 250                 255

Phe Leu Leu Gly Ser Gly Ser Asp Gln Ala Lys Gly Thr Asp Pro Leu
            260                 265                 270

Lys Asn His Gln Val His Arg Leu Thr Gly Gly Tyr Glu Glu Gly Gly
            275                 280                 285

Leu Asn Leu Ala Leu Ala Ala Gln Leu Asp Leu Ser Glu Asn Gly Asp
            290                 295                 300

Lys Thr Lys Asn Ser Thr Thr Glu Ile Ala Ala Thr Ala Ser Tyr Arg
305                 310                 315                 320

Phe Gly Asn Ala Val Pro Arg Ile Ser Tyr Ala His Gly Phe Asp Phe
                325                 330                 335

Ile Glu Arg Gly Lys Lys Gly Glu Asn Thr Ser Tyr Asp Gln Ile Ile
            340                 345                 350

Ala Gly Val Asp Tyr Asp Phe Ser Lys Arg Thr Ser Ala Ile Val Ser
            355                 360                 365

Gly Ala Trp Leu Lys Arg Asn Thr Gly Ile Gly Asn Tyr Thr Gln Ile
370                 375                 380

Asn Ala Ala Ser Val Gly Leu Arg His Lys Phe
385                 390                 395
```

<210> SEQ ID NO 280
<211> LENGTH: 347
<212> TYPE: PRT
<213> ORGANISM: Artificial Sequence
<220> FEATURE:
<223> OTHER INFORMATION: Major fimbrial subunit protein type I

<400> SEQUENCE: 280

```
Met Val Leu Lys Thr Ser Asn Ser Asn Arg Ala Phe Gly Val Gly Asp
1               5                   10                  15

Asp Glu Ser Lys Val Ala Lys Leu Thr Val Met Val Tyr Asn Gly Glu
            20                  25                  30
```

Gln Gln Glu Ala Ile Lys Ser Ala Glu Asn Ala Thr Lys Val Glu Asp
            35                  40                  45

Ile Lys Cys Ser Ala Gly Gln Arg Thr Leu Val Val Met Ala Asn Thr
 50                  55                  60

Gly Ala Met Glu Leu Val Gly Lys Thr Leu Ala Glu Val Lys Ala Leu
 65                  70                  75                  80

Thr Thr Glu Leu Thr Ala Glu Asn Gln Glu Ala Ala Gly Leu Ile Met
                 85                  90                  95

Thr Ala Glu Pro Lys Thr Ile Val Leu Lys Ala Gly Lys Asn Tyr Ile
            100                 105                 110

Gly Tyr Ser Gly Thr Gly Glu Gly Asn His Ile Glu Asn Asp Pro Leu
            115                 120                 125

Lys Ile Lys Arg Val His Ala Arg Met Ala Phe Thr Glu Ile Lys Val
130                 135                 140

Gln Met Ser Ala Ala Tyr Asp Asn Ile Tyr Thr Phe Val Pro Glu Lys
145                 150                 155                 160

Ile Tyr Gly Leu Ile Ala Lys Lys Gln Ser Asn Leu Phe Gly Ala Thr
                165                 170                 175

Leu Val Asn Ala Asp Ala Asn Tyr Leu Thr Gly Ser Leu Thr Thr Phe
            180                 185                 190

Asn Gly Ala Tyr Thr Pro Ala Asn Tyr Ala Asn Val Pro Trp Leu Ser
            195                 200                 205

Arg Asn Tyr Val Ala Pro Ala Ala Asp Ala Pro Gln Gly Phe Tyr Val
210                 215                 220

Leu Glu Asn Asp Tyr Ser Ala Asn Gly Gly Thr Ile His Pro Thr Ile
225                 230                 235                 240

Leu Cys Val Tyr Gly Lys Leu Gln Lys Asn Gly Ala Asp Leu Ala Gly
                245                 250                 255

Ala Asp Leu Ala Ala Gln Ala Ala Asn Trp Val Asp Ala Glu Gly
            260                 265                 270

Lys Thr Tyr Tyr Pro Val Leu Val Asn Phe Asn Ser Asn Asn Tyr Thr
            275                 280                 285

Tyr Asp Ser Asn Tyr Thr Pro Lys Asn Lys Ile Glu Arg Asn His Lys
            290                 295                 300

Tyr Asp Ile Lys Leu Thr Ile Thr Gly Pro Gly Thr Asn Asn Pro Glu
305                 310                 315                 320

Asn Pro Ile Thr Glu Ser Ala His Leu Asn Val Gln Cys Thr Val Ala
                325                 330                 335

Glu Trp Val Leu Val Gly Gln Asn Ala Thr Trp
            340                 345

<210> SEQ ID NO 281
<211> LENGTH: 428
<212> TYPE: PRT
<213> ORGANISM: Artificial Sequence
<220> FEATURE:
<223> OTHER INFORMATION: Mycoplasma fermentans macrophage activating
      lipopeptide

<400> SEQUENCE: 281

Met Lys Lys Ser Lys Lys Ile Leu Leu Gly Leu Ser Pro Ile Ala Ala
 1               5                  10                  15

Val Leu Pro Ala Val Ala Val Ser Cys Gly Asn Asn Asp Glu Ser Asn
             20                  25                  30

Ile Ser Phe Lys Glu Lys Asp Ile Ser Lys Tyr Thr Thr Thr Asn Ala
             35                  40                  45

```
Asn Gly Lys Gln Val Val Lys Asn Ala Glu Leu Leu Lys Leu Lys Pro
 50                  55                  60
Val Leu Ile Thr Asp Glu Gly Lys Ile Asp Asp Lys Ser Phe Asn Gln
65                  70                  75                  80
Ser Ala Phe Glu Ala Leu Lys Ala Ile Asn Lys Gln Thr Gly Ile Glu
                85                  90                  95
Ile Asn Ser Val Glu Pro Ser Ser Asn Phe Glu Ser Ala Tyr Asn Ser
                100                 105                 110
Ala Leu Ser Ala Gly His Lys Ile Trp Val Leu Asn Gly Phe Lys His
                115                 120                 125
Gln Gln Ser Ile Lys Gln Tyr Ile Asp Ala His Arg Glu Glu Leu Glu
                130                 135                 140
Arg Asn Gln Ile Lys Ile Gly Ile Asp Phe Asp Ile Glu Thr Glu
145                 150                 155                 160
Tyr Lys Trp Phe Tyr Ser Leu Gln Phe Asn Ile Lys Glu Ser Ala Phe
                    165                 170                 175
Thr Thr Gly Tyr Ala Ile Ala Ser Trp Leu Ser Glu Gln Asp Glu Ser
                180                 185                 190
Lys Arg Val Val Ala Ser Phe Gly Val Gly Ala Phe Pro Gly Val Thr
                195                 200                 205
Thr Phe Asn Glu Gly Phe Ala Lys Gly Ile Leu Tyr Tyr Asn Gln Lys
210                 215                 220
His Lys Ser Ser Lys Ile Tyr His Thr Ser Pro Val Lys Leu Asp Ser
225                 230                 235                 240
Gly Phe Thr Ala Gly Glu Lys Met Asn Thr Val Ile Asn Asn Val Leu
                245                 250                 255
Ser Ser Thr Pro Ala Asp Val Lys Tyr Asn Pro His Val Ile Leu Ser
                260                 265                 270
Val Ala Gly Pro Ala Thr Phe Glu Thr Val Arg Leu Ala Asn Lys Gly
                275                 280                 285
Gln Tyr Val Ile Gly Val Asp Ser Asp Gln Gly Met Ile Gln Asp Lys
                290                 295                 300
Asp Arg Ile Leu Thr Ser Val Leu Lys His Ile Lys Gln Ala Val Tyr
305                 310                 315                 320
Glu Thr Leu Leu Asp Leu Ile Leu Glu Lys Glu Glu Gly Tyr Lys Pro
                325                 330                 335
Tyr Val Val Lys Asp Lys Lys Ala Asp Lys Lys Trp Ser His Phe Gly
                340                 345                 350
Thr Gln Lys Glu Lys Trp Ile Gly Val Ala Glu Asn His Phe Ser Asn
                355                 360                 365
Thr Glu Glu Gln Ala Lys Ile Asn Asn Lys Ile Lys Glu Ala Ile Lys
                370                 375                 380
Met Phe Lys Glu Leu Pro Glu Asp Phe Val Lys Tyr Ile Asn Ser Asp
385                 390                 395                 400
Lys Ala Leu Lys Asp Gly Asn Lys Ile Asp Asn Val Ser Glu Arg Leu
                405                 410                 415
Glu Ala Ile Ile Ser Ala Ile Asn Lys Ala Ala Lys
                420                 425
```

<210> SEQ ID NO 282
<211> LENGTH: 143
<212> TYPE: PRT
<213> ORGANISM: Artificial Sequence
<220> FEATURE:
<223> OTHER INFORMATION: p19 protein of Mycobacterium tuberculosis

```
<400> SEQUENCE: 282

Ala Thr Thr Leu Pro Val Gln Arg His Pro Arg Ser Leu Phe Pro Glu
  1               5                  10                  15

Phe Ser Glu Leu Phe Ala Ala Phe Pro Ser Phe Ala Gly Leu Arg Pro
             20                  25                  30

Thr Phe Asp Thr Arg Leu Met Arg Leu Glu Asp Glu Met Lys Glu Gly
             35                  40                  45

Arg Tyr Glu Val Arg Ala Glu Leu Pro Gly Val Asp Pro Asp Lys Asp
         50                  55                  60

Val Asp Ile Met Val Arg Asp Gly Gln Leu Thr Ile Lys Ala Glu Arg
 65                  70                  75                  80

Thr Glu Gln Lys Asp Phe Asp Gly Arg Ser Glu Phe Ala Tyr Gly Ser
                 85                  90                  95

Phe Val Arg Thr Val Ser Leu Pro Val Gly Ala Asp Glu Asp Asp Ile
            100                 105                 110

Lys Ala Thr Tyr Asp Lys Gly Ile Leu Thr Val Ser Val Ala Val Ser
            115                 120                 125

Glu Gly Lys Pro Thr Glu Lys His Ile Gln Ile Arg Ser Thr Asn
            130                 135                 140
```